(12) United States Patent (10) Patent No.: US 9,617,244 B2
Guillemont et al. (45) Date of Patent: *Apr. 11, 2017

(54) ANTIBACTERIAL QUINOLINE DERIVATIVES

(71) Applicant: JANSSEN PHARMACEUTICA NV, Beerse (BE)

(72) Inventors: Jerome Emile Georges Guillemont, Val de Reuil (FR); Magali Madeleine Simone Motte, Val de Reuil (FR); David Francis Alain Lancois, Val de Reuil (FR); Sebastein Robert Gaston Thomas, Val de Reuil (FR); Wendy Mia Albert Balemans, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/391,034

(22) PCT Filed: Apr. 26, 2013

(86) PCT No.: PCT/EP2013/058697
§ 371 (c)(1),
(2) Date: Oct. 7, 2014

(87) PCT Pub. No.: WO2013/160431
PCT Pub. Date: Oct. 31, 2013

(65) Prior Publication Data
US 2015/0051244 A1 Feb. 19, 2015

(30) Foreign Application Priority Data
Apr. 27, 2012 (EP) .................................... 12165882

(51) Int. Cl.
*C07D 401/14* (2006.01)
*C07D 401/06* (2006.01)
*A61K 31/4709* (2006.01)
*A61K 45/06* (2006.01)

(52) U.S. Cl.
CPC ........ *C07D 401/14* (2013.01); *A61K 31/4709* (2013.01); *A61K 45/06* (2013.01); *C07D 401/06* (2013.01)

(58) Field of Classification Search
CPC  C07D 401/06; C07D 401/14; A61K 31/4709; A61K 45/06
USPC ......................................... 514/312; 546/157
See application file for complete search history.

(56) References Cited

U.S. PATENT DOCUMENTS 5,965,572 A 10/1999 Ellis et al.
9,133,167 B2 * 9/2015 Guillemont et al. ...... 514/235.2

FOREIGN PATENT DOCUMENTS

| WO | WO 00/34265 A2 | 6/2000 |
| WO | WO 2004/011436 A1 | 2/2004 |
| WO | WO 2005/070430 A1 | 8/2005 |
| WO | WO 2005/070924 A1 | 8/2005 |
| WO | WO 2005/075428 A1 | 8/2005 |
| WO | WO 2005/117875 A1 | 12/2005 |
| WO | WO 2005/123081 A2 | 12/2005 |
| WO | WO 2006/035051 A1 | 4/2006 |
| WO | WO 2006/067048 A1 | 6/2006 |
| WO | WO 2006/131519 A1 | 12/2006 |
| WO | WO 2007/000434 A1 | 1/2007 |
| WO | WO 2007/000435 A1 | 1/2007 |
| WO | WO 2007/000436 A1 | 1/2007 |
| WO | WO 2007/014885 A1 | 2/2007 |

(Continued)

OTHER PUBLICATIONS

Andrew "Difference between amoxicillin . . . " p. 1-2 from internet (2015).*
Levy "Antimicrobial proteins . . . " Blood, v.96(8) p. 2664-2672 (2000).*
Nascimento et al. "antibacterial . . . " Brazilian J. Microbiology v. 31, p. 247-256 (2000).*
"antimicrobial" Michigan State Univ. Website p. 1 (2011).*
Guillaume, M., et al., "Process Development of the Synthetic Route to R116301", Organic Process Research & Development 2007), vol. 11, pp. 1079-1086.
Ye, X., et al., "Discovery of a Novel Sulfonamide-Pyrazolopiperiine Series as Potent and Efficacious γ-Secretase Inhibitors", Bioorganic & Medicinal Chemistry Letters, (2010), vol. 20, pp. 2195-2199.

(Continued)

*Primary Examiner* — Celia Chang
(74) *Attorney, Agent, or Firm* — Thomas J. Dodd

(57) ABSTRACT

The present invention relates to novel substituted quinoline derivatives according to the general Formula (Ia) or Formula (Ib):

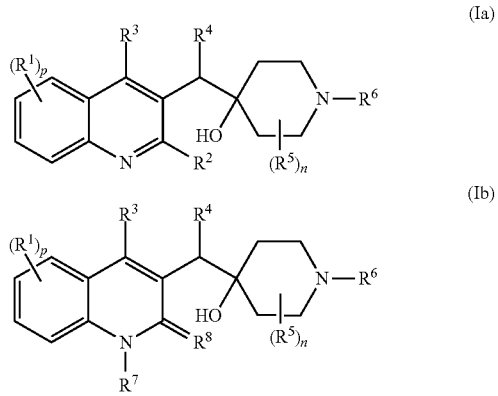

including any stereochemically isomeric form thereof, a pharmaceutically acceptable salt thereof, a N-oxide form thereof or a solvate thereof.

The claimed compounds are useful for the treatment of a bacterial infection. Also claimed is a composition comprising a pharmaceutically acceptable carrier and, as active ingredient, a therapeutically effective amount of the claimed compounds, the use of the claimed compounds or compositions for the manufacture of a medicament for the treatment of a bacterial infection and a process for preparing the claimed compounds.

26 Claims, No Drawings

(56) References Cited

FOREIGN PATENT DOCUMENTS

| WO | WO 2007/014934 A2 | 2/2007 |
|---|---|---|
| WO | WO 2007/014940 A2 | 2/2007 |
| WO | WO 2007/014941 A2 | 2/2007 |
| WO | WO 2008/068266 A1 | 6/2008 |
| WO | WO 2008/068267 A1 | 6/2008 |
| WO | WO 2008/068268 A1 | 6/2008 |
| WO | WO 2008/068269 A1 | 6/2008 |
| WO | WO 2008/068270 A1 | 6/2008 |
| WO | WO 2008/068272 A2 | 6/2008 |

OTHER PUBLICATIONS

Zurenko, G., et al., "In Vitro Activities of U-100592 and U-100766, Novel Oxazolidinone Antibacterial Agents", Antimicrobial Agents and Chemotherapy (1996), pp. 839-845.
International Search Report mailed Jun. 11, 2013 for Application No. PCT/EP2013/058703.
International Search Report mailed Jun. 13, 2013, for Application No. PCT/EP2013/058697.
Andries et al., Science, vol. 307, Jan. 14, 2005, pp. 223-227.

\* cited by examiner

ANTIBACTERIAL QUINOLINE DERIVATIVES

CROSS-REFERENCE TO RELATED APPLICATIONS

The present application claims priority of the benefits of the filing of Application Nos. EP 12165882.7 filed Apr. 27, 2012, and PCT/EP2013/058697 (WO2013/160431) filed Apr. 26, 2013. The complete disclosures of the aforementioned related patent applications are hereby incorporated herein by reference for all purposes.

The present invention relates to novel substituted quinoline derivatives useful for the treatment of bacterial diseases, including but not limited to diseases caused by pathogenic mycobacteria such as *Mycobacterium tuberculosis, M. bovis, M. leprae, M. avium* and *M. marinum*, or pathogenic Staphylococci or Streptococci.

BACKGROUND OF THE INVENTION

*Mycobacterium tuberculosis* is the causative agent of tuberculosis (TB), a serious and potentially fatal infection with a world-wide distribution. Estimates from the World Health Organization indicate that more than 8 million people contract TB each year, and 2 million people die from tuberculosis yearly. In the last decade, TB cases have grown 20% worldwide with the highest burden in the most impoverished communities. If these trends continue, TB incidence will increase by 41% in the next twenty years. Fifty years since the introduction of an effective chemotherapy, TB remains after AIDS, the leading infectious cause of adult mortality in the world. Complicating the TB epidemic is the rising tide of multi-drug-resistant strains, and the deadly symbiosis with HIV. People who are HIV-positive and infected with TB are 30 times more likely to develop active TB than people who are HIV-negative and TB is responsible for the death of one out of every three people with HIV/AIDS worldwide Existing approaches to treatment of tuberculosis all involve the combination of multiple agents. For example, the regimen recommended by the U.S. Public Health Service is a combination of isoniazid, rifampicin and pyrazinamide for two months, followed by isoniazid and rifampicin alone for a further four months. These drugs are continued for a further seven months in patients infected with HIV. For patients infected with multi-drug resistant strains of *M. tuberculosis*, agents such as ethambutol, streptomycin, kanamycin, amikacin, capreomycin, ethionamide, cycloserine, ciprofoxacin and ofloxacin are added to the combination therapies. There exists no single agent that is effective in the clinical treatment of tuberculosis, nor any combination of agents that offers the possibility of therapy of less than six months' duration.

There is a high medical need for new drugs that improve current treatment by enabling regimens that facilitate patient and provider compliance. Shorter regimens and those that require less supervision are the best way to achieve this. Most of the benefit from treatment comes in the first 2 months, during the intensive, or bactericidal, phase when four drugs are given together; the bacterial burden is greatly reduced, and patients become noninfectious. The 4- to 6-month continuation, or sterilizing, phase is required to eliminate persisting bacilli and to minimize the risk of relapse. A potent sterilizing drug that shortens treatment to 2 months or less would be extremely beneficial. Drugs that facilitate compliance by requiring less intensive supervision also are needed. Obviously, a compound that reduces both the total length of treatment and the frequency of drug administration would provide the greatest benefit.

Complicating the TB epidemic is the increasing incidence of multi-drug-resistant strains or MDR-TB. Up to four percent of all cases worldwide are considered MDR-TB—those resistant to the most effective drugs of the four-drug standard, isoniazid and rifampin. MDR-TB is lethal when untreated and cannot be adequately treated through the standard therapy, so treatment requires up to 2 years of "second-line" drugs. These drugs are often toxic, expensive and marginally effective. In the absence of an effective therapy, infectious MDR-TB patients continue to spread the disease, producing new infections with MDR-TB strains. There is a high medical need for a new drug with a new mechanism of action, which is likely to demonstrate activity against drug resistant, in particular MDR strains.

The term "drug resistant" as used hereinbefore or hereinafter is a term well understood by the person skilled in microbiology. A drug resistant *Mycobacterium* is a *Mycobacterium* which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs. MDR tuberculosis is a specific form of drug resistant tuberculosis due to a bacterium resistant to at least isoniazid and rifampicin (with or without resistance to other drugs), which are at present the two most powerful anti-TB drugs. Thus, whenever used hereinbefore or hereinafter "drug resistant" includes multi drug resistant.

Another factor in the control of the TB epidemic is the problem of latent TB. In spite of decades of tuberculosis (TB) control programs, about 2 billion people are infected by *M. tuberculosis*, though asymptomatically. About 10% of these individuals are at risk of developing active TB during their lifespan. The global epidemic of TB is fuelled by infection of HIV patients with TB and rise of multi-drug resistant TB strains (MDR-TB). The reactivation of latent TB is a high risk factor for disease development and accounts for 32% deaths in HIV infected individuals. To control TB epidemic, the need is to discover new drugs that can kill dormant or latent bacilli. The dormant TB can get reactivated to cause disease by several factors like suppression of host immunity by use of immunosuppressive agents like antibodies against tumor necrosis factor α or interferon-γ. In case of HIV positive patients the only prophylactic treatment available for latent TB is two-three months regimens of rifampicin, pyrazinamide. The efficacy of the treatment regime is still not clear and furthermore the length of the treatments is an important constraint in resource-limited environments. Hence there is a drastic need to identify new drugs, which can act as chemoprophylactic agents for individuals harboring latent TB bacilli. The tubercle bacilli enter healthy individuals by inhalation; they are phagocytosed by the alveolar macrophages of the lungs. This leads to potent immune response and formation of granulomas, which consist of macrophages infected with *M. tuberculosis* surrounded by T cells. After a period of 6-8 weeks the host immune response causes death of infected cells by necrosis and accumulation of caseous material with certain extracellular bacilli, surrounded by macrophages, epitheloid cells and layers of lymphoid tissue at the periphery. In case of healthy individuals, most of the mycobacteria are killed in these environments but a small proportion of bacilli still survive and are thought to exist in a non-replicating, hypometabolic state and are tolerant to killing by anti-TB drugs like isoniazid. These bacilli can remain in the altered physiological environments even for individual's lifetime without showing any clinical symptoms of disease. However, in 10% of the cases these latent bacilli may reactivate to cause disease. One of the hypothesis about development of these persistent bacteria is patho-physiological environment in human lesions namely, reduced oxygen tension, nutrient limitation, and acidic pH. These factors have been postulated to render these bacteria phenotypically tolerant to major anti-mycobacterial drugs.

In addition to the management of the TB epidemic, there is the emerging problem of resistance to first-line antibiotic agents. Some important examples include penicillin-resistant *Streptococcus pneumoniae*, vancomycin-resistant enterococci, methicillin-resistant *Staphylococcus aureus*, multi-resistant salmonellae.

The consequences of resistance to antibiotic agents are severe. Infections caused by resistant microbes fail to respond to treatment, resulting in prolonged illness and greater risk of death. Treatment failures also lead to longer periods of infectivity, which increase the numbers of infected people moving in the community and thus exposing the general population to the risk of contracting a resistant strain infection. Hospitals are a critical component of the antimicrobial resistance problem worldwide. The combination of highly susceptible patients, intensive and prolonged antimicrobial use, and cross-infection has resulted in infections with highly resistant bacterial pathogens.

Self-medication with antimicrobials is another major factor contributing to resistance. Self-medicated antimicrobials may be unnecessary, are often inadequately dosed, or may not contain adequate amounts of active drug.

Patient compliance with recommended treatment is another major problem. Patients forget to take medication, interrupt their treatment when they begin to feel better, or may be unable to afford a full course, thereby creating an ideal environment for microbes to adapt rather than be killed.

Because of the emerging resistance to multiple antibiotics, physicians are confronted with infections for which there is no effective therapy. The morbidity, mortality, and financial costs of such infections impose an increasing burden for health care systems worldwide.

Therefore, there is a high need for new compounds to treat bacterial infections, especially mycobacterial infections including drug resistant and latent mycobacterial infections, and also other bacterial infections especially those caused by resistant bacterial strains.

WO2004/011436, WO2005/070924, WO2005/070430, WO2005/075428 and WO2007/014885 disclose certain substituted quinoline derivatives having activity against Mycobacteria, in particular against *Mycobacterium tuberculosis*. WO2005/117875 describes substituted quinoline derivatives having activity against resistant Mycobacterial strains. WO2006/067048 describes substituted quinoline derivatives having activity against latent tuberculosis. One particular compound of these substituted quinoline derivatives is described in Science (2005), 307, 223-227 and its mode of action is described in WO2006/035051.

WO2006/131519, WO2007/000434, WO2007/000435, WO2007/000436, WO2007/014934, WO2007/014940 and WO2007/014941 disclose certain substituted quinoline derivatives having activity against bacteria such as *Staphylococcus* and *Streptococcus*.

WO2008/068266, WO2008/068267, WO2008/068268, WO2008/068269, WO2008/068270 and WO2008/068272 disclose certain substituted quinoline derivatives having activity against Mycobacteria, in particular against *Mycobacterium tuberculosis*, and also against bacteria such as *Staphylococcus* and *Streptococcus*.

Other substituted quinolines are disclosed in U.S. Pat. No. 5,965,572 (The United States of America) for treating antibiotic resistant infections and in WO00/34265 to inhibit the growth of bacterial microorganisms.

The purpose of the present invention is to provide novel compounds, in particular substituted quinoline derivatives, having the property of inhibiting bacterial growth especially of mycobacteria but also of other bacteria such as Streptococci and Staphylococci and the compounds are therefore useful for the treatment of bacterial diseases, particularly those diseases caused by pathogenic bacteria such as *Streptococcus pneumonia, Staphylococcus aureus* or *Mycobacterium tuberculosis* (including the latent disease and including drug resistant *M. tuberculosis* strains), *M. bovis, M leprae, M avium* and *M. marinum*.

SUMMARY OF THE INVENTION

The present invention relates to novel substituted quinoline derivatives according to formula (Ia) or (Ib):

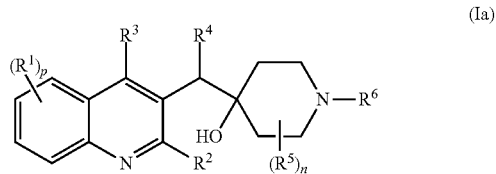

(Ia)

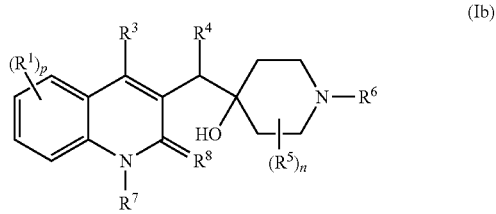

(Ib)

including any stereochemically isomeric form thereof, wherein
p is an integer equal to 1, 2, 3 or 4;
n is an integer equal to 1 or 2; provided that if n is 2 then both $R^5$ substituents are linked to the same carbon atom of the piperidine moiety;
$R^1$ is hydrogen, cyano, cyano$C_{1-6}$alkyl, formyl, carboxyl, halo, $C_{1-6}$alkyl, $C_{2-6}$alkenyl, $C_{2-6}$alkynyl, polyhalo$C_{1-6}$alkyl, hydroxy, hydroxy$C_{1-6}$alkyl, $C_{1-6}$alkyloxy, $C_{1-6}$alkyloxy$C_{1-6}$alkyl, $C_{1-6}$alkylthio, $C_{1-6}$alkylthio$C_{1-6}$alkyl, —C=N—$OR^{11}$, amino, mono or di($C_{1-6}$alkyl)amino, amino$C_{1-6}$alkyl, mono or di($C_{1-6}$alkyl)amino$C_{1-6}$alkyl, $C_{1-6}$alkylcarbonylamino$C_{1-6}$alkyl, $R^{9b}R^{10b}$N—C(=O)—, aryl$C_{1-6}$alkyl, arylcarbonyl, $R^{9a}R^{10a}$N—$C_{1-6}$alkyl, di(aryl)$C_{1-6}$alkyl, aryl, $C_{3-6}$cycloalkyl, $R^{9a}R^{10a}$N—, $R^{9a}R^{10a}$N—C(=O)—, $C_{1-4}$alkyl-S(=O)$_2$—, or Het;
$R^2$ is hydrogen, $C_{1-6}$alkyloxy, aryl, aryloxy, hydroxy, mercapto, $C_{1-6}$alkyloxy$C_{1-6}$alkyloxy, $C_{1-6}$alkylthio, mono or di($C_{1-6}$alkyl)amino, amino, pyrrolidino or a radical of formula

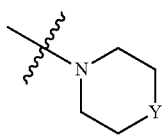

wherein Y is CH₂, O, S, NH or N—C_{1-6}alkyl;

R³ is hydrogen, halo, C_{1-6}alkyl, aryl or Het;

R⁴ is aryl¹ or Het;

R⁵ is aryl, arylC_{1-6}alkyl, C_{3-6}cycloalkyl, C_{3-6}cycloalkylC_{1-6}alkyl, Het, HetC_{1-6}alkyl, C_{1-6}alkyl, hydroxyC_{1-6}alkyl, aminoC_{1-6}alkyl, mono- or di(C_{1-4}alkyl)aminoC_{1-6}alkyl, aryl-NH—C_{1-6}alkyl, Het-NH—C_{1-6}alkyl, C_{2-6}alkenyl or halo;

R⁶ is hydrogen, C_{1-6}alkyl, arylC_{1-6}alkyl, Het¹, Het¹C_{1-6}alkyl or —C(=NH)—NH₂;

R⁷ is hydrogen or C_{1-6}alkyl;

R⁸ is oxo; or

R⁷ and R⁸ together form the radical —CH=CH—N=;

R^{9a} and R^{10a} together with the nitrogen atom to which they are attached form a radical selected from the group consisting of pyrrolidinyl, piperidinyl, piperazinyl, morpholinyl, 4-thiomorpholinyl, 2,3-dihydroisoindol-1-yl, thiazolidin-3-yl, 1,2,3,6-tetrahydropyridyl, hexahydro-1H-azepinyl, hexahydro-1H-1,4-diazepinyl, hexahydro-1,4-oxazepinyl, 1,2,3,4-tetrahydroisoquinolin-2-yl, pyrrolinyl, pyrrolyl, imidazolidinyl, pyrazolidinyl, 2-imidazolinyl, 2-pyrazolinyl, imidazolyl, pyrazolyl, triazolyl, pyridinyl, pyridazinyl, pyrimidinyl, pyrazinyl and triazinyl, each radical being optionally substituted with 1, 2, 3 or 4 substituents, each substituent being independently selected from C_{1-6}alkyl, polyhaloC_{1-6}alkyl, halo, arylC_{1-6}alkyl, hydroxy, C_{1-6}alkyloxy, amino, mono- or di(C_{1-6}alkyl)amino, C_{1-6}alkylthio, C_{1-6}alkylthioC_{1-6}alkyl, aryl, pyridyl or pyrimidinyl;

R^{9b} and R^{10b} each independently represent hydrogen, C_{1-6}alkyl, aryl or Het;

R¹¹ is hydrogen or C_{1-6}alkyl;

aryl is a homocycle selected from phenyl, naphthyl, acenaphthyl or tetrahydronaphthyl, each being optionally substituted with 1, 2 or 3 substituents, each substituent being independently selected from hydroxy, hydroxyC_{1-6}alkyl, halo, cyano, cyanoC_{1-6}alkyl, nitro, amino, mono- or di(C_{1-6}alkyl)amino, C_{1-6}alkyl, C_{2-6}alkenyl optionally substituted with phenyl, polyhaloC_{1-6}alkyl, C_{1-6}alkyloxy, C_{1-6}alkyloxyC_{1-6}alkyl, polyhaloC_{1-6}alkyloxy, carboxyl, C_{1-6}alkyloxycarbonyl, aminocarbonyl, morpholinyl or mono- or di(C_{1-6}alkyl)aminocarbonyl;

aryl¹ is a homocycle selected from phenyl, naphthyl, acenaphthyl or tetrahydronaphthyl, each being optionally substituted with 1, 2 or 3 substituents, each substituent being independently selected from hydroxy, hydroxyC_{1-6}alkyl, halo, cyano, cyanoC_{1-6}alkyl, nitro, amino, mono- or di(C_{1-6}alkyl)amino, C_{1-6}alkyl, polyhaloC_{1-6}alkyl, C_{1-6}alkyloxy, C_{1-6}alkyloxyC_{1-6}alkyl, C_{1-6}alkylthio, polyhaloC_{1-6}alkyloxy, carboxyl, C_{1-6}alkyloxycarbonyl, aminocarbonyl, Het, mono- or di(C_{1-6}alkyl)aminocarbonyl, or C_{1-4}alkyl-S(=O)₂—;

Het is a monocyclic heterocycle selected from N-phenoxypiperidinyl, piperidinyl, piperazinyl, morpholinyl, 4-thiomorpholinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle being optionally substituted with 1, 2 or 3 substituents, each substituent being independently selected from halo, hydroxy, C_{1-6}alkyl or C_{1-6}alkyloxy;

Het¹ is a monocyclic saturated heterocycle selected from pyrrolidinyl, piperidinyl, piperazinyl, morpholinyl, 4-thiomorpholinyl, imidazolidinyl, pyrazolidinyl; each monocyclic saturated heterocycle being optionally substituted with C_{1-6}alkyl or arylC_{1-6}alkyl;

the N-oxides thereof, the pharmaceutically acceptable salts thereof or the solvates thereof.

Whenever used herein, the term "compounds of formula (Ia) or (Ib)" or "compounds according to the invention" is meant to also include their pharmaceutically acceptable salts or their N-oxide forms or their solvates.

The compounds of formula (Ia) and (Ib) are interrelated in that e.g. a compound according to formula (Ib), with R⁸ equal to oxo and R⁷ equal to hydrogen, is the tautomeric equivalent of a compound according to formula (Ia) with R² equal to hydroxy (keto-enol tautomerism).

In the definition of Het, it is meant to include all the possible isomeric forms of the heterocycles, for instance, pyrrolyl comprises 1H-pyrrolyl and 2H-pyrrolyl.

The aryl, aryl¹, Het or Het¹ listed in the definitions of the substituents of the compounds of formula (Ia) or (Ib) (see for instance R⁴ or R⁶) as mentioned hereinbefore or hereinafter may be attached to the remainder of the molecule of formula (Ia) or (Ib) through any ring carbon or heteroatom as appropriate, if not otherwise specified. Thus, for example, when Het is imidazolyl, it may be 1-imidazolyl, 2-imidazolyl, 4-imidazolyl and the like.

Lines drawn from substituents into ring systems indicate that the bond may be attached to any of the suitable ring atoms.

The pharmaceutically acceptable salts as mentioned hereinbefore or hereinafter are meant to comprise the therapeutically active non-toxic acid addition salt forms which the compounds according to formula (Ia) or formula (Ib) are able to form. Said acid addition salts can be obtained by treating the base form of the compounds according to formula (Ia) or formula (Ib) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds of formula (Ia) or (Ib) containing acidic protons may be converted into their therapeutically active non-toxic metal or amine addition salt forms by treatment with appropriate organic and inorganic bases. The pharmaceutically acceptable salts as mentioned hereinbefore or hereinafter are meant to also comprise the therapeutically active non-toxic metal or amine addition salt forms (base addition salt forms) which the compounds of formula (Ia) or (Ib) are able to form. Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like.

Conversely, said acid or base addition salt forms can be converted into the free forms by treatment with an appropriate base or acid.

The term pharmaceutically acceptable salt also comprises the quaternary ammonium salts (quaternary amines) which the compounds of formula (Ia) or (Ib) are able to form by reaction between a basic nitrogen of a compound of formula (Ia) or (Ib) and an appropriate quaternizing agent, such as, for example, an optionally substituted $C_{1-6}$alkylhalide, aryl$C_{1-6}$alkylhalide, $C_{1-6}$alkylcarbonylhalide, arylcarbonylhalide, Het$C_{1-6}$alkylhalide or Hetcarbonylhalide, e.g. methyliodide or benzyliodide. Preferably, Het represents a monocyclic heterocycle selected from furanyl or thienyl; or a bicyclic heterocycle selected from benzofuranyl or benzothienyl; each monocyclic and bicyclic heterocycle may optionally be substituted with 1, 2 or 3 substituents, each substituent being independently selected from the group of halo, alkyl and aryl. Preferably, the quaternizing agent is a $C_{1-6}$alkylhalide. Other reactants with good leaving groups may also be used, such as $C_{1-6}$alkyl trifluoromethanesulfonates, $C_{1-6}$alkyl methanesulfonates, and $C_{1-6}$alkyl p-toluenesulfonates. A quaternary amine has a positively charged nitrogen. Pharmaceutically acceptable counterions include chloro, bromo, iodo, trifluoroacetate, acetate, triflate, sulfate, sulfonate. Preferably, the counterion is iodo. The counterion of choice can be introduced using ion exchange resins.

Preferably, the term pharmaceutically acceptable salt means the pharmaceutically acceptable acid and base additional salts as mentioned hereinabove.

The term solvate comprises the hydrates and solvent addition forms which the compounds of formula (Ia) or (Ib) are able to form, as well as the salts thereof. Examples of such forms are e.g. hydrates, alcoholates and the like.

In the framework of this application, a compound according to the invention is inherently intended to comprise all stereochemically isomeric forms thereof. The term "stereochemically isomeric forms" as used hereinbefore or hereinafter defines all the possible stereoisomeric forms which the compounds of formula (Ia) and (Ib), and their N-oxides, pharmaceutically acceptable salts, solvates or physiologically functional derivatives may possess. Unless otherwise mentioned or indicated, the chemical designation of compounds denotes the mixture of all possible stereochemically isomeric forms. In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art. Stereochemically isomeric forms of the compounds of formula (Ia) and (Ib) are obviously intended to be embraced within the scope of this invention.

Of special interest are those compounds of formula (Ia) or (Ib) which are stereochemically pure.

Following CAS-nomenclature conventions, when stereogenic centers of known absolute configuration are present in a molecule, an R or S descriptor is assigned (based on Cahn-Ingold-Prelog sequence rule) to the lowest-numbered chiral center, the reference center.

Where the absolute configuration of a stereogenic centre is not known such centers are indicated herein arbitrarily as R* or S* if the relevant compound is stereochemically pure or as RS* if the compound is a stereochemical mixture. In many cases with the compounds according to the invention the configuration of the carbon atom on the piperidine ring to which the $R^5$ substituent is known from the literature or from the mode of synthesis of the piperidine moiety; in this case the relevant carbon atom is indicated as R or S according to the known stereochemical configuration of the atom. It is readily possible using standard analytical techniques to establish whether the $R^5$ substituent and the 4-hydroxy substituent on the piperidine ring are in the same plane (i.e. cis) or on opposite planes (i.e. trans), thus allowing one establish the absolute configuration for the carbon atom at the 4-position of the piperidine ring, i.e. R or S; otherwise this carbon atom is identified as R* or S*. indicating an unknown absolute configuration. The carbon atom intermediate to the piperidine ring and the quinoline is arbitrarily identified as R* or S* if the configuration is unknown.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, when a compound of formula (Ia) or (Ib) is for instance specified as a specific enantiomer, this means that the compound is substantially free of the other enantiomers.

Compounds of either formula (Ia) and (Ib) and some of the intermediate compounds invariably have at least two stereogenic centers in their structure which may lead to at least 4 stereochemically different structures. In the structures below, the at least two stereogenic centers are indicated with *.

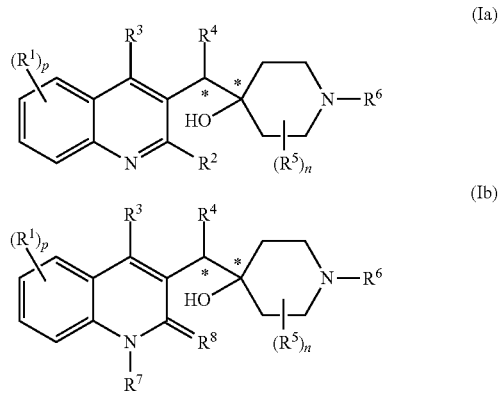

Except for those compounds of formula (Ia) or (Ib) wherein n is 2 and the two $R^5$ substituents are identical, the present compounds also have invariable an additional chiral center at the carbon atom of the piperidine moiety carrying the $R^5$ substituent(s). This implies at least 8 stereochemically different structures.

The compounds of either formula (Ia) and (Ib) may be synthesized in the form of mixtures, in particular racemic mixtures, of enantiomers which can be separated from one another following art-known resolution procedures. The racemic compounds of either formula (Ia) and (Ib) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of either formula (Ia) and (Ib) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of formula (Ia) or (Ib) are meant to comprise those compounds of formula (Ia) or (Ib) wherein e.g. an enol group is converted into a keto group (keto-enol tautomerism). Tautomeric forms of the compounds of formula (Ia) and (Ib) or of intermediates of the present invention are intended to be embraced by the ambit of this invention.

The N-oxide forms of the present compounds are meant to comprise the compounds of formula (Ia) or (Ib) wherein one or several tertiary nitrogen atoms are oxidized to the so-called N-oxide.

The compounds of formula (Ia) and (Ib) may be converted to the corresponding N-oxide forms following art-known procedures for converting a trivalent nitrogen into its N-oxide form. Said N-oxidation reaction may generally be carried out by reacting the starting material of formula (Ia) or (Ib) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

In the framework of this application, a compound according to the invention is inherently intended to comprise all isotopic combinations of its chemical elements. In the framework of this application, a chemical element, in particular when mentioned in relation to a compound according to formula (Ia) or (Ib), comprises all isotopes and isotopic mixtures of this element, either naturally occurring or synthetically produced, either with natural abundance or in an isotopically enriched form. In particular, when hydrogen is mentioned, it is understood to refer to $^1H$, $^2H$, $^3H$ and mixtures thereof; when carbon is mentioned, it is understood to refer to $^{11}C$, $^{12}C$, $^{13}C$, $^{14}C$ and mixtures thereof; when nitrogen is mentioned, it is understood to refer to $^{13}N$, $^{14}N$, $^{15}N$ and mixtures thereof; when oxygen is mentioned, it is understood to refer to $^{14}O$, $^{15}O$, $^{16}O$, $^{17}O$, $^{18}O$ and mixtures thereof; and when fluor is mentioned, it is understood to refer to $^{18}F$, $^{19}F$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to formula (Ia) or (Ib), a pharmaceutically acceptable salt thereof or an N-oxide form thereof or a solvate thereof, which contains at least one radioactive atom. For example, a compound can be labelled with positron or with gamma emitting radioactive isotopes. For radioligand-binding techniques (membrane receptor assay), the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. Preferably, the radioactive atom is selected from the group of hydrogen, carbon and halogen.

In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

In the framework of this application, $C_{1-6}$alkyl represents a straight or branched saturated hydrocarbon radical having from 1 to 6 carbon atoms such as for example methyl, ethyl, propyl, 2-methyl-ethyl, pentyl, hexyl and the like. A preferred subgroup of $C_{1-6}$alkyl is $C_{1-4}$alkyl which represents a straight or branched saturated hydrocarbon radical having from 1 to 4 carbon atoms such as for example methyl, ethyl, propyl, 2-methyl-ethyl and the like.

In the framework of this application $C_{2-6}$alkenyl is a straight or branched hydrocarbon radical having from 2 to 6 carbon atoms containing a double bond such as ethenyl, propenyl, butenyl, pentenyl, hexenyl and the like; $C_{2-6}$alkynyl is a straight or branched hydrocarbon radical having from 2 to 6 carbon atoms containing a triple bond such as ethynyl, propynyl, butynyl, pentynyl, hexynyl and the like; $C_{3-6}$cycloalkyl is a cyclic saturated hydrocarbon radical having from 3 to 6 carbon atoms and is generic to cyclopropyl, cyclobutyl, cyclopentyl and cyclohexyl.

In the framework of this application, halo is a substituent selected from the group of fluoro, chloro, bromo and iodo. Preferably, halo is bromo, fluoro or chloro; in particular chloro or bromo.

In the framework of this application, polyhalo$C_{1-6}$alkyl is defined as mono- or polyhalosubstituted $C_{1-6}$alkyl, for example, methyl with one or more fluoro atoms, for example, difluoromethyl or trifluoromethyl, 1,1-difluoroethyl and the like. In case more than one halo atom is attached to a $C_{1-6}$alkyl group within the definition of polyhalo$C_{1-6}$alkyl, they may be the same or different.

An interesting embodiment relates to a compound of formula (Ia) or (Ib) having the following formula

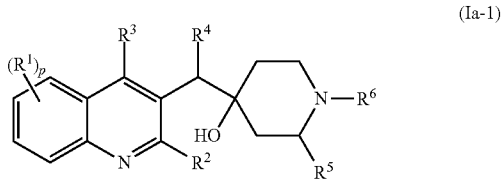

(Ia-1)

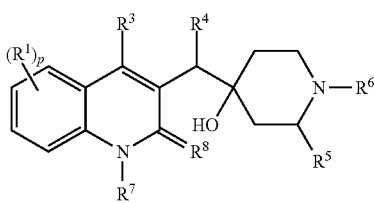

(Ib-1)

An interesting embodiment relates to a compound of formula (Ia) or (Ib) having the following formula

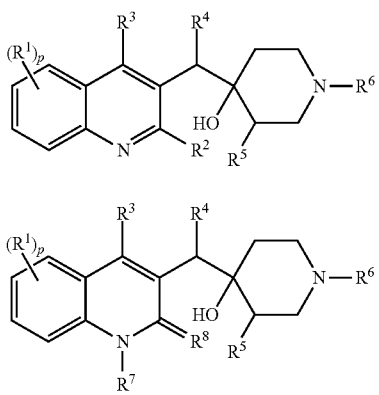

(Ia-2)

(Ib-2)

An interesting embodiment relates to a compound of formula (Ia) or (Ib), (Ia-1) or (Ib-1), or (Ia-2) or (Ib-2), wherein $R^1$ is hydrogen, cyano, carboxyl, halo, $C_{1-6}$alkyl, $C_{2-6}$alkenyl, polyhalo$C_{1-6}$alkyl, hydroxyl, hydroxy$C_{1-6}$alkyl, $C_{1-6}$alkyloxy, amino, mono or di($C_{1-6}$alkyl)amino, amino$C_{1-6}$alkyl, mono or di($C_{1-6}$alkyl)amino$C_{1-6}$alkyl, $R^{9b}R^{10b}N$—C(O)—, aryl, $R^{9a}R^{10a}N$—, $R^{9a}R^{10a}N$—C(O)—, $C_{1-4}$alkyl-S(=O)$_2$—, or Het; in particular $R^1$ is hydrogen, cyano, carboxyl, halo, $C_{1-6}$alkyl, $C_{2-6}$alkenyl, polyhalo$C_{1-6}$alkyl, hydroxy$C_{1-6}$alkyl, $C_{1-6}$alkyloxy, amino$C_{1-6}$alkyl, $R^{9b}R^{10b}N$—C(O)—, aryl, $C_{1-4}$alkyl-S(=O)$_2$—, or Het; more in particular $R^1$ is hydrogen, carboxyl, halo, $C_{1-6}$alkylthio, amino$C_{1-6}$alkyl or Het A second interesting embodiment relates to a compound of formula (Ia) or (Ib), (Ia-1) or (Ib-1), or (Ia-2) or (Ib-2), or a subgroup thereof as mentioned hereinbefore as an interesting embodiment, wherein p is 1 or 2; in particular p is 1.

A third interesting embodiment relates to a compound of formula (Ia), (Ia-1) or (Ia-2) or any subgroup thereof as mentioned hereinbefore as an interesting embodiment, wherein $R^2$ is hydrogen, $C_{1-6}$alkyloxy, $C_{1-6}$alkylthio, mono or di($C_{1-6}$alkyl)amino, amino or a radical of formula

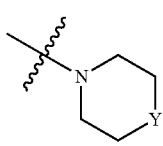

wherein Y is CH$_2$, O, S, NH or N—C$_{1-6}$alkyl; in particular $R^2$ is $C_{1-6}$alkyloxy, $C_{1-6}$alkylthio, mono or di($C_{1-6}$alkyl) amino, or a radical of formula

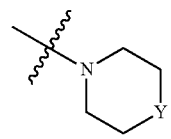

wherein Y is CH$_2$ or O; more in particular $R^2$ is $C_{1-6}$alkyloxy or $C_{1-6}$alkylthio; even more in particular $R^2$ is $C_{1-6}$alkyloxy especially methyloxy.

A fourth interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein $R^3$ is hydrogen, halo or $C_{1-6}$alkyl; in particular $R^3$ is hydrogen.

A fifth interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein $R^4$ is aryl$^1$; in particular $R^4$ is phenyl or naphthyl, each being optionally substituted with 1, 2 or 3 substituents, each substituent being independently selected from halo, cyano, $C_{1-6}$alkyl, polyhalo$C_{1-6}$alkyl, $C_{1-6}$alkyloxy, $C_{1-6}$alkylthio, $C_{1-4}$alkyl-S(=O)$_2$—; more in particular $R^4$ is phenyl optionally substituted with 1, 2 or 3 substituents, each substituent being independently selected from halo, cyano, $C_{1-6}$alkyl, polyhalo$C_{1-6}$alkyl, $C_{1-6}$alkyloxy, $C_{1-6}$alkylthio or $C_{1-4}$alkyl-S(=O)$_2$—; even more in particular $R^4$ is phenyl optionally substituted with 1 substituent, said substituent being selected from halo, cyano, $C_{1-4}$alkyl-S(=O)$_2$— or $C_{1-6}$alkylthio.

A sixth interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein $R^4$ is Het; in particular $R^4$ is a monocyclic heterocycle selected from N-phenoxypiperidinyl, piperidinyl, piperazinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; each monocyclic heterocycle being optionally substituted with 1, 2 or 3 substituents, each substituent being independently selected from halo, hydroxy, $C_{1-6}$alkyl or $C_{1-6}$alkyloxy; more in particular $R^4$ is a monocyclic heterocycle selected from piperidinyl, pyrazolyl, furanyl or pyridinyl, especially pyrazolyl or pyridinyl; each monocyclic heterocycle being optionally substituted with 1 substituent selected from halo, hydroxy, $C_{1-6}$alkyl or $C_{1-6}$alkyloxy, in particular hydroxy.

A seventh interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein $R^5$ is aryl, aryl$C_{1-6}$alkyl, $C_{3-6}$cycloalkyl$C_{1-6}$alkyl, Het$C_{1-6}$alkyl, $C_{1-6}$alkyl, hydroxy$C_{1-6}$alkyl or $C_{2-6}$alkenyl; in particular $R^5$ is aryl, aryl$C_{1-6}$alkyl, $C_{3-6}$cycloalkyl$C_{1-6}$alkyl, Het$C_{1-6}$alkyl or $R^5$ is $C_{1-6}$alkyl, hydroxy$C_{1-6}$alkyl or $C_{2-6}$alkenyl; more in particular $R^5$ is aryl or aryl$C_{1-6}$alkyl; even more in particular $R^5$ is optionally substituted phenyl, optionally substituted naphthyl, or phenyl$C_{1-6}$alkyl wherein said phenyl is optionally substituted; even further in particular $R^5$ is phenyl, phenyl substituted with 1 or 2 substituent each independently being selected from halo or $C_{1-6}$alkyl, naphthyl, naphthyl substituted with 1 or 2 substituent each being independently selected from halo or $C_{1-6}$alkyl, phenyl$C_{1-6}$alkyl or phenyl$C_{1-6}$alkyl wherein said phenyl is substituted with 1 or 2 substituents each being independently selected from halo or $C_{1-6}$alkyl; still further in particular $R^5$ is phenyl; phenyl substituted with 1 or 2 substituents each being independently selected from halo or $C_{1-6}$alkyl; phenyl$C_{1-6}$alkyl; or phenyl$C_{1-6}$alkyl wherein said phenyl is substituted with 1 or 2 substituent each being independently selected from halo or $C_{1-6}$alkyl; in particular $R^5$ is phenyl; phenyl substituted with 1 or 2 substituents each being independently selected from halo or $C_{1-6}$alkyl; benzyl; or benzyl wherein the phenyl moiety is substituted with 1 or 2 substituents each being independently selected from halo or $C_{1-6}$alkyl.

An eighth interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein $R^6$ is hydrogen, $C_{1-6}$alkyl, aryl$C_{1-6}$alkyl, Het$^1$, or —C(=NH)—NH$_2$; in particular $R^6$ is hydrogen, $C_{1-6}$alkyl or aryl$C_{1-6}$alkyl; more in particular $R^6$ is hydrogen, $C_{1-6}$alkyl or aryl$C_{1-6}$alkyl wherein aryl is optionally substituted phenyl; even more in particular $R^6$ is hydrogen, $C_{1-6}$alkyl or phenyl$C_{1-6}$alkyl; even further in particular $R^6$ is hydrogen, $C_{1-6}$alkyl or benzyl; and especially $R^6$ is hydrogen.

A ninth interesting embodiment relates to a compound of formula (Ia) or (Ib), (Ia-1) or (Ib-1), or (Ia-2) or (Ib-2) or any subgroup thereof as mentioned hereinbefore as an interesting embodiment, wherein $R^7$ is hydrogen or ethyl and $R^8$ is oxo; in particular $R^7$ is hydrogen and $R^8$ is oxo.

A tenth interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein the compound is a compound of formula (Ia).

An eleventh interesting embodiment relates to a compound of formula (Ia) or (Ib), (Ia-1) or (Ib-1), or (Ia-2) or (Ib-2), or any subgroup thereof as mentioned hereinbefore as interesting embodiment, wherein the compound is a compound of formula (Ib).

A twelfth interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein $R^1$ is placed in position 6 of the quinoline ring.

In the framework of this application, the quinoline ring of the compounds of formula (Ia) or (Ib) is numbered as follows:

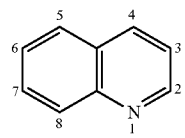

A thirteenth interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein n is 1.

A fourteenth interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein n is 2; and in particular $R^5$ is $C_{1-6}$alkyl.

A fifteenth interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein n is 1 and $R^5$ is placed in position 2 of the piperidine ring.

A sixteenth interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein n is 1 and $R^5$ is placed in position 3 of the piperidine ring.

A seventeenth interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein aryl is naphthyl or phenyl, more preferably phenyl, each being optionally substituted with one or two substituents each being independently selected from halo, for example chloro; cyano; alkyl for example methyl; or alkyloxy for example methyloxy.

An eighteenth interesting embodiment relates to a compound of formula (Ia) or (Ib), (Ia-1) or (Ib-1), or (Ia-2) or (Ib-2), or any subgroup thereof as mentioned hereinbefore as interesting embodiment, wherein aryl$^1$ is naphthyl or phenyl, more preferably phenyl, each optionally substituted with one or two substituents selected from halo, for example chloro; cyano; $C_{1-6}$alkyl for example methyl; alkyloxy, for example methyloxy; $C_{1-6}$alkylthio for example methylthio; or $C_{1-4}$alkyl-S(=O)$_2$— for example methyl-S(=O)$_2$—.

A nineteenth interesting embodiment relates to a compound of formula (Ia) or (Ib), (Ia-1) or (Ib-1), or (Ia-2) or (Ib-2), or any subgroup thereof as mentioned hereinbefore as an interesting embodiment, wherein Het is pyridinyl or pyrazolyl.

A twentieth interesting embodiment relates to a compound of formula (Ia) or any subgroup thereof as mentioned hereinbefore as interesting embodiment, wherein one or more, preferably all, of the following definitions apply:
p is 1;
n is 1;
$R^1$ is halo, in particular bromo, chloro or fluoro; $C_{1-6}$alkylthio, in particular methylthio; $C_{1-4}$alkyl-S(=O)$_2$—, in particular methyl-S(=O)$_2$—; or Het, in particular pyridinyl;
$R^2$ is $C_{1-6}$alkyloxy, in particular methyloxy;
$R^3$ is hydrogen;
$R^4$ is phenyl optionally substituted with halo, e.g. chloro, in either the 3- or 4-position;
$R^5$ is aryl in particular phenyl optionally substituted with one or two substituents selected from halo, for example fluoro, and $C_{1-6}$alkyl, for example methyl; aryl$C_{1-6}$alkyl for example benzyl optionally substituted on the phenyl ring with one or two substituents selected from halo, for example fluoro, and $C_{1-6}$alkyl, for example methyl; $C_{3-6}$cycloalkyl$C_{1-6}$alkyl for example $C_{3-6}$cycloalkylmethyl in particular cyclohexylmethyl; Het$C_{1-6}$alkyl for example Hetmethyl in particular pyridinylmethyl; or $C_{1-6}$alkyl for example methyl; and wherein $R^5$ is placed in position 2 of the piperdine ring; and
$R^6$ is Hydrogen.

A twenty first interesting embodiment relates to a compound of formula (Ib) or any subgroup thereof as mentioned hereinbefore as interesting embodiment, wherein one or more, preferably all, of the following definitions apply:
p is 1;
n is 1;
$R^1$ is halo, in particular bromo, chloro or fluoro;
$R^3$ is hydrogen;
$R^4$ is phenyl optionally substituted with halo, e.g. chloro, in either the 3- or 4-position;
$R^5$ is $C_{3-6}$cycloalkyl$C_{1-6}$alkyl for example $C_{3-6}$cycloalkylmethyl in particular cyclohexylmethyl;
$R^6$ is hydrogen;
$R^7$ is hydrogen; and
$R^8$ is oxo.

As indicated above the compound of formula (Ia) or (Ib) has two or three chiral centres and therefore is capable of forming respectively four or eight enantiomers. When the compound of formula (Ia) or (Ib) is prepared from the reaction of a quinoline derivative and a piperidone derivative, as described below, the configuration of the $R^5$ substituent on the piperidine ring may be known, either from the literature or from the method of synthesis, i.e. as having the R or S configuration for a pure compound, or may be unknown as having the R* or S* configuration for a pure compound, hence limiting the potential stereoisomers to a maximum of four, thus facilitating separation and isolation of such isomers.

The cis and trans configuration of pure isomers are determined by proton NMR. Such pure isomers are designated herein as 1, 2, 3 or 4 according to the order that they are separated and isolated in the synthesis protocol for example by chromatography. Such designations are made either in respect of the synthesis protocol conducted in the last stage if the separation and isolation occurs during such a stage, or the protocol conducted in an earlier stage if the separation and isolation occurs during that stage and the last stage uses a separated and isolated pure stereoisomer. In order to identify unambiguously the relevant stereoisomer, the synthesis protocol in particular the chromatographic conditions under which the relevant stereoisomer is separated and isolated are give herein for each such compound.

The compounds of formula (Ia) or (Ib) may also be obtained as a mixture of two enantiomers. It is preferred to prepare the compounds in a stereospecific manner such that for example the asymmetric carbon atom carrying the $R^5$ substituent(s) on the piperidine ring has a known absolute configuration (for example 2R or 2S) or unknown pure absolute configuration (for example 2R* or 2S*), hence limiting the potential stereoisomers to a maximum of four, thus facilitating separation and isolation of such isomers. When pure isomers are not physically separated, the mixture of two enantiomers is indicated as A or B. A or B depends on whether it is first isolated in the synthesis protocol (i.e. A) or second (i.e. B).

In certain cases, one may obtain a mixture of two isomers of undetermined absolute configuration. Such mixtures may be identified as M1, M2, M3 or M4 when the carbon atom carrying the $R^5$ substituent on the piperidine ring has a mixture of RS isomers. Such mixtures may be identified as S1 or S2 when the carbon atom carrying two identical $R^5$ substituents on the piperidine ring has a mixture of unknown isomers. These mixtures are numbered according to the order that they are separated and isolated in the synthesis protocol.

Preferred compounds according to the present invention are selected from the following compounds:

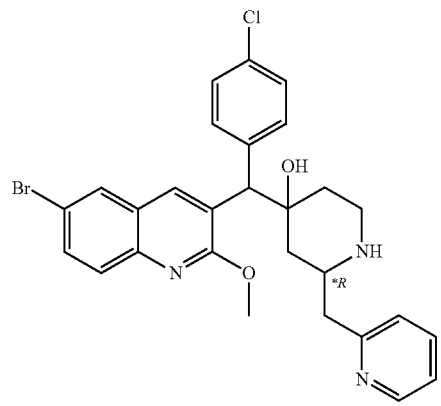

(2R*), cis-1

-continued

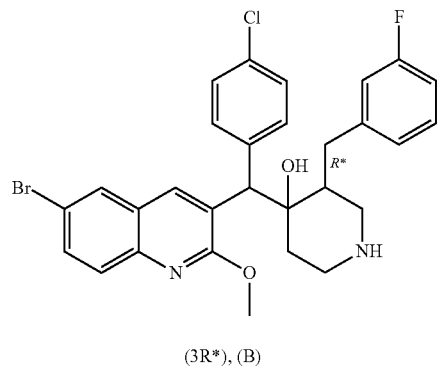

(3R*), (B)

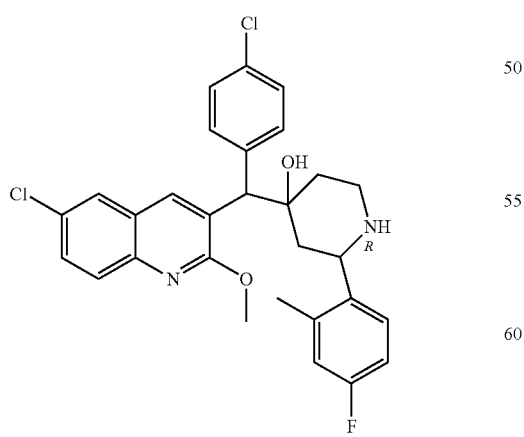

(2R), trans-3

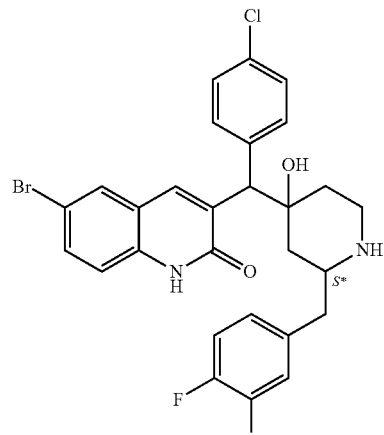

(2S*), cis-1

-continued
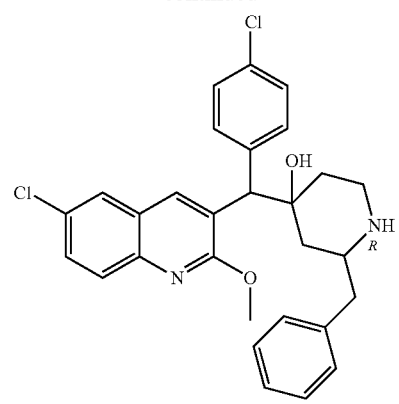
(2R), trans-3
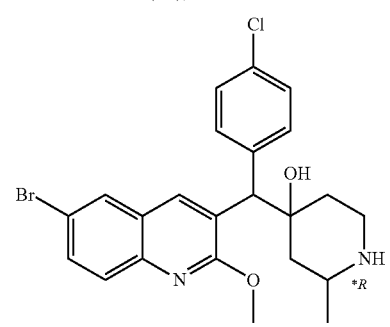
(2R*), cis-2
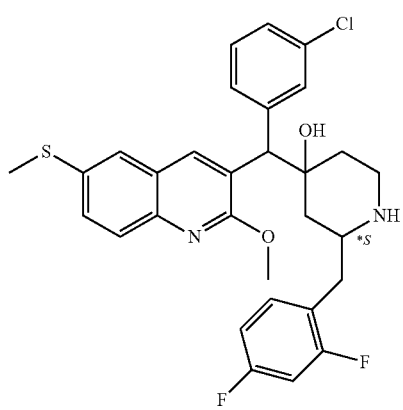
(2S*), cis-2
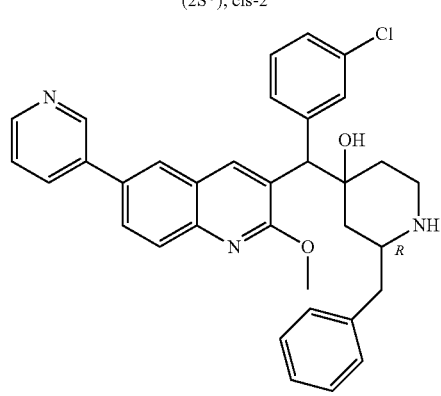
(2R), cis-1
-continued
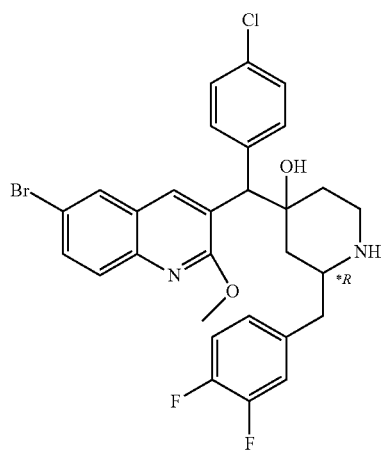
(2R*), cis-2
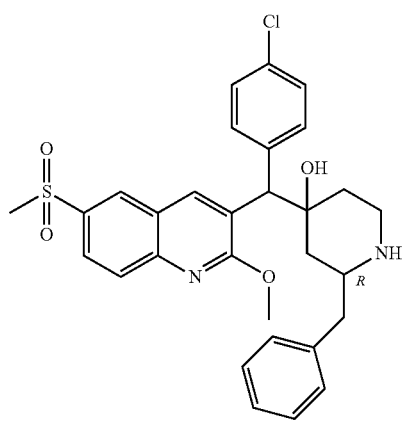
(2R), cis-3
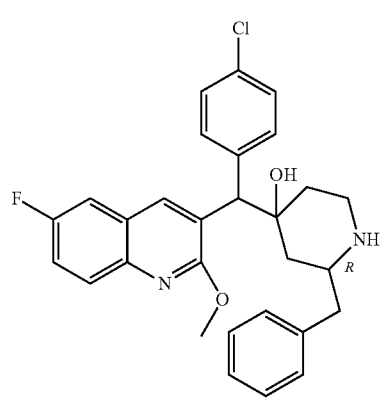
(2R), cis-1

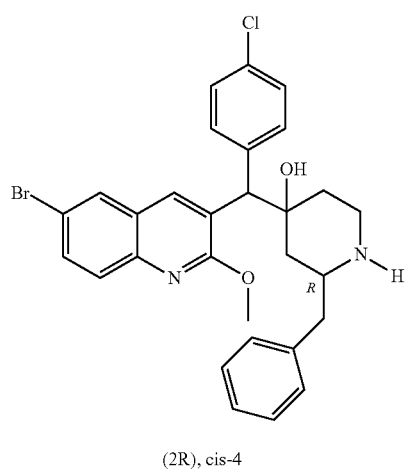
(2R), cis-4
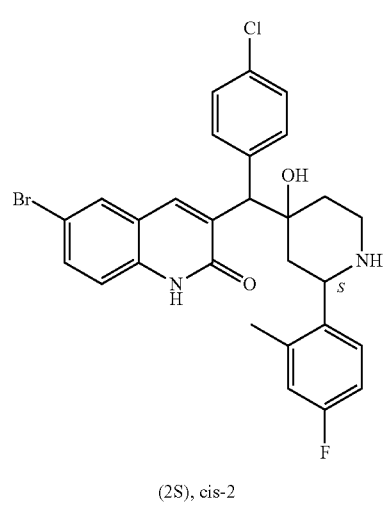
(2S), cis-2
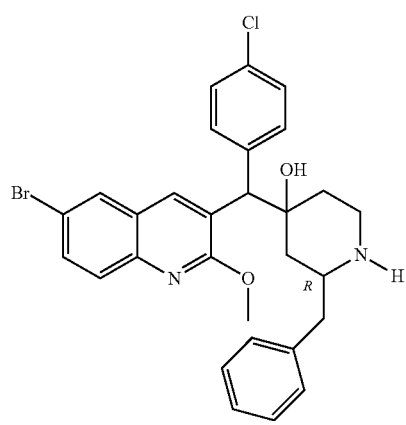
(2R), trans-2
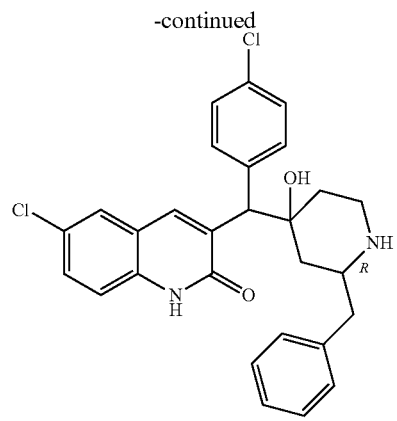
(2R), trans-3
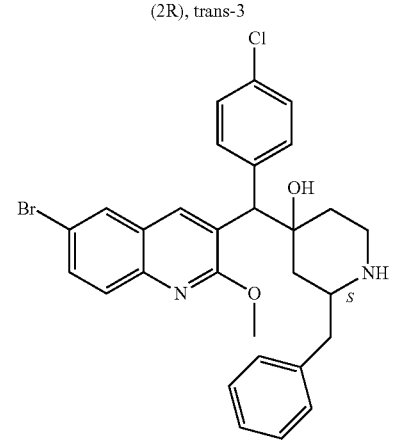
(2S), cis-4
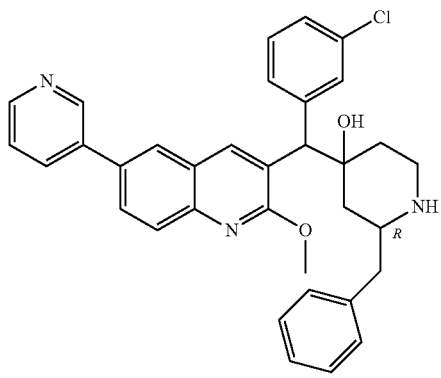
(2R), cis-4
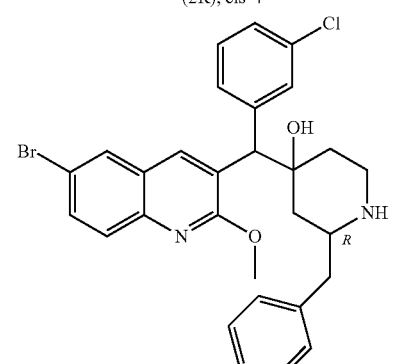
(2R), cis-4

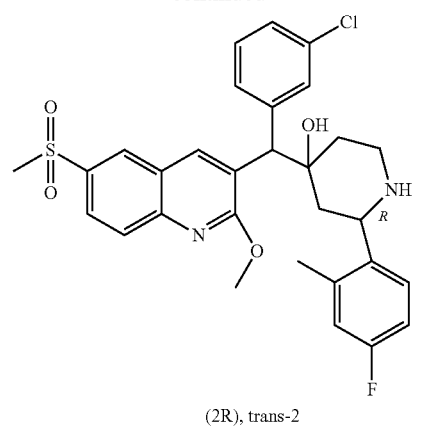
(2R), trans-2
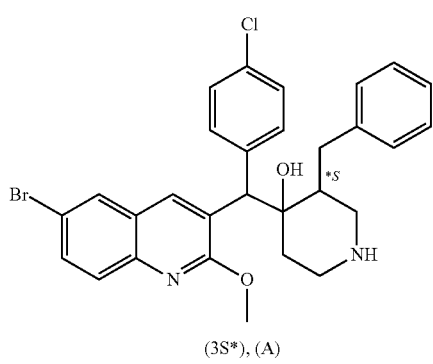
(3S*), (A)
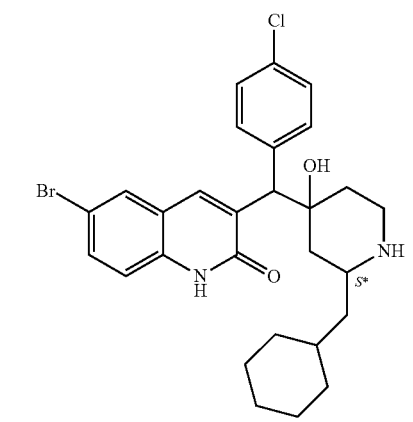
(2S*), (A)
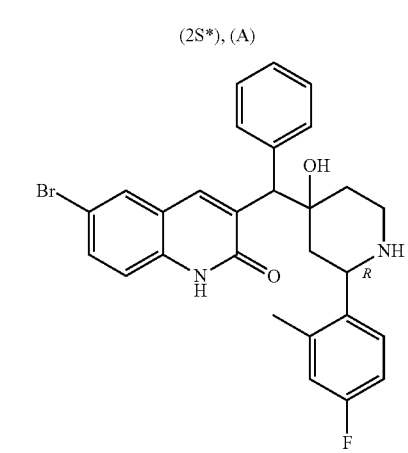
(2R), trans-2

(3S*), (A)
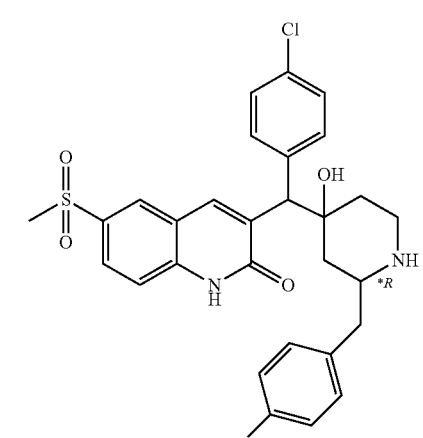
(2R*), cis-2
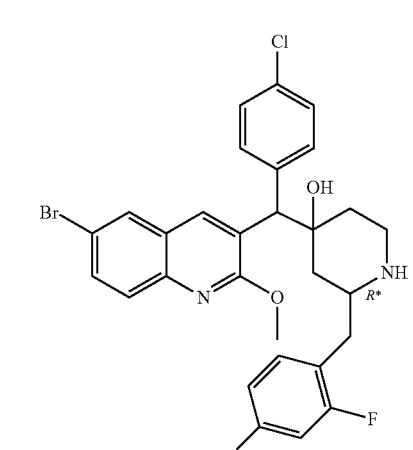
(2R*), cis-3

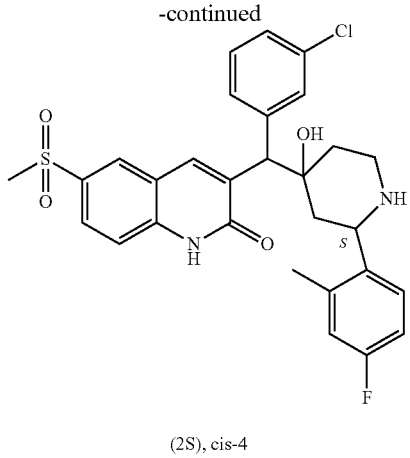

(2S), cis-4 including any stereochemically isomeric form thereof a N-oxide thereof, a pharmaceutically acceptable salt thereof or a solvate thereof.

Pharmacology

The compounds according to the invention have surprisingly been shown to be suitable for the treatment of a bacterial infection including a mycobacterial infection, particularly those diseases caused by pathogenic mycobacteria such as *Mycobacterium tuberculosis* (including the latent and drug resistant form thereof), *M. bovis, M. avium, M leprae* and *M. marinum*. The present invention thus also relates to compounds of formula (Ia) or (Ib) as defined hereinabove and their stereochemically isomeric forms, the pharmaceutically acceptable salts thereof or the N-oxide forms thereof or the solvates thereof, for use as a medicine, in particular for use as a medicine for the treatment of a bacterial infection including a mycobacterial infection.

Further, the present invention also relates to the use of a compound of formula (Ia) or (Ib) and their stereochemically isomeric forms, the pharmaceutically acceptable salts thereof or the N-oxide forms thereof or the solvates thereof, as well as any of the pharmaceutical compositions thereof as described hereinafter for the manufacture of a medicament for the treatment of a bacterial infection including a mycobacterial infection.

Accordingly, in another aspect, the invention provides a method of treating a patient suffering from, or at risk of, a bacterial infection, including a mycobacterial infection, which comprises administering to the patient a therapeutically effective amount of a compound or pharmaceutical composition according to the invention.

In addition to their activity against mycobacteria, the compounds according to the invention are also active against other bacteria. In general, bacterial pathogens may be classified as either gram-positive or gram-negative pathogens. Antibiotic compounds with activity against both gram-positive and gram-negative pathogens are generally regarded as having a broad spectrum of activity. The compounds of the present invention are regarded as active against gram-positive and/or gram-negative bacterial pathogens, in particular against gram-positive bacterial pathogens. In particular, the present compounds are active against at least one gram-positive bacterium, preferably against several gram-positive bacteria, more preferably against one or more gram-positive bacteria and/or one or more gram-negative bacteria.

The present compounds have bactericidal or bacteriostatic activity.

Examples of gram-positive and gram-negative aerobic and anaerobic bacteria, include Staphylococci, for example *S. aureus*; Enterococci, for example *E. faecalis*; Streptococci, for example *S. pneumoniae, S. mutans, S. pyogens*; Bacilli, for example *Bacillus subtilis;* Listeria, for example *Listeria monocytogenes; Haemophilus*, for example *H. influenza; Moraxella*, for example *M. catarrhalis; Pseudomonas*, for example *Pseudomonas aeruginosa*; and *Escherichia*, for example *E. coli*. Gram-positive pathogens, for example Staphylococci, Enterococci and Streptococci are particularly important because of the development of resistant strains which are both difficult to treat and difficult to eradicate from for example a hospital environment once established. Examples of such strains are methicillin resistant *Staphylococcus aureus* (MRSA), methicillin resistant coagulase negative staphylococci (MRCNS), penicillin resistant *Streptococcus pneumoniae* and multiple resistant *Enterococcus faecium*.

The compounds of the present invention also show activity against resistant bacterial strains.

The compounds of the present invention are especially active against *Streptococcus pneumoniae* and *Staphylococcus aureus*, including resistant *Staphylococcus aureus* such as for example methicillin resistant *Staphylococcus aureus* (MRSA).

Therefore, the present invention also relates to the use of a compound of formula (Ia) or (Ib) and their stereochemically isomeric forms, the pharmaceutically acceptable salts thereof or the N-oxide forms thereof or the solvates thereof, as well as any of the pharmaceutical compositions thereof as described hereinafter for the manufacture of a medicament for the treatment of a bacterial infection including an infection caused by Staphylococci and/or Streptococci.

Accordingly, in another aspect, the invention provides a method of treating a patient suffering from, or at risk of, a bacterial infection, including an infection caused by Staphylococci and/or Streptococci, which comprises administering to the patient a therapeutically effective amount of a compound or pharmaceutical composition according to the invention.

Without being bound to any theory, it is taught that the activity of the present compounds lies in inhibition of the F1F0 ATP synthase, in particular the inhibition of the F0 complex of the F1F0 ATP synthase, more in particular the inhibition of subunit c of the F0 complex of the F1F0 ATP synthase, leading to killing of the bacteria by depletion of the cellular ATP levels of the bacteria. Therefore, in particular, the compounds of the present invention are active on those bacteria of which the viability depends on proper functioning of F1F0 ATP synthase.

Bacterial infections which may be treated by the present compounds include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynaecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients.

Whenever used hereinbefore or hereinafter, that the compounds can treat a bacterial infection it is meant that the compounds can treat an infection with one or more bacterial strains.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight, even more preferably from 0.1 to 50% by weight of the active ingredient(s), and, from 1 to 99.95% by weight, more preferably from 30 to 99.9% by weight, even more preferably from 50 to 99.9% by weight of a pharmaceutically acceptable carrier, all percentages being based on the total weight of the composition.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the mycobacterial disease indicated. However, in general, satisfactory results will be obtained when the compound according to the invention is administered at a daily dosage not exceeding 1 gram, e.g. in the range from 10 to 50 mg/kg body weight.

Given the fact that the compounds of formula (Ia) or Formula (Ib) are active against bacterial infections, the present compounds may be combined with other antibacterial agents in order to effectively combat bacterial infections.

Therefore, the present invention also relates to a combination of (a) a compound according to the invention, and (b) one or more other antibacterial agents.

The present invention also relates to a combination of (a) a compound according to the invention, and (b) one or more other antibacterial agents, for use as a medicine.

The present invention also relates to the use of a combination or pharmaceutical composition as defined directly above for the treatment of a bacterial infection.

A pharmaceutical composition comprising a pharmaceutically acceptable carrier and, as active ingredient, a therapeutically effective amount of (a) a compound according to the invention, and (b) one or more other antibacterial agents, is also comprised by the present invention.

The weight ratio of (a) the compound according to the invention and (b) the other antibacterial agent(s) when given as a combination may be determined by the person skilled in the art. Said ratio and the exact dosage and frequency of administration depends on the particular compound according to the invention and the other antibacterial agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (Ia) or (Ib) and another antibacterial agent may range from 1/10 to 10/1, more in particular from 1/5 to 5/1, even more in particular from 1/3 to 3/1.

The compounds according to the invention and the one or more other antibacterial agents may be combined in a single preparation or they may be formulated in separate preparations so that they can be administered simultaneously, separately or sequentially. Thus, the present invention also relates to a product containing (a) a compound according to the invention, and (b) one or more other antibacterial agents, as a combined preparation for simultaneous, separate or sequential use in the treatment of a bacterial infection.

The other antibacterial agents which may be combined with the compounds of formula (Ia) or (Ib) are for example antibacterial agents known in the art. The other antibacterial agents comprise antibiotics of the β-lactam group such as natural penicillins, semisynthetic penicillins, natural cephalosporins, semisynthetic cephalosporins, cephamycins, 1-oxacephems, clavulanic acids, penems, carbapenems, nocardicins, monobactams; tetracyclines, anhydrotetracyclines, anthracyclines; aminoglycosides; nucleosides such as N-nucleosides, C-nucleosides, carbocyclic nucleosides, blasticidin S; macrolides such as 12-membered ring macrolides, 14-membered ring macrolides, 16-membered ring macrolides; ansamycins; peptides such as bleomycins, gramicidins, polymyxins, bacitracins, large ring peptide antibiotics containing lactone linkages, actinomycins, amphomycin, capreomycin, distamycin, enduracidins, mikamycin, neocarzinostatin, stendomycin, viomycin, virginiamycin; cycloheximide; cycloserine; variotin; sarkomycin A; novobiocin; griseofulvin; chloramphenicol; mitomycins; fumagillin; monensins; pyrrolnitrin; fosfomycin; fusidic acid; D-(p-hydroxyphenyl)glycine; D-phenylglycine; enediynes.

Specific antibiotics which may be combined with the present compounds of formula (Ia) or (Ib) are for example benzylpenicillin (potassium, procaine, benzathine), phenoxymethylpenicillin (potassium), phenethicillin potassium, propicillin, carbenicillin (disodium, phenyl sodium, indanyl sodium), sulbenicillin, ticarcillin disodium, methicillin sodium, oxacillin sodium, cloxacillin sodium, dicloxacillin, flucloxacillin, ampicillin, mezlocillin, piperacillin sodium, amoxicillin, ciclacillin, hectacillin, sulbactam sodium, talampicillin hydrochloride, bacampicillin hydrochloride, pivmecillinam, cephalexin, cefaclor, cephaloglycin, cefadroxil, cephradine, cefroxadine, cephapirin sodium, cephalothin sodium, cephacetrile sodium, cefsulodin sodium, cephaloridine, cefatrizine, cefoperazone sodium, cefamandole, vefotiam hydrochloride, cefazolin sodium, ceftizoxime sodium, cefotaxime sodium, cefmenoxime hydrochloride, cefuroxime, ceftriaxone sodium, ceftazidime, cefoxitin, cefmetazole, cefotetan, latamoxef, clavulanic acid, imipenem, aztreonam, tetracycline, chlortetracycline hydrochloride, demethylchlortetracycline, oxytetracycline, methacycline, doxycycline, rolitetracycline, minocycline, daunorubicin hydrochloride, doxorubicin, aclarubicin, kanamycin sulfate, bekanamycin, tobramycin, gentamycin sulfate, dibekacin, amikacin, micronomicin, ribostamycin, neomycin sulfate, paromomycin sulfate, streptomycin sulfate, dihydrostreptomycin, destomycin A, hygromycin B, apramycin, sisomicin, netilmicin sulfate, spectinomycin hydrochloride, astromicin sulfate, validamycin, kasugamycin, polyoxin, blasticidin S, erythromycin, erythromycin estolate, oleandomycin phosphate, tracetyloleandomycin, kitasamycin, josamycin, spiramycin, tylosin, ivermectin, midecamycin, bleomycin sulfate, peplomycin sulfate, gramicidin S, polymyxin B, bacitracin, colistin sulfate, colistinmethanesulfonate sodium, enramycin, mikamycin, virginiamycin, capreomycin sulfate, viomycin, enviomycin, vancomycin, actinomycin D, neocarzinostatin, bestatin, pepstatin, monensin, lasalocid, salinomycin, amphotericin B, nystatin, natamycin, trichomycin, mithramycin, lincomycin, clindamycin, clindamycin palmitate hydrochloride, flavophospholipol, cycloserine, pecilocin, griseofulvin, chloramphenicol, chloramphenicol palmitate, mitomycin C, pyrrolnitrin, fosfomycin, fusidic acid, bicozamycin, tiamulin, siccanin.

Other antimycobacterial agents which may be combined with the compounds of formula (Ia) or (Ib) are for example rifampicin (=rifampin); isoniazid; pyrazinamide; amikacin; ethionamide; ethambutol; streptomycin; para-aminosalicylic acid; cycloserine; capreomycin; kanamycin; thioacetazone; PA-824; quinolones/fluoroquinolones such as for example moxifloxacin, gatifloxacin, ofloxacin, ciprofloxacin, sparfloxacin; macrolides such as for example clarithromycin, clofazimine, amoxycillin with clavulanic acid; rifamycins; rifabutin; rifapentine; the compounds disclosed in WO2004/011436.

General Preparation

The compounds according to the invention can generally be prepared by a succession of steps, each of which is known to the skilled person.

Compounds of formula (Ia) wherein $R^6$ is hydrogen, said compounds being represented by formula (Ia-1), can be prepared by deprotecting an intermediate of formula (II-a) wherein $P^1$ is a suitable protecting group such as a $C_{1-6}$alkyloxycarbonyl group especially a tert-butyloxycarbonyl group, for example with a suitable acid such as trifluoroacetic acid or hydrochloric acid in a suitable solvent such as dichloromethane or iso-propanol; alternatively $P^1$ may represent an aryl$C_{1-6}$alkyloxycarbonyl group such as benzyloxycarbonyl and deprotection may be effected by treatment with boron tribromide in a suitable solvent such as dichloromethane.

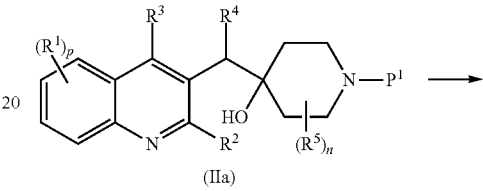

(IIa)

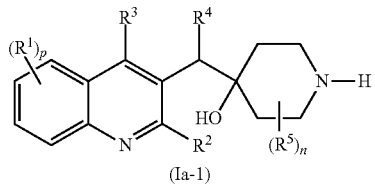

(Ia-1)

Compounds of formula (Ib) wherein $R^6$ is hydrogen, $R^7$ is hydrogen and $R^8$ is oxo, said compounds being represented by formula (Ib-2), can be prepared by deprotecting an intermediate of formula (IIa) with a suitable acid for example hydrochloric acid or trifluoroacetic acid in a suitable solvent such as tetrahydrofuran or iso-propanol.

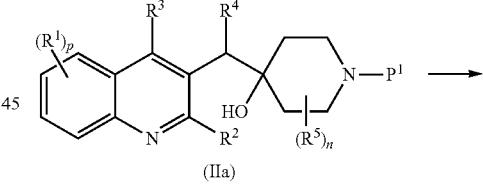

(IIa)

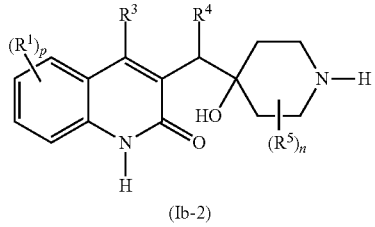

(Ib-2)

Compounds of formula (Ia) wherein $R^5$ is a hydroxymethyl group, said compounds being represented by formula (Ia-3), can be prepared by treating an intermediate of formula (IV-a) wherein $P^3$ is a suitable protecting group such as an alkylsilyl group for example the tert-butyldimethylsilyl group, with a quaternary ammonium salt such as tetrabutylammonium chloride in a suitable solvent such as tetrahydrofuran.

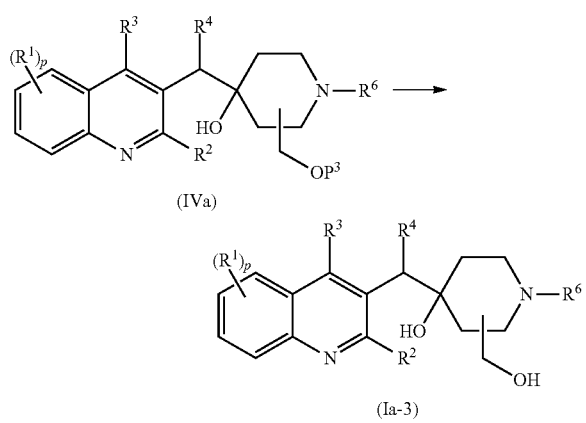

(IVa)

(Ia-3)

Compounds of formula (Ia) can be prepared by reacting an intermediate of formula (Va) with a compound of formula (VIa) for example in the presence of n-butyl-lithium in hexane in a solvent system comprising for example diisopropylamine in tetrahydrofuran. Alternatively, the reaction can be effected for example in the presence of n-butyl-lithium in a solution of N-(1-methylethyl)-2-propanamine in tetrahydrofuran. Both reactions are preferably effected at a low temperature for example about −70° to −78° C.

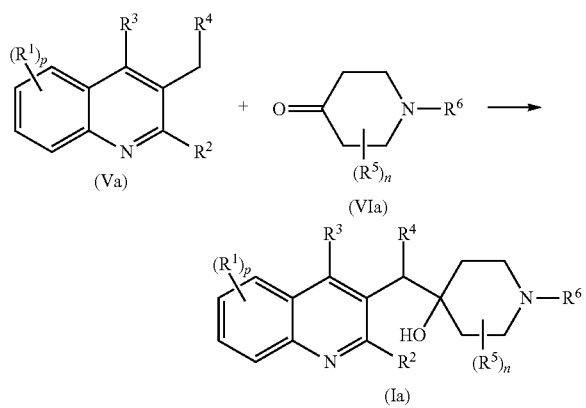

(Va) + (VIa) → (Ia)

It is considered within the knowledge of the skilled man to explore the appropriate temperatures, dilutions, and reaction times in order to optimize the above reactions in order to obtain a desired compound.

The compounds of formula (Ia) or (Ib) may further be prepared by converting compounds of formula (Ia) or (Ib) into each other according to art-known group transformation reactions.

The compounds of formula (Ia) or (Ib) may be converted to the corresponding N-oxide forms following art-known procedures for converting a trivalent nitrogen into its N-oxide form. Said N-oxidation reaction may generally be carried out by reacting the starting material of formula (Ia) or (Ib) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (Ia) or (Ib) wherein $R^1$ represents halo, e.g. bromo, can be converted into a compound of formula (Ia) or (Ib) wherein $R^1$ represents Het, by reaction with Het-B(OH)$_2$ in the presence of a suitable catalyst, such as for example Pd(OAc)$_2$ or Pd(PPh$_3$)$_4$, in the presence of a suitable base, such as for example K$_3$PO$_4$ or Na$_2$CO$_3$, and a suitable solvent, such as for example toluene or 1,2-dimethoxyethane (DME).

Similarly, compounds of formula (Ia) or (Ib) in which $R^1$ is halo, for example bromo, may be converted into compounds of formula (Ia) or (Ib) in which $R^1$ is alkyl, for example methyl, by treatment with an appropriate alkylating agent such as CH$_3$B(OH)$_2$ or (CH$_3$)$_4$Sn in the presence of a suitable catalyst, such as for example Pd(PPh$_3$)$_4$, in a suitable solvent such as for example toluene or 1,2-dimethoxyethane (DME).

Compounds of formula (Ia) or (Ib) wherein $R^1$ is halo, in particular bromo, or aryl $C_{1-6}$ alkyl, can be converted into a compound of formula (Ia) or (Ib) wherein $R^1$ is hydrogen, by reaction with HCOONH$_4$ in the presence of a suitable catalyst such as for example palladium/carbon, and in the presence of a suitable solvent, such as for example an alcohol, e.g. methanol. Alternatively, such conversion can be effected for example using n-butyl-lithium in a suitable solvent such as diethyl ether.

Compounds of formula (Ia) or (Ib) wherein $R^1$ is halo in particular bromo or chloro and $R^6$ is other than hydrogen for example an aryl$C_{1-6}$alkyl group such as 1-ethylphenyl, can be converted into a compound of formula (Ia) or (Ib) wherein $R^1$ is hydrogen and $R^6$ is hydrogen by hydrogenation with palladium/carbon in the presence of acetic acid in a suitable solvent such as methanol.

Compounds of formula (Ia) or (Ib) wherein $R^1$ is halo, in particular bromo, can also be converted into a compound wherein $R^1$ is formyl, by reaction with N,N-dimethylformamide in the presence of n-butyl-lithium and a suitable solvent, such as for example tetrahydrofuran. These compounds can then further be converted into a compound of formula (Ia) or (Ib) wherein $R^1$ is —CH$_2$—OH by reaction with a suitable reducing agent, such as for example NaBH$_4$, and in the presence of a suitable solvent, such as for example an alcohol, e.g. methanol, and tetrahydrofuran.

Compounds of formula (Ia) or (Ib) wherein $R^1$ is $C_{2-6}$alkenyl, can be prepared by reacting a compound of formula (Ia) or (Ib) wherein $R^1$ is halo, e.g. bromo and the like, with tributyl($C_{2-6}$alkenyl)tin, such as for example tributyl(vinyl)tin, in the presence of a suitable catalyst, such as for example Pd(PPh$_3$)$_4$, in the presence of a suitable solvent, such as for example N,N-dimethylformamide. This reaction is preferably performed at elevated temperature.

Compounds of formula (Ia) or (Ib) wherein $R^1$ is $R^{9a}R^{10a}N$—, can be prepared from a compound of formula (Ia) or (Ib) wherein $R^1$ is halo, e.g. bromo and the like, by reaction with $R^{9a}R^{10a}NH$ or a functional derivative thereof in the presence of a suitable catalyst, such as for example tris(dibenzylideneacetone)palladium, a suitable ligand, such as for example 2-(di-t-butylphosphino)biphenyl, a suitable base, such as for example sodium t-butoxide, and a suitable solvent, such as for example toluene. For example, when $R^1$ represents pyridinyl the initial said compound of formula (Ia) or (Ib) may be reacted with a pyridine compound such as the boronic acid 1,3-propanediol cyclic ester in the presence of a suitable catalyst such as tetrakis(triphenylphosphine)-palladium and a suitable base such as potassium carbonate and in a suitable solvent such as 1,2-dimethoxyethane.

Compounds of formula (Ia) or (Ib) wherein $R^1$ is —C=N—$OR^{11}$, can be prepared from a compound of formula (Ia) or (Ib) wherein $R^1$ is formyl, by reaction with hydroxylamine hydrochloride or $C_{1-6}$alkoxylamine hydrochloride in the presence of a suitable solvent, such as for example pyridine.

Compounds of formula (Ia) or (Ib) wherein $R^1$ is —$CH_2$—$NH_2$, can be prepared from a compound of formula (Ia) or (Ib) wherein $R^1$ is formyl, by reduction in the presence of $H_2$, a suitable catalyst, such as for example palladium/carbon, and a suitable solvent, such as for example $NH_3$/alcohol, e.g. $NH_3$/methanol. Compounds of formula (Ia) or (Ib) wherein $R^1$ is —$CH_2$—$NH_2$ can be converted into a compound of formula (Ia) or (Ib) wherein $R^1$ is —$CH_2$—$N(C_{1-6}alkyl)_2$ by reaction with a suitable aldehyde or ketone reagent, such as for example paraformaldehyde or formaldehyde, in the presence of sodium cyanoborohydride, acetic acid and a suitable solvent, such as for example acetonitrile.

Compounds of formula (Ia) or (Ib) wherein $R^1$ is $R^{9a}R^{10a}N$—$CH_2$—, can be prepared by reacting a compound of formula (Ia) or (Ib) wherein $R^1$ is formyl, with a suitable reagent of formula $R^{9a}R^{10a}N$—H in the presence of a suitable reducing agent, such as for example $BH_3CN$, a suitable solvent, such as for example acetonitrile and tetrahydrofuran, and a suitable acid, such as for example acetic acid.

Compounds of formula (Ia) or (Ib) wherein $R^1$ is amino, can be prepared by reacting a compound of formula (Ia) or (Ib) wherein $R^1$ is carboxyl, with a suitable azide, such as for example diphenylphosphorylazide (DPPA), and a suitable base, such as for example triethylamine, in a suitable solvent, such as for example toluene. The obtained product undergoes a Curtius reaction, and by adding trimethylsilylethanol a carbamate intermediate is formed. In a next step, this intermediate is reacted with tetrabutylammonium bromide (TBAB) in a suitable solvent, such as for example tetrahydrofuran to obtain the amino derivative.

Compounds of formula (Ia) or (Ib) wherein $R^1$ is aminocarbonyl, mono or di(alkyl)aminocarbonyl or $R^{9a}R^{10a}N$—C(=O)—, can be prepared by reacting a compound of formula (Ia) or (Ib) wherein $R^1$ is carboxyl, with a suitable amine, a suitable coupling reagent such as for example hydroxybenzotriazole, a suitable activating reagent such as for example 1,1'-carbonyldiimidazole or N,N'-dicyclohexylcarbodiimide or 1-(3-dimethylaminopropyl)-3-ethylcarbodiimide, a suitable base, such as for example triethylamine, and a suitable solvent, such as for example tetrahydrofuran and methylene chloride.

Compounds of formula (Ia) or (Ib) wherein $R^1$ is arylcarbonyl, can be prepared by reacting in a first step (a) a compound of formula (Ia) or (Ib) wherein $R^1$ is halo, e.g. bromo and the like, with a suitable arylaldehyde in the presence of n-butyl-lithium and a suitable solvent, such as for example tetrahydrofuran. This reaction is preferably performed at low temperature such as for example −70° C. In a next step (b), the product obtained in step (a) is oxidized with a suitable oxidizing agent, such as for example manganese oxide, in the presence of a suitable solvent, such as for example methylene chloride.

Compounds of formula (Ia) or (Ib) wherein $R^4$ is phenyl substituted with halo, can be converted into a compound of formula (Ia) or (Ib) wherein $R^4$ is phenyl substituted with Het, by reaction with Het-$B(OH)_2$ in the presence of a suitable catalyst, such as for example $Pd(PPh_3)_4$, in the presence of a suitable base, such as for example $Na_2CO_3$, and a suitable solvent, such as for example toluene or 1,2-dimethoxyethane (DME) and an alcohol, for example methanol.

Compounds of formula (Ia) wherein $R^2$ is methoxy, can be converted into a corresponding compound of formula (Ib) wherein $R^8$ is hydrogen and $R^9$ is oxo, by hydrolysis in the presence of a suitable acid, such as for example hydrochloric acid, and a suitable solvent, such as for example dioxane or tetrahydrofuran.

Compounds of formula (Ia) or (Ib) wherein $R^6$ is hydrogen can be converted into corresponding compounds of formula (Ia) or (Ib) wherein $R^6$ is other than hydrogen using conventional techniques. For example a compound of formula (Ia) or (Ib) wherein $R^6$ is $C_{1-6}$alkyl can be prepared by alkylation of a compound of formula (Ia) or (Ib) wherein $R^6$ is hydrogen, for example in the case where $R^6$ is methyl by treatment with aqueous formaldehyde in the presence of sodium triacetoxyborohydride in a suitable solvent such as dichloromethane.

Compounds of formula (Ia) or (Ib) wherein $R^6$ is other than hydrogen can be converted into a corresponding compound of formula (Ia) or (Ib) wherein $R^6$ is hydrogen using conventional techniques. For example, a compound of formula (Ia) or (Ib) wherein $R^6$ is an aryl$C_{1-6}$ alkyl group for example an ethyl-1-phenyl group can be converted in to a corresponding compound of formula (Ia) or (Ib) wherein $R^6$ is hydrogen by hydrogenation in the presence of palladium/carbon in a suitable solvent such as methanol.

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC, chiral chromatography. Individual diastereoisomers or individual enantiomers can also be obtained by Supercritical Fluid Chromatography (SCF).

The starting materials and the intermediates are compounds that are either commercially available or may be prepared according to conventional reaction procedures generally known in the art. Piperidone compounds useful as starting materials in the above processes can be prepared for example in accordance with the procedures described in Xiaocong M. Ye el, Bioorganic & Medicinal Chemistry Letters, 20 (2010) 2195-2199, Michel Guillaume et al, Organic Process Research and Development 2007, 11, 1079-1086 and WO 2005/123081. Various procedures for the preparation of compounds useful as the quinoline starting materials are described in the WO specifications herein referred to above.

In particular, the intermediates of formula (II-a) can be prepared according to the following reaction scheme (1):

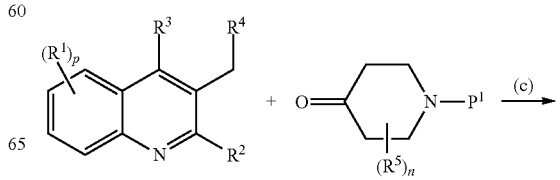

-continued

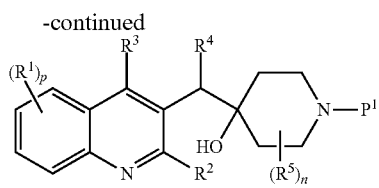

In reaction scheme (1), the quinoline compound is reacted with a piperidin-4-one derivative for example with n-butyllithium in hexane in a suitable solvent such as tetrahydrofuran.

The quinoline starting material used in scheme (1) can be prepared in conventional manner for example in accordance with the following scheme (1-a) when $R^3$ is hydrogen:

Scheme 1-a

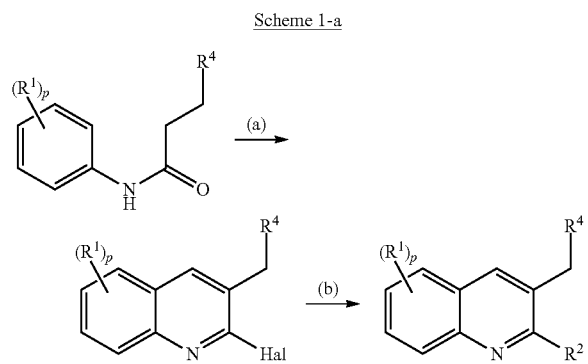

In scheme (1-a), step (a) comprises the cyclisation of a benzene propanamide compound with conversion of the oxo group to a halo (Hal) group preferably chloro for example by treatment with phosphorus oxychloride in a suitable solvent such as dimethylformamide.

In step (b), the resulting halo (Hal) group can be converted into the appropriate $R^2$ group in conventional manner for example by treatment with an alkoxide compound such as sodium methoxide to form a $C_{1-6}$alkyloxy group especially a methyloxy group, in a suitable solvent such as methanol.

The quinoline starting material used in scheme (1) can be prepared in accordance with the following scheme (1-b) when $R^3$ is halo especially chloro:

Scheme 1-b

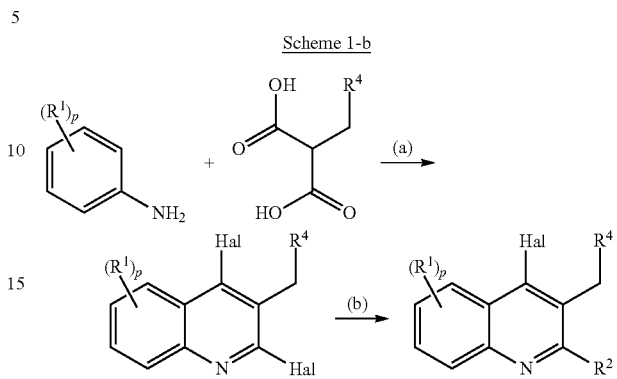

In scheme (1-b), step (a) comprises the reaction of an aminobenzene derivative with a benzenepropanoic acid derivative in the presence of a halogenating agent especially a chlorinating agent such as phosphorus trichloride at an elevated temperature for example about 80° C.

In step (b) the 2-Hal group can be converted into the desired $R^2$ group in conventional manner for example with an appropriate alkyloxylating agent such as a sodium alkoxide for example sodium methoxide to introduce an alkyloxy group preferably in a suitable solvent such methanol.

The quinoline starting material used in scheme (1) can be prepared in accordance with the following scheme (1-c) when $R^3$ is alkyl, aryl or Het:

Scheme 1-c

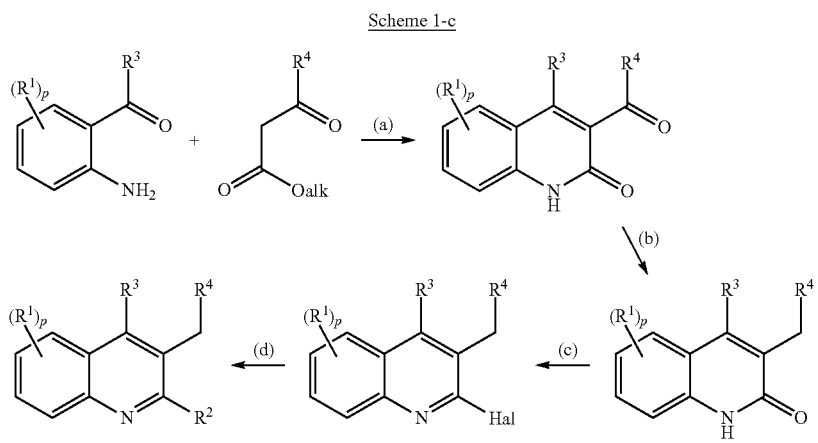

In Scheme (1-c), step (a) comprises the reaction of an aminophenylalkanone with an appropriate β-oxobenzene (or heterocyclyl)-propanoic acid alkyl (alk) ester preferably the benzenepropanoic acid ester for example the ethyl ester at an elevated temperature for example about 180° C.

In step (b) the resulting quinoline derivative is reduced to convert the oxo group attached to the 3-position of the quinoline nucleus to a methylene (—$CH_2$—) group for example by reaction with hydrazine in a suitable solvent such as 1,2-ethanediol, preferably at an elevated temperature such as about 100° C., followed by the addition of a base such as potassium hydroxide.

In step (c) the 2-oxo group can be converted into a halo (Hal) group for example a chloro group in conventional manner by treatment with an appropriate halogenating agent such as phosphorus oxychloride in the presence of benzyltriethylammonium chloride in an appropriate solvent such acetone, preferably at an elevated temperature such as 80° C.

In step (d) the 2-halo group can be converted in conventional manner into the desired $R^2$ group for example with an appropriate alkyloxylating agent such as a sodium alkoxide for example sodium methoxide to introduce an alkyloxy group preferably in a suitable solvent such methanol.

The piperidin-4-one derivatives used in Scheme 1 are generally known and may be prepared by processes known, or analogous to those known, in the literature. For example, such derivatives can be prepared according to the following reaction scheme (2).

Scheme 2

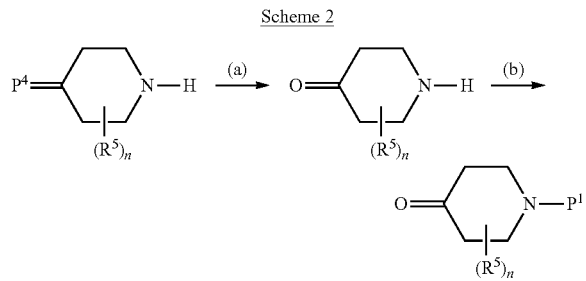

In step (a), a piperidine derivative in which $P^4$ represents a precursor group for the oxo group such as a $C_{1-4}$ alkylenedioxydioxy group especially the 1,2-ethylenedioxy group is treated to convert the precursor group to the desired oxo group for example by treatment with an acid such as hydrochloric acid to effect conversion of the $C_{1-4}$ alkylenedioxy group to the oxo group. In step (b) the protecting group $P^1$ can be introduced in conventional manner. Thus, for example, when the $P^1$ group is a $C_{1-6}$alkyloxycarbonyl group, the piperidin-4-one compound can be reacted with an appropriate di-$C_{1-6}$alkyl dicarbonate such as di-tert-butyl dicarbonate in the presence of a base such as triethylamine and in a suitable solvent such as tetrahydrofuran. This process is especially appropriate for the preparation of compound in which $R^5$ is a cyclohexylmethyl group, the initial compound being obtained by reduction of the corresponding phenylmethyl compound, for example, by hydrogenation in the presence of a rhenium/aluminium oxide catalyst and in a suitable solvent such as methanol.

Alternatively the above piperidin-4-one derivative can be prepared by reduction of a corresponding 3,4-dihydropyridine compound according to reaction scheme (3):

Scheme 3

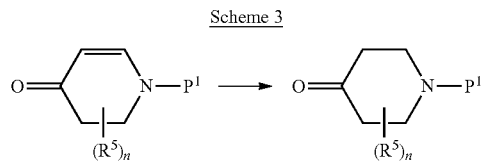

In this reaction the 3,4-dihydropyridine compound is reduced for example with a reducing agent such as lithium hydrotris(1-methylpropyl) (1-) borate in a suitable solvent such as tetrahydrofuran, preferably at a temperature of about −78° C.

The above piperidin-4-one compound wherein $R^5$ is a $C_{2-6}$alkenyl group especially an ethenyl group, can be prepared according to reaction scheme (4) in which $R_b$ is a $C_{1-4}$alkyl group:

Scheme 4

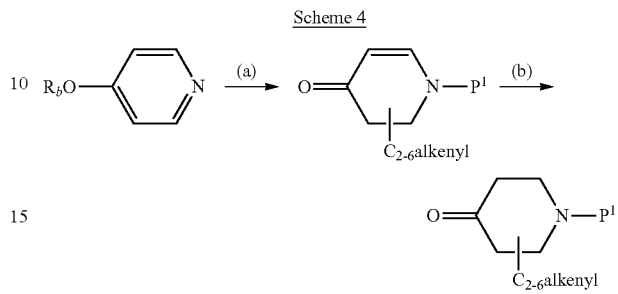

In stage (a) the initial pyridine compound is treated to introduce the protecting group $P^1$ in conventional manner. Thus for example when the $P^1$ protecting group is a $C_{1-6}$alkyloxycarbonyl group, the pyridine compound can be reacted with an appropriate di-$C_{1-6}$alkyl dicarbonate such as di-tert-butyl dicarbonate in a suitable solvent such as tetrahydrofuran. The protected compound is then reacted with an appropriate alkenylmagnesium halide Grignard reagent such as vinyl magnesium bromide in a suitable solvent such as tetrahydrofuran. The resulting compound can then be reduced in stage (b) to the piperidin-4-one as described above.

The above alkenyl piperidin-4-one intermediate compounds in which $R^5$ is vinyl can be used to prepare intermediates of formula (IIa) in which $R^5$ is a hydroxymethyl group according to the following reaction scheme (5):

Scheme 5

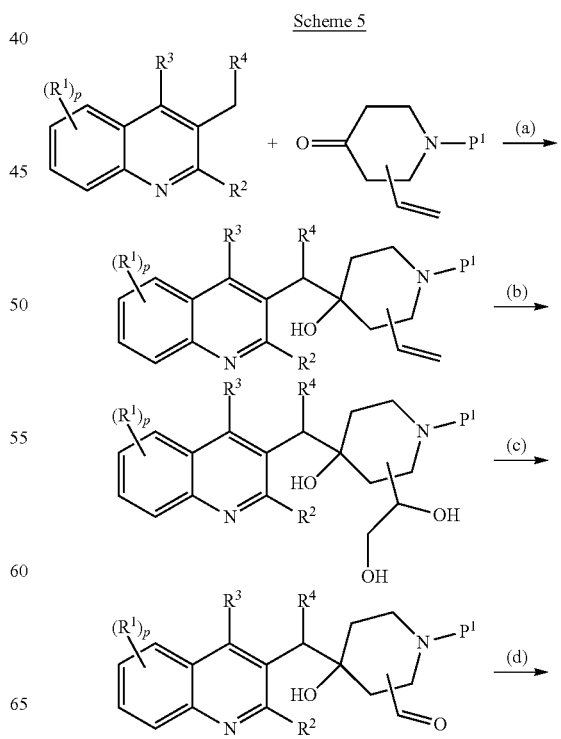

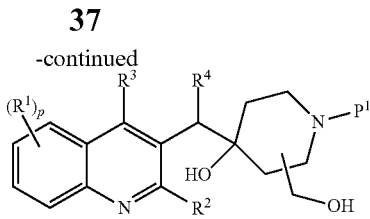

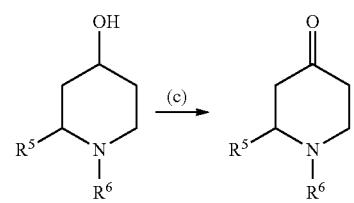

In stage (a), the piperidin-4-one compound is reacted with an appropriate quinoline as described above using for example n-butyl-lithium in hexane in a solvent system comprising for example diisopropylamine in tetrahydrofuran. The reaction is preferably effected at a low temperature for example at about −78° C.

In stage (b), the conversion of the ethenyl group to a 1,2-dihydroxyethyl group may be effected by oxidation for example by treatment with osmium oxide in n-butanol in the presence of a base such as 4-methylmorpholine-4-oxide and a suitable solvent such as tetrahydrofuran.

In stage (c), the 1,2-dihydroxyethyl group is converted to an aldehyde group by treatment with for example sodium periodate in a suitable solvent such as tetrahydrofuran.

In stage (d), the aldehyde compound is reduced to a hydroxymethyl compound for example with a reducing agent such as sodium borohydride in a suitable solvent such as methanol.

Piperidin-4-one compounds in which $R^5$ is in the 2-position and is for example a Het group such as pyridyl especially 3-pyridyl and $R^6$ is for example a phenyl-1-ethyl group can be prepared according to the following reaction scheme (6):

Scheme 6

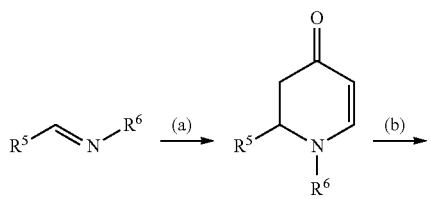

In step (a), the starting methanamine is reacted with a mixture of a 3 Å molecular sieve, 1,1-bi-2-naphthol and triphenyl borate in a suitable solvent such as dichloromethane and the resulting reaction mixture mixed with 1-methyloxy-3-(trimethylsilyloxy)-1,3-butadiene and reacted at a low temperature for example −78° C.

In step (b), the conversion is effected by treating the starting material with L-Selectride (lithium tri-sec-butyl (hydrido)borate(1-)) in a suitable solvent such as tetrahydrofuran at a low temperature for example at about −78° C. to reduce the double bond in the piperidine ring and convert the oxo group to a hydroxy group.

In step (c), the hydroxy compound is oxidized for example by treatment with Dess-Martin periodinane (1,1,1-triacetoxy-1,1-dihydro-1,2-benziodoxol-3 (1H)-one) in a suitable solvent for example dichloromethane.

Compounds of formula (IVa) can be prepared according to the following reaction scheme (7):

Scheme 7

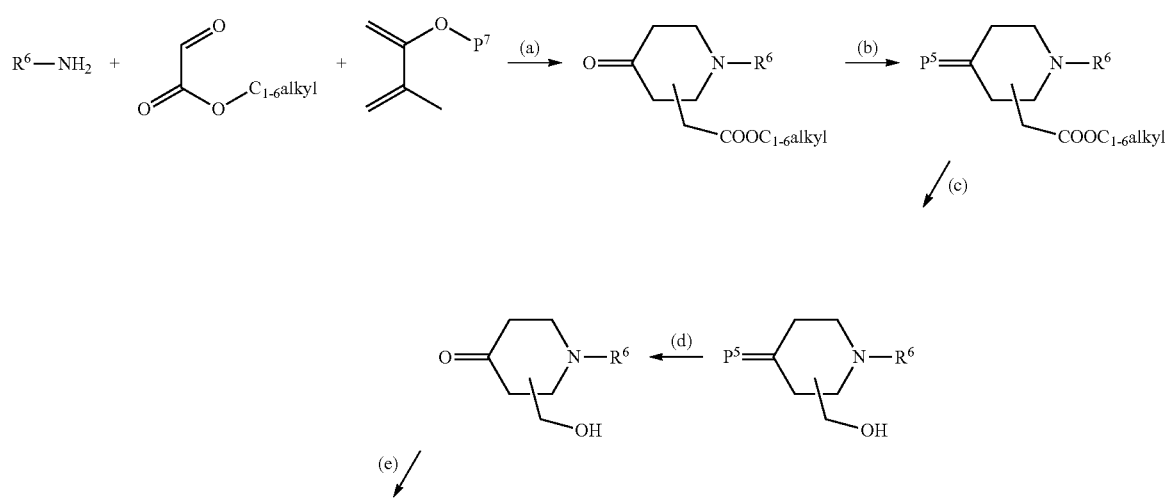

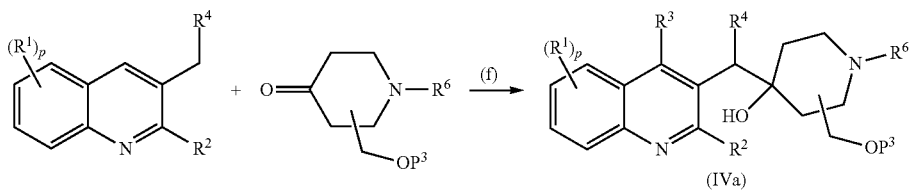

(IVa)

In step (a), the piperidin-4-one is formed by reaction of the above reagents, namely $R^6$—$NH^2$, a glyoxylate ester and a butadiene derivative in which $P^7$ is a protecting group such as a $triC_{1-6}$alkyl (e.g. methyl)silyl group, in the presence of trifluoroacetic acid, boron trifluoride and a 3 Å molecular sieve in a suitable solvent such as dichloromethane, preferably at a low temperature such as about −78'C.

In step (b), an oxo protecting group $P^5$ such as a 4,4-di-$C_{1-6}$alkyl (e.g. ethyl) group is introduced for example by treatment with a tri-$C_{1-6}$alkyl (e.g. ethyl) orthoformate in the presence of an acid such as p-toluenesulphonic acid in a suitable solvent such as ethanol.

In step (c), the protected piperidine compound is reduced to convert the ester group to a hydroxymethyl group for example with lithium aluminium hydride in a suitable solvent such as diethyl ether.

In step (d), the $P^5$ protecting group is removed for example by treatment with an acid such as trifluoroacetic acid, in a suitable solvent for example water.

In step (e), the hydroxymethyl group is protected for example with a tri-$C_{1-6}$alkyl (e.g. tert-butyldimethyl)silyl group which may be introduced for example by treatment with the appropriate tri-$C_{1-6}$ alkyl (e.g. tert-butyldimethyl) silyl halide, for example chloride in the presence of for example imidazole, in a suitable solvent such as dimethylformamide.

In step (f), the protected piperidine compound obtained in step (e) is reacted with a quinoline derivative in conventional manner, as described above.

EXPERIMENTAL PART

The following examples illustrate the present invention.

Experimental Part

Hereinafter, "BuLi" is defined as n-butyllithium, "Cyclo" is defined as cyclohexane, "DCM" is defined as dichloromethane, "DIPE" is defined as diisopropyl ether, "DME" is defined as 1,2-dimethoxyethane, "DMF" is defined as N,N-dimethylformamide, "ETIP" is defined as a 1:1 mixture of ethanol and 2-propanol, "EtOAc" is defined as ethyl acetate, "EtOH" is defined as ethanol, "iPA" is defined as isopropylamine, "iPrOH" is defined as 2-propanol, "MeOH" is defined as methanol, "TFA" is defined as trifluoroacetic acid, "THF" is defined as tetrahydrofuran, "SFC" is defined as Supercritical Fluid Chromatography. Unless otherwise indicated, SFC is conducted using a mobile phase with a flow rate of 50 ml/minute, the column being held at a temperature of 35° C. and an outlet pressure of 100 bars.

A. Preparation of the Intermediate Compounds

Example A1 a) Preparation of Intermediate 1

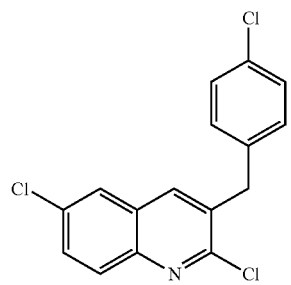 [SMILES: Clc1ccc(Cc2cc3cc(Cl)ccc3nc2Cl)cc1]

DMF (12.45 ml) was added dropwise to phosphorus oxychloride 99% (755.015 mmol) at 5° C. then 4-chloro-N-(4-chlorophenyl)-benzenepropanamide (107.859 mmol) was added portionwise at 5° C. The resulting mixture was heated at 80° C. overnight then cooled to room temperature and poured into water and ice. The precipitate was filtered off, washed with water, and taken up in DIPE. The precipitate was filtered off and dried (vacuum, 60° C.), yielding 32.1 g of intermediate 1.

b) Preparation of Intermediate 2

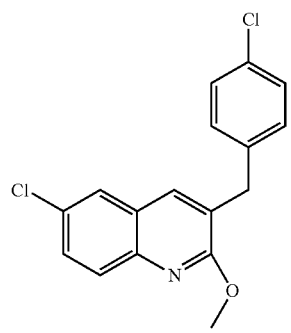 [SMILES: COc1nc2ccc(Cl)cc2cc1Cc1ccc(Cl)cc1]

Sodium methoxide 30% in MeOH, (132.7 ml, 0.696 mol) was added to a solution of intermediate 1 (32.1 g, 0.1 mol) in MeOH (623 ml). The mixture was stirred at 80° C. overnight, then cooled to room temperature and the solvent was evaporated under reduced pressure. The mixture was poured into water and ice and the precipitate was filtered off, and washed with water. The powder was dried under vacuum at 60° C. affording a brown solid. This residue (26.31 g) was purified by flash chromatography over silica gel (15-40 μm, 400 g, DCM/Cyclo: 50/50). The pure fractions were collected and evaporated to dryness affording a yellow solid, yielding 15.7 g of intermediate 2.

c) Preparation of Intermediate 3

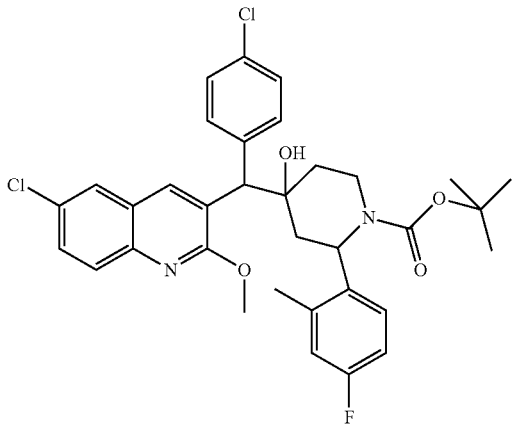

(2R)

BuLi 1.6M in hexane (4.7 ml, 7.54 mmol) was added slowly at −20° C. under N₂ flow to a solution of diisopropylamine (1.06 ml, 7.54 mmol) in THF (11 ml). The mixture was stirred at −20° C. for 20 minutes, then cooled to −70° C. A solution of intermediate 2 (2 g, 6.285 mmol) in THF (20 ml) was added slowly. The mixture was stirred at −70° C. for 1.30 hour. A solution of (2R)-2-(4-fluoro-2-methylphenyl)-4-oxo-1-piperidinecarboxylic acid, 1,1-dimethylethyl ester (2.32 g, 7.54 mmol) in THF (23 ml) was added slowly. The mixture was stirred at −70° C. for 2 hours, hydrolyzed at −30° C. with ice water, and extracted with EtOAc. The organic layer was separated, washed with brine, dried over MgSO₄, filtered, and the solvent was evaporated. The crude product (4.3 g) was purified by flash chromatography over silica gel (15-40 μm, 90 g, Cyclo/EtOAc 85/15). The pure fractions were collected and evaporated to dryness, yielding 3.8 g of intermediate 3. The residue was not 100% pure but used without further purification.

Example A2 a) Preparation of Intermediate 4

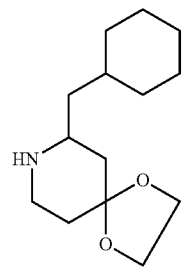 [SMILES: C1CCC(CC2CC3(CCN2)OCCO3)CC1]

The following method and work-up were performed twice. A mixture of 7-(phenylmethyl)-1,4-dioxa-8-azaspiro[4.5]decane (0.375 mol) in MeOH (500 ml) was hydrogenated for 16 hours at 125° C. (H₂ pressure: 100 atm) with 5% Rh/Al₂O₃ (15 g) as a catalyst. After uptake of H₂ (3 equiv), the catalyst was filtered off and the filtrate was evaporated, yielding 178 g (99%) of intermediate 4, used in the next reaction step without further purification.

b) Preparation of Intermediate 5

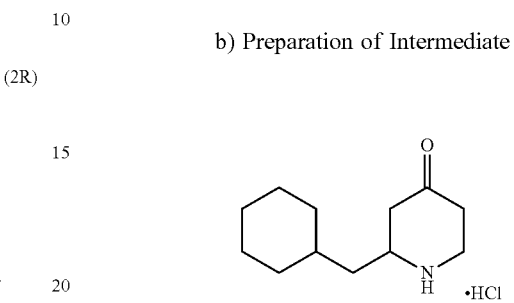

Intermediate 4 (41.0 mmol) in hydrochloric acid (100 ml) was stirred at reflux for 4 hours. The mixture was cooled to room temperature and poured into ice and basified with 10% aqueous solution of potassium carbonate. The mixture was extracted with EtOAc, the organic layer was separated, washed with water then brine, dried (MgSO₄) and evaporated to dryness, yielding 9.3 g of intermediate 5.

c) Preparation of Intermediates 6 and 7

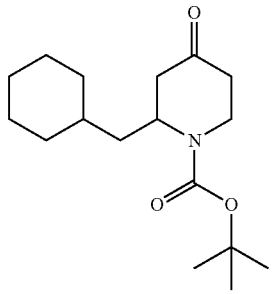

Intermediate 6 (2S*)
Intermediate 7 (2R*)

A solution of intermediate 5 (9.3 g, 47.6 mmol), di-tert-butyl dicarbonate (10.4 g, 47.6 mmol) and triethylamine (13.2 ml, 95.2 mmol) in THF (100 ml) was stirred overnight at room temperature then the mixture was poured into water and extracted with EtOAc. The organic layer was separated, washed with water then brine, dried over MgSO₄, filtered and the solvent was evaporated to dryness. The residue (12.9 g) was purified by flash chromatography over silica gel (20-45 μm, 450 g, Cyclo/EtOAc 80/20). The pure fractions were collected and evaporated to dryness. The residue (9.8 g) was purified by SFC on a Chiralpak AD-HTM column (5 μm 20×250 mm) with a flow rate of 50 ml/minutes, the column being maintained at a temperature of 35° C. and an outlet pressure of 100 bars. The mobile phase is CO₂ 90% MeOH 10% in isocratic mode. The pure fractions were collected and evaporated to dryness, yielding 4.34 g of intermediate 6 and 4.47 g of intermediate 7.

d) Preparation of Intermediates 8 and 9

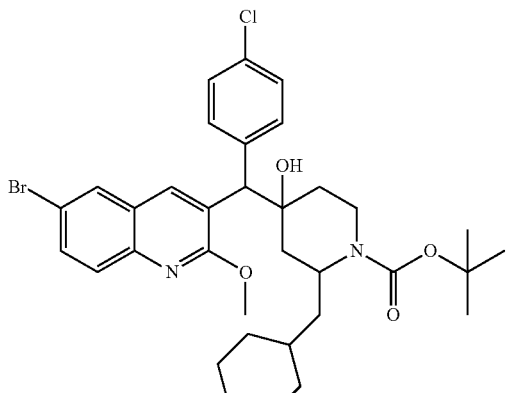

Intermediate 8 (2S*), (A)-1
Intermediate 9 (2S*), (B)-2

BuLi 1.6 M in hexane (4.74 ml, 7.58 mmol) was added dropwise under $N_2$ flow to a solution of diisopropylamine (1.07 ml, 7.58 mmol) in THF (10 ml) at −20° C. The mixture was stirred for 20 minutes at −20° C. then cooled to −78° C. A solution of 6-bromo-3-[(4-chlorophenyl)methyl]-2-methoxy-quinoline (2.29 g, 6.32 mmol) in THF (23 ml) was added then stirred at −78° C. for 1 hour. A solution of intermediate 6 (2.24 g, 7.58 mmol) in THF (22 ml) was added at −78° C. then stirred for 2 hours at −78° C. Water and EtOAc were added, the organic layer was separated, washed with water then brine, dried over $MgSO_4$, filtered and the solvent was evaporated to dryness. The residue (4.8 g) was purified by chromatography over silica gel (15-40 µm, 200 g, Cyclo/EtOAc 90/10). The pure fractions were collected and evaporated to dryness, yielding respectively 1 g of fraction F1 and 0.45 g of fraction F2. F1 was purified by high-performance liquid chromatography (Irregular SiOH 15-40 µm 300 g MERCK), mobile phase (DCM 98% EtOAc 2%), yielding 0.628 g of intermediate 9 and 0.21 g of intermediate 8.

Example A3

Preparation of Intermediates 10, 11, 12 and 13

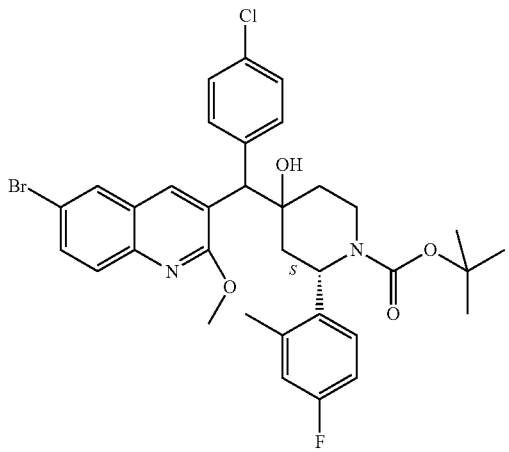

Intermediate 11 (2S), trans, (A)-1
Intermediate 10 (2S), cis, (A)-2
Intermediate 12 (2S), trans, (B)-3
Intermediate 13 (2S), cis, (B)-4

BuLi 1.6 M in hexane (0.0056 mol) was added slowly at −20° C. to a solution of N-(1-methylethyl)-2-propanamine (0.0056 mol) in THF (8 ml) under $N_2$ flow. The mixture was stirred at −20° C. for 20 minutes, then cooled to −70° C. A solution of 6-bromo-3-[(4-chlorophenyl)methyl]-2-methoxy-quinoline (0.0047 mol) in THF (17 ml) was added slowly. The mixture was stirred at −70° C. for 1 hour and 30 minutes. A solution of (2R)-2-(4-fluoro-2-methylphenyl)-4-oxo-1-piperidinecarboxylic acid, 1,1-dimethylethyl ester, (0.0052 mol) in THF (16 ml) was added slowly. The mixture was stirred at −70° C. for 2 hours, poured into ice water at −30° C. and extracted with EtOAc. The organic layer was separated, dried ($MgSO_4$), filtered and the solvent was evaporated. The residue was purified by column chromatography over silica gel (eluent: Cyclo/EtOAc 90/10; 15-40 µm). Two fractions were collected and the solvent was evaporated, yielding respectively F1 0.8 g of intermediate 11 and 0.8 g of F2. F2 was purified by SFC (eluent: $CO_2$/iPrOH/MeOH/iPA 85/7.5/7.5/0.3). Three fractions were collected and the solvent was evaporated, yielding respectively 0.111 g (3.5%) of intermediate 10, 0.303 g (10%) of intermediate 12 and 0.083 g (3%) of intermediate 13.

Example A4 a) Preparation of Intermediate 14

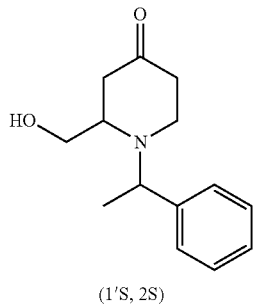 [SMILES: CC(c1ccccc1)N1CCC(=O)CC1CO]

(1'S, 2S)

A solution of (2S)-4,4-diethoxy-1-[(1S)-1-phenylethyl]-,2-piperidinemethanol, (1.4 g, 4.55 mmol) in TFA (6.5 ml) and water (0.5 ml) was stirred at 0° C. for 4 hours. The mixture was poured into 10% aqueous $K_2CO_3$ solution (basic pH). The organic layer was separated, washed with water, dried ($MgSO_4$) and evaporated to dryness, yielding 1 g (94%) of intermediate 14.

b) Preparation of Intermediate 15

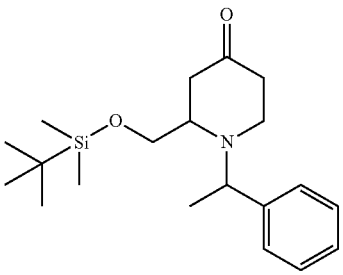

(1'S, 2S)

A solution of intermediate 14 (1.0 g, 4.29 mmol), tert-butyldimethylsilyl chloride (0.775 g, 5.14 mmol) and imidazole (0.35 g, 5.14 mmol) in DMF (10 ml) was stirred at room temperature for 5 hours. The mixture was poured into water, extracted with EtOAc, the organic layer was separated, washed with water then brine, dried (MgSO₄) and evaporated to dryness. The residue (1.44 g) was purified by flash chromatography over silica gel (15-40 μm, 90 g, Cyclo 100 to Cyclo/EtOAc 90/10) The pure fractions were collected and evaporated to dryness, yielding 1.2 g of intermediate 15.

c) Preparation of Intermediate 16

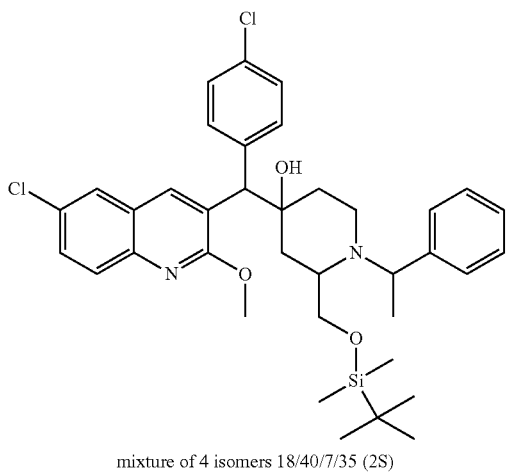 [SMILES: COc1nc2ccc(Cl)cc2cc1C(c1ccc(Cl)cc1)C1(O)CCN(C(C)c2ccccc2)C(CO[Si](C)(C)C(C)(C)C)C1]

mixture of 4 isomers 18/40/7/35 (2S)

BuLi 1.6 M in hexane (2.81 ml, 4.49 mmol) was added dropwise under N₂ flow to a solution of diisopropylamine (0.631 ml, 4.49 mmol) in THF (6 ml) at −20° C. The mixture was stirred for 20 minutes at −20° C. then cooled to −78° C. A solution of intermediate 2 (1.32 g, 4.14 mmol) in THF (13 ml) was added then stirred at −78° C. for 1 hour. A solution of intermediate 15 (1.2 g, 3.45 mmol) in THF (12 ml) was added at −78° C. then stirred for 1 hour at −78° C. Water and EtOAc were added, the organic layer was separated, washed with water then brine, dried over MgSO₄, filtered and the solvent was evaporated to dryness, yielding 1.42 g (61.8%) of intermediate 16.

Example A5 a) Preparation of Intermediates 17 and 18

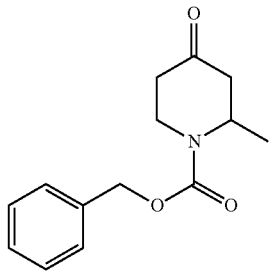

Intermediate 17 (*R)
Intermediate 18 (*S)

Lithium hydrotris(1-methylpropyl)-borate (1-) (1:1) (28.539 mmol) was added dropwise under nitrogen to a solution of 3,4-dihydro-2-methyl-4-oxo-1(2H)-pyridinecarboxylic acid, phenylmethyl ester (28.539 mmol) in THF at −78° C. and the reaction mixture was stirred for 5 hours at −78° C. Water and EtOAc were added at −78° C. The organic layer was separated, washed with water then brine, dried over MgSO₄, filtered and the solvent was evaporated to dryness. The residue (11.9 g) was purified by column chromatography over silica gel (SiO₂ 20-45 μm, eluent: Cyclo/EtOAc: 75/25). The pure fractions were collected and the solvent was evaporated to dryness to give 4.1 g of a mixture of enantiomers. The pure mixture was purified by chiral SFC (Chiralpack AD-H, eluent: CO₂/MeOH: 80/20). The pure fractions were collected and the solvent was evaporated to dryness, yielding 1.7 g (24.1%) of intermediate 17 and 1.9 g (27.0%) of intermediate 18.

b) Preparation of Intermediates 19 and 20

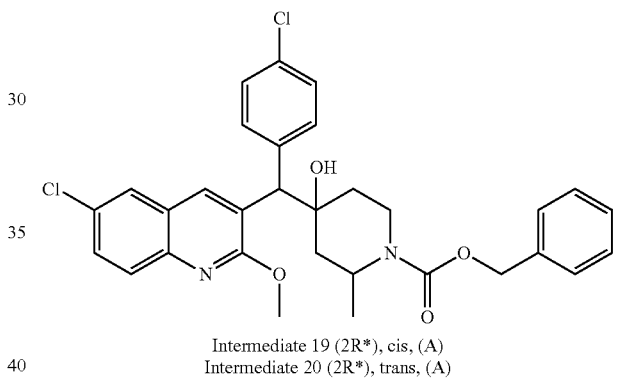

Intermediate 19 (2R*), cis, (A)
Intermediate 20 (2R*), trans, (A)

BuLi 1.6 M in hexane (1.6M) was added dropwise under N₂ flow to a solution of diisopropylamine in THF anhydrous (8 ml) at −20° C. The mixture was stirred for 20 minutes at −20° C. then cooled to −78° C. A solution of 6-bromo-3-[(4-chlorophenyl)methyl]-2-methoxy-quinoline (4.718 mmol) in THF (17 ml) was added then stirred at −78° C. for 2 hours. A solution of intermediate 17 (5.661 mmol) in THF (14 ml) was added at −78° C. The reaction mixture was stirred for 1 hour at −78° C. Water and EtOAc were added at −78° C. The organic layer was separated, washed with water then brine, dried over MgSO₄, filtered and the solvent was evaporated to dryness. The residue (3.1 g) was purified by chromatography over silica gel (15-40 μm, 450 g, Cyclo/EtOAc: 85/15) The pure fractions were collected and evaporated to dryness to give 1.45 g of a mixture containing three isomers 56/40/4. This mixture was separated into its enantiomers by SFC on a Chiralpak AD-HTM column (5 μm 20×250 mm) with a flow rate of 50 ml/minute, the column being maintained at a temperature of 35° C. and an outlet pressure of 100 bars. The mobile phase is CO₂ 50% iPrOH 50% and iPA 0.3% (in methanol) in isocratic mode. The pure fractions were collected and evaporated to dryness, yielding 0.72 g of intermediate 20 and 0.46 g of intermediate 19.

Example A6 a) Preparation of Intermediate 21

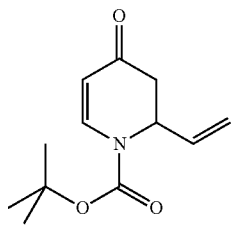 [SMILES: C=CC1CC(=O)C=CN1C(=O)OC(C)(C)C]

Di-tert-butyl dicarbonate (58.333 mmol) was added portionwise under a $N_2$ atmosphere and with rapid stirring to a solution of 4-methoxypyridine (58.333 mmol) in THF (60 ml). The mixture was cooled to 0° C., vinylmagnesium bromide (70 mmol) was added dropwise and the mixture was stirred for 3 hours at room temperature. HCl (1N) (about 150 ml) was added at 5° C. (ambient temperature of 25° C.) and the mixture was stirred for 10 minutes. The mixture was extracted with EtOAc. The organic layer was washed with 10% aqueous $NaHCO_3$ solution then brine, dried over $MgSO_4$, filtered and evaporated to dryness, yielding 10.7 g (82.1%) of intermediate 21.

b) Preparation of Intermediates 22 and 23

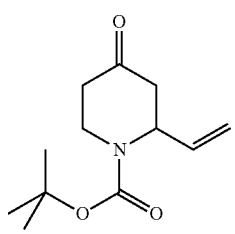

Intermediate 22 (2R*)
Intermediate 23 (2S*)

Lithium hydrotris(1-methylpropyl)-borate(1-) (1:1) (47.9 ml, 47.9 mmol) was added dropwise under $N_2$ to a solution of intermediate 21 (10.7 g, 47.9 mmol) in THF (110 ml) at −78° C. and the mixture stirred at the same temperature for 3 hours. Water and EtOAc were added, the organic layer was separated, washed with water then brine, dried over $MgSO_4$, filtered and the solvent was evaporated to dryness. The residue (19.5 g) was purified by Normal phase on irregular SiOH (20-45 μm 450 g MATREX), mobile phase (80% Cyclo, 20% EtOAc). The pure fractions were collected and the solvent was evaporated. The residue (4.3 g) was separated into its enantiomers by chiral SFC on Chiralpak AD-H, 250×20 mm, mobile phase (90% $CO_2$, 10% MeOH). The pure fractions were collected and the solvent was evaporated to dryness, yielding 1.9 g (17.6%) of intermediate 22 and 1.5 g (13.9%) of intermediate 23.

c) Preparation of Intermediate 24

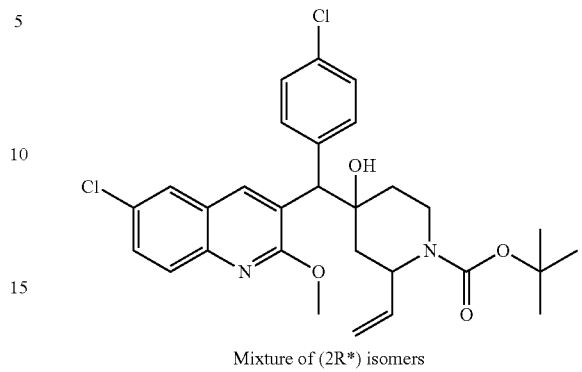

Mixture of (2R*) isomers

BuLi 1.6 M in hexane (5.27 ml, 8.43 mmol) was added dropwise under $N_2$ flow to a solution of diisopropylamine (1.19 ml, 8.43 mmol) in THF (12 ml) at −20° C. The mixture was stirred for 20 minutes at −20° C. then cooled to −78° C. A solution of intermediate 2 (2.24 g, 7.03 mmol) in THF (22 ml) was added then stirred at −78° C. for 1 hour. A solution of intermediate 22 (1.9 g, 8.43 mmol) in THF (19 ml) was added at −78° C. then stirred for 2 hours at −78° C. Water and EtOAc were added, the organic layer was separated, washed with water then brine, dried over $MgSO_4$, filtered and the solvent was evaporated to dryness. The residue (4.5 g) was purified by flash chromatography over silica gel (15-40 μm, 90 g, Cyclo 100/0 to Cyclo/EtOAc 90/10 then Cyclo/EtOAc 80/20) The pure fractions were collected and evaporated to dryness, yielding 1.15 g of intermediate 24, mixture of (2R*).

d) Preparation of Intermediate 25

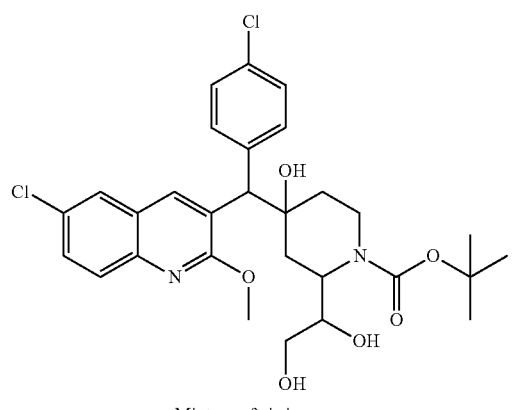

Mixture of cis isomers

A solution of intermediate 24 (3.238 mmol), osmium oxide in butanol 2.5% (0.0486 mmol) and 4-methylmorpholine-4-oxide (4.857 mmol) in THF (16 ml) and water (4 ml) was stirred at room temperature overnight. The solution was poured into a saturated $Na_2S_2O_3$ solution then extracted with EtOAc. The organic layer was separated, washed with water, dried over $MgSO_4$, filtered and the solvent was evaporated to dryness, yielding 1.8 g (96.2%) of intermediate 25.

e) Preparation of Intermediate 26

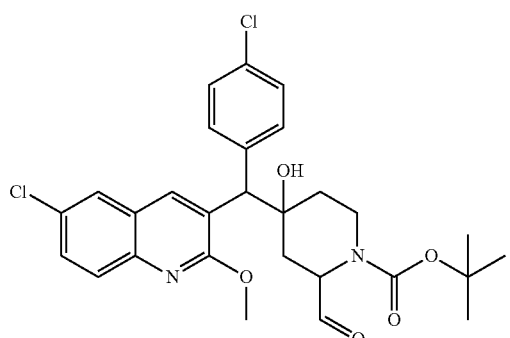

Mixture of cis (2R*) isomers

Sodium periodate (3.584 mmol) was added to a solution of intermediate 25 (3.117 mmol) in THF (20 ml) and water (10 ml) at room temperature and the mixture was stirred for 3 hours. Water and EtOAc were added. The organic layer was separated, washed with water and brine, dried (MgSO$_4$), filtered and evaporated to dryness. The residue of 1.86 g (109%) was purified by flash chromatography over silica gel (15-40 µm, 90 g, Cyclo 100/0 to Cyclo/EtOAc 80/20). The pure fractions were collected and evaporated to dryness, yielding 1.47 g (86.5%) of intermediate 26.

f) Preparation of Intermediates 27 and 28

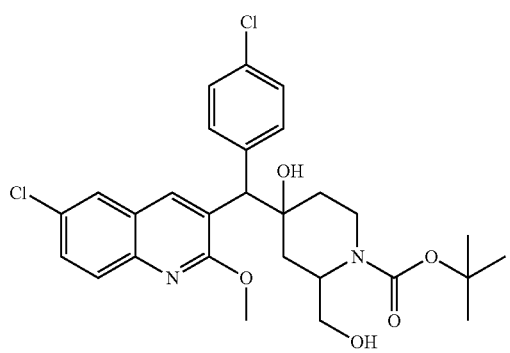

Intermediate 27 (2R*), cis, A-2
Intermediate 28 (2R*), cis, A-1

Sodium borohydride (36.4 mg, 0.962 mmol) was added to a solution of intermediate 26 (700 mg, 1.28 mmol) in MeOH (10 ml) at 0° C. then stirred for one hour at 0° C. Water and EtOAc were added. The organic layer was separated, washed with brine, dried (MgSO$_4$) and evaporated to dryness. The residue (0.66 g) was purified by chiral SFC on Chiralpak AD-H, 5 µm, 250×20 mm; mobile phase (0.3% iPA, 70% CO$_2$, 30% EtOH 50% iPrOH 50%). The pure fractions were collected and the solvent was evaporated, yielding 212 mg (30.2%) of intermediate 28 and 383 mg (54.5%) of intermediate 27.

Example A7 a) Preparation of Intermediate 29

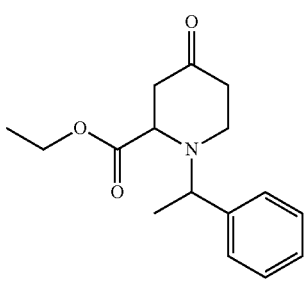

Mixture of 2 isomers

Ethyl glyoxylate (85.083 mmol) was refluxed for 30 minutes to depolymerize the reagent, then it was poured under N$_2$ into a suspension of molecular sieve (4 Å, 25 g) in DCM (150 ml) at 0° C. (S)-(–)-α-methylbenzylamine (85.083 mmol) was added at 0° C., the mixture was stirred for 45 minutes at 0° C. then cooled to –78° C. TFA (85.083 mmol), boron trifluoride diethyl etherate (85.083 mmol) and trimethyl[(1-methylene-2-propen-1-yl)oxy]-silane (85.083 mmol) were added successively at –78° C. with stirring with a period of 5 minutes between each addition. The reaction mixture was stirred at –78° C. then allowed to reach –30° C. and the reaction mixture was stirred for 2 hours at –30° C. Water (40 ml) was added and the mixture was stirred for 30 minutes. An additional amount of water was added (50 ml) and the mixture was allowed to stand overnight. KH$_2$PO$_4$ was added portionwise to a pH of 4-5. The reaction mixture was filtered through a pad of celite which was washed with DCM. The organic layer was separated, washed with water, dried (MgSO$_4$) and evaporated to dryness. The residue was purified by Normal phase on irregular SiOH (20-45 µm 1000 g MATREX); mobile phase (80% Cyclo, 20% EtOAc). The pure fractions were collected and the solvent was evaporated, yielding 7.7 g of fraction F1 and 5.5 g of fraction F2. Fraction F2 was taken up in DCM and HCl 3N and the resulting solution was stirred for 30 minutes then poured into 10% aqueous K$_2$CO$_3$ solution (basic). The organic layer was separated, washed with water, dried (MgSO$_4$) and evaporated to dryness, yielding 5.9 g of intermediate 29.

b) Preparation of Intermediates 30 and 31

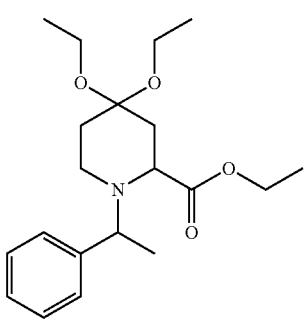

Intermediate 30 (1'S, 2R)
Intermediate 31 (1'S, 2S)

A mixture of intermediate 29 (5.9 g, 21.43 mmol), triethyl orthoformate (35.7 ml, 0.214 mol) and p-toluenesulfonic acid, monohydrate (5.54 g, 32.14 mmol) in EtOH (60 ml) was stirred overnight at room temperature. The reaction mixture was neutralized with sodium bicarbonate (pH=7-8) and extracted with DCM twice. The organic layer was separated, washed with water, dried (MgSO₄) and evaporated to dryness. The residue was purified by flash chromatography over silica gel (15-40 μm, 200 g, Cyclo 100 to Cyclo/EtOAc 90/10) to yield two fraction which were collected and the solvent was evaporated to dryness, yielding respectively 4.75 g of intermediate 30 and 1.5 g of intermediate 31.

c) Preparation of Intermediate 32

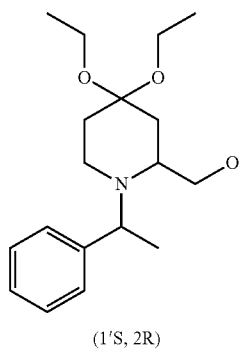 [SMILES: CCOC1(OCC)CCN(C(C)c2ccccc2)C(CO)C1]

(1'S, 2R)

A solution of intermediate 30 (4.75 g, 13.6 mmol) in diethyl ether (30 ml) was added dropwise under N₂ to a suspension of lithium aluminum hydride (0.774 g, 20.4 mmol) in diethyl ether (20 ml) at such a rate that the solution gently refluxed. The reaction mixture was then stirred overnight at room temperature. The reaction mixture was cooled to 0° C., EtOAc (50 ml) then water (15 ml) were added carefully. After stirring for 10 minutes, the reaction mixture was filtered through a short pad of celite and washed with EtOAc. The filtrate was washed with brine, dried (MgSO₄) and evaporated to dryness, yielding 4.2 g of intermediate 32.

d) Preparation of Intermediate 33

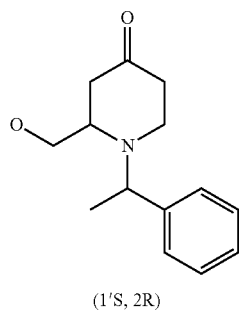 [SMILES: CC(c1ccccc1)N1CCC(=O)CC1CO]

(1'S, 2R)

A solution of intermediate 32 (1.9 g, 6.18 mmol) in TFA (9 ml) and water (1 ml) was stirred at 0° C. for 4 hours. The mixture was poured into 10% aqueous K₂CO₃ solution (basic pH). The organic layer was separated, washed with water, dried (MgSO₄) and evaporated to dryness, yielding 2.7 g of intermediate 33.

e) Preparation of Intermediate 34

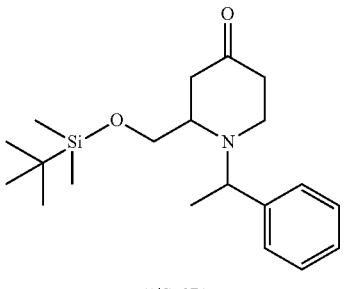

(1'S, 2R)

A solution of intermediate 33 (4.5 g, 19.3 mmol), tert-butyldimethylsilyl chloride (3.49 g, 23.1 mmol) and imidazole (1.58 g, 23.1 mmol) in DMF (45 ml) was stirred at room temperature overnight. The mixture was poured into water, extracted with EtOAc, the organic layer was separated, washed with water then brine, dried (MgSO₄) and evaporated to dryness. The residue was purified by flash chromatography over silica gel (15-40 μm, 200 g, Cyclo 100/0 to Cyclo/EtOAc 90/10) The pure fractions were collected and evaporated to dryness, yielding 5.3 g of intermediate 34.

f) Preparation of Intermediate 35

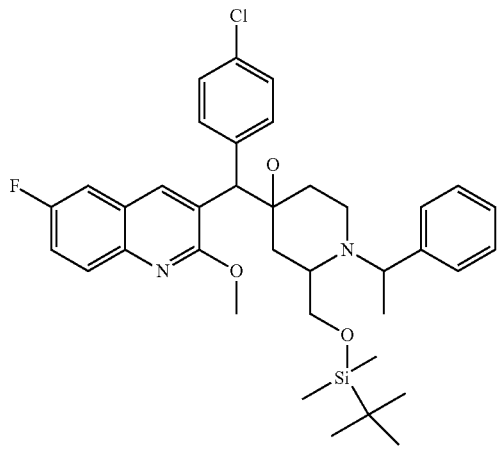

Mixture of (2R) isomers 65/35

BuLi (1.6M in hexane, 13.3 ml, 21.2 mmol) was added dropwise under N₂ flow to a solution of diisopropylamine (2.98 ml, 21.2 mmol) in THF (30 ml) at −20° C. The mixture was stirred for 20 minutes at −20° C. then cooled to −78° C. A solution of intermediate 37 (6.41 g, 21.2 mmol) in THF (65 ml) was added then stirred at −78° C. for 1 hour. A solution of intermediate 34 (6.15 g, 17.7 mmol) in THF (60 ml) was added at −78° C. then stirred for 1 hour at −78° C. Water and EtOAc were added, the organic layer was separated, washed with water then brine, dried over MgSO₄, filtered and the solvent was evaporated to dryness. The residue (13.4 g) was purified by flash chromatography over silica gel (15-40 nm, 400 g, DCM 100/0 to DCM/EtOAc 97/3 then 90/10). The pure fractions were collected and evaporated to dryness. The residue was purified by normal phase chromatography on irregular SiOH (20-45 nm, 450 g MATREX); mobile phase (gradient from 95% DCM, 5% EtOAc to 90% DCM, 10% EtOAc, then toluene/EtOAc 80/20). The pure fractions were collected and the solvent was evaporated, yielding 1.02 g of intermediate 35.

Example A8 a) Preparation of Intermediate 36

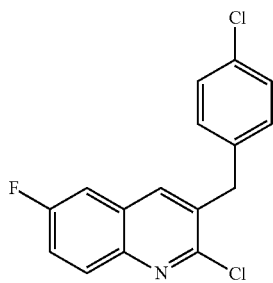 [SMILES: Fc1ccc2nc(Cl)c(Cc3ccc(Cl)cc3)cc2c1]

DMF (17.7 ml, 0.23 mol) was slowly added dropwise to phosphorus oxychloride (100 ml, 1.06 mol) at 0° C. 4-chloro-N-(4-fluorophenyl)-benzenepropanamide (42.2 g, 0.15 mol) was added portionwise at 0° C. and the mixture was then allowed to reach room temperature. The mixture was stirred overnight at 85° C. and then cooled to 40° C. to avoid precipitation, and poured into water/ice portionwise keeping the temperature below 25° C. The mixture was stirred for 1 hour then the precipitate was filtered off, taken up in 2-propanol at 5° C., filtered off again and dried at 60° C. to obtain a yellow solid, yielding 33.76 g of intermediate 36.

b) Preparation of Intermediate 37

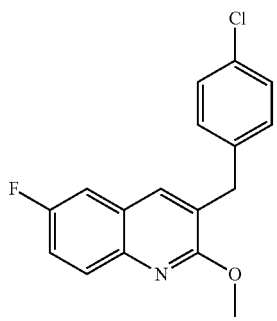 [SMILES: COc1nc2ccc(F)cc2cc1Cc1ccc(Cl)cc1]

Sodium methoxide 30% in MeOH, 148 ml, 0.77 mol) was added to a solution of intermediate 36 (33.76 g, 0.11 mmol) in MeOH (550 mL). The mixture was stirred at 60° C. overnight, then cooled to room temperature and the solvent was evaporated under reduced pressure. Water was added, and the precipitate was filtered off, and washed with iPrOH. The powder was dried under vacuum at 60° C., yielding 24.54 g of intermediate 37. The filtrate was extracted with DCM, dried over MgSO$_4$, filtered and concentrated, yielding 4.33 g of intermediate 37.

Example A9 a) Preparation of Intermediate 38

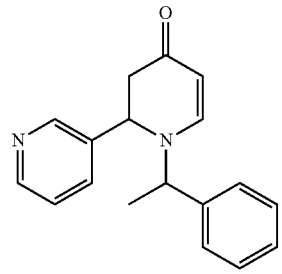 [SMILES: CC(c1ccccc1)N1C=CC(=O)CC1c1cccnc1]

1,1'Bi-2-naphthol (5.48 g) and triphenyl borate (5.56 g) was added to a suspension of 4 Å molecular sieve activated powder (50 g) in DCM (200 ml) under N$_2$ at room temperature. The mixture was stirred for 2 hours and then cooled to 0° C. and a solution of α-methyl-N-(3-pyridinylmethylene)-benzenemethanamine (αR) (4.03 g) in DCM (20 ml) was added and stirred for 10 minutes at 0° C. The mixture was cooled to −78° C. and 1-methyloxy-3-(trimethylsiloxy)-1,3-butadiene (4.86 ml) was added dropwise and the reaction mixture stirred for 2 hours at −78° C. and overnight at −20° C. Water was added and the mixture was filtered through a short pad of celite. The organic layer was separated and HCl 3N was added. The mixture was stirred for 5 minutes. The aqueous layer was basified with K$_2$CO$_3$ (solid) and back extracted with DCM. The organic layer was separated and dried (MgSO$_4$). The residue (3.1 g) was purified by flash chromatography over silica gel (15-40 μm, 90 g) from DCM to DCM/MeOH/NH$_4$OH: 95/5/0.1. The pure fractions were collected and evaporated to dryness, yielding 1.6 g of intermediate 38.

b) Preparation of Intermediate 39

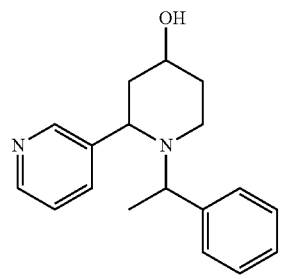 [SMILES: CC(c1ccccc1)N1CCC(O)CC1c1cccnc1]

L-Selectride (R) (6.9 ml, 6.9 mmol) was added dropwise under N$_2$ to a solution of intermediate 38 (1.6 g, 5.75 mmol) in THF (30 ml) at −78° C. and the mixture stirred at the same temperature for 2 hours. Water and EtOAc were added, the organic layer was separated, washed with water then brine, dried over MgSO$_4$, filtered and the solvent was evaporated to dryness. The residue was purified by flash chromatography over silica gel (15-40 μm, 90 g), from DCM 100/0 to DCM/MeOH/NH$_4$OH: 95/5/0.1. The pure fractions were collected and evaporated to dryness, yielding 2.1 g of intermediate 39.

c) Preparation of Intermediate 40

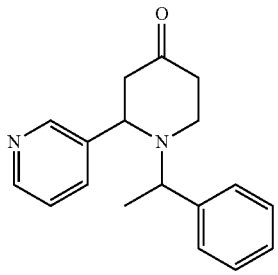 [SMILES: CC(c1ccccc1)N1CCC(=O)CC1c1cccnc1]

Dess-Martin periodinane (27.3 ml, 13.1 mmol) was added to a solution of intermediate 39 (1.85 g, 6.55 mmol) in DCM (40 ml) at 0° C. and the mixture was stirred at 0° C. for 30 minutes and at room temperature for 1 hour. 10% aqueous $K_2CO_3$ solution was added, the organic layer was separated, washed with water then brine, dried over $MgSO_4$, filtered and the solvent was evaporated to dryness. The residue was taken up in DCM, the precipitate was filtered off and the filtrate was purified by flash chromatography over silica gel (15-40 μm, 90 g), from DCM 100/0 to DCM/MeOH 99/1). The pure fractions were collected and evaporated to dryness, yielding 0.9 g of intermediate 40.

Example A10

Preparation of Intermediates 41, 42, 43 and 44

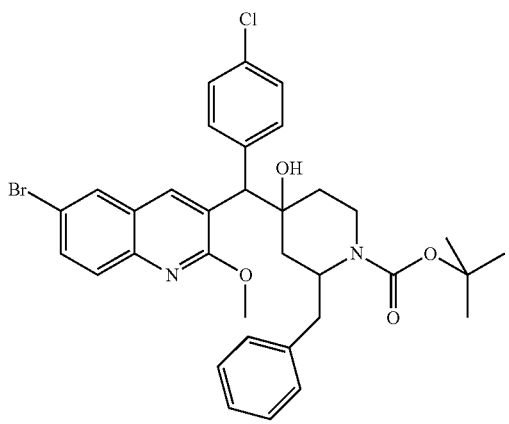

Intermediate 41 (2R), cis, (A)
Intermediate 42 (2R), trans, (A)
Intermediate 43 (2R), trans, (B)
Intermediate 44 (2R), cis, (B)

BuLi 1.6M in hexane (26.7 mmol; 16.7 ml) was added dropwise under $N_2$ flow to a solution of diisopropylamine (26.7 mmol; 3.8 ml) in THF (55 ml) at −20° C. The mixture was stirred 20 minutes at −20° C. then cooled to −78° C. A solution of 6-bromo-3-[(4-chlorophenyl)methyl]-2-methoxy-quinoline (24.75 mmol, 9 g) in THF (90 ml) was added then stirred at −78° C. for 1 hour. A solution of (2R)-4-oxo-2-(phenylmethyl)-1-piperidinecarboxylic acid, 1,1-dimethylethyl ester (19.04 mmol; 5.51 g) in THF (55 ml) was added at −78° C. then stirred for 1 hour at −78° C. Water and EtOAc were added at −50° C. Purification of the residue (6.17 g) was carried out by flash chromatography over silica gel (20-45 μm, 450 g, Cyclo/EtOAc 90/10). The pure fractions were collected and evaporated to dryness, yielding respectively 3.45 g of fraction intermediate 41 and 3.3 g of fraction F2 (mixture).

Fraction F2 was purified by SFC on a Chiralpak AD-HTM column (5 μm 20×250 mm) with a flow rate of 50 ml/minutes, the column being held at a temperature of 35° C. and a outlet pressure of 100 bars. The mobile phase is $CO_2$ 60% iPrOH 40% and iPA 0.3% (in methanol) in isocratic mode. The pure fractions were collected and evaporated to dryness, yielding respectively 0.60 g of intermediate 42, 0.45 g of intermediate 43 and 2.25 g of intermediate 44.

Example A11

Preparation of Intermediates 45, 46 47 and 48

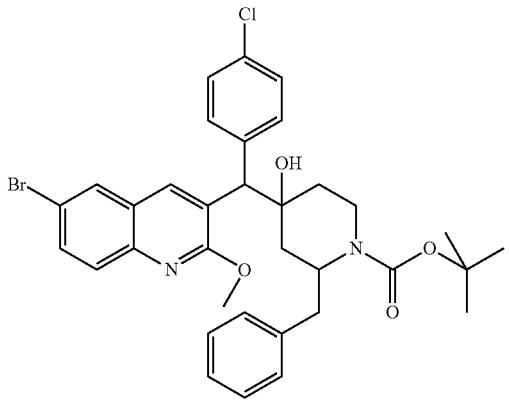

Intermediate 45 (2S), trans, (B)
Intermediate 46 (2S), cis, (A)
Intermediate 47 (2S), trans, (A)
Intermediate 48 (2S), cis, (B)

BuLi 1.6M in hexane (9.19 mmol) was added dropwise under $N_2$ flow to a solution of diisopropylamine (9.19 mmol) in THF (19 ml) at −20° C. The mixture was stirred for 20 minutes at −20° C. then cooled to −78° C. A solution of 6-bromo-3-[(4-chlorophenyl)methyl]-2-methoxy-quinoline in THF (30 ml) was added then stirred at −78° C. for 1 hour. A solution of (2S)-4-oxo-2-(phenylmethyl)-1-piperidinecarboxylic acid, 1,1-dimethylethyl ester, (10 mmol) in THF (29 ml) was added at −78° C. then stirred for 1.5 hour at −78° C. Water and EtOAc were added at −50° C. The organic layer was separated, washed with water then brine, dried over $MgSO_4$, filtered and the solvent was evaporated to dryness. The residue (6.1 g) was purified by column chromatography over silica gel ($SiO_2$ 15-40 μm, eluent: DCM: 100). The pure fractions were collected and the solvent was evaporated to dryness, yielding respectively 1.0 g, (18%) of intermediate 46 and 1.1 g of fraction F2 (mixture of 3 isomers). F2 was purified by SFC (Chiralpack AD-H, $CO_2$/ MeOH/iPrOH/IPA: 70/15/15/0.3). The pure fractions were collected and the solvent was evaporated to dryness, yielding respectively 0.11 g (2%) of intermediate 45, 0.03 g of intermediate 46, 0.07 g (1.3%) of intermediate 47 and 0.55 g (10%) of intermediate 48.

Example A12

Preparation of Intermediates 49, 50 and 51

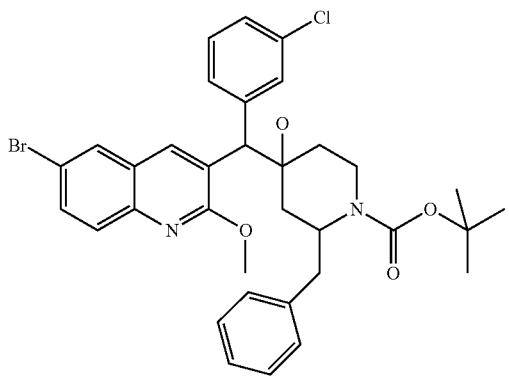

Intermediate 49 (2R), cis, (A)
Intermediate 50 (2R), cis, (B)
Intermediate 51 mixture of isomers BuLi 1.6M in hexane (9.1 mmol) was added dropwise under $N_2$ flow to a solution of diisopropylamine (9.1 mmol) in THF (20 ml) at −20° C. The mixture was stirred for 20 minutes at −20° C. then cooled to −78° C. A solution of 6-bromo-3-[(3-chlorophenyl)methyl]-2-methoxy-quinoline (8.27 mmol) in THF (30 ml) was added then stirred at −78° C. for 1 hour. A solution of (2R)-4-oxo-2-(phenylmethyl)-1-piperidinecarboxylic acid, 1,1-dimethylethyl ester (8.27 mmol) in THF (25 ml) was added at −78° C. then stirred for 1 hour at −78° C. Water and EtOAc were added at −50° C. The organic layer was separated, washed with water then brine, dried over $MgSO_4$, filtered and the solvent was evaporated to dryness. The residue was purified by column chromatography over silica gel (Merck 200 g, $SiO_2$ 15-40 μm, eluent: Cyclo/EtOAc: 85/15). The pure fractions were collected and the solvent was evaporated to dryness. The residue (3.15 g, 59%) was purified by column chromatography over silica gel ($SiO_2$ 15-40 μm, eluent: DCM 100). The pure fractions were collected and the solvent was evaporated to dryness, yielding respectively 1.1 g (20%) of intermediate 49, 0.5 g (9%) of intermediate 51 (mixture of isomers) and 1.0 g (19%) of intermediate 50.

Example A13

Preparation of Intermediates 52, 53, 54 and 55

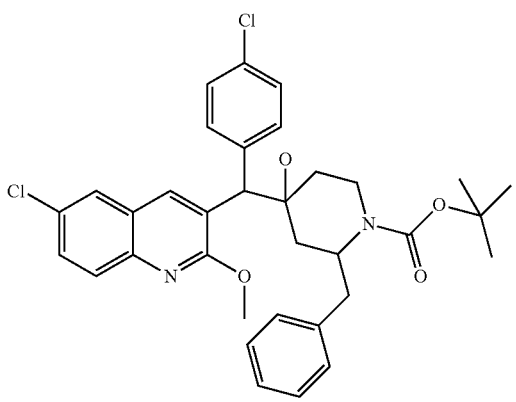

Intermediate 52 (2R), trans, (B)-3
Intermediate 53 (2R), trans, (A)-1
Intermediate 54 (2R), cis, (A)-2
Intermediate 55 (2R), cis, (B)-4

BuLi 1.6M in hexane (7.07 ml, 11.31 mmol) was added slowly at −20° C. under $N_2$ flow to a solution of diisopropylamine (1.59 ml, 11.31 mmol) in THF (16 ml). The mixture was stirred at −20° C. for 20 minutes, and then cooled at −70° C. A solution of intermediate 2 (3 g, 9.43 mmol) in THF (30 ml) was added slowly. The mixture was stirred at −70° C. for 1.5 hour. A solution of (2R)-4-oxo-2-(phenylmethyl)-1-piperidinecarboxylic acid, 1,1-dimethylethyl ester (3.27 g, 11.31 mmol) in THF (33 ml) was added slowly. The mixture was stirred at −70° C. for 2 hours, hydrolyzed at −30° C. with ice water, and extracted with EtOAc. The organic layer was separated, dried over $MgSO_4$, filtered, and the solvent was evaporated. The residue (6.21 g) was purified by high-performance liquid chromatography on irregular SiOH (20-45 μm, 450 g MATREX); mobile phase (Cyclo 90% EtOAc 10%). Two fractions were collected and the solvent was evaporated, yielding respectively 1300 mg of fraction F1 and 1300 mg of fraction F2.

F1 was purified by high-performance liquid chromatography (Chiralpak IC 5 μm 250×20 mm); mobile phase (iPA 0.3%; $CO_2$ 60% iPrOH 40%). Two fractions were collected and the solvent was evaporated, yielding 150 mg of intermediate 53 and 1020 mg of intermediate 54.

F2 was purified by high-performance liquid chromatography (Chiralpak AD-H 5 μm 250×20 mm); mobile phase (iPA 0.3%; $CO_2$ 70% iPrOH 30%), yielding 120 mg of intermediate 52 and 800 mg of intermediate 55.

Example A14 a) Preparation of Intermediate 56

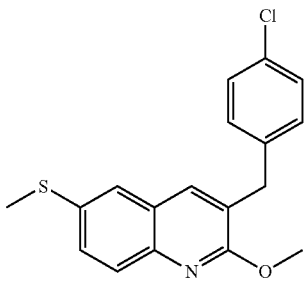 [SMILES: COc1nc2ccc(SC)cc2cc1Cc1ccc(Cl)cc1]

BuLi 1.6M in hexane (66.2 mmol, 41.3 ml) was added dropwise under $N_2$ to a solution of 6-bromo-3-[(4-chlorophenyl)methyl]-2-methoxy-quinoline (55.1 mmol; 20 g) in THF (135 ml) at −70° C. then the mixture was stirred for 1.5 hour. A solution of methyl disulfide (137.8 mmol; 12.4 ml) in THF (15 ml) was added at −78° C. then the mixture was allowed to reach room temperature and stirred for 2 hours. Water and EtOAc were added to the mixture. The organic layer was extracted, washed with water then brine, dried over $MgSO_4$ and the solvent was evaporated. The residue crystallized on standing and was taken up in DIPE, filtered off and dried (vacuum 60° C.), yielding 11.23 g of intermediate 56. The filtrate was evaporated and the residue was purified by flash chromatography over silica gel (15-40 μm, 450 g, DCM/Cyclo 30/70). The pure fractions were collected and evaporated to dryness, yielding 5.45 g of intermediate 56.

b) Preparation of Intermediates 57 and 58

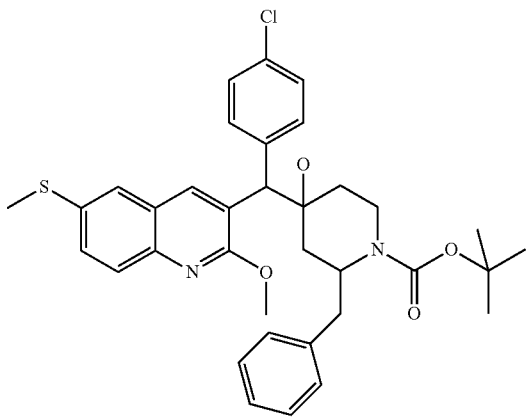

Intermediate 57 (2R), cis, (B)-3
Intermediate 58 (2R), cis, (A)-1

The following reaction was carried out twice:
BuLi 1.6M in hexane (23 ml, 8.37 mmol) was added slowly at −20° C. under $N_2$ flow to a solution of diisopropylamine (1.17 ml, 8.37 mmol) in THF (12 ml). The mixture was stirred at −20° C. for 20 minutes, then cooled at −70° C. A solution of intermediate 56 (2.3 g, 6.97 mmol) in THF (23 ml) was added slowly. The mixture was stirred at −70° C. for 1.5 hour. A solution of (2R)-4-oxo-2-(phenylmethyl)-1-piperidinecarboxylic acid, 1,1-dimethylethyl ester (3.03 g, 10.46 mmol) in THF (30 ml) was added slowly. The mixture was stirred at −70° C. for 2 hours, hydrolyzed at −30° C. with ice water, and extracted with EtOAc. The organic layer was separated, washed with brine, dried over $MgSO_4$, filtered, and the solvent was evaporated.

The residue was purified by normal phase chromatography on irregular SiOH (20-45 μm 450 g MATREX); mobile phase (90% Cyclo, 10% EtOAc), yielding respectively fraction F1 comprising 0.73 g of intermediate 58, fraction F2 comprising a mixture of isomers and fraction F3 comprising starting material (2R)-4-oxo-2-(phenylmethyl)-1-piperidinecarboxylic acid, 1,1-dimethylethyl ester.

Fraction F2 was purified by chiral SFC on Chiralpak AD-H (5 μm 250×20 mm); mobile phase (0.3% iPA, 65% $CO_2$, 35% EtOH), yielding respectively fraction F2/1 comprising 280 mg of the (2R),trans,(A)-2 isomer, fraction F2/2 comprising 980 mg (11.4%) of intermediate 57 and fraction F2/3 comprising 370 mg of the (2R),trans,(B)-4 isomer.

c) Preparation of Intermediate 59

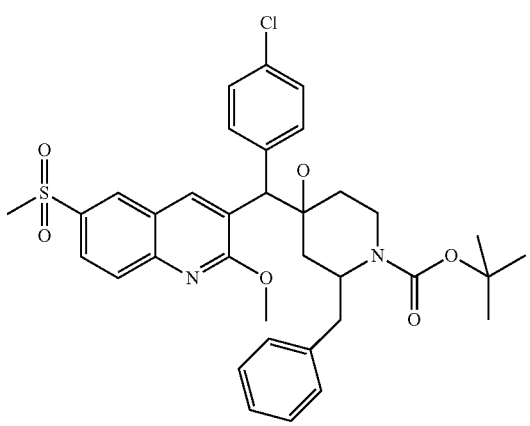

(2R), cis, (B)

A mixture of intermediate 57 (0.98 g, 1.58 mmol) and 3-chloroperoxybenzoic acid (1.17 g, 4.75 mmol) in DCM (20 ml) was stirred overnight at room temperature. The mixture was poured into 10% aqueous $K_2CO_3$ solution and extracted with DCM. The organic layer was separated, washed with water, dried over $MgSO_4$, filtered and the solvent was evaporated to dryness, yielding 1.02 g (99.0%) of intermediate 59.

Example A15

Preparation of Intermediates 60, 61 and 62

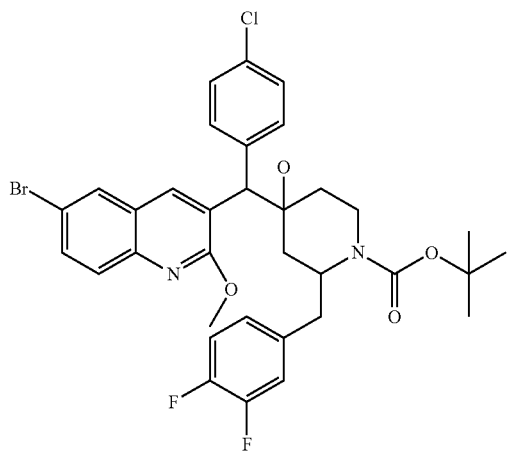

Intermediate 60 (2R), cis, (B)
Intermediate 61 (2R), cis, (A)
Intermediate 62 (2R), trans, (A)

BuLi 1.6M in hexane (5.17 ml, 8.27 mmol) was added slowly at −20° C. under $N_2$ flow to a solution of diisopropylamine (1.16 ml, 8.27 mmol) in THF (12 ml). The mixture was stirred at −20° C. for 20 minutes, then cooled to −70° C. A solution of intermediate 66 (2.5 g, 6.89 mmol) in THF (25 ml) was added slowly. The mixture was stirred at −70° C. for 1.5 hour. A solution of 6-bromo-3-[(4-chlorophenyl)methyl]-2-methoxy-quinoline (2.47 g, 7.58 mmol) in THF (25 ml) was added slowly. The mixture was stirred at −70° C. for 2 hours, hydrolyzed at −30° C. with ice water, and extracted with EtOAc. The organic layer was separated, dried over $MgSO_4$, filtered, and the solvent was evaporated. The residue (4.15 g) was purified by column chromatography over silica gel (15-40 μm, 450 g), Cyclo/EtOAc, 80/20. The pure fractions were collected and the solvent was evaporated to dryness, yielding respectively 1.18 g of fraction F1, and 1.04 g of intermediate 62.

F1 was purified by SFC (eluent: $MeOH/CO_2$/iPA, 30/70/0.3, Chiralpack AD-H). The pure fractions were collected and the solvent was evaporated to dryness, yielding respectively 100 mg of intermediate 61 and 730 mg of intermediate 60.

Example A16 a) Preparation of Intermediates 63 and 64

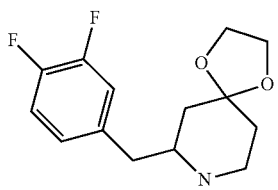

Intermediate 63 (R)
Intermediate 64 (S)

A mixture of 7-[(3,4-difluorophenyl)methyl]-1,4-dioxa-8-azaspiro[4.5]decane (0.657 mol) in MeOH (200 ml) was concentrated at 60° C. and the resulting residue (177 g) was separated into enantiomers by chiral separation (Chiralpak AD, eluent:heptane/EtOH 30/70). Two product fractions were collected and the solvents were evaporated, yielding respectively 80.0 g (90%) of intermediate 63 (R) and 84 g (95%) of intermediate 64 (S).

b) Preparation of Intermediate 65

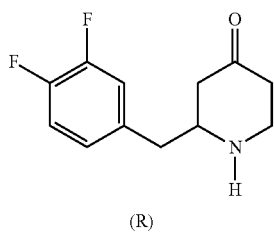 [SMILES: O=C1CCNC(Cc2ccc(F)c(F)c2)C1 ; "(R)"]
(R)

Intermediate 63 (11 mmol) in HCl 6N (30 ml) was stirred at 75° C. overnight. Then, the mixture was stirred at room temperature and poured into glass. The solution was basified with NaOH (30%) (portionwise). The mixture was extracted with DCM, dried with MgSO$_4$ and concentrated under reduced pressure, yielding 3.6 g (96%) of intermediate 65.

c) Preparation of Intermediate 66

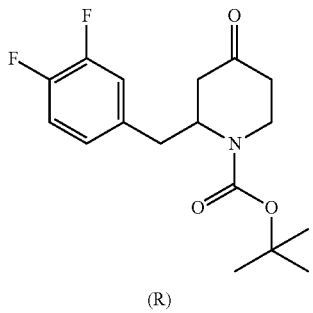 [SMILES: CC(C)(C)OC(=O)N1CCC(=O)CC1Cc1ccc(F)c(F)c1 ; "(R)"]
(R)

To a solution of intermediate 65 (3.7 g, 16.43 mmol) in THF (164 ml) was added triethylamine (2.29 ml, 16.43 mmol) then di-tert-butyl dicarbonate (3.59 g, 16.43 mmol). The mixture was stirred at room temperature overnight. Water and EtOAc were added to the mixture. The organic layer was washed with water, dried over MgSO$_4$, filtered and concentrated under reduced pressure, yielding 5.3 g (99.2%) of intermediate 66.

Example A17

Preparation of Intermediates 67 and 68

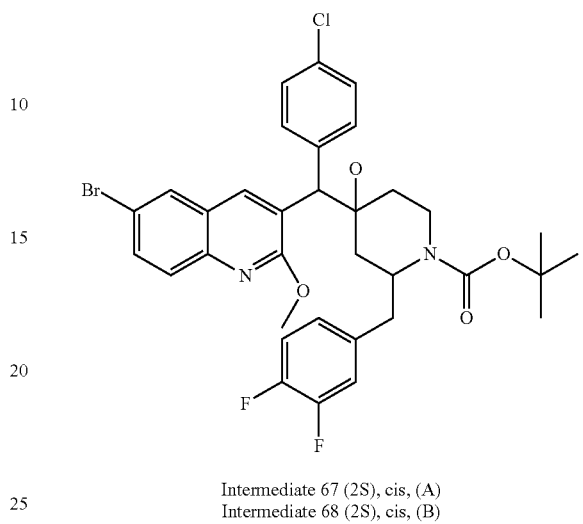

Intermediate 67 (2S), cis, (A)
Intermediate 68 (2S), cis, (B)

BuLi 1.6M in hexane (5.17 ml, 8.27 mmol) was added slowly at −20° C. under N$_2$ flow to a solution of diisopropylamine (1.16 ml, 8.27 mmol) in THF (12 ml). The mixture was stirred at −20° C. for 20 minutes, and then cooled at −70° C. A solution of 6-bromo-3-[(4-chlorophenyl)methyl]-2-methoxy-quinoline (2.5 g, 6.89 mmol) in THF (25 ml) was added slowly. The mixture was stirred at −70° C. for 1.5 hour. A solution of intermediate 70 (S) (2.47 g, 7.58 mmol) in THF (25 ml) was added slowly. The mixture was stirred at −70° C. for 2 hours, hydrolyzed at −30° C. with ice water, and extracted with EtOAc. The organic layer was separated, dried over MgSO$_4$, filtered, and the solvent was evaporated. The residue (4.6 g) was purified by column chromatography over silica gel (eluent: Cyclo/EtOAc, 95/5, 15-40 μm, 450 g). The pure fractions were collected and the solvent was evaporated to dryness yielding respectively 310 mg of intermediate 67 and 720 mg of intermediate 68.

Example A18 a) Preparation of Intermediate 69

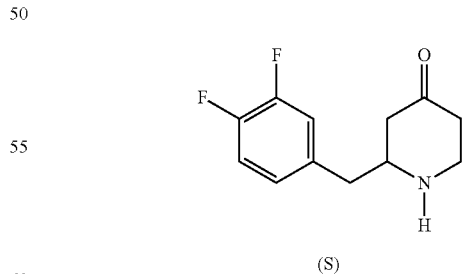
(S)

Intermediate 64 (11 mmol) in HCl 6N (30 ml) was stirred at 75° C. overnight. Then, the mixture was stirred at room temperature and poured into glass. The solution was basified with NaOH (30%) (portionwise). The mixture was extracted with DCM, dried with MgSO$_4$ and concentrated under reduced pressure, yielding 4.32 g (99%) of intermediate 69.

b) Preparation of Intermediate 70

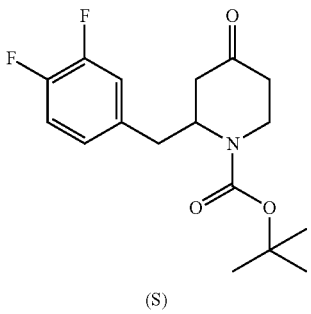 [SMILES: CC(C)(C)OC(=O)N1CCC(=O)CC1Cc1ccc(F)c(F)c1 ; "(S)"]

(S)

To a solution of intermediate 69 (4.32 g, 19.18 mmol) in THF (192 ml) was added triethylamine (2.67 ml, 19.18 mmol) then di-tert-butyl dicarbonate (4.19 g, 19.18 mmol). The mixture was stirred at room temperature overnight. Water and EtOAc were added to the mixture. The organic layer was washed with water, dried over $MgSO_4$, filtered and concentrated under reduced pressure, yielding 6.1 g (97.8%) of intermediate 70.

Example A19

Preparation of Intermediates 71 and 72

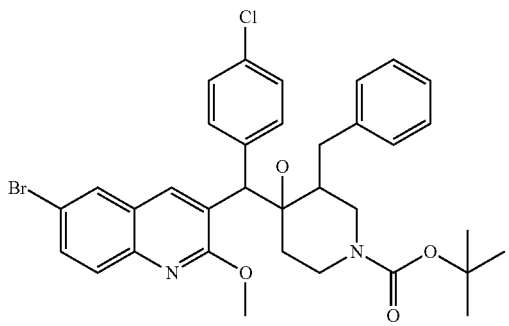

Intermediate 71 (3R*), (A)
Intermediate 72 mixture of 3 isomers

BuLi 1.6M in hexane (0.829 mmol) was added dropwise under $N_2$ flow to a solution of diisopropylamine (0.829 mmol) in THF (1 ml) at −20° C. The mixture was stirred for 20 minutes at −20° C., and then cooled to −78° C. A solution of 6-bromo-3-[(4-chlorophenyl)methyl]-2-methoxy-quinoline (0.691 mmol) in THF (2 ml) was added then stirred at −78° C. for 2 hours. A solution of (3R)-4-oxo-3-(phenylmethyl)-1-piperidinecarboxylic acid, 1,1-dimethylethyl ester (0.691 mmol) in THF (2 ml) was added at −78° C. then stirred for 2 hours at −78° C. Water and EtOAc were added at −78° C. The organic layer was separated, washed with water then brine, dried over $MgSO_4$, filtered and the solvent was evaporated to dryness. The residue (0.45 g) was purified by column chromatography over silica gel (Kromasil 10 μm, eluent: Cyclo/EtOAc: 90/10). The pure fractions were collected and the solvent was evaporated to dryness, yielding respectively 43 mg (9.5%) of intermediate 71 and 80 mg (17.8%) of intermediate 72 [mixture of 3 isomers].

Example A20 a) Preparation of Intermediate 73

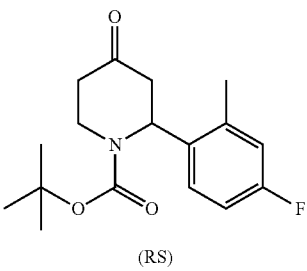 [SMILES: Cc1cc(F)ccc1C1CC(=O)CCN1C(=O)OC(C)(C)C]

(RS)

2-(4-fluoro-2-methylphenyl)-3,4-dihydro-4-oxo-1(2H)-pyridinecarboxylic acid, 1,1-dimethylethyl ester (21 g, 68.774 mmol) in EtOAc (400 ml) was hydrogenated under a 1 Bar pressure of $H_2$ with Pd 10% (3 g) as a catalyst. The catalyst was filtered through a pad of celite and then washed with EtOAc. The filtrate was evaporated. The residue (22.9 g) was purified by flash chromatography over silica gel (15-40 μm, 400 g, Cyclo/EtOAc: 90/10 to 85/15). The pure fractions were collected and the solvent was evaporated to dryness, yielding 17.4 g (82%) of intermediate 73.

b) Preparation of Intermediates 74 and 75

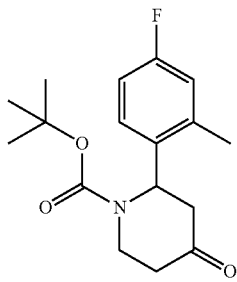

Intermediate 74 (R)
Intermediate 75 (S)

Intermediate 73 (84 g, 273.291 mmol) was purified by chromatography on Chiralpak ADTM (20 μm, 450 g) with a flow rate of 80 ml/min. The mobile phase is heptene/isopropanol 98.5/1.5. The pure fractions were collected and evaporated to dryness, yielding 41 g of intermediate 74 and 41.1 g of intermediate 75.

c) Preparation of Intermediates 76, 77, 78 and 79

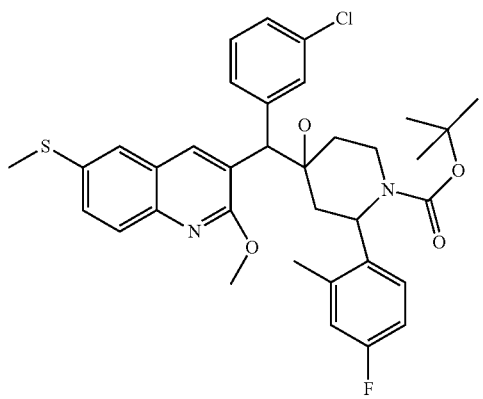

Intermediate 76 (2S), trans, (A)
Intermediate 77 (2S), trans, (B)
Intermediate 78 (2S), cis, (A)
Intermediate 79 (2S), cis, (B)

BuLi 1.6M in hexane (13.6 ml, 21.7 mmol) was added slowly at −20° C. under $N_2$ flow to a solution of diisopropylamine (3.05 ml, 21.7 mmol) in THF (31 ml). The mixture was stirred at −20° C. for 20 minutes, and then cooled at −70° C. A solution of intermediate 81 (5.5 g, 16.67 mmol) in THF (55 ml) was added slowly. The mixture was stirred at −70° C. for 1.5 hour. A solution of intermediate 75 (6.15 g, 20.01 mmol) in THF (61 ml) was added slowly. The mixture was stirred at −70° C. for 2 hours, hydrolyzed at −30° C. with ice water, and extracted with EtOAc. The organic layer was separated, dried over $MgSO_4$, filtered, and the solvent was evaporated. The residue was purified by chromatography over silica gel (15-40 μm, 450 g, Cyclo/EtOAc: 80/20). The desired fractions were collected and evaporated to dryness, yielding 2.15 g of intermediate 76 and 1.73 g of fraction F3.

Purification of fraction F3 was carried out by SFC on a Chiralpak AD-H column (5 μm, 21×250 mm) with a flow rate of 50 ml/min., the column being held at a temperature of 35° C. and an outlet pressure of 100 bars. The mobile phase was $CO_2$ 85% iPrOH 15% and iPA 0.3% (in methanol) in isocratic mode. The desired pure fractions were collected and evaporated to dryness, yielding respectively 355 mg of intermediate 78, 411 mg of intermediate 77 and 250 mg of intermediate 79.

d) Preparation of Intermediate 80

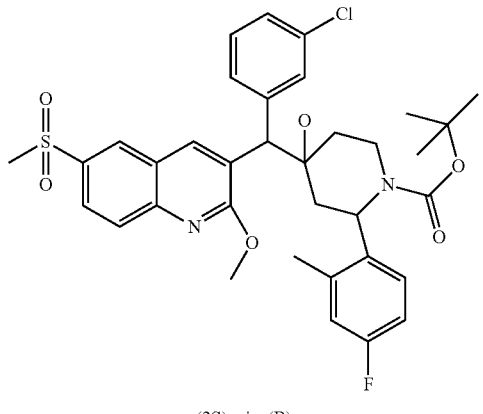

(2S), cis, (B)

A solution of intermediate 79 (0.25 g, 0.39 mmol) and 3-chloroperbenzoic acid (0.29 g, 1.18 mmol) in DCM (2.5 ml) was stirred overnight. The mixture was poured into 10% aqueous $K_2CO_3$ solution and extracted with DCM. The organic layer was separated, washed with water, dried over $MgSO_4$, filtered and the solvent was evaporated to dryness yielding 255 mg (97.1%) of intermediate 80.

Example A21

Preparation of Intermediate 81

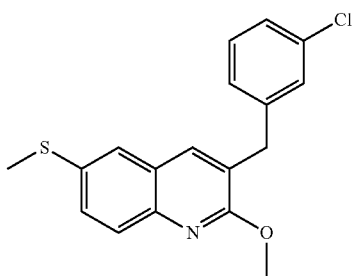 [SMILES: COc1nc2ccc(SC)cc2cc1Cc1cccc(Cl)c1]

BuLi 1.6M in hexane, (20.7 ml, 33.09 mmol) was added dropwise to a solution of 6-bromo-3-[(3-chlorophenyl)methyl]-2-methoxy-quinoline (10 g, 27.57 mmol) in THF (100 ml) at −70° C. under $N_2$ flow and the mixture was stirred for 1.5 hour. Then, a solution of methyl disulfide (6.21 ml, 68.94 mmol) in THF (30 ml) was added slowly at −70° C., and the mixture was allowed to reach room temperature and stirred for 2 hours. Water and EtOAc were added at room temperature. The organic layer was separated, washed with water then brine, dried over $MgSO_4$, filtered and the solvent was evaporated to dryness. The residue was crystallized from DIPE, and the precipitate was filtered off, yielding 6.4 g. (70%) of intermediate 81.

Example A22

Preparation of Intermediates 82, 83 and 84

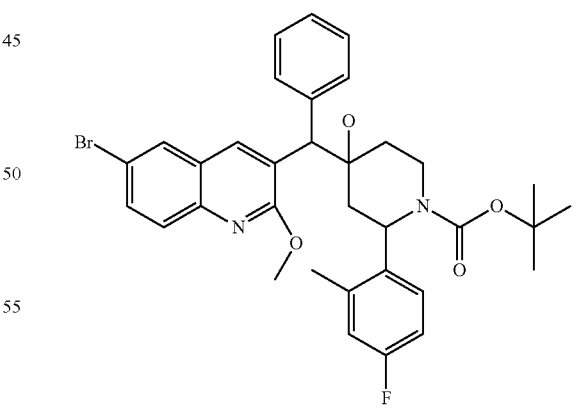

Intermediate 82 (2R), trans, (A)
Intermediate 83 (2R), trans, (B)
Intermediate 84 (2R), cis, (A)

BuLi 1.6M in hexane (6.9 ml, 11.09 mmol) was added slowly at −20° C. under $N_2$ flow to a solution of diisopropylamine (1.6 ml, 11.1 mmol) in THF (16 ml). The mixture was stirred at −20° C. for 20 minutes, and then cooled to −70° C. A solution of 6-bromo-2-methoxy-3-(phenylmethyl)-quinoline (2.8 g, 8.53 mmol) in THF (28 ml) was added slowly. The mixture was stirred at −70° C. for 1.5 hour. A solution of (2R)-2-(4-fluoro-2-methylphenyl)-4-oxo-1-piperidinecarboxylic acid, 1,1-dimethylethyl ester (3.15 g, 10.24 mmol) in THF (31 ml) was added slowly. The mixture was stirred at −70° C. for 2 hours, hydrolyzed at −30° C. with ice water, and extracted with EtOAc. The organic layer was separated, dried over MgSO$_4$, filtered, and the solvent was evaporated. The residue (6.39 g) was purified by chromatography over silica gel (15-40 nm, 450 g, Cyclo/EtOAc 90/10) The pure fractions were collected and evaporated to dryness yielding respectively fractions F1 (2.64 g), F2 (0.125 g) and F3 (0.174 g). Purification of F1 was carried out by SFC on a Chiralpak AD-HTM column (5 μm 20×250 mm) with a flow rate of 50 ml/minutes, the column being held at a temperature of 35° C. and an outlet pressure of 100 bars. The mobile phase was CO$_2$ 75% ethanol 25% and iPA 0.3% (in methanol) in isocratic mode. The pure fractions were collected and evaporated to dryness, yielding respectively 1.393 g of intermediate 82, 514 mg of intermediate 83 and 192 mg of intermediate 84.

Example A23 a) Preparation of Intermediate 86

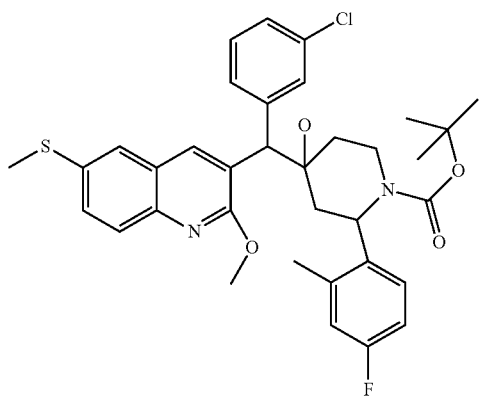

Mixture of 4 isomers

BuLi 1.6M in hexane (13.6 ml, 21.7 mmol) was added slowly at −20° C. under N$_2$ flow to a solution of diisopropylamine (3.05 ml, 21 mmol) in THF (31 ml). The mixture was stirred at −20° C. for 20 minutes and cooled to −70° C. A solution of intermediate 81 (5.5 g, 16.7 mmol) in THF (55 ml) was added slowly. The mixture was stirred at −70° C. for 1.5 hour. A solution of intermediate 74 (6.15 g, 20 mmol) in THF (61 ml) was added slowly. The mixture was stirred at −70° C. for 2 hours, hydrolyzed at −30° C. with ice water, and extracted with EtOAc. The organic layer was separated, dried over MgSO$_4$, filtered, and the solvent was evaporated. The residue (12 g) was purified by chromatography over silica gel (15-40 μm, 450 g, Cyclo/EtOAc 98/2). The pure fractions were collected and evaporated to dryness yielding 7.87 g (74%) of intermediate 86.

b) Preparation of Intermediate 87

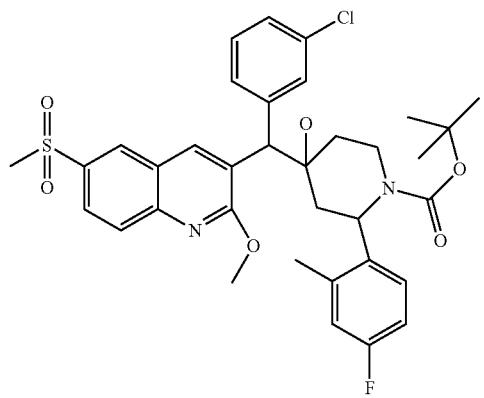 [SMILES: COc1nc2ccc(S(C)(=O)=O)cc2cc1C(c1cccc(Cl)c1)C1(O)CCN(C(=O)OC(C)(C)C)C(c2ccc(F)cc2C)C1]

A solution of intermediate 86 (5.8 g, 9.1 mmol) and 3-chloro-benzenecarboperoxoic acid (6.73 g, 27.31 mmol) in DCM (58 ml) was stirred overnight. The mixture was poured into 10% aqueous K$_2$CO$_3$ solution and extracted with DCM. The organic layer was separated, washed with water, dried over MgSO$_4$, filtered and the solvent was evaporated to dryness, yielding 6.07 g of intermediate 87.

Example A24 a) Preparation of Intermediate 88

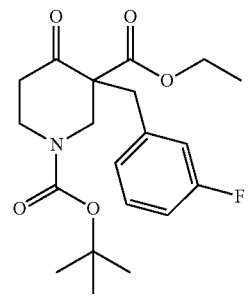 [SMILES: CCOC(=O)C1(Cc2cccc(F)c2)CN(C(=O)OC(C)(C)C)CCC1=O]

NaH 60% in oil (0.62 g, 15.48 mmol) was added portionwise to a solution of 1,3-(4-oxo-piperidine)-dicarboxylic acid, 1-(1,1-dimethylethyl) 3-ethyl ester (2 g, 7.37 mmol) suspended in THF (20 ml) cooled at 0° C. The mixture was stirred for 30 minutes at 0° C. and then allowed to warm to ambient temperature and stirred for a further 1 hour. 3-fluorobenzylbromide (1.36 ml, 11.06 mmol) was added and the resulting solution was stirred at room temperature overnight. Water and then EtOAc were added. The organic layer was extracted, washed with brine, dried over MgSO$_4$, filtered and concentrated. The residue (2.78 g) was purified by Normal phase on irregular SiOH (15-40 μm, 300 g); mobile phase (85% heptane, 15% EtOAc). The pure fractions were collected and the solvent was evaporated, yielding 1 g (35.7%) of intermediate 88.

b) Preparation of Intermediate 89

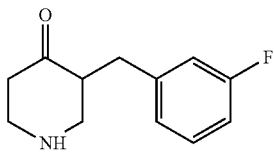 [SMILES: O=C1CCNCC1Cc1cccc(F)c1]

A solution of intermediate 88 (1 g, 2.64 mmol) in HCl 6N (8 ml) and MeOH (1.5 ml) was heated to reflux temperature with stirring for 20 hours. After cooling to room temperature, the mixture was basified to pH 10 with NaOH 6N (2.5 ml) and extracted with DCM (3 times). The combined organic layers were dried over MgSO$_4$, filtered and concentrated, HCl 6N (8 ml) and MeOH (1.5 ml) were added to the residue and the resulting mixture was then heated to reflux temperature and stirring for 20 hours. After cooling to room temperature, the mixture was basified to pH 10 with NaOH 6N (2.5 ml) and extracted with DCM (3 times). The combined organic layers were dried over MgSO$_4$, filtered and concentrated, yielding 260 mg (47.6%) of intermediate 89.

c) Preparation of Intermediates 90 and 91

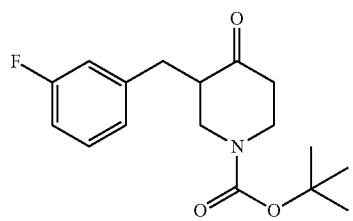

Intermediate 90 (3R*)
Intermediate 91 (3S*)

A solution of intermediate 89 (10.4 g, 42.7 mmol), di-tert-butyl dicarbonate (9.31 g, 42.7 mmol) and triethylamine (11.9 ml, 85.3 mmol) in THF (100 ml) was stirred overnight at room temperature. The mixture was poured into water and extracted with EtOAc. The organic layer was separated, washed with water then brine, dried over MgSO$_4$, filtered and the solvent was evaporated to dryness. The residue (13.1 g) was purified by flash chromatography over silica gel (20-45 μm, 450 g, Cyclo/EtOAc 80/20) The pure fractions were collected and evaporated to dryness. The residue (12 g) was purified by SFC on a Chiralpak AD-HTM column (5 μm 20×250 mm) with a flow rate of 50 ml/min., the column was held at a temperature of 35° C. and an outlet pressure of 100 bars. The mobile phase was CO$_2$ 95% methanol 5% and isopropylamine 0.3% (in methanol) in isocratic mode. The pure fractions were collected and evaporated to dryness, yielding 4.8 g (35.6%) of intermediate 90 and 5.2 g (39.6%) of intermediate 91.

d) Preparation of Intermediates 92 and 93

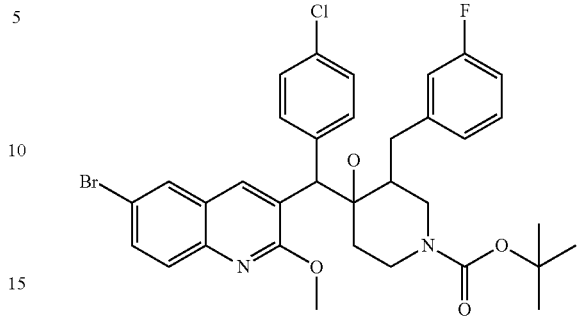

Intermediate 92 (3R*), (B)-2
Intermediate 93 (3R*), (A)-1

BuLi 1.6M in hexane (4.14 ml, 6.62 mmol) was added dropwise under N$_2$ flow to a solution of diisopropylamine (0.93 ml, 6.62 mmol) in THF (10 ml) at −20° C. The mixture was stirred 20 minutes at −20° C. then cooled to −78° C. A solution of 6-bromo-3-[(4-chlorophenyl)methyl]-2-methoxy-quinoline (2 g, 5.52 mmol) in THF (20 ml) was added then stirred at −78° C. for 1 hour. A solution of intermediate 90 (2 g, 6.62 mmol) in THF (20 ml) was added at −78° C. then stirred for 2 hours at −78° C. Water and EtOAc were added. The organic layer was separated, washed with water then brine, dried over MgSO$_4$, filtered and the solvent was evaporated to dryness.

The residue (4.2 g) was purified by high-performance liquid chromatography (irregular SiOH (20-45 μm 450 g, MATREX); mobile phase (DCM 80%/Cyclo 20%). Two fractions were collected and the solvent was evaporated, yielding respectively 950 mg of intermediate 93 and 1500 mg of intermediate 92.

Example A25 a) Preparation of Intermediates 94 and 95

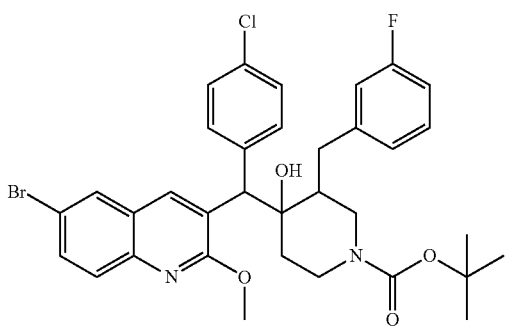

Intermediate 94 (3S*), (A)-1
Intermediate 95 (3S*), (B)-2

BuLi 1.6M in hexane (4.14 ml, 6.62 mmol) was added dropwise under N$_2$ flow to a solution of diisopropylamine (0.93 ml, 6.62 mmol) in THF (10 ml) at −20° C. The mixture was stirred for 20 minutes at −20° C. then cooled to −78° C. A solution of 6-bromo-3-[(4-chlorophenyl)methyl]-2-methoxy-quinoline (2 g, 5.52 mmol) in THF (20 ml) was added then stirred at −78° C. for 1 hour. A solution of intermediate 91 (2 g, 6.62 mmol) in THF (20 ml) was added at −78° C., then stirred for 1 hour at −78° C. Water and EtOAc were added. The organic layer was separated, washed with water then brine, dried over MgSO$_4$, filtered and the solvent was evaporated to dryness. The residue (4.3 g) was purified by high-performance liquid chromatography on irregular SiOH (20-45 μm 450 g MATREX); mobile phase (DCM 80%/Cyclo 20%). Two fractions were collected and the solvent was evaporated, yielding respectively 820 mg of intermediate 94 and 1.6 g of intermediate 95.

Example A26 a) Preparation of Intermediate 96

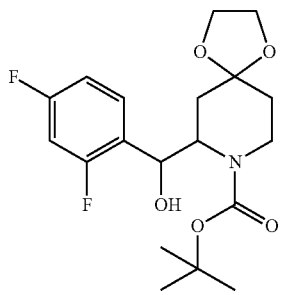 [SMILES: CC(C)(C)OC(=O)N1CCC2(CC1C(O)c1ccc(F)cc1F)OCCO2]

BuLi 1.3M in Cyclo (70 ml, 91 mmol) was added dropwise to a solution of 4,4-(ethylenedioxy)-1-tert-butoxycarbonylpiperidine (17 g, 70 mmol) and N,N,N',N'-tetramethylethylenediamine (10.5 ml, 100 mmol) in diethyl ether (110 ml) at −70° C. and the mixture was stirred at −70° C. under N$_2$ for 3 hours. A solution of 2,4-difluorobenzaldehyde (8.4 ml, 77 mmol) in diethyl ether (15 ml) was added at such a rate that the temperature remained under −60° C. The mixture was stirred for 3 hours at −70° C. 10% aqueous NH$_4$Cl solution (130 ml) was added, then EtOAc was added and the organic layer was separated, dried (MgSO$_4$) and concentrated. The crude product was purified by chromatography over silica gel using Cyclo/EtOAc 70/30 as eluent. The pure fractions were collected and the solvent was evaporated, yielding 9.3 g of intermediate 96.

b) Preparation of Intermediate 97

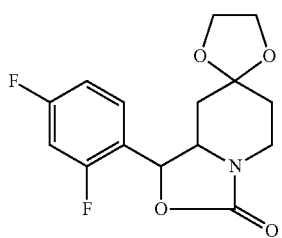 [SMILES: O=C1OC(c2ccc(F)cc2F)C2CC3(CCN12)OCCO3]

A mixture of intermediate 96 (6.7 g, 17.4 mmol) and potassium tert-butoxide (0.2 g, 1.74 mmol) in iPrOH (20 ml) was stirred and refluxed for 2 hours and then cooled to room temperature. Water was added and the residue was extracted with DCM, decanted, dried over MgSO$_4$ and concentrated. The crude product was purified by chromatography over silica gel using Cyclo/EtOAc 70/30 as eluent. The pure fractions were collected and the solvent was evaporated, yielding 4.4 g (81.3%) of intermediate 97.

c) Preparation of Intermediate 98

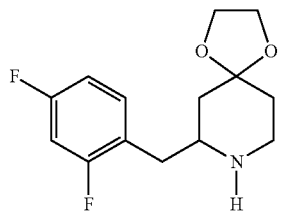 [SMILES: Fc1ccc(CC2CC3(CCN2)OCCO3)c(F)c1]

A solution of intermediate 97 (7.5 g, 24.1 mmol) in MeOH (150 ml) was hydrogenated (3 bars) at 50° C. with Pd/C 10% (2 g) as a catalyst for 12 hours. The catalyst was filtered off and the filtrate was evaporated. The crude product was purified by chromatography over silica gel using DCM/MeOH/NH$_4$OH 97/3/0.1 as eluent. The pure fractions were collected and the solvent was evaporated, yielding 1.5 g (23.1%) of intermediate 98.

d) Preparation of Intermediate 99

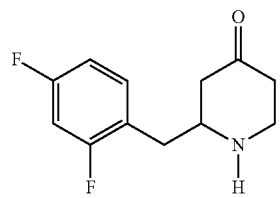

Intermediate 98 (4.2 g, 15.6 mmol) in HCl 6N (80 ml) was stirred at reflux for 12 hours. The mixture was cooled down to room temperature and poured into ice, basified and saturated with K$_2$CO$_3$ solution. The mixture was extracted with EtOAc, the organic layer was separated, washed with water then brine, dried (MgSO$_4$) and evaporated to dryness, yielding 3.5 g (99.6%) of intermediate 99.

e) Preparation of Intermediates 100 and 101

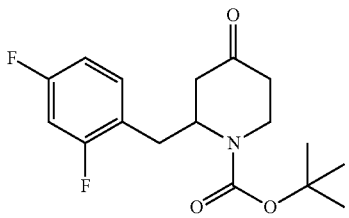

Intermediate 100 (R)*
Intermediate 101 (S)*

A solution of intermediate 99 (3.5 g, 15.5 mmol), di-tert-butyl dicarbonate (3.4 g, 15.5 mmol) and triethylamine (2.2 ml, 15.5 mmol) in THF (50 ml) was stirred overnight at room temperature. The mixture was poured into water and extracted with EtOAc. The organic layer was separated, washed with water then brine, dried over MgSO$_4$, filtered and the solvent was evaporated to dryness. The residue was purified by high-performance liquid chromatography (Chiralpak AD-H, 250×20 mm); mobile phase (iPA 0%; CO$_2$ 90% MeOH 10%). Two fractions were collected and the solvent was evaporated, yielding 2900 mg of intermediate 100 and 2700 mg of intermediate 101.

f) Preparation of Intermediate 102 and 103

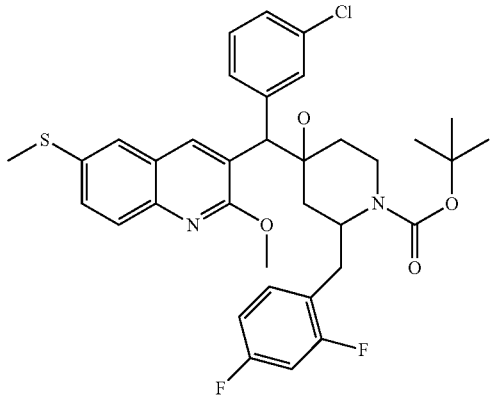

Intermediate 102 (2S*), cis, (A)-1
Intermediate 103 (2S*), cis, (B)-2

BuLi 1.6M in hexane (6.1 mmol; 3.85 ml) was added dropwise under N$_2$ flow to a solution of diisopropylamine (6.1 mmol; 0.90 ml) in THF (15 ml) at −20° C. The mixture was stirred for 20 minutes at −20° C. then cooled to −78° C. A solution of intermediate 81 (5.12 mmol, 1.7 g) in THF (30 ml) was added then stirred at −78° C. for 1 hour. A solution of intermediate 101 (6.14 mmol; 2 g) in THF (30 ml) was added at −78° C. then stirred for 1 hour at −78° C. Water and EtOAc were added at −70° C. The organic layer was separated, washed with water and brine, dried (MgSO$_4$) and evaporated to dryness. The crude product was purified by flash chromatography over silica gel (Cyclo/EtOAc: 90/10). The pure mixture was collected and evaporated to dryness. The residue was purified by high-performance liquid chromatography (Chiracel OD-H, 5 µm, 250×20 mm); mobile phase (iPA 0%; CO$_2$ 70% MeOH 30%), yielding respectively 95 mg of fraction F1 comprising the (2S*),trans,A)-3 and (2S*),trans,(B)-4 isomers, fraction F2 comprising 500 mg of intermediate 102 and fraction F3 comprising 730 mg of intermediate 103.

Example A27

Preparation of Intermediates 104, 105, 106 and 107

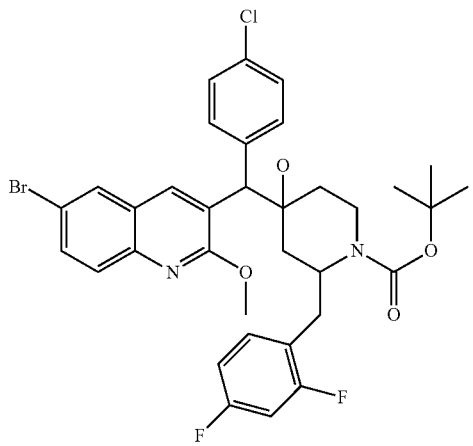

Intermediate 104 (2R*), trans, (A)1
Intermediate 105 (2R*), trans, (B)-2
Intermediate 106 (2R*), cis, (A)-3
Intermediate 107 (2R*), cis, (B)-4

BuLi 1.6M in hexane (6.1 mmol; 3.85 ml) was added dropwise under N$_2$ flow to a solution of diisopropylamine (6.1 mmol, 0.90 ml) in THF (15 ml) at −20° C. The mixture was stirred for 20 minutes at −20° C. then cooled to −78° C. A solution of 6-bromo-3-[(4-chlorophenyl)methyl]-2-methoxy-quinoline (5.12 mmol, 1.86 g) in THF (30 ml) was added then stirred at −78° C. for 1 hour. A solution of intermediate 100 (6.14 mmol, 2 g) in THF (30 ml) was added at −78° C. then stirred for 1 hour at −78° C. Water and EtOAc were added at −70° C. The organic layer was separated, washed with water and brine, dried (MgSO$_4$) and evaporated to dryness. The crude product was purified by flash chromatography over silica gel (Cyclo/EtOAc 90/10). The pure mixture was collected and evaporated to dryness. The residue (1.7 g) was purified by high-performance liquid chromatography (Chiralpak AD-H, 5 µm, 250×20 mm); mobile phase (iPA 0%; CO$_2$ 70% EtOH 15% iPrOH 15%), yielding 38 mg of intermediate 104, 18 mg of intermediate 105, 670 mg of intermediate 106 and 460 mg of intermediate 107.

Example A28

Preparation of Intermediate 108

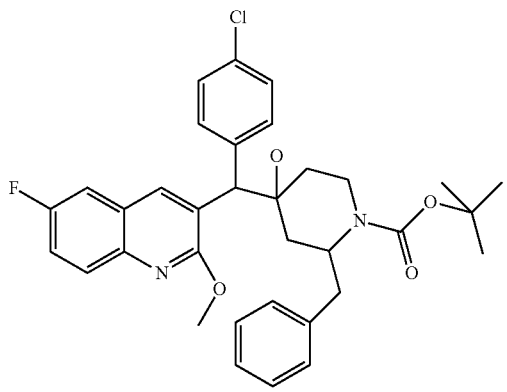

Mixture of R isomers

BuLi 1.6M in hexane (3.76 ml, 6 mmol) was added slowly at −20° C. under N$_2$ flow to a solution of diisopropylamine (0.84 ml, 6 mmol) in THF (9 ml). The mixture was stirred at −20° C. for 20 minutes, and then cooled at −70° C. A solution of intermediate 37 (1.5 g, 4.9 mmol) in THF (15 ml) was added slowly. The mixture was stirred at −70° C. for 1.5 hour. A solution of (2R)-4-oxo-2-(phenylmethyl)-1-piperidinecarboxylic acid, 1,1-dimethylethyl ester, (1.85 g, 6 mmol) in THF (19 ml) was added slowly. The mixture was stirred at −70° C. for 2 hours, hydrolyzed at −30° C. with ice water, and extracted with EtOAc. The organic layer was separated, washed with brine, dried over MgSO$_4$, filtered, and the solvent was evaporated. The residue was purified by flash chromatography over silica gel (15-40 µm, 90 g, Cyclo/EtOAc, 90/10). The pure fractions were collected and evaporated to dryness, yielding 1.3 g of intermediate 108.

Example A29 a) Preparation of Intermediate 109

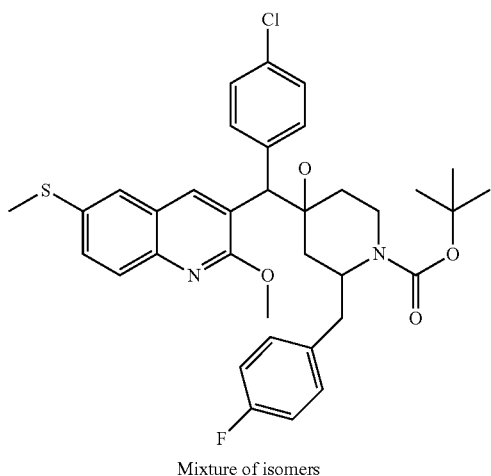 [SMILES: COc1nc2ccc(SC)cc2cc1C(c1ccc(Cl)cc1)C1(O)CCN(C(=O)OC(C)(C)C)C(Cc2ccc(F)cc2)C1]

Mixture of isomers

BuLi 1.6M in hexane (7.28 mmol; 4.6 ml) was added dropwise under N$_2$ flow to a solution of diisopropylamine (7.28 mmol; 1.02 ml) in THF (10 ml) at −20° C. The mixture was stirred for 20 minutes at −20° C. then cooled down to −78° C. A solution of intermediate 56 (6.07 mmol, 2 g) in THF (20 ml) was added then stirred at −78° C. for 1 hour. A solution of intermediate 117 (7.28 mmol, 2.24 g) in THF (20 ml) was added at −78° C. then stirred for 1 hour at −78° C. Water and EtOAc were added at −70° C. The organic layer was separated, washed with water and brine, dried (MgSO$_4$) and evaporated to dryness. The residue was purified by flash chromatography over silica gel (15-40 μm, 90 g, Cyclo/EtOAc 80/20). The pure fractions were collected and evaporated to dryness, yielding 2.3 g of intermediate 109.

b) Preparation of Intermediate 110

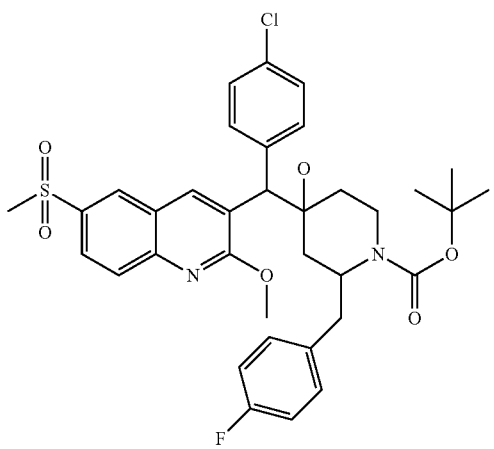 [SMILES: COc1nc2ccc(S(C)(=O)=O)cc2cc1C(c1ccc(Cl)cc1)C1(O)CCN(C(=O)OC(C)(C)C)C(Cc2ccc(F)cc2)C1]

A mixture of intermediate 109 (2.3 g, 3.609 mmol) and 3-chloro-benzenecarboperoxoic acid (1.87 g, 10.9 mmol) in DCM (100 ml) was stirred overnight at room temperature. The mixture was poured into 10% aqueous K$_2$CO$_3$ solution and extracted with DCM. The organic layer was separated, washed with water, dried over MgSO$_4$, filtered and the solvent was evaporated to dryness, yielding 2.6 g of intermediate 110.

Example A30

Preparation of Intermediates 111 and 112

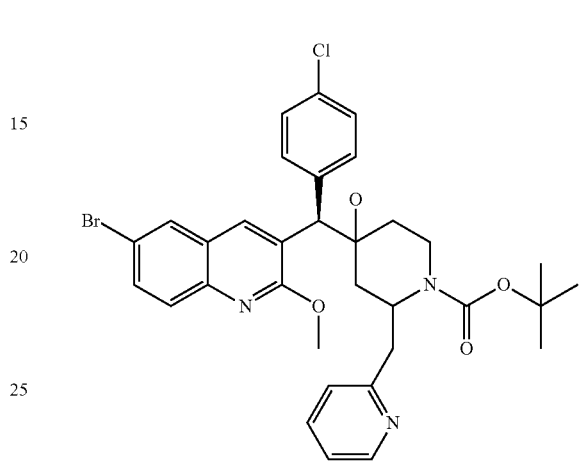

Intermediate 111 (2R*), cis, (A)-1
Intermediate 112 (2R*), cis, (B)-2

BuLi 1.6M in hexane (1.37 ml, 2.19 mmol) was added dropwise under N$_2$ flow to a solution of diisopropylamine (0.31 ml, 2.19 mmol) in THF (3 ml) at −20° C. The mixture was stirred for 20 minutes at −20° C. then cooled to −78° C. A solution of 6-bromo-3-[(4-chlorophenyl)methyl]-2-methoxy-quinoline (0.79 g, 2.19 mmol) in THF (8 ml) was added then stirred at −78° C. for 40 minutes. A solution of intermediate 123 (0.53 g, 1.83 mmol) in THF (5 ml) was added at −78° C. then stirred for 40 minutes at −78° C. Water and EtOAc were added, the organic layer was separated, washed with water then brine, dried over MgSO$_4$, filtered and the solvent was evaporated to dryness. The residue (1.3 g) was purified by high-performance liquid chromatography (irregular SiOH 15-40 μm 300 g MERCK); mobile phase (Cyclo 80% EtOAc 20%). Two fractions were collected and the solvent was evaporated, yielding respectively 0.29 g of intermediate 111 and 0.35 g of intermediate 112.

Example A31 a) Preparation of Intermediate 113

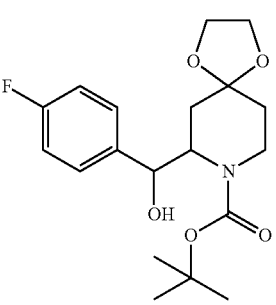 [SMILES: CC(C)(C)OC(=O)N1CCC2(CC1C(O)c1ccc(F)cc1)OCCO2]

BuLi 1.3M in Cyclo (70 ml, 91 mmol) was added dropwise under N$_2$ to a solution of 4,4-(ethylenedioxy)-1-tert-butoxycarbonylpiperidine (17 g, 70 mmol) and N,N,N',N'-tetramethylethylenediamine (10.5 ml, 70 mmol) in diethyl ether (110 ml) at −70° C. The mixture was stirred at −70° C. for 3 hours. A solution of 4-fluorobenzaldehyde (7.4 ml, 77 mmol) in diethyl ether (15 ml) was added at such a rate that the temperature remained under −60° C. and then the mixture was stirred for 3 hours at −70° C. 10% aqueous NH$_4$Cl solution (130 ml) was added. The mixture was stirred at room temperature overnight. The precipitate was filtered off and dried (60° C., vacuum). The residue was purified by high-performance liquid chromatography (irregular SiOH 20-45 μm 450 g MATREX); mobile phase (Cyclo 60% EtOAc 40%). The pure fractions were collected and the solvent was evaporated, yielding 11 g of intermediate 113.

b) Preparation of Intermediate 114

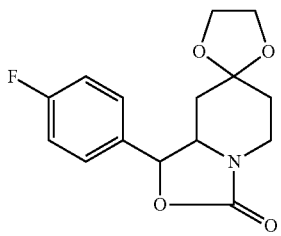 [SMILES: O=C1OC(c2ccc(F)cc2)C2CC3(CCN12)OCCO3]

A mixture of intermediate 113 (12.9 g, 35.11 mmol) and potassium tert-butoxide (0.394 g, 3.511 mmol) in iPrOH (80 ml) was stirred and refluxed for 2 hours then cooled to room temperature. The resulting suspension was cooled to 0° C., stirred for 30 minutes and filtered off. The precipitate was washed with cold iPrOH (20 mL) and dried (50° C., vacuum). The residue was purified by chromatography over a silica gel column SiO$_2$ (15-40 um, 450 g) Cyclo/EtOAc 60/40. The pure fractions were collected and the solvent was evaporated, yielding 2 g of intermediate 114.

c) Preparation of Intermediate 115

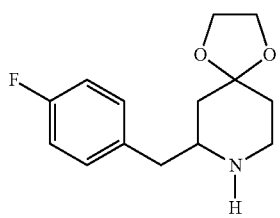 [SMILES: Fc1ccc(CC2CC3(CCN2)OCCO3)cc1]

A solution of intermediate 114 (8.5 g, 37.17 mmol) in MeOH (120 ml) was hydrogenated (3 bars) at 50° C. with Pd/C 10% dry (3 g) as a catalyst for 4 hours. The catalyst was filtered off and the filtrate was evaporated, yielding 7.1 g (97.5%) of intermediate 115.

d) Preparation of Intermediate 116

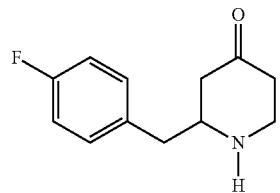 [SMILES: O=C1CCNC(Cc2ccc(F)cc2)C1]

Intermediate 115 (18.3 mmol) in HCl 6N (50 ml) was stirred at reflux for 4 hours. The mixture was cooled to room temperature and poured into ice and basified with 10% aqueous K$_2$CO$_3$ solution. The mixture was extracted with EtOAc, the organic layer was separated, washed with water then brine, dried (MgSO$_4$) and evaporated to dryness, yielding 9.4 g (82.6%) of intermediate 116.

e) Preparation of Intermediates 117 and 118

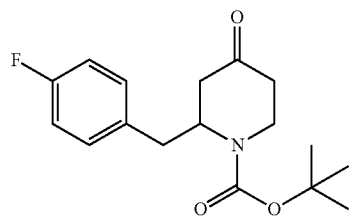

Intermediate 117 (2R*)
Intermediate 118 (2S*)

A solution of intermediate 116 (7.5 g, 36.19 mmol), di-tert-butyl dicarbonate (7.9 g, 36.19 mmol) and triethylamine (5.03 ml, 36.19 mmol) in THF (85 ml) was stirred overnight at room temperature. The mixture was poured into water and extracted with EtOAc. The organic layer was separated, washed with water then brine, dried over MgSO$_4$, filtered and the solvent was evaporated to dryness. The residue (14.7 g) was purified by high-performance liquid chromatography on irregular SiOH 20-45 μm, 1000 g MATREX; mobile phase (Cyclo 70% EtOAc 30%). The pure fractions were collected and the solvent evaporated to dryness. The residue (12.4 g) was purified by high-performance liquid chromatography (Chiralpak AD-H, 5 μm, 250×20 mm); mobile phase (iPA 0%; CO$_2$ 90% MeOH 10%). Two fractions were collected and the solvent was evaporated, yielding 5.2 g (37.3%) of intermediate 117 and 5.4 g (38.7%) of intermediate 118.

Example A32 a) Preparation of Intermediate 119

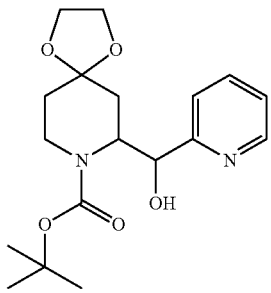 [SMILES: CC(C)(C)OC(=O)N1CCC2(CC1C(O)c1ccccn1)OCCO2]

BuLi 1.6M in hexane (8.29 ml, 13.3 mmol) was added dropwise to a solution of 2-bromopyridine (1.26 ml, 13.3 mmol) in diethyl ether (15 ml) at −78° C. under N₂ flow then the mixture was stirred 45 minutes at −78° C. A solution of 7-formyl-1,4-dioxa-8-azaspiro[4.5]decane-8-carboxylic acid, 1,1-dimethylethyl ester (3 g, 11.1 mmol) in diethyl ether (30 ml) was added dropwise then the mixture was stirred at −78° C. for 4 hours. Water and EtOAc were added, the organic layer was separated, washed with water then brine, dried over MgSO₄, filtered and the solvent was evaporated to dryness. The residue was purified by chromatography over silica gel (15-40 μm, 200 g), DCM/MeOH/NH₄OH: 97/3/0.1. The pure fractions were collected and the solvent was evaporated to dryness, yielding 1.4 g of intermediate 119.

b) Preparation of Intermediate 120

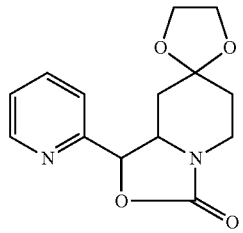 [SMILES: O=C1OC(c2ccccn2)C2CC3(CCN12)OCCO3]

A mixture of intermediate 119 (1.1 g, 3.14 mmol) and potassium tert-butoxide (0.035 g, 0.314 mmol) in iPrOH (4 ml) was stirred and refluxed for 2 hours and then cooled to room temperature. The mixture was poured into water and extracted with EtOAc. The organic layer was separated, washed with water then brine, dried over MgSO₄, filtered and the solvent was evaporated to dryness, yielding 0.74 g (85.3%) of intermediate 120.

c) Preparation of Intermediate 121

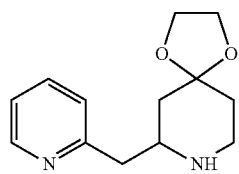 [SMILES: c1ccc(CC2CC3(CCN2)OCCO3)nc1]

A solution of intermediate 120 (0.74 g, 2.68 mmol) in MeOH (10 ml) was hydrogenated (3 bars) at 50° C. with Pd/C 10% dry (0.1 g) as a catalyst for 2 hours. The catalyst was filtered off and the filtrate was evaporated, yielding 0.52 g (82.9%) of intermediate 121.

d) Preparation of Intermediate 122

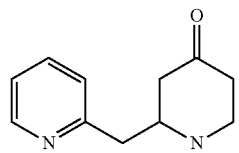 [SMILES: O=C1CCNC(Cc2ccccn2)C1]

Intermediate 121 (1.15 g, 4.91 mmol) in HCl 6N (10 ml) was stirred at 100° C. for 5 hours then cooled to room temperature. The mixture was poured into NaOH 3N and extracted with DCM (three times). The organic layer was separated, washed with water, dried over MgSO₄, filtered and the solvent was evaporated to dryness, yielding 0.6 g (67.1%) of intermediate 122.

e) Preparation of Intermediates 123 and 124

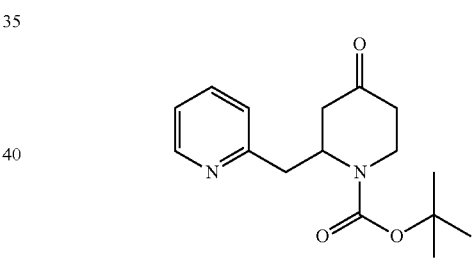

A solution of intermediate 122 (0.6 g, 3.15 mmol), di-tert-butyl dicarbonate (0.69 g, 3.15 mmol) and triethylamine (0.44 ml, 3.15 mmol) in THF (10 ml) was kept overnight at room temperature then the mixture was poured into water and extracted with EtOAc. The organic layer was separated, washed with water then brine, dried over MgSO₄, filtered and the solvent was evaporated to dryness.

The residue was purified by chromatography over silica gel (15-40 μm, 30 g), DCM/MeOH/NH₄OH: 97/3/0.1. The pure fractions were collected and the solvent was evaporated to dryness. The residue (0.45 g) was combined with a fraction made in a similar way, and then purified by high-performance liquid chromatography (Chiralpak AD-H, 5 μm 250×20 mm); mobile phase (CO₂ 90% MeOH 10%). Two fractions were collected and the solvent was evaporated, yielding 533 mg of intermediate 123 and 506 mg of intermediate 124.

Example A33

Preparation of Intermediate 125 and 126

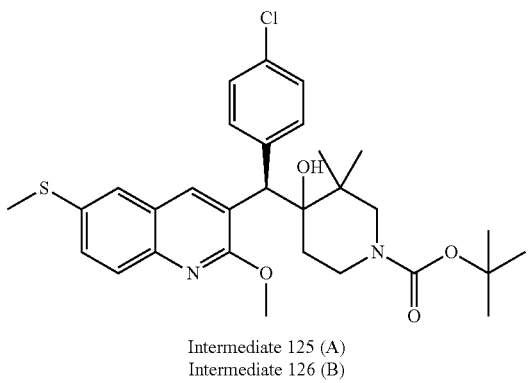 [SMILES: COc1nc2ccc(SC)cc2cc1[C@@H](c1ccc(Cl)cc1)C1(O)CCN(C(=O)OC(C)(C)C)CC1(C)C]

Intermediate 125 (A)
Intermediate 126 (B)

BuLi 1.6M in hexane (3.41 ml, 5.46 mmol) was added dropwise under $N_2$ flow to a solution of diisopropylamine (0.767 ml, 5.46 mmol) in THF (8 ml) at −20° C. The mixture was stirred for 20 minutes at −20° C. then cooled to −78° C. A solution of intermediate 56 (1.5 g, 4.55 mmol) in THF (15 ml) was added then stirred at −78° C. for 1 hour. A solution of 3,3-dimethyl-4-oxo-1-piperidinecarboxylic acid, 1,1-dimethylethyl ester (1.24 g, 5.46 mmol) in THF (12 ml) was added at −78° C. then stirred for 2 hours at −78° C. Water and EtOAc were added, the organic layer was separated, washed with water then brine, dried over $MgSO_4$, filtered and the solvent was evaporated to dryness. The residue (2.8 g) was purified by Normal phase on Irregular SiOH 15-40 μm 300 g Merck, mobile phase (85% Cyclo, 15% EtOAc). The pure fractions were collected and the solvent was evaporated. The residue (2 g) was purified by chiral SFC on Chiralpak AD-H (5 μm 250×20 mm); mobile phase (iPA 0.3%, 70% $CO_2$, 30% EtOH). Two fractions were collected and the solvent was evaporated, yielding 0.58 g (22.9%) of intermediate 125 and 0.87 g (34.3%) of intermediate 126.

Example A34

Preparation of Intermediate 127

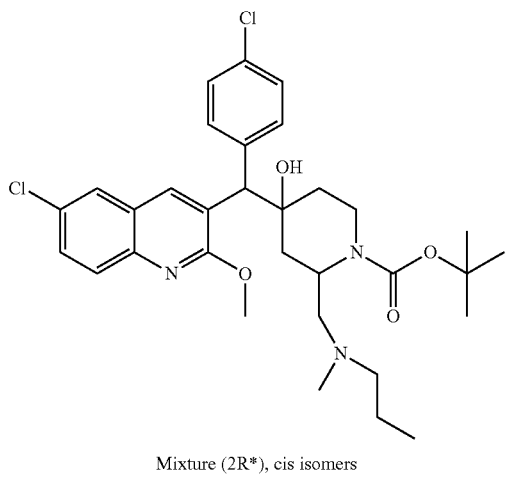 [SMILES: CCCN(C)CC1CC(O)(C(c2ccc(Cl)cc2)c2cc3cc(Cl)ccc3nc2OC)CCN1C(=O)OC(C)(C)C]

Mixture (2R*), cis isomers

A solution of intermediate 26 (0.917 mmol) sodium triacetoxyborohydride (1.833 mmol) and N-methylpropylamine (1.833 mmol) in THF (10 ml) and acetic acid (2.75 mmol) was stirred for 4 hours. 10% aqueous $K_2CO_3$ solution and EtOAc were added, the organic layer was separated, washed with water then brine, dried over $MgSO_4$, filtered and the solvent was evaporated to dryness, yielding 0.49 g (88.7%) of intermediate 127.

Example A35 a) Preparation of Intermediate 128

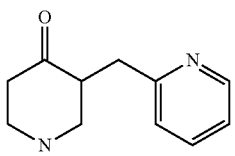 [SMILES: O=C1CCNCC1Cc1ccccn1]

A solution of 4-oxo-3-(2-pyridinylmethyl)-1,3-piperidinedicarboxylic acid, 1-(1,1-dimethylethyl) 3-ethyl ester (13 g, 35.869 mmol) in HCl 6N (88 ml) and MeOH (15 ml) was heated to reflux temperature with stirring for 20 hours. After cooling to room temperature, the mixture was basified to pH 10 with NaOH 6N (2.5 ml) and extracted with DCM (3 times). The combined organic layers were dried over $MgSO_4$, filtered and concentrated, yielding 4.52 g of intermediate 128.

b) Preparation of Intermediates 129 and 130

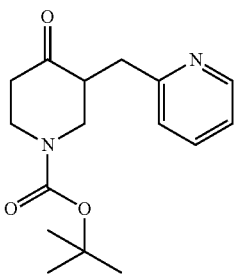

Intermediate 129 R*
Intermediate 130 S*

Triethylamine (6.61 ml, 47.52 mmol) and then di-tert-butyl dicarbonate (5.2 g, 23.8 mmol) were added to a solution of intermediate 128 (4.52 g, 23.76 mmol) in THF (60 ml). The resulting mixture was stirred overnight at room temperature. The solution was poured into water and extracted with EtOAc. The organic layer was separated, washed with brine, dried over $MgSO_4$, filtered, and the solvent was evaporated. The residue (6.8 g) was purified by Normal phase on Irregular SiOH (15-40 μm, 300 g Merck); mobile phase (90% $CO_2$, 10% (MeOH 50% iPrOH 50%)). The pure fractions were collected and the solvent was evaporated. The residue was purified by chiral SFC on Chiralpak AD; mobile phase (90% $CO_2$, 5% MeOH, 5% iPrOH, 0.3% iPa). Two fractions were collected and the solvent was evaporated, yielding 2.2 g (31.89%) of intermediate 129 and 2 g (29.0%) of intermediate 130.

c) Preparation of Intermediate 131

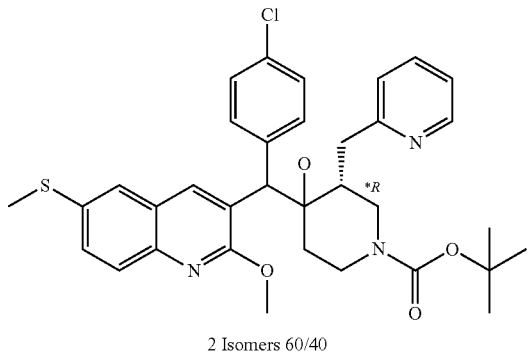 [SMILES: COc1nc2ccc(SC)cc2cc1C(c1ccc(Cl)cc1)C1(O)CCN(C(=O)OC(C)(C)C)C[C@H]1Cc1ccccn1]

2 Isomers 60/40

BuLi 1.6M in hexane (1.94 ml, 3.1 mmol) was added slowly at −20° C. under N₂ flow to a solution of diisopropylamine (0.43 ml, 3.1 mmol) in THF (4.5 ml). The mixture was stirred at −20° C. for 20 minutes, then cooled to −70° C. A solution of intermediate 56 (0.85 g, 2.58 mmol) in THF (9 ml) was added slowly. The mixture was stirred at −70° C. for 90 minutes. A solution of intermediate 129 (0.9 g, 3.11 mmol) in THF (9 ml) was added slowly. The mixture was stirred at −70° C. for 2 hours, hydrolyzed at −30° C. with ice water, and extracted with EtOAc. The organic layer was separated, washed with brine, dried over MgSO₄, filtered, and the solvent was evaporated. The residue was purified by flash chromatography over silica gel (30 g, 15-40μ, Cyclo/EtOAc 85/15). The pure fractions were collected and the solvent was evaporated, yielding 0.9 g (56.1%) of intermediate 131.

d) Preparation of Intermediate 132

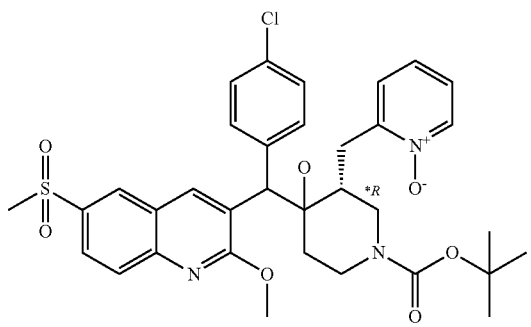 [SMILES: COc1nc2ccc(S(C)(=O)=O)cc2cc1C(c1ccc(Cl)cc1)C1(O)CCN(C(=O)OC(C)(C)C)C[C@H]1Cc1cccc[n+]1[O-]]

A mixture of intermediate 131 (0.9 g, 1.45 mmol) and chloroperoxybenzoic acid (1.07 g, 4.35 mmol) in DCM (20 ml) was stirred overnight at room temperature. The mixture was poured into 10% aqueous K₂CO₃ solution and extracted with DCM. The organic layer was separated, washed with water, dried over MgSO₄, filtered and the solvent was evaporated to dryness, yielding 805 mg (83%) of intermediate 132.

Example A36 a) Preparation of Intermediate 133

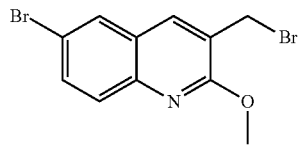

6-bromo-2-methoxy-3-methyl-quinoline (7.9 g, 31.34 mmol), N-bromosuccinimide (5.58 g; 31.34 mmol) and benzoyl peroxide (0.76 g, 3.13 mmol) were added in 1,2-dichloroethane (79 ml). The mixture was stirred at 80° C. overnight, poured into water, basified with 10% aqueous K₂CO₃ solution and extracted with DCM. The organic layer was dried over MgSO₄, filtered and evaporated under reduced pressure to dryness. The residue (10.08 g) was purified by Normal phase on Irregular SiOH (20-45 μm 450 g Matrex); mobile phase, gradient from 90% heptane, 10% EtOAc to 85% heptane, 15% EtOAc. The pure fractions were collected and concentrated, yielding 5.90 g of intermediate 133.

b) Preparation of Intermediate 134

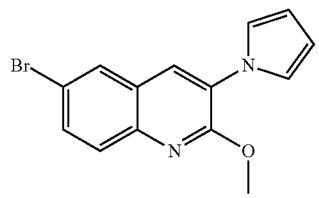 [SMILES: COc1nc2ccc(Br)cc2cc1-n1cccc1]

A solution of intermediate 133 (1.49 g, 0.0045 mol), pyrazole (0.34 g, 0.005 mol), K₂CO₃ (0.68 g, 0.005 mol) in acetonitrile was stirred and refluxed overnight. The solution was cooled to room temperature and poured into ice water. DCM was added and the organic layer was extracted, dried over MgSO₄, filtered off and concentrated. The residue was purified by flash chromatography over silica gel (heptane/EtOAc 80/20). Pure fractions were collected and evaporated to give 1.2 g (82%) of intermediate 134.

c) Preparation of Intermediate 135

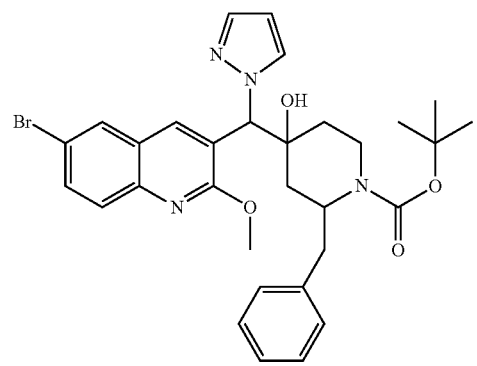 [SMILES: COc1nc2ccc(Br)cc2cc1C(n1cccn1)C1(O)CCN(C(=O)OC(C)(C)C)C(Cc2ccccc2)C1]

85

BuLi 1.6M in hexane (1.9 ml, 3.1 mmol) was added dropwise to diisopropylamine (0.43 ml, 3.1 mmol) in THF (3 ml) stirred under $N_2$ at −20° C. The mixture was stirred for 20 minutes at −20° C. then cooled to −78° C. Intermediate 134 (0.82 g, 2.6 mmol) in THF (8 ml) was added dropwise, and the resulting red solution was stirred at −78° C. for 1 hour. (2R)-4-oxo-2-(phenylmethyl)-1-piperidinecarboxylic acid, 1,1-dimethylethyl ester (0.89 g, 3.1 mmol) in THF (8 ml) was added and the mixture was stirred at −78° C. for 1 hour. Water was added. The aqueous layer was extracted with EtOAc. The combined organic layers were washed with water and brine, dried over $MgSO_4$, filtered and concentrated under reduced pressure. The residue (1.83 g). was purified by Normal phase on Irregular SiOH (15-40 μm 300 g MERCK); mobile phase 90% Cyclo, 10% EtOAc. The pure fractions were collected and the solvent was evaporated. The residue (0.486 g) was purified by chiral SFC on Chiralpak AD-H (5 μm, 250×20 mm); mobile phase, gradient from 0.3% iPa, 75% $CO_2$, 25% MeOH to 0.3% iPa, 75% $CO_2$, 25% MeOH). The pure fractions were collected and the solvent was evaporated, yielding 20.18 g of intermediate 135.

B. Preparation of the Final Compounds

Example B1

Preparation of Compounds 1, 2, 3 and 4

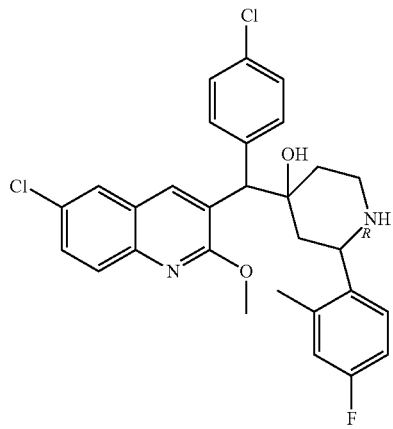

Compound 1 (2R), cis-1
Compound 2 (2R), trans-2
Compound 3 (2R), trans-3
Compound 4 (2R), cis-4

Trifluoroacetic acid (12 ml) was added to a solution of intermediate 3 (3.8 g, 6.07 mmol) in DCM (38 ml). The reaction mixture was stirred at room temperature for 3 hours and basified with 10% aqueous potassium carbonate solution. The organic layer was extracted with DCM, dried over $MgSO_4$, filtered and concentrated. The residue (3.6 g) was purified by high-performance liquid chromatography (Cartridge, 15-40 μm, 90 g); mobile phase ($NH_4OH$ 0.3%; DCM 95% MeOH 5%), yielding respectively 160 mg of fraction F1 and 2.7 g of fraction F2.

Fraction F2 was purified by high-performance liquid chromatography (Chiralpak AD-H, 5 μm, 250×20 mm); mobile phase (iPA 0.3%; $CO_2$ 60% MeOH 40%), yielding respectively 2.15 g of fraction F2/1 and 150 mg of compound 1.

Fraction F2/1 was purified by high-performance liquid chromatography (Chiralpak AD-H, 5 μm, 250×20 mm); mobile phase (iPA 0.3%; $CO_2$ 75% MeOH 12.5% iPrOH 12.5%), yielding respectively 1.2 g of compound 2, melting point 126° C. and 620 mg of compound 3, melting point 146° C. and 135 mg of compound 4.

86

Compound 1: optical rotation: −153.8° (589 nm, c 0.342 w/v %, DMF, 20° C.)

Compound 2: optical rotation: +76.76° (589 nm, c 0.37 w/v %, DMF, 20° C.)

Compound 3: optical rotation: −182.79° (589 nm, c 0.3835 w/v %, DMF, 20° C.)

Compound 4: optical rotation: +140.04° (589 nm, c 0.2835 w/v %, DMF, 20° C.)

Example B2

Preparation of Compound 5

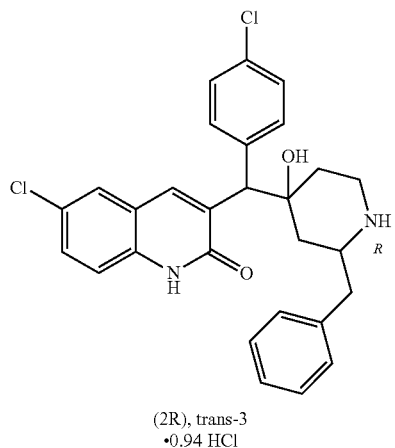

(2R), trans-3
•0.94 HCl

A solution of compound 37 (0.052 g, 0.102 mmol) and hydrochloric acid (3N, 0.6 ml) in THF (0.6 ml) was stirred overnight at 70° C. The mixture was cooled to room temperature and the precipitate was filtered, washed with water and dried under vacuum at 60° C., yielding 41 mg of compound 5, melting point: >250° C.

Example B3

Preparation of Compound 6

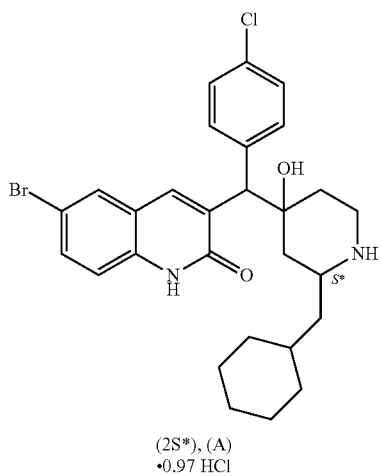 [SMILES: O=c1[nH]c2ccc(Br)cc2cc1C(c1ccc(Cl)cc1)C1(O)CCNC(CC2CCCCC2)C1]

(2S*), (A)
•0.97 HCl

A mixture of intermediate 8 (0.45 g, 0.684 mmol) in hydrochloric acid (5 ml) and THF (5 ml) was stirred at 60° C. overnight then cooled to room temperature. The precipitate was filtered off and dried (vacuum, 60° C.), yielding 0.165 g of compound 6, melting point: >250° C.

Example B4

Preparation of Compound 7

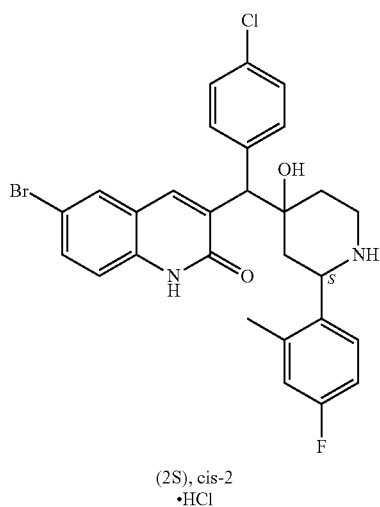

(2S), cis-2
·HCl

A mixture of intermediate 10 (0.0002 mol) and trifluoroacetic acid (0.004 mol) in DCM (1.6 ml) was stirred at room temperature for 2 hours, poured into 10% aqueous potassium carbonate solution and extracted with DCM. The organic layer was washed with water, dried (MgSO$_4$), filtered and the solvent was evaporated to dryness. 0.037 g of fumaric acid (in 2-propanone) was added portionwise to the residue. The mixture was stirred at room temperature for 1 hour. The precipitate was filtered off, washed with 2-propanone and dried at 60° C. in vacuo. The residue (0.073 g) was dissolved in DCM. The mixture was basified with 10% aqueous potassium carbonate solution and dissolved in diethyl ether. HCl 5N (in 2-propanone) was added dropwise. The mixture was filtered off and dried in vacuo. The residue was dissolved in THF (1 ml) and HCl 3N (1 ml) was added. The mixture was stirred at 70° C. overnight and cooled to room temperature. Ice and water were added. The mixture was stirred at 0° C. for 15 minutes. The precipitate was filtered off and dried at 60° C. in vacuo, yielding 0.02 g (20%) of compound 7, optical rotation: +78.57° (589 nm, c 0.224 w/v %, DMF, 20° C.).

Example B5 a) Preparation of Compounds 8 and 9

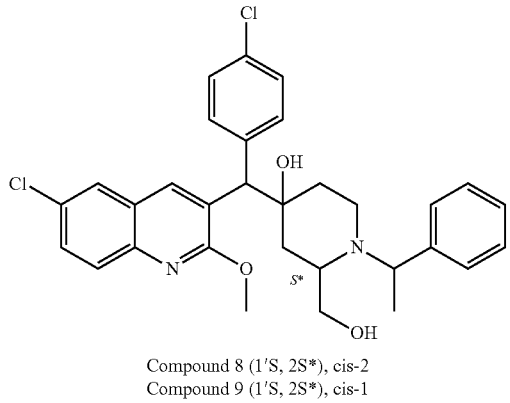 [SMILES: COc1nc2ccc(Cl)cc2cc1C(c1ccc(Cl)cc1)C1(O)CCN(C(C)c2ccccc2)C(CO)C1]

Compound 8 (1'S, 2S*), cis-2
Compound 9 (1'S, 2S*), cis-1

A solution of intermediate 16 (0.52 g, 0.781 mmol) and tetrabutylammonium fluoride 1M in THF (0.781 ml, 0.781 mmol) in THF (10 ml) was stirred at 0° C. for 2 hours. Water and EtOAc were added, the organic layer was separated, washed with water then brine, dried over MgSO$_4$, filtered and the solvent was evaporated to dryness. The residue (0.52 g) was purified by chiral SFC on (Chiralpak AD-H, 5 nm, 250×20 mm); mobile phase (gradient from 0.3% iPA, 60% CO$_2$, 40% EtOH to 0.3% iPA, 60% CO$_2$, 40% EtOH). Two fractions were collected and the solvent was evaporated, yielding 134 mg of compound 8 and 193 mg of F1. F1 was crystallized from MeOH, yielding 135 mg (31.3%) of compound 9, melting point 182° C.

b) Preparation of Compound 10

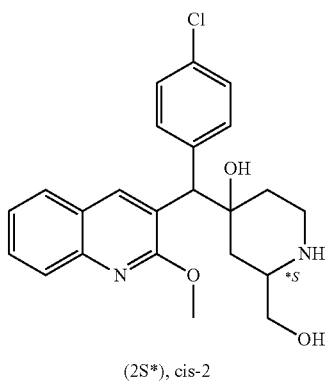 [SMILES: COc1nc2ccccc2cc1C(c1ccc(Cl)cc1)C1(O)CCNC(CO)C1]

(2S*), cis-2

A mixture of compound 8 (0.243 mmol) in MeOH (5 ml) and EtOAc (5 ml) was hydrogenated (Patm) at room temperature with Pd/C (25 mg) as a catalyst for 1.30 hour then 2 hours and overnight. The catalyst was filtered through a short pad of celite, the celite was washed with EtOAc, the filtrate was washed with 10% aqueous potassium carbonate solution then brine, dried (MgSO$_4$) and evaporated to dryness. The residue was purified by reverse phase chromatography on Nucleodur-Sphinx rp 5 μm 21×150 mm; mobile phase (gradient from 30% NH$_4$HCO$_3$ 0.5%, 70% MeOH to 0% NH$_4$HCO$_3$ 0.5%, 100% MeOH). The pure fractions were collected and the solvent was evaporated, yielding 27 mg of compound 10.

Example B6

Preparation of Compound 11

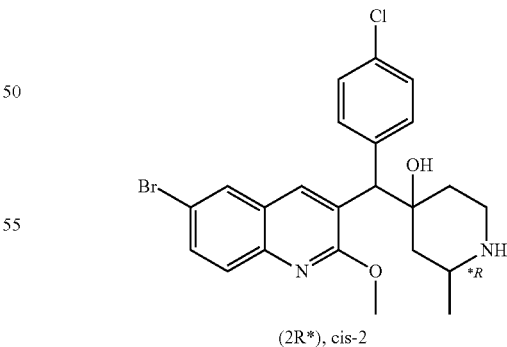

(2R*), cis-2

Boron tribromide (3.77 ml, 3.77 mmol) was added dropwise to a solution of intermediate 19 (0.46 g, 0.754 mmol) in DCM (10 ml) at 5° C. and the reaction mixture was stirred for 3 hours and allowed to reach about 15° C. The reaction mixture was poured into 10% aqueous potassium carbonate solution and extracted with DCM. The organic layer was separated, dried over MgSO$_4$, filtered and the solvent was evaporated to dryness. The residue was purified by chromatography on a SiOH column (3.5 μm 30×150 mm); from DCM/MeOH/NH$_4$OH 98/2/0.2 to DCM/MeOH/NH$_4$OH 90/10/1). The pure fractions were collected and evaporated to dryness. The residue (0.11 g) was crystallized from DIPE, yielding 0.054 g of compound 11, melting point 143° C., optical rotation: +189.15° (589 nm, c 0.3225 w/v %, DMF, 20° C.).

Example B7

Preparation of Compound 12

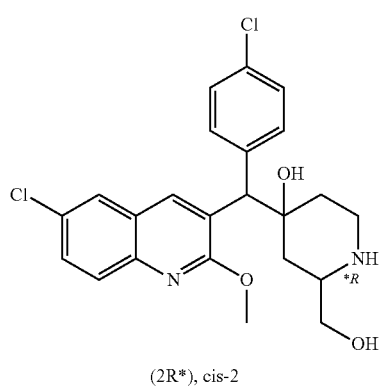 [SMILES: COc1nc2ccc(Cl)cc2cc1C(c1ccc(Cl)cc1)C1(O)CCNC(CO)C1]

(2R*), cis-2

A solution of intermediate 27 (0.7 mmol) in HCl/iPrOH 5-6M (4 ml) was stirred at 0° C. for 2 hours. The gel-like residue was taken up in EtOAc and 10% aqueous potassium carbonate solution. The organic layer was separated, washed with water then brine, dried over MgSO$_4$, filtered and the solvent was evaporated to dryness. The residue was crystallized from DIPE, yielding 137 mg of compound 12, melting point: 135° C., optical rotation: −134.65° (589 nm, c 0.303 w/v %, DMF, 20° C.).

Example B8

Preparation of Compounds 13 and 14

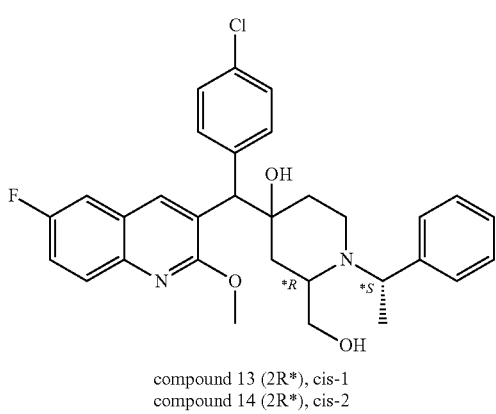 [SMILES: COc1nc2ccc(F)cc2cc1C(c1ccc(Cl)cc1)C1(O)CCN([C@@H](C)c2ccccc2)C(CO)C1]

compound 13 (2R*), cis-1
compound 14 (2R*), cis-2

A solution of intermediate 35 (1.02 g, 1.571 mmol) and tetrabutylammonium fluoride 1M in THF (1.57 ml, 1.57 mmol) in THF (20 ml) was stirred at 0° C. for 2 hours. Water and EtOAc were added, the organic layer was separated, washed with water then brine, dried over MgSO$_4$, filtered and the solvent was evaporated to dryness. The residue (0.9 g) was purified by chiral SFC on (Chiralpak AD-H, 5 μm, 250×20 mm); mobile phase (0.3% iPA, 70% CO$_2$, 30% EtOH). The pure fractions were collected and the solvent was evaporated, yielding respectively 0.245 g of compound 13, optical rotation +99.45° (589 nm, c 0.2735 w/v %, DMF, 20° C.) and 0.4 g of compound 14, melting point 162° C., optical rotation −87.9° (589 nm, c 0.281 w/v %, DMF, 20° C.).

Example B9

Preparation of Compound 15

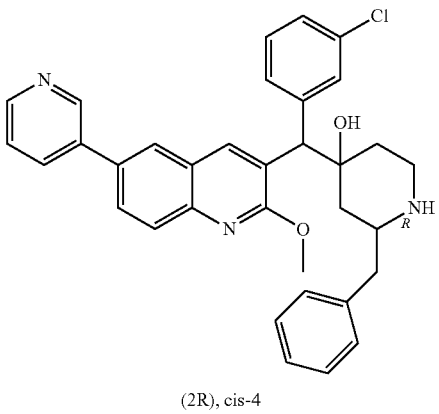

(2R), cis-4

A mixture of compound 34 (0.362 mmol), pyridine-3-boronic acid 1,3-propanediol cyclic ester (0.544 mmol), tetrakis(triphenylphosphine)palladium (0.0362 mmol) and potassium carbonate 2M (0.725 mmol) in DME was stirred under N$_2$ at 90° C. for 2 hours then overnight at room temperature. The reaction mixture was poured into water and extracted with EtOAc. The organic layer was separated, washed with water then brine, dried over MgSO$_4$, filtered and the solvent was evaporated to dryness. The crude product was crystallized from MeOH, yielding 0.075 g of compound 15, melting point: 220° C.

Example B10

Preparation of Compound 16

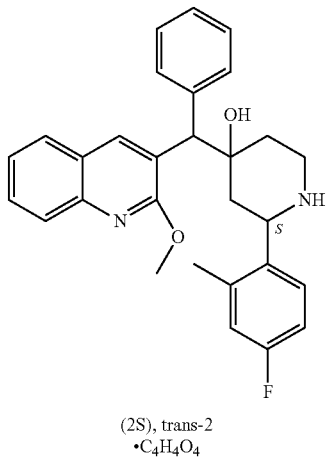

(2S), trans-2
·C$_4$H$_4$O$_4$

A solution of compound 248 (0.15 g, 0.28 mmol), ammonium formate (0.088 g, 1.401 mmol) and Pd/C (0.15 g, 1.41 mmol) in MeOH (3 ml) was heated at reflux for 2 hours. The mixture was cooled to room temperature, and then the solution was filtered over celite and washed with DCM. The filtrate was washed with water and brine, dried over MgSO$_4$, filtered and concentrated. Fumaric acid (0.056 g, 0.48 mmol) was added portionwise to a solution of pure product (0.110 g, 0.24 mmol) in acetone (4 ml). The mixture was stirred overnight at room temperature. The precipitate was filtered off, washed with acetone, and dried under vacuum at 60° C., yielding, 0.085 g of compound 16, melting point 166-168° C.

Example B11

Preparation of Compounds 17 and 18

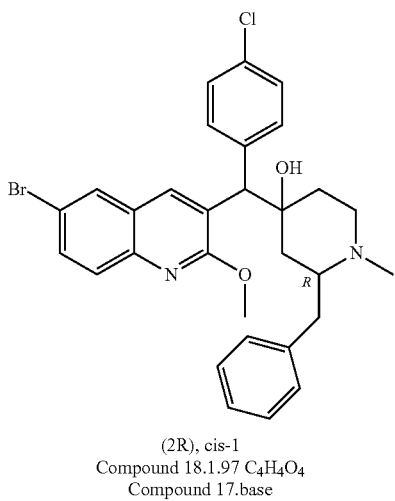

(2R), cis-1
Compound 18.1.97 C$_4$H$_4$O$_4$
Compound 17.base

Intermediate 41 was deprotected in an analogous manner to Example B1. The deprotected compound (0.0009 mol) was mixed with formaldehyde (0.0038 mol) in DCM (9 ml) and stirred at room temperature for 15 minutes. Sodium triacetoxyborohydride (0.0023 mol) was added. The mixture was stirred at room temperature overnight. Water was added. The mixture was extracted with DCM. The organic layer was separated, dried (MgSO$_4$), filtered and the solvent was evaporated under reduced pressure. The residue (0.416 g) was purified by column chromatography over silica gel (eluent: DCM/MeOH 97/3; 15-40 µm). The pure fractions were collected and the solvent was evaporated, yielding compound 17 (0.1 g) which was converted into the (E)-2-butenedioic acid salt. The precipitate was filtered, washed with DIPE and dried in vacuo, yielding 0.078 g of compound 18.

Example B12

Preparation of Compound 19

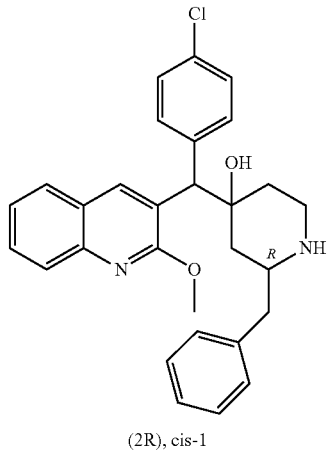

(2R), cis-1

Intermediate 41 was deprotected in an analogous manner to Example B1. BuLi (0.0025 mol) was added dropwise at −78° C. to a solution of the deprotected compound (0.0007 mol) in diethyl ether (4 ml). The solution was stirred at −78° C. for 4 hours. Water was added. The mixture was extracted with EtOAc. The organic layer was separated, dried (MgSO$_4$), filtered and the solvent was evaporated under reduced pressure. The residue (0.357 g) was purified by reverse phase column chromatography over silica gel (eluent: DCM/MeOH/NH$_4$HCO$_3$ 0.5% from 80/20 to 100/0; Sunfire 5 µm). The pure fractions were collected and the solvent was evaporated. The residue was purified by column chromatography over Kromasil, 10 µm (eluent: DCM/MeOH/NH$_4$OH 96/4/0.1);). The pure fractions were collected and the solvent was evaporated, yielding 0.046 g of compound 19.

Example B13

Preparation of Compound 20

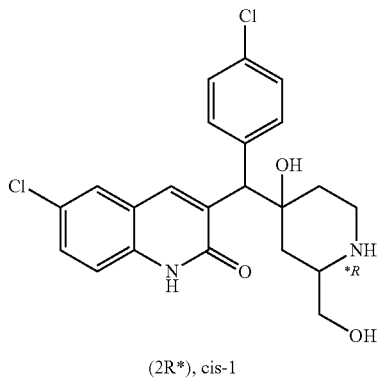 [SMILES: O=c1[nH]c2ccc(Cl)cc2cc1C(c1ccc(Cl)cc1)C1(O)CCNC(CO)C1]

(2R*), cis-1

A solution of intermediate 28 (0.387 mmol) in HCl/iPrOH (2 ml) was stirred at 0° C. for 2 hours and then evaporated to dryness. The residue was crystallized from diethyl ether. The residue was taken up in EtOAc and 10% aqueous potassium carbonate solution, the organic layer was separated, washed with water then brine, dried over MgSO$_4$, filtered and the solvent was evaporated to dryness. The residue was crystallized from diethyl ether, yielding 6 mg of compound 20, melting point: 232° C.

Example B14

Preparation of Compounds 21, 22, 23 and 24

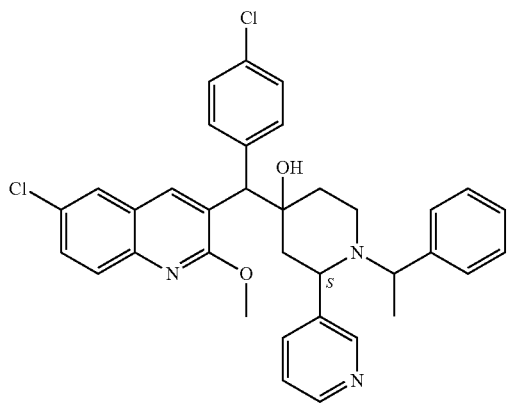

Compound 21 (2S), trans-1
Compound 22 (2S), trans-2
Compound 23 (2S), cis-3
Compound 24 (2S), cis-4

BuLi 1.6 M in hexane (1.93 ml, 3.09 mmol) was added dropwise under $N_2$ flow to a solution of diisopropylamine (0.434 ml, 3.091 mmol) in THF (4 ml) at −20° C. The mixture was stirred for 20 minutes at −20° C. then cooled to −78° C. A solution of intermediate 2 (0.757 g, 2.38 mmol) in THF (4 ml) was added then stirred at −78° C. for 1 hour. A solution of intermediate 40 (0.8 g, 2.85 mmol) in THF (4 ml) was added at −78° C. then stirred for 3 hours at −78° C. Water and EtOAc were added, the organic layer was separated, washed with water then brine, dried over $MgSO_4$, filtered and the solvent was evaporated to dryness. The residue was purified by flash chromatography over silica gel (15-40 µm, 50 g, from DCM 100/0 to DCM/MeOH/$NH_4$OH: 98.5/1.5/0.1) The pure fractions were collected and evaporated to dryness. The residue was purified by chiral SFC on Chiralpak AD-H, 5 µm, 250×20 mm; mobile phase (0.3% iPA, 50% $CO_2$, 50% ETIP), yielding respectively 0.089 g of compound 21, 0.124 g of compound 22, 0.177 g of compound 23 and 0.218 g of compound 24.

Example B15

Preparation of Compounds 25 and 26

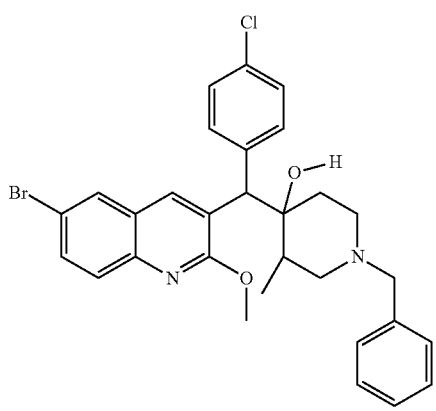

Compound 25 (A).1.94 $C_4H_4O_4$
Compound 26 (B).1.24 $C_4H_4O_4$

BuLi 1.6 M in hexane (0.0033 mol) was added dropwise at −20° C. to a solution of N-(1-methylethyl)-2-propanamine (0.0033 mol) in THF (7 ml) under $N_2$ flow. The mixture was stirred at −20° C. for 20 minutes, then cooled to −70° C. A solution of 6-bromo-3-[(4-chlorophenyl)methyl]-2-methoxy-quinoline (0.0027 mol) in THF (10 ml) was added. The mixture was stirred at −70° C. for 1 hour. A solution of 3-methyl-1-(phenylmethyl)-4-piperidinone (0.003 mol) in THF (6 ml) was added dropwise. The mixture was stirred at −70° C. for 2 hours. Water was added. The mixture was extracted with EtOAc. The organic layer was washed with saturated NaCl solution, dried ($MgSO_4$), filtered and the solvent was evaporated. The residue (1.3 g) was purified by SFC (eluent: $CO_2$/MeOH/iPA 90/10/0.5). Two fractions were collected and the solvent was evaporated, yielding 0.16 g (10%) of fraction F1 and 0.2 g (13%) of fraction F2. Fraction F1 was dissolved in butenedioic acid (0.066 g) and converted into the (E)-2-butenedioic acid salt with 2-propanone (4 ml). The precipitate was taken up in diethyl ether, filtered off and dried, yielding 0.115 g (5%) of compound 25, melting point 154° C. Fraction F2 was dissolved in butenedioic acid (0.082 g) and converted into the (E)-2-butenedioic acid salt with 2-propanone (4 ml). The precipitate was taken up in diethyl ether, filtered off, yielding 0.24 g (12%) of compound 26, melting point 238° C.

Example B16

Preparation of Compounds 27 and 28

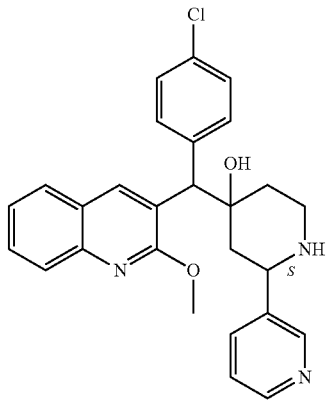

Compound 27 (2S), cis-3

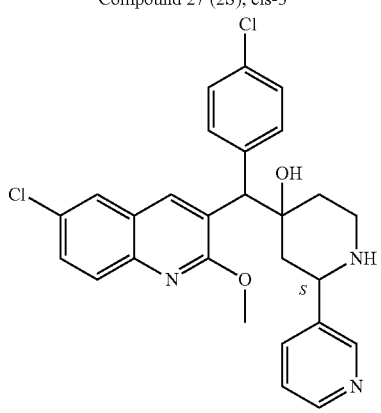

Compound 28 (2S), cis-3

A mixture of compound 23 (0.296 mmol) in MeOH (5 ml) and acetic acid (0.4 ml) was hydrogenated (Patm) at room temperature with Pd/C 10% dry (35 mg) as a catalyst for 3 hours. 10% Aqueous potassium carbonate solution and EtOAc were added, the mixture was filtered through a short pad of celite, the organic layer was separated, washed with brine, dried (MgSO$_4$) and evaporated to dryness. The residue was purified by flash chromatography over silica gel (15-40 μm, 10 g, from DCM to DCM/MeOH/NH$_4$OH: 90/10/0.2). The pure fractions were collected and evaporated to dryness. The residue was purified by reverse phase chromatography on X-Terra-C18 (10 μm, 19×150 mm); mobile phase gradient from 30% NH$_4$HCO$_3$ 0.5%, 70% MeOH to 0% NH$_4$HCO$_3$ 0.5%, 100% MeOH), yielding 20 mg of compound 27 and 25 mg of compound 28.

Example B17 a) Preparation of Compound 29

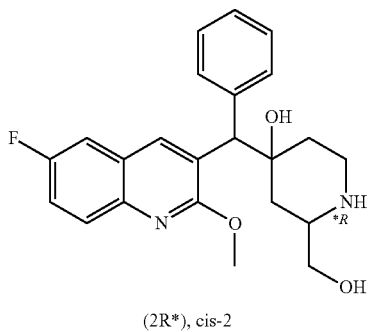

(2R*), cis-2

A mixture of compound 14 (0.654 mmol) in MeOH (5 ml) was hydrogenated (Patm) at room temperature with Pd/C (35 mg) as a catalyst for 90 minutes. The catalyst was filtered off and the filtrate was evaporated to dryness. The residue (260 mg) was purified by chiral SFC on Chiralpak AD-H 5 nm 250×20 mm; mobile phase (0.3% iPA, 70% CO$_2$, 30% EtOH). The pure fractions were collected and the solvent was evaporated. The residue (225 mg) was crystallized from DIPE, yielding 166 mg of compound 29, melting point: 135° C.

b) Preparation of Compound 30

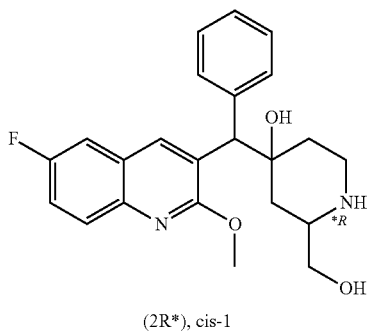

(2R*), cis-1

A mixture of compound 13 (0.374 mmol) in MeOH (5 ml) and THF (2 ml) was hydrogenated (Patm) at room temperature with Pd/C (20 mg) as a catalyst for 90 minutes. The catalyst was filtered off and the filtrate was evaporated to dryness. The residue (140 mg) was purified by normal phase chromatography on stability silica 5 nm 150×30.0 mm); mobile phase (gradient from 0.4% NH$_4$OH, 96% DCM, 4% MeOH to 1.5% NH$_4$OH, 85% DCM, 15% MeOH). The pure fractions were collected and the solvent was evaporated, yielding 55 mg of compound 30.

Example B18

Preparation of Compound 31

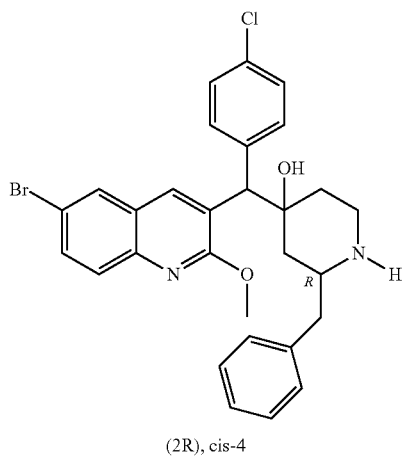

(2R), cis-4

A solution of intermediate 44 (3.76 mmol, 2.45 g) in TFA (8 ml) and DCM (25 ml) was stirred at room temperature for 4 hours. The mixture was poured out into 10% aqueous K$_2$CO$_3$ solution and extracted with DCM. The organic layer was separated, washed with water, dried over MgSO$_4$, filtered and the solvent was evaporated to dryness. The residue was crystallized from MeOH, yielding 1 g of compound 31. The filtrate was recrystallized from MeOH, yielding a further 0.7 g of compound 31, melting point: 183° C.

Example B19

Preparation of Compound 32

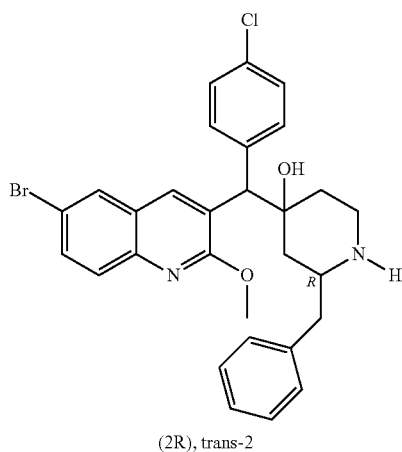

(2R), trans-2

A solution of intermediate 42 (0.0002 mol) in TFA (1.5 ml) and DCM (1.5 ml) was stirred at room temperature for 1 hour. The mixture was poured into 10% aqueous K$_2$CO$_3$ solution and extracted with DCM. The organic layer was separated, washed with water, dried over MgSO$_4$, filtered off and the solvent was evaporated to dryness, yielding 0.115 g (91%) of compound 32.

Example B20

Preparation of Compound 33

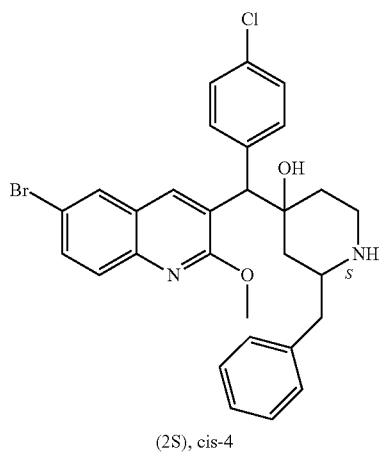

(2S), cis-4

A solution of intermediate 48 in TFA and DCM was stirred at room temperature for 1 hour. The mixture was poured into 10% aqueous K$_2$CO$_3$ solution and extracted with DCM. The organic layer was separated, washed with water, dried over MgSO$_4$, filtered and the solvent was evaporated to dryness. The residue (0.47 g, 100%) was crystallized from DIPE, yielding 0.317 g (71%) of compound 33, melting point 177° C., optical rotation: +232.66° (589 nm, c 0.297 w/v %, DMF, 20° C.).

Example B21

Preparation of Compound 34

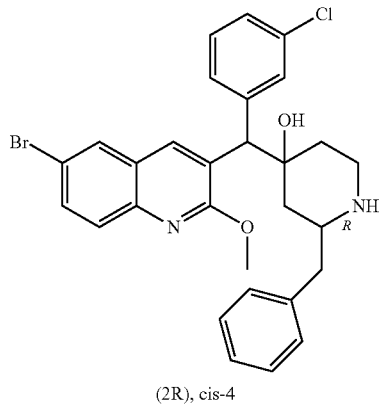

(2R), cis-4

A solution of intermediate 50 in TFA and DCM was stirred at room temperature for 2 hours. The mixture was poured into 10% aqueous K$_2$CO$_3$ solution and extracted with DCM. The organic layer was separated, washed with water, dried over MgSO$_4$, filtered and the solvent was evaporated to dryness. The residue (0.86 g, 100%) was purified by column chromatography over silica gel (SiO$_2$, 15-40 μm), eluent: DCM/iPrOH/NH$_4$OH: 97/3/0.1). The pure fractions were collected and the solvent was evaporated to dryness, yielding respectively 0.63 g of fraction F1 and 0.25 g of fraction F2. F2 was purified by SFC (eluent: CO$_2$/MeOH/iPA: 70/30/0.5). The pure fractions were collected and the solvent was evaporated to dryness, yielding F2/1 0.025 g and F2/2 0.188 g. F1 was combined with F2/2 to give 0.818 g of compound 34.

Example B22 a) Preparation of Compound 35

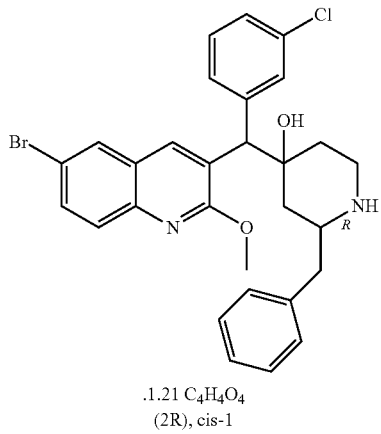

.1.21 C$_4$H$_4$O$_4$
(2R), cis-1

A solution of intermediate 49 (1.69 mmol) in TFA (2.2 ml) and DCM (11 ml) was stirred at room temperature for 2 hours. The mixture was poured into 10% aqueous K$_2$CO$_3$ solution and extracted with DCM. The organic layer was separated, washed with water, dried over MgSO$_4$, filtered and the solvent was evaporated to dryness. The residue (0.95 g, 100%) (0.4 g, 0.72 mmol) was dissolved in 2-propanone (4 ml) and converted into the (E)-2-butenedioic acid salt (1 eq, 0.085 g) dissolved into acetone/EtOH: 50/50:2 ml, yielding 0.40 g of compound 35, melting point: 145° C.

b) Preparation of Compound 36

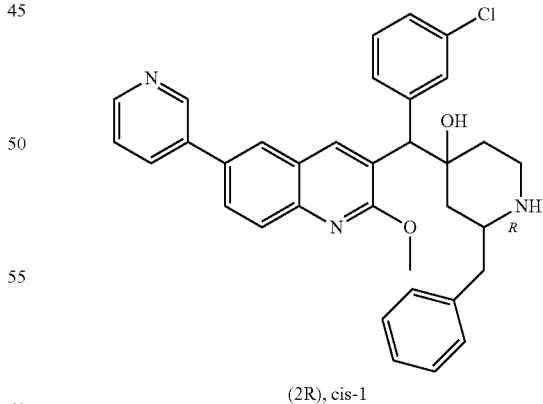

(2R), cis-1

A mixture of compound 35 (0.525 mmol), pyridine-3-boronic acid 1,3-propanediol cyclic ester (0.788 mmol), tetrakis(triphenylphosphine)palladium(0) (0.0525 mmol) and K$_2$CO$_3$ 2 M (1.051 mmol) in DME (4 ml) was stirred under N$_2$ at 90° C. for 2 hours then overnight at room temperature. The reaction mixture was poured into water and extracted with EtOAc. The organic layer was separated, washed with water then brine, dried over MgSO₄, filtered and the solvent was evaporated to dryness. The residue (0.32 g) was purified by column chromatography over silica gel (SiO₂ 3.5 μm), eluent: DCM/MeOH/NH₄OH aqueous: 98/2/0.2 to 92/8/0.8. The pure fractions were collected and the solvent was evaporated to dryness. The residue (0.225 g, 77.8%) was crystallized from DIPE, yielding 0.107 g (37.0%) of compound 36, melting point: 120° C.

Example B23

Preparation of Compound 37

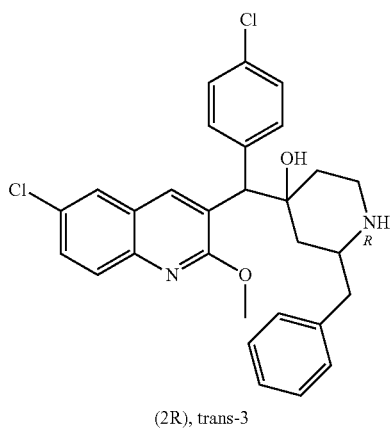

(2R), trans-3

Trifluoroacetic acid (0.36 ml) was added to a solution of intermediate 52 (0.12 g, 0.198 mmol) in DCM (1.2 ml). The reaction mixture was stirred at room temperature for 3 hours and basified with 10% aqueous K₂CO₃ solution. The organic layer was extracted with DCM, dried over MgSO₄, filtered and concentrated. A part (50 mg) of the residue (100 mg) was crystallized from DIPE and dried under vacuum at 60° C., yielding 25 mg of compound 37, melting point: 107° C.

Example B24

Preparation of compound 38

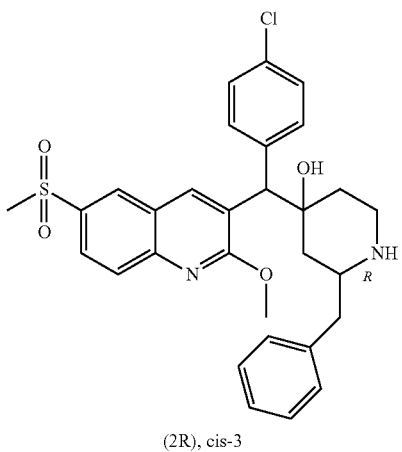

(2R), cis-3

Trifluoroacetic acid (3 ml) was added to a solution of intermediate 59 (1.02 g, 1.57 mmol) in DCM (10 ml). The reaction mixture was stirred at room temperature for 3 hours and basified with 10% aqueous K₂CO₃ solution. The organic layer was extracted with DCM, dried over MgSO₄, filtered and concentrated. The residue was crystallized from DIPE and dried under vacuum at 60° C. The residue (966 mg) was purified by normal phase chromatography on Cartridge (15-40 μm, 30 g); mobile phase (0.5% NH₄OH, 95% DCM, 5% MeOH). The pure fractions were collected and the solvent was evaporated. The residue (670 mg) was crystallized from DIPE and dried under vacuum at 60° C., yielding 0.535 g (62.0%) of compound 38, melting point 130° C.

Example B25

Preparation of Compound 39

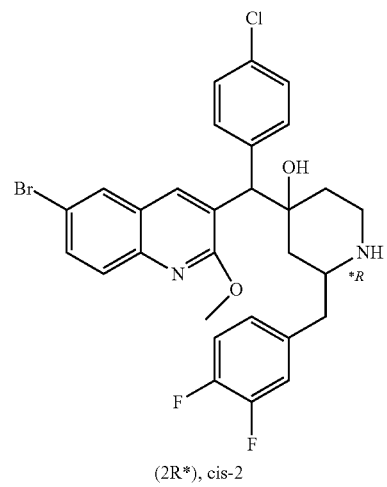 [SMILES: COc1nc2ccc(Br)cc2cc1C(c1ccc(Cl)cc1)C1(O)CCNC(Cc2ccc(F)c(F)c2)C1]

(2R*), cis-2

A solution of intermediate 60 (730 mg, 1.06 mmol) and TFA (1.96 ml, 25.46 mmol) in DCM (10 ml) was stirred at room temperature for 3 hours. The mixture was poured into 10% aqueous K₂CO₃ solution and extracted with DCM. The organic layer was separated, washed with water, dried over MgSO₄, filtered and the solvent was evaporated to dryness. The product was crystallized from MeOH, yielding 492 mg (79%) of compound 39, melting point 106° C., optical rotation: −115.3° (589 nm, c 0.3365 w/v %, DMF, 20° C.).

Example B26

Preparation of Compound 40

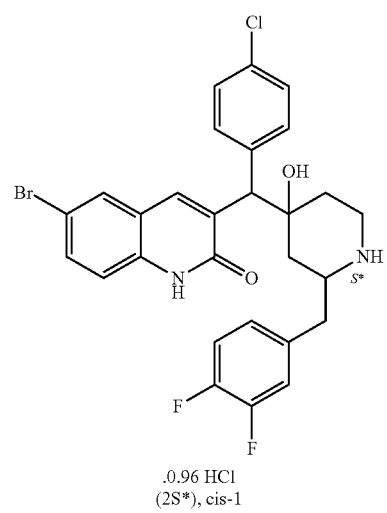 [SMILES: O=c1[nH]c2ccc(Br)cc2cc1C(c1ccc(Cl)cc1)C1(O)CCNC(Cc2ccc(F)c(F)c2)C1]

.0.96 HCl
(2S*), cis-1

A solution of intermediate 67 (1.18 mmol) and TFA (2.18 ml, 28.26 mmol) in DCM (10 ml) was stirred at room temperature for 3 hours. The mixture was poured into 10% aqueous K₂CO₃ solution and extracted with DCM. The organic layer was separated, washed with water, dried over MgSO₄, filtered and the solvent was evaporated to dryness. The residue was dissolved in diethyl ether (6 ml) and HCl 5N in iPrOH was added slowly, drop by drop to obtain a white precipitate. The solid was filtered off and dried under vacuum, as the product was a mixture of quinoline and quinolone (60/40). The residue was dissolved in THF (6 ml) and HCl 3N (6 ml) was added, and the mixture was stirred at 70° C. overnight. The reaction mixture was cooled to room temperature and ice-water was added. The solution was stirred for 15 minutes at 0° C., and the precipitate was filtered and dried under vacuum at 60° C., yielding 415 mg (61%) of compound 40, melting point 224° C., optical rotation: +48.62° (589 nm, c 0.3435 w/v %, DMF, 20° C.).

Example B27

Preparation of Compound 41

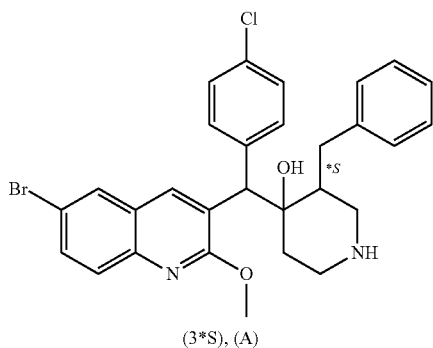 [SMILES: COc1nc2ccc(Br)cc2cc1C(c1ccc(Cl)cc1)C1(O)CCNCC1Cc1ccccc1]

(3*S), (A)

A solution of intermediate 71 (65 mg, 0.0997 mmol) in TFA (0.2 ml) and DCM (2 ml) was stirred at room temperature for 2 hours. The mixture was poured into 10% aqueous K₂CO₃ solution and extracted with DCM. The organic layer was separated, washed with water, dried over MgSO₄, filtered and the solvent was evaporated to dryness, yielding 40 mg (72.8%) of compound 41.

Example B28

Preparation of Compound 42

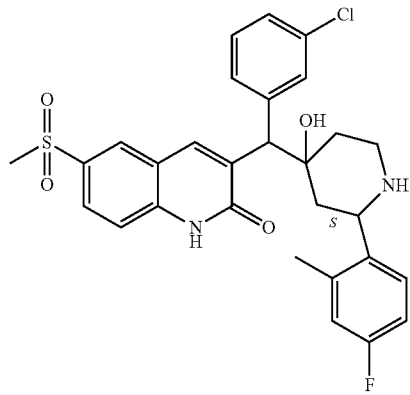

.0.77 HCl
(2S), cis-4

A solution of intermediate 80 (255 mg, 0.38 mmol) and HCl 3N (2.6 ml) in THF (2.6 ml) was stirred overnight at 70° C. The mixture was cooled to room temperature and poured into ice water. The solution was stirred 30 minutes and the precipitate was filtered, washed with water and dried under vacuum at 60° C. The residue was crystallized from DIPE, filtered and dried under vacuum at 60° C., yielding 211 mg (95.0%) of compound 42, melting point>250° C.

Example B29 a) Preparation of Compound 61

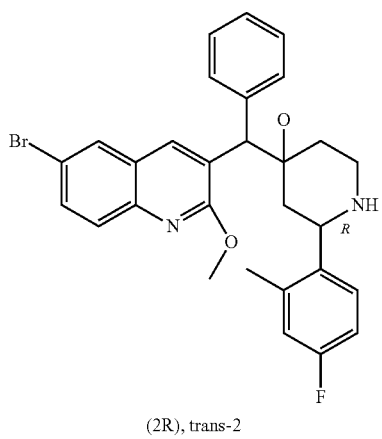

(2R), trans-2

Trifluoroacetic acid (1.5 ml) was added to a solution of intermediate 83 (0.514 g, 0.809 mmol) in DCM (5 ml). The reaction mixture was stirred at room temperature for 3 hours and basified with 10% aqueous K₂CO₃ solution. The organic layer was extracted with DCM, dried over MgSO₄, filtered and concentrated. A part (240 mg) of the residue (430 mg) was crystallized from DIPE and dried under vacuum at 60° C., yielding 161 mg of compound 61.

b) Preparation of Compound 43

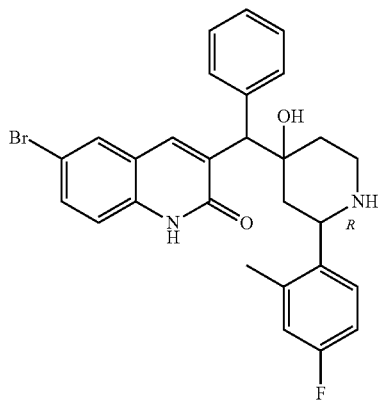

.0.84 HCl
(2R), trans-2

A solution of compound 61 (0.24 g, 0.448 mmol) and HCl 3N (2.5 ml) in THF (2.5 ml) was stirred overnight at 70° C. The mixture was cooled to room temperature and poured into ice water. The solution was stirred for 30 minutes and the precipitate was filtered, washed with water and dried under vacuum at 60° C. The residue was crystallized from DIPE, filtered and dried under vacuum at 60° C., yielding 215 mg (86.9%) of compound 43, melting point: >250° C.

Example B30

Preparation of Compounds 44, 45, 46 and 47

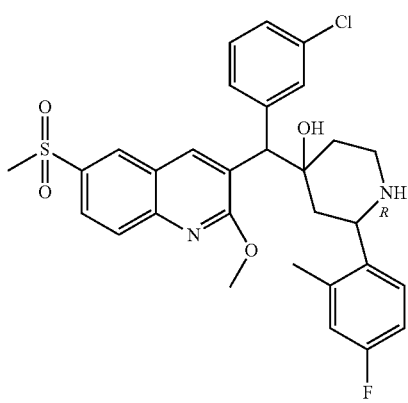

Compound 44 (2R), trans-1
Compound 45 (2R), trans-2
Compound 46 (2R), cis-3
Compound 47 (2R), cis-4

Trifluoroacetic acid (20 ml) was added to a solution of intermediate 87 (6.07 g, 9.07 mmol) in DCM (61 ml). The reaction mixture was stirred at room temperature for 3 hours and basified with 10% aqueous $K_2CO_3$ solution. The organic layer was extracted with DCM, dried over $MgSO_4$, filtered and concentrated. The residue (5.15 g) was purified by flash chromatography over silica gel (15-40 μm, 90 g, DCM/MeOH/NH$_4$OH: 97/3/0.1) The pure fractions were collected and evaporated to dryness. The residue (3.6 g) was purified by SFC on a Chiralpak AD-HTM column (5 μm, 20×250 mm) with a flow rate of 50 ml/min., the column being held at a temperature of 35° C. and a outlet pressure of 100 bars. The mobile phase is $CO_2$ 65% EtOH 17.5% iPrOH 17.5% and iPA 0.3% (in MeOH) in isocratic mode. The pure fractions were collected and evaporated to dryness, yielding respectively 1.52 g of compound 44, melting point: 148° C., optical rotation: +46.5° (589 nm, c 0.329 w/v %, DMF, 20° C.; 900 mg of compound 45, melting point: 160° C., optical rotation: −162.08° (589 nm, c 0.327 w/v %, DMF, 20° C.; 250 mg of fraction F3 and 180 mg of fraction F4. A part (125 mg) of fraction F3 was crystallized from DIPE and dried at 60° C. under vacuum, yielding 61 mg of compound 46, melting point: 145° C., optical rotation: +126.22° (589 nm, c 0.286 w/v %, DMF, 20° C.

A part (90 mg) of fraction F4 was crystallized from DIPE and dried at 60° C. under vacuum, yielding 51 mg of compound 47, melting point: 174° C., optical rotation: −141.92° (589 nm, c 0.291 w/v %, DMF, 20° C.

Example B31

Preparation of Compound 48

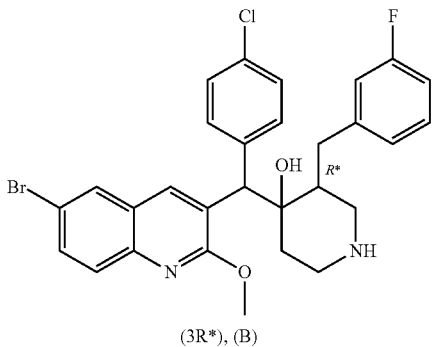 [SMILES: COc1nc2ccc(Br)cc2cc1C(c1ccc(Cl)cc1)C1(O)CCNCC1Cc1cccc(F)c1]

(3R*), (B)

A solution of intermediate 92 (1.1 g, 1.64 mmol) in TFA (3.5 ml) and DCM (11 ml) was stirred at room temperature for 4 hours. The mixture was poured into 10% aqueous $K_2CO_3$ solution and extracted with DCM. The organic layer was separated, washed with water, dried over $MgSO_4$, filtered and the solvent was evaporated to dryness. The residue (0.95 g) was crystallized from DIPE, filtered off and dried (vacuum, 60° C.), yielding 0.718 g of compound 48, melting point: 221° C.

Example B32

Preparation of Compound 49

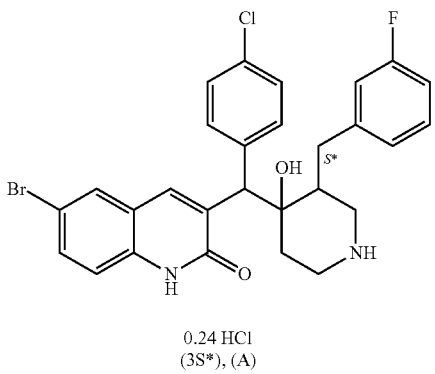 [SMILES: O=c1[nH]c2ccc(Br)cc2cc1C(c1ccc(Cl)cc1)C1(O)CCNCC1Cc1cccc(F)c1]

0.24 HCl
(3S*), (A)

A mixture of intermediate 94 (0.4 g, 0.597 mmol) in HCl 3N (4 ml) and THF (4 ml) was stirred at 60° C. overnight then cooled to room temperature. The mixture was poured into 10% aqueous $K_2CO_3$ solution and extracted with EtOAc. The organic layer was separated, washed with water then brine, dried ($MgSO_4$), filtered and evaporated to dryness. The residue was crystallized from DIPE, yielding 0.27 g (80%) of compound 49, melting point: 183° C.

Example B33

Preparation of Compound 50

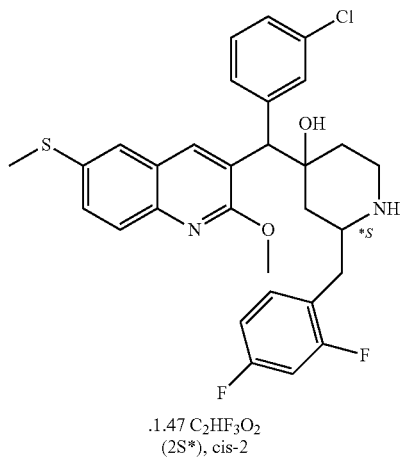 [SMILES: COc1nc2ccc(SC)cc2cc1C(c1cccc(Cl)c1)C1(O)CCNC(Cc2ccc(F)cc2F)C1]

.1.47 C₂HF₃O₂
(2S*), cis-2

At 0° C., TFA (0.3 ml) was added dropwise to a mixture of intermediate 103 (0.1 g, 0.153 mmol) in DCM (10 ml). The mixture was stirred at room temperature for 12 hours. The solvent was evaporated. The residue was taken up in DIPE and the precipitate was filtered off, yielding 102 mg (84.1%) of compound 50, melting point: 208° C., optical rotation: +109.94° (589 nm, c 0.322 w/v %, DMF, 20° C.).

Example B34

Preparation of Compound 51

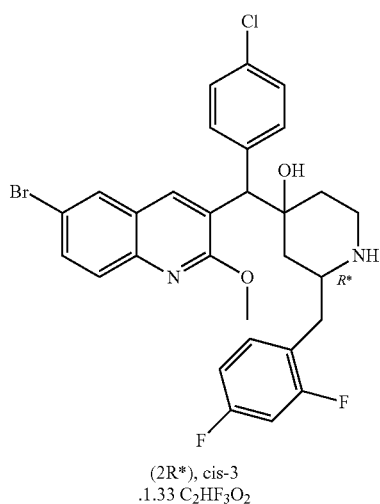 [SMILES: COc1nc2ccc(Br)cc2cc1C(c1ccc(Cl)cc1)C1(O)CCNC(Cc2ccc(F)cc2F)C1]

(2R*), cis-3
.1.33 C₂HF₃O₂

At 0° C., TFA (1 ml) was added dropwise to a mixture of intermediate 106 (0.31 g, 0.451 mmol) in DCM (15 ml). The mixture was stirred at room temperature for 12 hours. The solvent was evaporated. The residue was taken up in DIPE and the precipitate was filtered off, air-dried, yielding 290 mg (87%) of compound 51, melting point 176° C., optical rotation: −101.43° (589 nm, c 0.28 w/v %, DMF, 20° C.).

Example B35

Preparation of Compounds 52, 53, 54 and 55

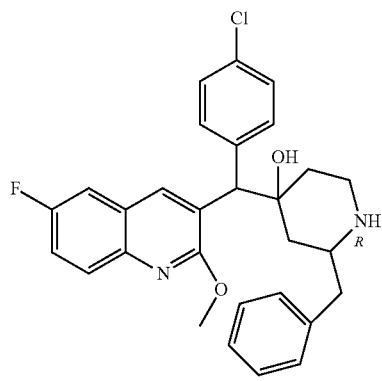

Compound 52 (2R), cis-1
Compound 53 (2R), cis-2
Compound 54 0.6 C₄H₄O₄, (2R), trans-3
Compound 55 1.1 C₄H₄O₄, (2R), trans-4

Trifluoroacetic acid (4 ml) was added to a solution of intermediate 108 (1.3 g, 2.2 mmol) in DCM (13 ml). The reaction mixture was stirred at room temperature for 3 hours and basified with 10% aqueous $K_2CO_3$ solution. The organic layer was extracted with DCM, dried over $MgSO_4$, filtered and concentrated. The residue (0.95 g.) was purified by high-performance liquid chromatography (Chiralpak AD-H, 5 μm, 250×20 mm), mobile phase: iPA 0.3%; $CO_2$ 60% EtOH 20% iPrOH 20%, yielding respectively 263 mg of fraction F1 and 550 mg of fraction F2.

Fraction F2 was purified by high-performance liquid chromatography (Chiralpak AD-H, 5 μm, 250×20 mm), mobile phase: iPA 0.3%; $CO_2$ 70% EtOH15% iPrOH 15%, yielding 49 mg of fraction F2/1, 273 mg of fraction F2/2, 55 mg of fraction F2/3 and 98 mg of fraction F2/4.

A part of F1 (197 mg) of was crystallized from DIPE, filtered and dried under vacuum at 60° C., yielding 97 mg of compound 52, melting point: 176° C.

A part of F2/2 (199 mg) was crystallized from DIPE, filtered and dried under vacuum at 60° C., yielding 167 mg of compound 53, melting point: 102° C.

Fumaric acid (0.013 g, 0.112 mmol) was added portionwise to a solution of pure product F2/3 (0.055 g, 0.112 mmol) in acetone (1 ml). The mixture was stirred overnight at room temperature. The precipitate was filtered off, washed with acetone, and dried under vacuum at 60° C., yielding 36 mg of compound 54, melting point: 209° C.

Fumaric acid (0.023 g, 0.199 mmol) was added portionwise to a solution of pure product F2/4 (0.098 g, 0.199 mmol) in acetone (1 ml). The mixture was stirred overnight at room temperature. The precipitate was filtered off, washed with acetone, and dried under vacuum at 60° C., yielding 63 mg of compound 55, melting point: 120° C.

Example B36

Preparation of Compounds 56, 57, 58 and 59

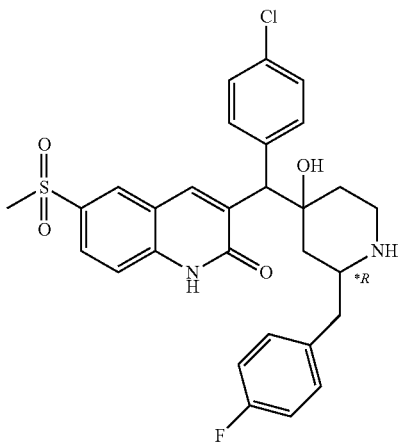

Compound 56 (2R*), cis-1
Compound 57 (2R*), cis-2
Compound 58 (2R*), trans-3
Compound 59 (2R*), trans-4

A solution of intermediate 110 (1.15 g, 1.718 mmol) and HCl 3N (HCl 3N, 5 ml) in THF (5 ml) was stirred overnight at 70° C. The mixture was cooled to room temperature, DCM and $K_2CO_3$ powder were added to obtain a basic pH. The organic phase was collected, dried with $MgSO_4$ and solvent was evaporated. A part of the residue (990 mg) was precipitated in DCM. The residue was purified by normal phase chromatography on irregular SiOH 15-40 μm 300 g MERCK; mobile phase ($NH_4OH$ 1%, 90% DCM, 10% MeOH) to give respectively fraction F1 (160 mg) then F2 (165 mg). The filtrate was purified by Normal phase on Irregular SiOH (15-40 μm, 300 g MERCK); mobile phase ($NH_4OH$ 1%, 90% DCM, 10% MeOH) to give respectively fraction F3 (90 mg) then fraction F4 (60 mg).

Fractions F1, F2, F3 and F4 were crystallised in $CH_3CN$/DiPE, yielding respectively 133 mg of compound 56, melting point: 140° C., optical rotation: −65.4° (589 nm, c 0.367 w/v %, DMF, 20° C.); 116 mg of compound 57, melting point: 100° C., optical rotation: +121.07° (589 nm, c 0.261 w/v %, DMF, 20° C.); 46 mg of compound 58, melting point: 192° C., optical rotation: +59.23° (589 nm, c 0.287 w/v %, DMF, 20° C.); and 49 mg of compound 59, melting point: 182° C., optical rotation: −70.18° (589 nm, c 0.285 w/v %, DMF, 20° C.

Example B37

Preparation of Compound 60

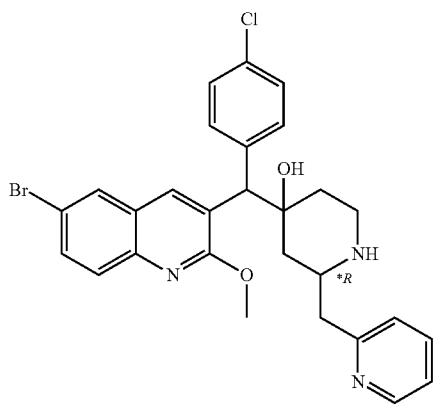

(2R*), cis-1

A solution of intermediate 111 (0.29 g, 0.444 mmol) in TFA (0.9 ml) and DCM (5 ml) was stirred at room temperature for 2 hours. The mixture was poured into 10% aqueous $K_2CO_3$ solution and extracted with DCM. The organic layer was separated, washed with water, dried over $MgSO_4$, filtered and the solvent was evaporated to dryness. The residue (0.25 g) was crystallized from DIPE to give 0.11 g (44.8%) of compound 60, melting point: 161° C., optical rotation: +245.07° (589 nm, c 0.2685 w/v %, DMF, 20° C.).

Example B38

Preparation of Compound 62

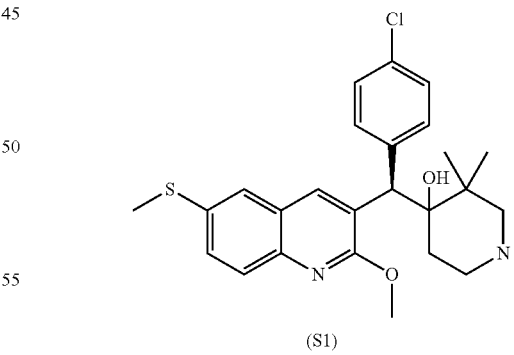

(S1)

A solution of intermediate 125 (0.2 g, 0.359 mmol) in TFA (0.6 ml) and DCM (5 ml) was stirred at room temperature for 2 hours. The mixture was poured into 10% aqueous $K_2CO_3$ solution and extracted with DCM. The organic layer was separated, washed with water, dried over $MgSO_4$, filtered and the solvent was evaporated to dryness, yielding 0.088 g (53.6%) of compound 62.

Example B39

Preparation of Compounds 63 and 64

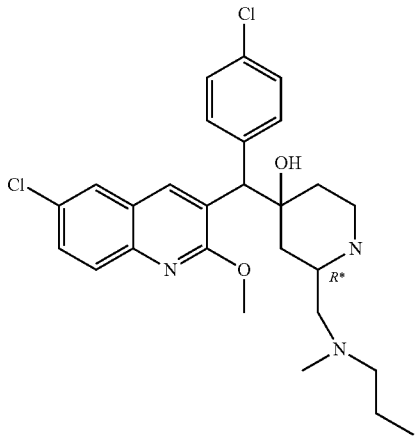

Compound 63 (2R*), cis-1
Compound 64 (2R*), cis-2, .1.1 C₄H₄O₄

TFA (1.5 ml) was added to a mixture of intermediate 127 (0.813 mmol) in DCM at 0° C. then the reaction mixture was stirred overnight at room temperature. The mixture was poured into 10% aqueous K$_2$CO$_3$ solution and extracted with DCM. The organic layer was separated, washed with water, dried over MgSO$_4$, filtered and the solvent was evaporated to dryness. The residue (0.45 g) was purified by flash chromatography over silica gel (15-40 µm, 30 g, from DCM to DCM/CH$_3$OH/NH$_4$OH: 92/8/0.5) The pure fractions were collected and evaporated to dryness. The residue (0.3 g) was purified by chiral SFC on Chiralpak AD-H (5 µm, 250×20 mm), mobile phase, 0.3% iPA, 60% CO$_2$, 40% EtOH. Two fractions were collected and the solvent was evaporated, yielding 98 mg of fraction 1 and 120 mg of fraction 2.

Fraction 1 was crystallized from DIPE to give 34 mg of compound 63.

Fraction 2 was dissolved in 2-propanone and converted into the (E)-2-butenedioic acid salt (1:2) with a solution of (E)-2-butenedioic acid in 2-propanone/EtOH (1/1) to give compound 64.

Example B40

Preparation of Compounds 65 and 66

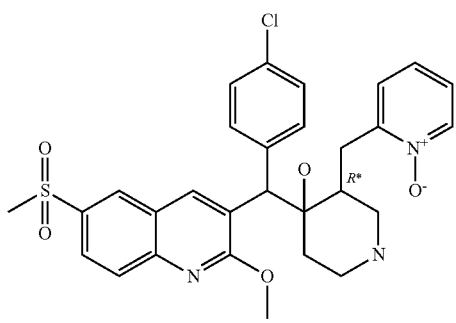

Compound 65 (3R*), (A)
Compound 66 (3R*), (B)

Trifluoroacetic acid (2.4 ml) was added to a solution of intermediate 132 (0.805 g, 1.2 mmol) in DCM (8 ml). The reaction mixture was stirred at room temperature for 3 hours and basified with 10% aqueous K$_2$CO$_3$ solution. The organic layer was extracted with DCM, dried over MgSO$_4$, filtered and concentrated. The residue was crystallized from DIPE and dried under vacuum at 60° C.

The residue (689 mg) was purified by Normal phase on Cartridge (15-40 µm, 30 g); mobile phase, 0.5% NH$_4$OH, 95% DCM, 5% MeOH. Two fractions were collected and the solvent was evaporated, yielding 170 mg of fraction 1 and 240 mg of fraction 2.

Fraction 1 was crystallized from DIPE, filtered and dried under vacuum at 60° C., yielding 138 mg of compound 65.

Fraction 2 was crystallized from DIPE, filtered and dried under vacuum at 60° C., yielding 164 mg of compound 66.

Example B41

Preparation of Compound 67

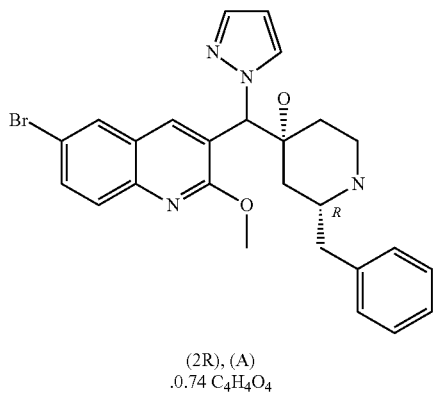

(2R), (A)
.0.74 C₄H₄O₄

(0.11 g, 0.17 mmol) in TFA (0.3 ml) and DCM (1 ml) were stirred at room temperature for 4 hours. The mixture was basified with a solution of 10% aqueous K$_2$CO$_3$ solution. The aqueous layer was extracted with DCM. The combined organic layers were washed with a 10% aqueous K$_2$CO$_3$ solution, dried over MgSO$_4$, filtered and concentrated under reduced pressure. The residue (0.09 g) was diluted in acetone (0.9 ml). Fumaric acid (20 mg) in EtOH/acetone 1/1 (0.6 ml) was added. The precipitate was filtered off and dried under reduced pressure (60° C.), yielding 71 mg (68.6%) of compound 67.

The following final compounds were prepared according to the methods described above. The compounds which are described in the Examples in Section B above are indicated with an asterisk against the relevant B example; the other compounds are prepared in an analogous manner to the relevant specified B example. The chromatographic conditions used for the preparation of the respective compounds, either in the final stage or in an earlier stage, are indicated below the relevant formula. Where two or more chromatographic conditions are recited then these are performed sequentially in the order given.

TABLE 1

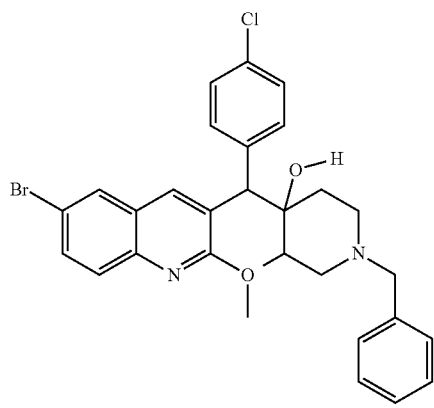 [SMILES: COc1nc2ccc(Br)cc2cc1C(c1ccc(Cl)cc1)C1(O)CCN(Cc2ccccc2)CC1C]

SFC (CO₂/MeOH/iPA 90/10/0.5)
Co. 25; fumarate; (A); Ex. B15*
Co. 26; fumarate; (B); Ex. B15*

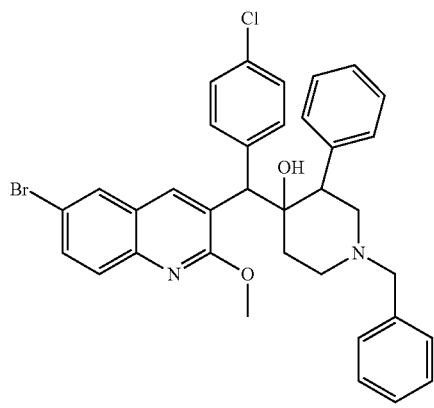 [SMILES: COc1nc2ccc(Br)cc2cc1C(c1ccc(Cl)cc1)C1(O)CCN(Cc2ccccc2)CC1c1ccccc1]

Silica gel, DCM/MeOH 98/2; 15-40 µm, then
MeOH/NH₄HCO₃ 0.5%, 88/12; 5 µm
Co. 68; (B); Ex. B31
Co. 69; (A); Ex. B31

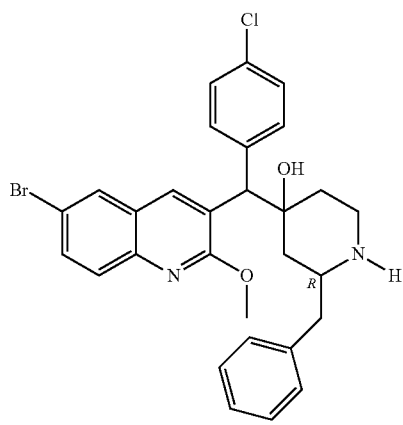

Silica gel, 15-40 µm, Cyclo/DCM: 30/70
Co. 70; (2R), cis-1; Ex. B18
SFC (Chiralpak AD-H, CO₂/iPrOH/iPA:
70/30/0.3)
Co. 31; (2R), cis-4; Ex. B18*
Co. 71; (2R), trans-3; Ex. B19
Co. 32; (2R), trans-2; Ex. B19*

TABLE 1-continued

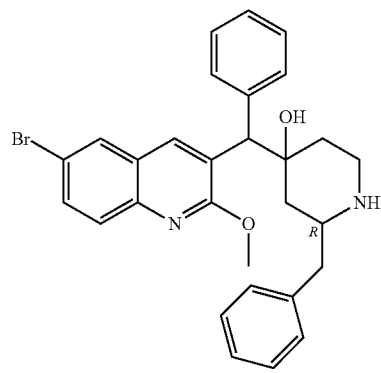

SFC (Chiralpak AD-H, CO₂/EtOH/iPA:
80/20/0.3)
Co. 72; (2R), cis-1; Ex. B18
Co. 73; (2R), trans-2; Ex. B19
Co. 74; (2R), cis-3; Ex. B18

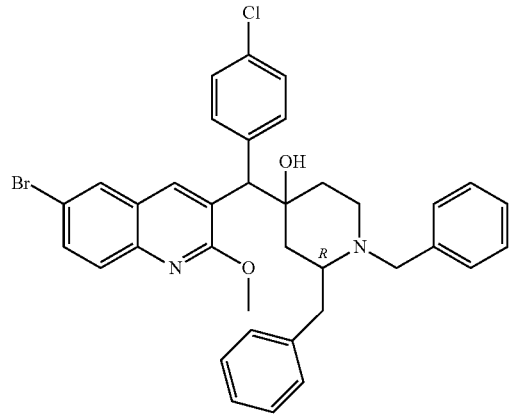

SFC (Chiralpak AD-H, CO₂/iPrOH/iPA:
70/30/0.3)
Co. 75; (2R), cis-4; Ex. B14
SiO₂ 15-40 µm, Cyclo/DCM: 30/70
Co. 76; fumarate; (2R), cis-1; Ex. B14

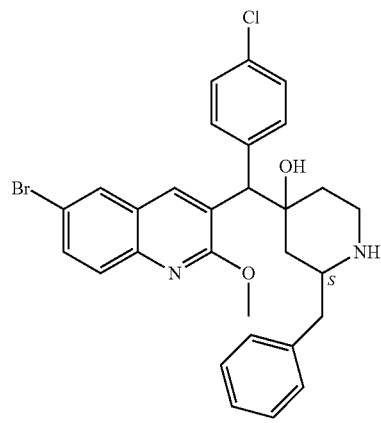

Silica gel, 15-40 µm, DCM: 100
Co. 77; fumarate; (2S), cis-1; Ex. B20
SFC (Chiralpak AD-H, CO₂/MeOH/iPrO/iPA:
70/15/15/0.3)
Co. 78; (2S), trans-2; Ex. B18
Co. 79; (2S), trans-3; Ex. B18
Co. 33; (2S), cis-4; Ex. B20*

TABLE 1-continued
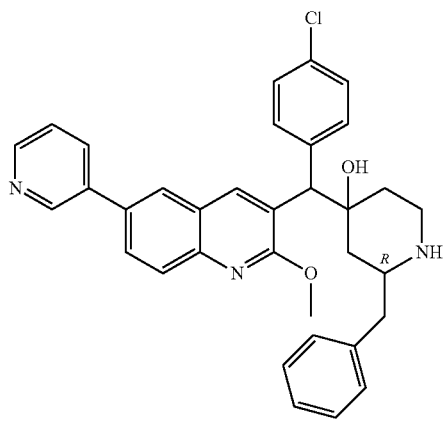
Silica gel, SI60, 15-40 μm, 25 g, DCM/MeOH
90/10
Co. 80; (2R), cis-1; Ex. B9
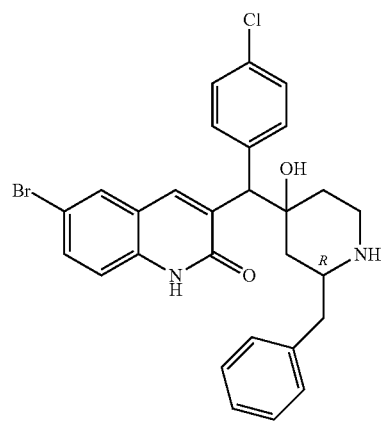
Silica gel, SI60, 15-40 μm, 25 g, DCM/MeOH
85/15
Co. 81; (2R), cis-1; Ex. B26
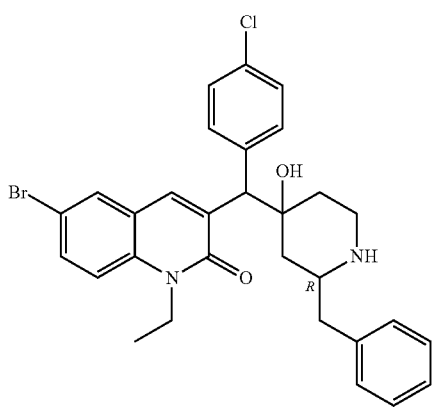
Sunfire C18-5 μm-19 × 150 mm;
MeOH/NH₄HCO₃ 85/15
Co. 82; (2R), cis-2; Ex. B2
Co. 83; (2R), cis-1; Ex. B2
TABLE 1-continued
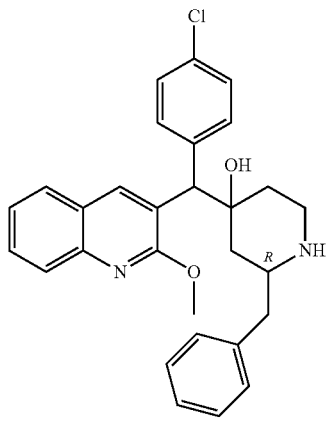
Chromasil 10 μm, 65 g; DCM/MeOH/NH₄OH
96/4/0.1
Co. 19; (2R), cis-1; Ex. B12*
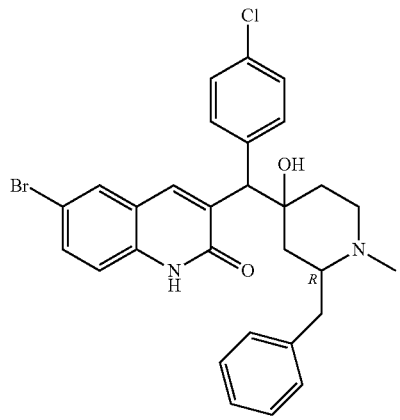
Silica gel (Merck 200 g, SiO₂ 15-40 μm,
Cyclo/DCM: 30/70 to 10/90).
Co. 84; (2R), cis-1; Ex. B2
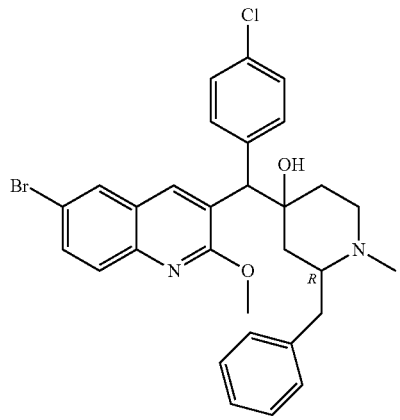
Silica gel (Merck 200 g, SiO₂ 15-40 μm,
Cyclo/DCM: 30/70 to 10/90).
Co. 17; fumarate; (2R), cis-1; Ex. B11*
Co. 18; ; AAA; (2R), cis-1; Ex. B11*

TABLE 1-continued

Silica gel, 15-40 μm, DCM 100
Co. 35; fumarate; (2R), cis-1; Ex. B22*
Co. 34; (2R), cis-4; Ex. B21*

Silica gel, 15-40 μm, DCM 100
Co. 85; hydrochloride; (2R), cis-1; Ex. B2
Co. 86; hydrochloride; (2R), cis-4; Ex. B2

Silica gel, Cyclo/EtOAc 80/20 and then SFC
Chiralpak AD, CO₂ 50%, EtOH 50%, iPA
0.3%
Co. 87; (2R), cis-3; Ex. B20
Co. 88; fumarate; (2R), trans-2; Ex. B19
Co. 89; (2R), cis-1; Ex. B20

Silica gel, 15-40 μm, DCM 100
Co. 36; (2R), cis-1; Ex. B22*
Co. 15; (2R), cis-4; Ex. B9*

Silica gel, 15-40 μm, Cyclo/EtOAc: 90/10
Co. 90; fumarate; (2R), cis-1; Ex. B33
SFC (Chiralpack AD-H, CO₂/EtOH/iPA: 65/35/0.3)
Co. 91; (2R), cis-2; Ex. B33
Co. 92; (2R), trans-3; Ex. B19
SiO₂, 15-40 μm, Cyclo/EtOAc: 90/10
Co. 93; fumarate; (2R), trans-4; Ex. B19

Silica gel, 20-45 μm, 450 g; Cyclo 90% EtOAc
10% then SFC Chiralpak AD-H, 5 μm,
250 × 20 mm iPA 0.3%; CO₂ 70% iPrOH 30%
Co. 37; (2R), trans-3; Ex. B23*
Co. 94; fumarate; (2R), cis-4; Ex. B20
SiOH 20-45 μm, 450 g; Cyclo 90% EtOAc 10%
then Chiralpak IC 5 μm, 250 × 20 mm, iPA 0.3%;
CO₂ 60% iPrOH 40%
Co. 95; fumarate; (2R), cis-2; Ex. B18
Co. 96; (2R), trans-1; Ex. B23

TABLE 1-continued

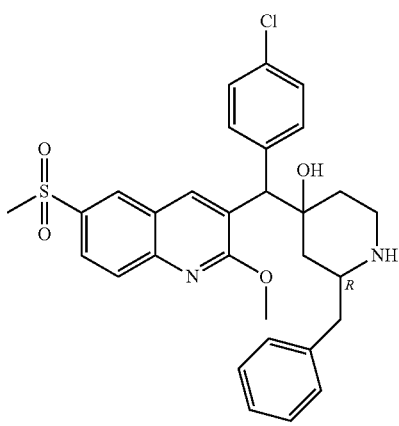

Silica gel, 20-45 µm 450 g; Cyclo 90% EtOAc
10% then Chiralpak IC, 5 µm, 250 × 20 mm, iPA
0.3%; CO$_2$ 60% iPrOH 40%
Co. 97; (2R), cis-1; Ex. B24
SFC (Chiralpak AD-H 5 µm, 250 × 20 mm)
Mobile phase (0.3% iPA, 65% CO$_2$, 35%
EtOH)
SFC (Chiralpak AD-H 5 µm, 250 × 20 mm, 0.3%
iPA, 65% CO$_2$, 35% EtOH)
Co. 38; (2R), cis-3; Ex. B24*

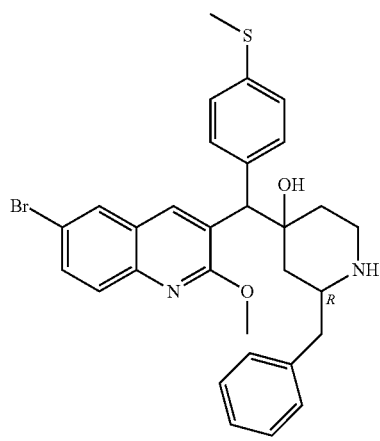

SFC (Chiralpak AD-H, CO$_2$/EtOH/iPA:
70/30/0.3)
Co. 98; (2R), cis-2; Ex. B18
Co. 99; (2R), cis-3; Ex. B18
Co. 100; (2R), trans-4; Ex. B19
Co. 101; (2R), trans-1; Ex. B19

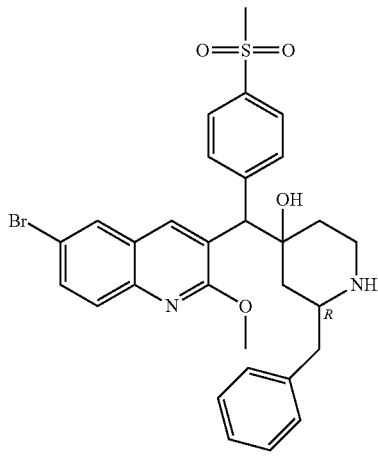

SFC (Chiralpak AD-H, CO$_2$/EtOH/iPA:
70/30/0.3)
Co. 102; (2R), cis-2; Ex. B18
Co. 103; (2R), cis-3; Ex. B18

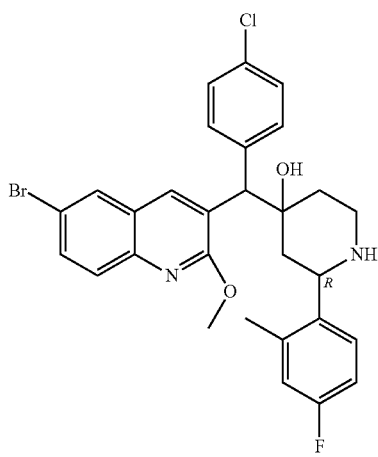

Silica gel, 15-40 µm, Cyclo/EtOAc, 90/10
Co. 104; (2R), trans-1; Ex. B1
SFC (Chiralpak AD, CO$_2$/iPOH/MeOH/iPA
75/12.5/12.5/0.3)
Co. 105; (2R), trans-3; Ex. B1

TABLE 1-continued

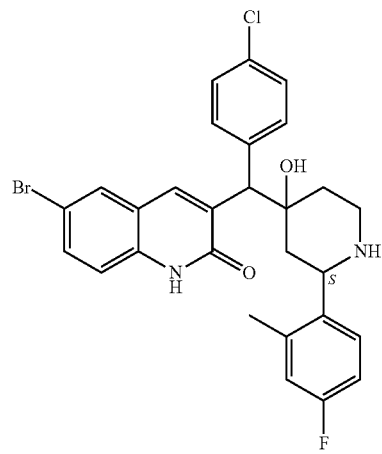

Silica gel, 15-40 µm, Cyclo/EtOAc, 90/10,
Co. 106; hydrochloride; (2S), trans-1;
Ex. B4
SFC (Chiralpak AD, CO₂/iPOH/MeOH/iPA
85/7.5/7.5/0.3)
Co. 107; hydrochloride; (2S), cis-4; Ex. B4
Co 7; hydrochloride; (2S), cis-2; Ex. B4*
Co. 108; fumarate; (2S), trans-3; Ex. B4

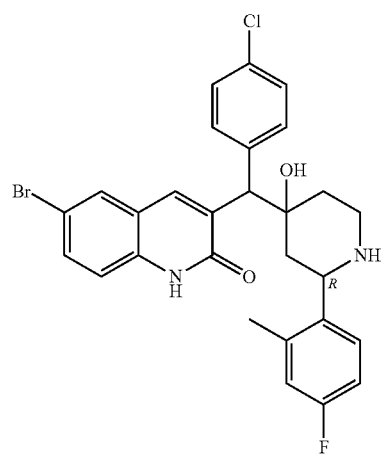

SFC (Chiralpak AD, CO₂/iPOH/MeOH/iPA
75/12.5/12.5/0.3)
Co. 109; hydrochloride; (2R), cis-4; Ex. B4
Co. 110; hydrochloride; (2R), cis-2; Ex. B4

TABLE 1-continued

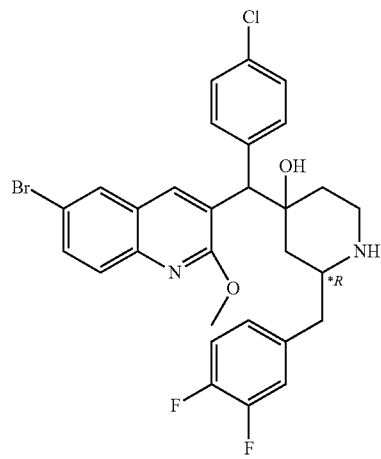

Silica gel, Cyclo/EtOAc, 80/20, 15-40 µm, 450 g
Co. 111; (2R*), trans-3; Ex. B25
SFC (Chiralpak AD-H: MeOH/CO₂/iPA,
30/70/0.3)
Co. 39; (2R*), cis-2; Ex. B25*
Co. 112; (2R*), cis-1; Ex. B25

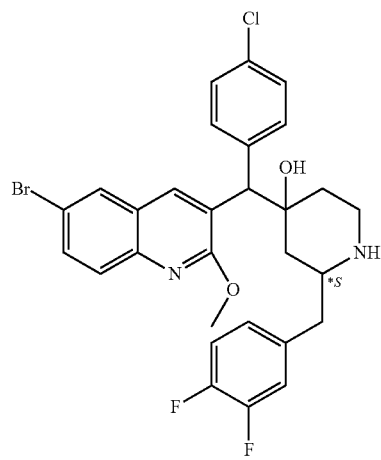

Silica gel, B-6720, Cyclo/EtOAc, 95/5, 15-40
µm, 450 g
Co. 113; fumarate; (2S*), cis-2; Ex. B25

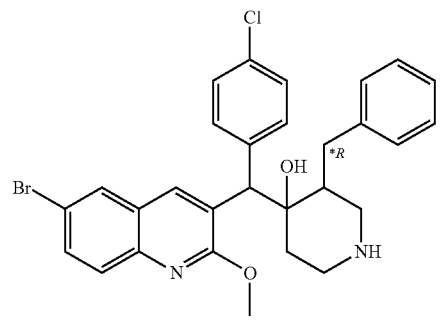

Silica gel, B6778, Kromasil 10 µm,
Cyclo/EtOAc: 90/10
Co. 114; (3R*), (A); Ex. B27

TABLE 1-continued

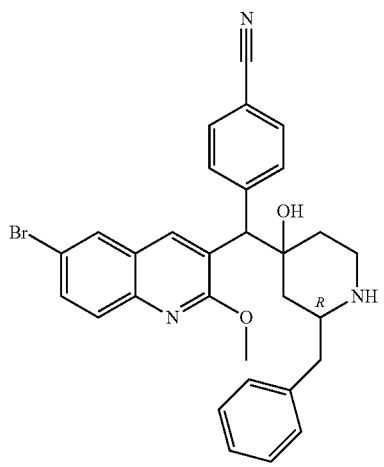

Silica gel, 15-40 µm, Cyclo/EtOAc: 80/20
Co. 115; fumarate; (2R), cis-2; Ex. B18
Co. 116; (2R), cis-1; Ex. B18

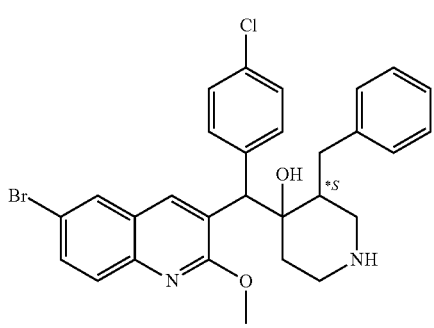

Kromasil, 10 µm, Cyclo/EtOAc: 90/10
Co. 41; (3S*), (A); Ex. B27*
Co. 117; mixture; Ex. B27

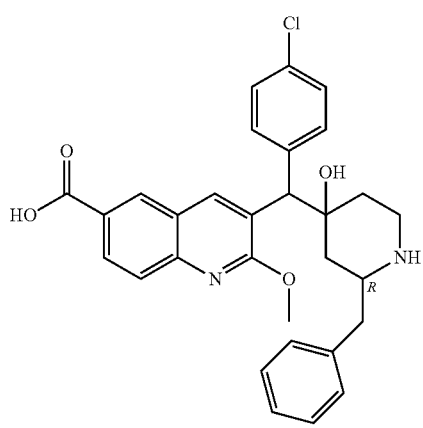

Flash Silica gel, B6927, 20-45 µm, 450 g,
Cyclo/EtOAc 90/10
Co. 118; trifluoroacetate; (2R), cis-1;
Ex. B18

TABLE 1-continued

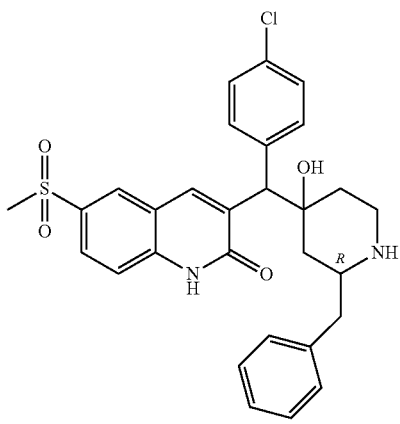

Silica gel, 15-40 µm, 450 g, Cyclo/EtOAc 90/10
Co. 119; fumarate; (2R), cis-1; Ex. B28
SFC Chiralpak AD-H (5 µm 20 × 250 mm)
CO$_2$ 60% iPrOH 40% and iPA 0.3%
Co. 120; (2R), cis-4; Ex. B28

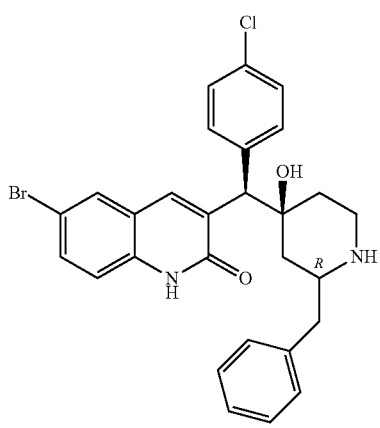

Silica gel, 15-40 µm, 450 g, Cyclo/EtOAc 90/10
then SFC Chiralpak AD-H (5 µm 20 × 250 mm),
CO$_2$ 60% iPrOH 40% and iPA 0.3%
Co. 121; hydrochloride; (2R), trans-2;
Ex. B26
Co. 122; hydrochloride; (2R), cis-4; Ex. B26

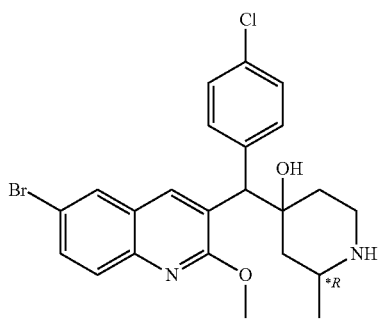

SFC Chiralpak AD-H (5 µm 20 × 250 mm),
CO$_2$ 50% iPrOH 50% and iPA 0.3%
Co. 123; (2R*), trans-1; Ex. B6
Co. 11; (2R*), cis-2; Ex. B6*

TABLE 1-continued

SFC Chiralpak AD-H (5 μm 20 × 250 mm), CO2 50% iPrOH 50% and iPA 0.3%
Co. 124; (2S*), cis-1; Ex. B6
Co. 125; (2S*), trans-2; Ex. B6

SFC Chiralpak AD-HTM (5 μm, 20 × 250 mm) CO2 60% EtOH 40% and iPA 0.3% (in MeOH)
Co. 126; hydrochloride; (2S*), trans-2; Ex. B26
Co. 127; hydrochloride; (2S*), trans-3; Ex. B26
Cyclo/EtOAc, 95/5, 15-40 μm
Co. 40; hydrochloride; (2S*), cis-1; Ex. B26*

SFC Chiralpak AD-H (5 μm, 20 × 250 mm), CO2 60% iPrOH 40% and iPA 0.3% (in MeOH) in isocratic mode
Co. 128; hydrochloride; (2R), trans-3; Ex. B2

SFC Chiralpak AD-H (5 μm 20 × 250 mm), CO2 50% iPrOH 50% and iPA 0.3%, then SFC (B6817), Chiralpak AD-H (5 μm, 20 × 250 mm), CO2 50% iPrOH 50% and iPA 0.3% (in MeOH) in isocratic mode.
Co. 129; hydrochloride; (2R*), trans-1; Ex. B3
Co. 130; hydrochloride; (2R*), cis-2; Ex. B3

SFC Chiralpak AD-H (5 μm 20 × 250 mm), CO2 50% iPrOH 50% and iPA 0.3%, then SFC (B6817), Chiralpak AD-H (5 μm, 20 × 250 mm), CO2 50% iPrOH 50% and iPA 0.3% (in MeOH) in isocratic mode.
Co. 131; hydrochloride; (2S*), cis-1; Ex. B3
Co. 132; hydrochloride; (2S*), trans-2; Ex. B3

Silica gel, 15-40 μm, 450 g, Cyclo/EtOAc: 90/10 then Kromasil 10 μm, 60 g, DCM/Cyclo: 50/50
Co. 133; hydrochloride; (2R*), cis-1; Ex. B26
Co. 134; hydrochloride; (2R*), cis-2; Ex. B26

TABLE 1-continued

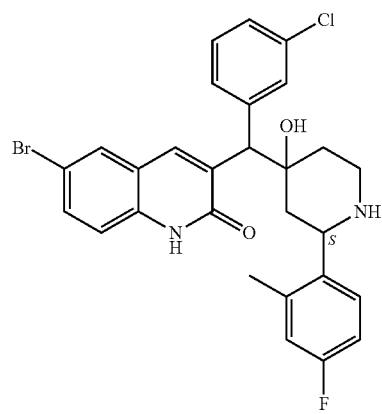

SFC Chiralpak AD-H (5 μm, 20 × 250 mm), CO$_2$
75% EtOH 25% and iPA 0.3%
Co. 135; hydrochloride; (2S), cis-4; Ex. B4
Co. 136; hydrochloride; (2S), trans-3; Ex. B4
Co. 137; hydrochloride; (2S), cis-2; Ex. B4
Cyclo/EtOAc 100:0 to Cyclo/EtOAc 70:30
Co. 138; hydrochloride; (2S), trans-1; Ex. B4

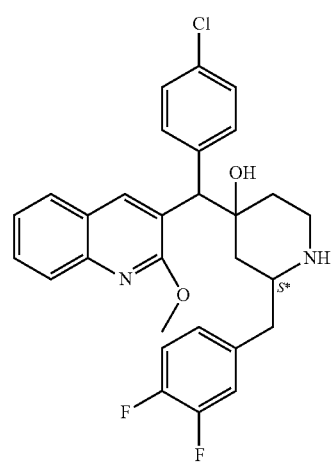

Silica gel, Cyclo/EtOAc, 95/5, 15-40 μm
Co. 139; fumarate; (2S*), cis-1; Ex. B34
SFC Chiralpak AD-H (5 μm, 20 × 250 mm),
CO$_2$ 60% EtOH 40% and iPA 0.3% (in MeOH)
Co. 140; (2S*), cis-4; Ex. B34

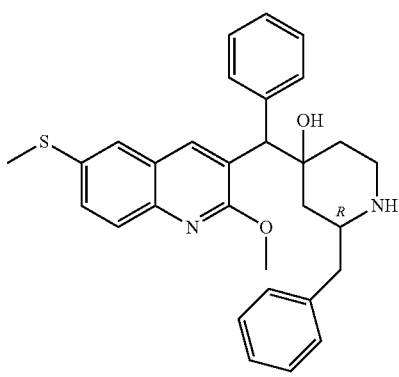

Silica gel, 15-40 μm, 90 g, DCM/EtOAc 97/3
Co. 141; fumarate; (2R), cis-1; Ex. B24
SFC Chiralpak AD-H (5 μm, 21 × 250 mm), CO$_2$
80% MeOH 20% and iPA 0.3%
Co. 142; (2R), cis-4; Ex. B24

TABLE 1-continued

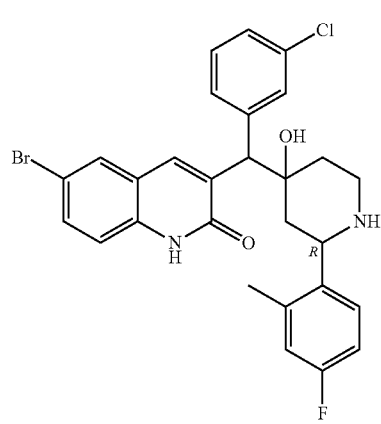

SFC Chiralpak AD-H (5 μm, 20 × 250 mm),
CO$_2$ 65% iPrOH 35% and iPA 0.3%
Co. 143; hydrochloride; (2R), cis-4;
Ex. B4
Co. 144; hydrochloride; (2R), cis-3;
Ex. B4
Co. 145; hydrochloride; (2R), trans-2;
Ex. B4
Kromasil, 10 μm, 15-40 μm, 90 g,
DCM/MeOH/NH$_4$OH: 95/5/0.1
Co. 146; hydrochloride; (2R), trans-1;
Ex. B4

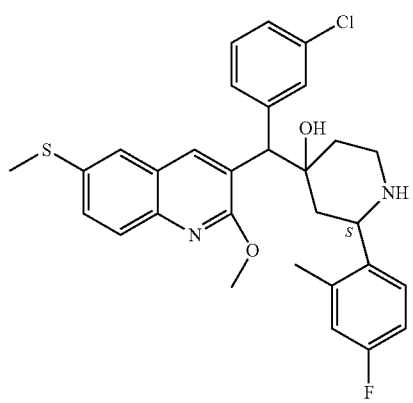

SFC Chiralpak AD-H (5 μm, 21 × 250 mm), CO$_2$
85% iPrOH 15% and iPA 0.3%
Co. 147; (2S), trans-2; Ex. B1
Silica gel, 15-40 μm, 450 g, Cyclo/EtOAc: 80/20
Co. 148; (2S), trans-1; Ex. B1

TABLE 1-continued

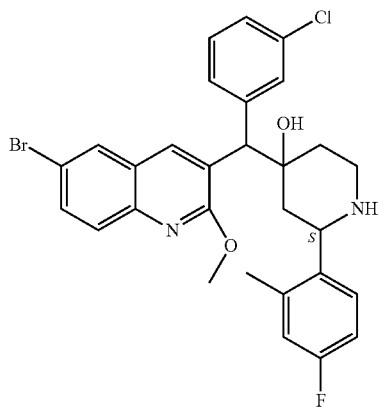

SFC Chiralpak AD-H (5 μm, 20 × 250 mm),
CO$_2$ 75% EtOH 25% and iPA 0.3%
Co. 149; fumarate; (2S)cis-4; Ex. B1
Co. 150; fumarate; (2S), trans-3; Ex. B1
Co. 151; fumarate; (2S), cis-2; Ex. B1
Silica gel, Cyclo/EtOAc 100:0 to Cyclo/EtOAc 70:30
Co. 152; fumarate; (2S), trans-1; Ex. B1

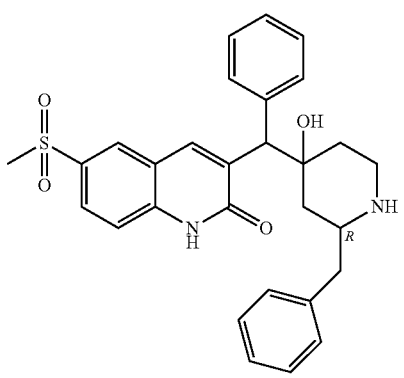

Silica gel, 15-40 μm, 90 g, DCM/EtOAc 97/3
Co. 153; (2R), cis-1; Ex. B36
SFC Chiralpak AD-H (5 μm 21 × 250 mm), CO$_2$
80% MeOH 20% iPA 0.3% (in MeOH)
Co. 154; (2R), trans-2; Ex. B36
Co. 155; (2R), trans-3; Ex. B36
Co. 156; (2R), cis-4; Ex. B36

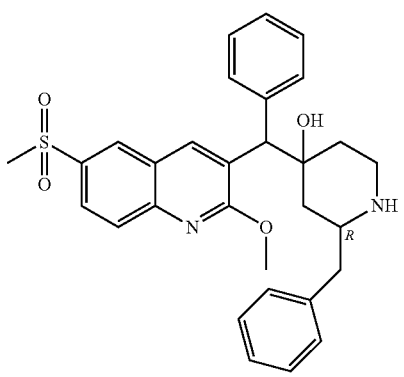

Silica gel, 15-40 μm, 90 g, DCM/EtOAc 97/3
Co. 157; (2R), cis-1; Ex. B24
SFC Chiralpak AD-H (5 μm, 21 × 250 mm),
CO$_2$ 80% MeOH 20% iPA 0.3% (in MeOH)
Co. 158; (2R), cis-4; Ex. B24

TABLE 1-continued

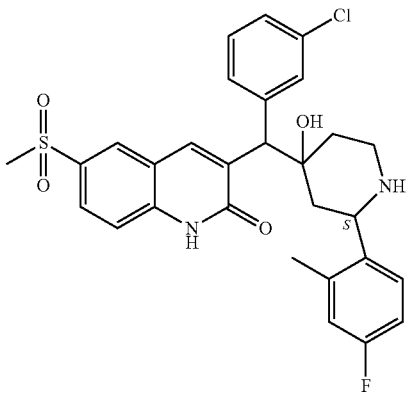

SFC Chiralpak AD-H (5 μm 21 × 250 mm), CO$_2$
85% iPrOH 15% and iPA 0.3% (in MeOH)
Co. 159; hydrochloride; (2S), cis-3; Ex. B28
Co. 42; hydrochloride; (2S), cis-4; Ex. B28*

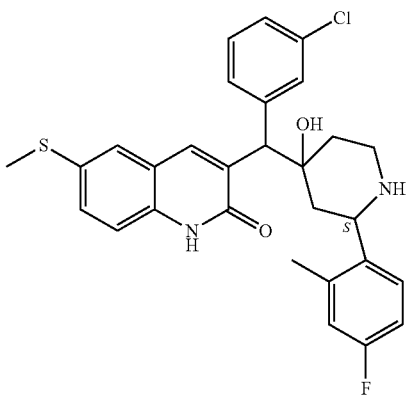

SFC Chiralpak AD-H (5 μm, 21 × 250 mm),
CO$_2$ 85% iPrOH 15% and iPA 0.3% (in MeOH)
Co. 160; hydrochloride; (2S), trans-2; Ex. B28
Co. 161; hydrochloride; (2S), cis-3; Ex. B28
Silica gel, 15-40 μm, 450 g, Cyclo/EtOAc: 80/20
Co. 162; hydrochloride; (2S), trans-1; Ex. B28

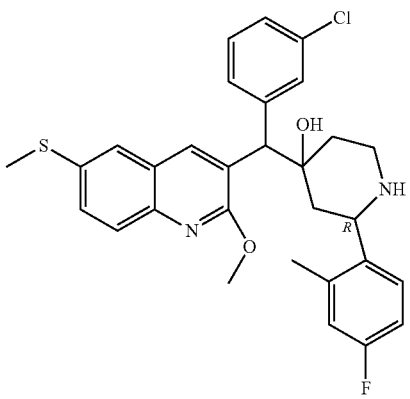

SFC Chiralpak AD-H (5 μm, 20 × 250 mm), CO$_2$
70% iPrOH 15%, MeOH 15% and iPA 0.3% (in MeOH)
Co. 163; (2R), trans-1; Ex. B1
Co. 164; fumarate; (2R), cis-3; Ex. B1
Co. 165; fumarate; (2R), cis-4; Ex. B1
Co. 166; fumarate; (2R), trans-2; Ex. B1

TABLE 1-continued

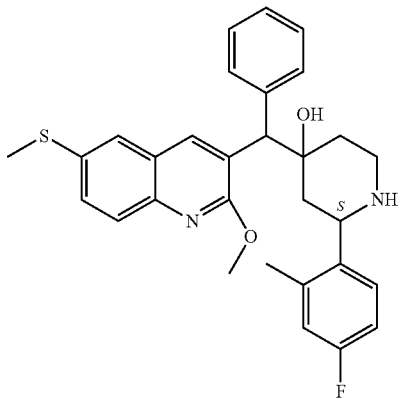

SFC Chiralpak AD-H (5 µm, 20 × 250 mm),
CO$_2$ 65% EtOH 17.5% iPrOH 17.5% and iPA
0.3% (in MeOH)
Co. 167; (2S), trans-1; Ex. B24
Co. 168; (2S), trans-2; Ex. B24
Co. 169; fumarate; (2S), cis-3; Ex. B24
Co. 170; fumarate; (2S), cis-4; Ex. B24

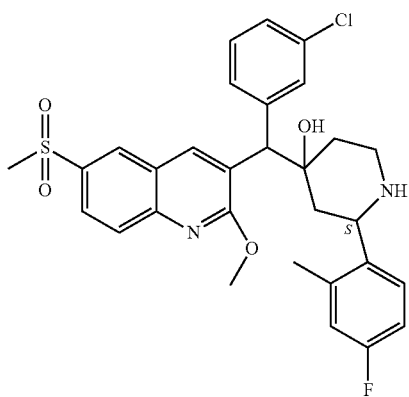

SFC Chiralpak AD-H (5 µm, 21 × 250 mm), CO$_2$
85% iPrOH 15% and iPA 0.3% (in MeOH) in
isocratic mode
Co. 171; (2S), trans-2; Ex. B30
Co. 172; (2S), trans-1; Ex. B30

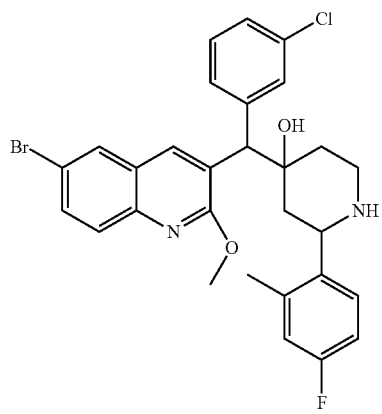 [SMILES: COc1nc2ccc(Br)cc2cc1C(c1cccc(Cl)c1)C1(O)CCNC(c2ccc(F)cc2C)C1]

Silica gel Kromasil, 10 µm, 15-40 µm, 90 g,
DCM/MeOH/NH$_4$OH: 95/5/0.1
Co. 173; (2R), trans-1; Ex. B1

TABLE 1-continued

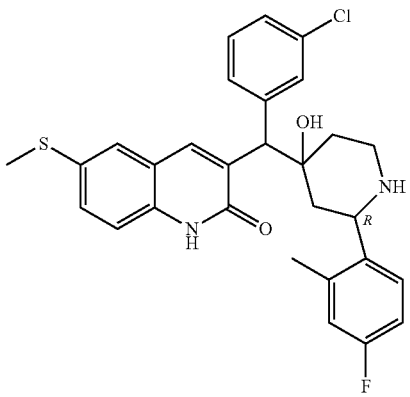

SFC Chiralpak AD-H (5 µm, 20 × 250 mm), CO$_2$
70% MeOH 30% and iPA 0.3% (in MeOH)
Co. 174; (2R), cis-1; Ex. B28
Co. 175; (2R), cis-2; Ex. B28
Co. 176; (2R), trans-3; Ex. B28
Co. 177; hydrochloride; (2R), trans-4;
Ex. B28

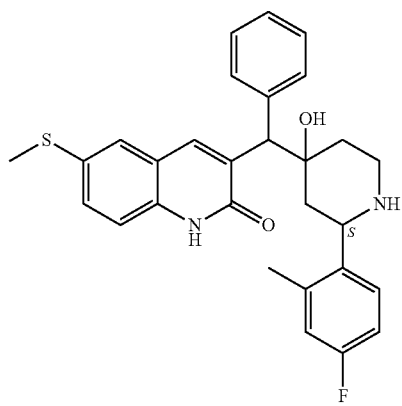

SFC Chiralpak AD-H (5 µm 20 × 250 mm),
CO$_2$ 60% iPrOH 40% and iPA 0.3% (in
MeOH)
Co. 178; (2S), trans-1; Ex. B28
Co. 179; (2S), trans-2; Ex. B28
Co. 180; (2S), cis-3; Ex. B28
Co. 181; (2S), cis-4; Ex. B28

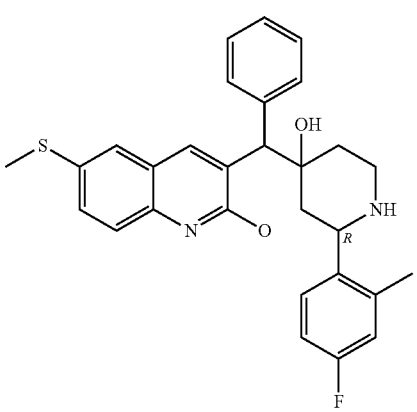

SFC Chiralpak AD-H (5 µm 21 × 250 mm), CO$_2$
60% iPrOH 40% and iPA 0.3% (in MeOH)
Co. 182; hydrochloride; (2R), trans-1;
Ex. B28
Co. 183; hydrochloride; (2R), trans-3;
Ex. B28

TABLE 1-continued

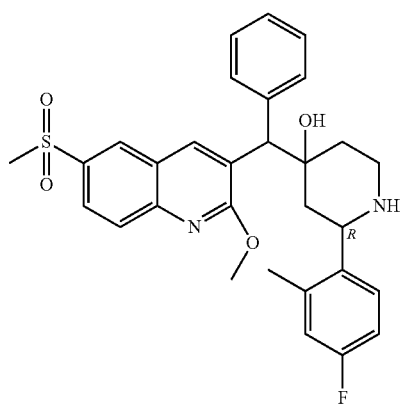

SFC Chiralpak AD-H (5 μm 20 × 250 mm),
CO$_2$ 60% iPrOH 40% and iPA 0.3% (in MeOH)
Co. 184; (2R), trans-1; Ex. B30
Co. 185; (2R), cis-2; Ex. B30
Co. 186; (2R), trans-3; Ex. B30
Co. 187; (2R), cis-4; Ex. B30

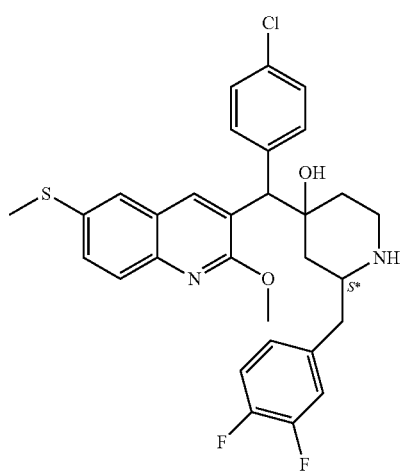

Silica gel, Cyclo/EtOAc 80/20 and then SFC
Chiralpak AD, CO$_2$ 50%, EtOH 50%, iPA 0.3%
Co. 188; fumarate; (2S*), cis-1; Ex. B33
Co. 189; (2S*), cis-4; Ex. B33

TABLE 1-continued

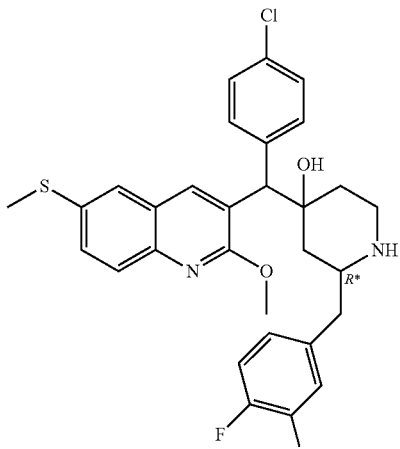

SFC Chiralpak AD-H (5 μm, 20 × 250 mm),
CO$_2$ 60% EtOH 20% iPrOH 20% and iPA 0.3% (in MeOH)
Co. 190; (2R*), cis-1; Ex. B33
SFC Chiralpak AD-H (5 μm 20 × 250 mm),
CO$_2$ 95% MeOH 5% and iPA 0.3% (in MeOH)
Co. 191; (2R*), cis-3; Ex. B33

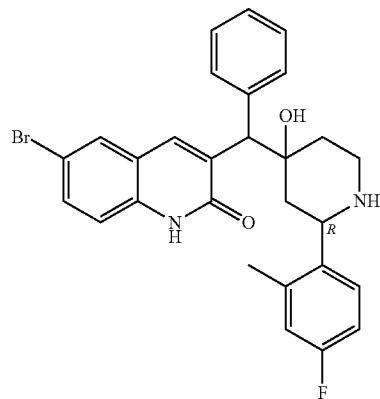

SFC Chiralpak AD-H (5 μm, 20 × 250 mm), CO$_2$
75% EtOH 25% and iPA 0.3% (in MeOH)
Co. 192; hydrochloride; (2R), trans-1; Ex. B29
Co. 43; hydrochloride; (2R), trans-2; Ex. B29*

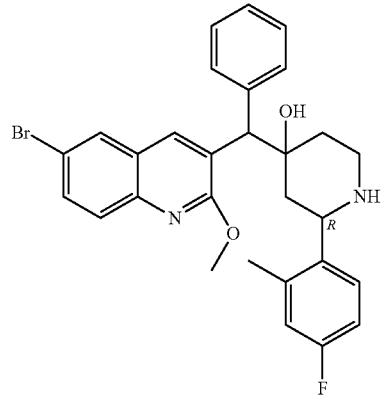

SFC Chiralpak AD-H (5 μm 20 × 250 mm),
CO$_2$ 75% EtOH 25% and iPA 0.3% (in MeOH)
Co. 193; (2R), trans-1; Ex. B1
Co. 61; (2R), trans-2; Ex. B29*
Co. 194; (2R), cis-3; Ex. B1

TABLE 1-continued

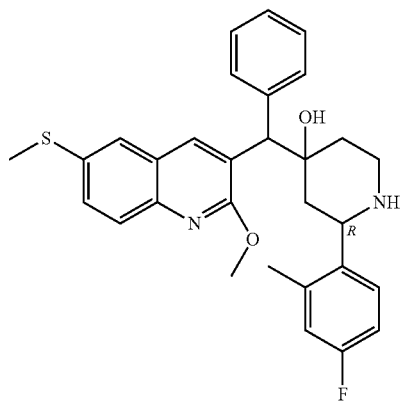

SFC Chiralpak AD-H (5 μm 21 × 250 mm), CO₂
60% iPrOH 40% and iPA 0.3% (in MeOH)
Co. 195; (2R), trans-1; Ex. B33
Co. 196; (2R), cis-2; Ex. B33
Co. 197; (2R), trans-3; Ex. B33
Co. 198; (2R), cis-4; Ex. B33

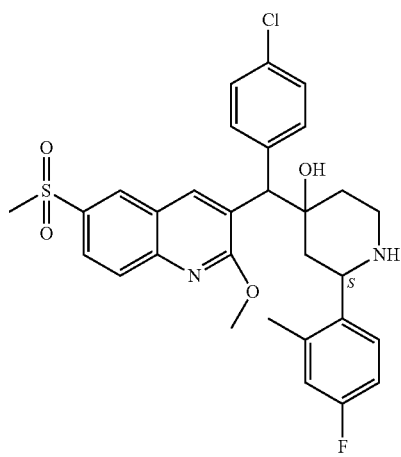

SFC Chiralpak AD-H (5 μm 20 × 250 mm),
CO₂ 60% EtOH 40% and iPA 0.3% (in MeOH)
Co. 199; (2S), trans-2; Ex. B30
SFC Chiralpak AD-H (5 μm 20 × 250 mm),
CO₂ 75% EtOH 25% and iPA 0.3% (in MeOH)
Co. 200; (2S), trans-4; Ex. B30
Silica gel, 15-40 μm, 90 g,
DCM/MeOH/NH₄OH: 97/3/0.1
Co. 201; fumarate; (2S), cis-1; Ex. B30
SFC Chiralpak AD-H (5 μm, 20 × 250 mm),
CO₂ 60% EtOH 40% and iPA 0.3% (in MeOH)
Co. 202; (2S), cis-3; Ex. B30

TABLE 1-continued

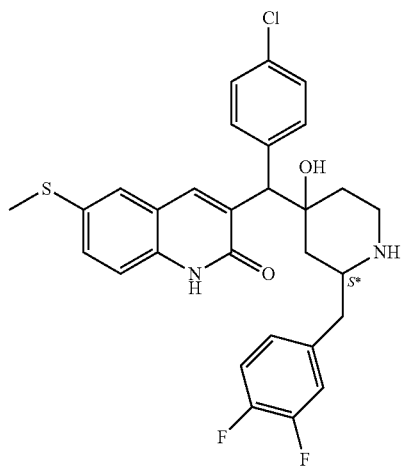

SFC Chiralpak AD-H (5 μm 20 × 250 mm), CO₂
60% EtOH 20% iPrOH 20% and iPA 0.3% (in
MeOH)
Co. 203; (2S*), cis-1; Ex. B33
SFC Chiralpak AD-H (5 μm 20 × 250 mm), CO₂
95% MeOH 5% and iPA 0.3% (in MeOH)
Co. 204; hydrochloride; (2S*), cis-4;
Ex. B33

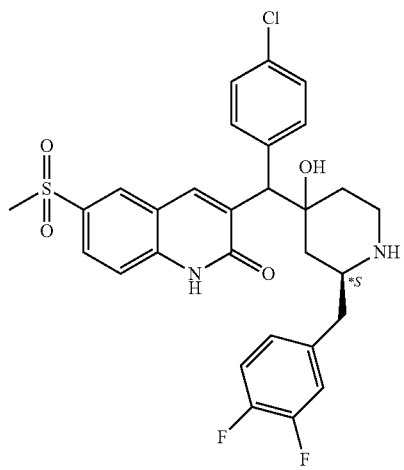

SiO₂, 20-45 μm, 450 g, Cyclo/EtOAc 90/10
Co. 205; hydrochloride; (2S*), cis-1;
Ex. B36
SFC Chiralpak AD-H (5 μm, 20 × 250 mm),
CO₂ 95% MeOH 5% and iPA 0.3% (in MeOH)
in isocratic mode.
Co. 206; hydrochloride; (2S*), trans-3;
Ex. B36
Silica gel, 20-45 μm, 450 g, Cyclo/EtOAc 90/10
Co. 207; hydrochloride; (2S*), trans-2;
Ex. B36
SFC Chiralpak AD-H (5 μm, 20 × 250 mm),
CO₂ 95% MeOH 5% and iPA 0.3% (in MeOH)
Co. 208; hydrochloride; (2S*), cis-4;
Ex. B36

TABLE 1-continued

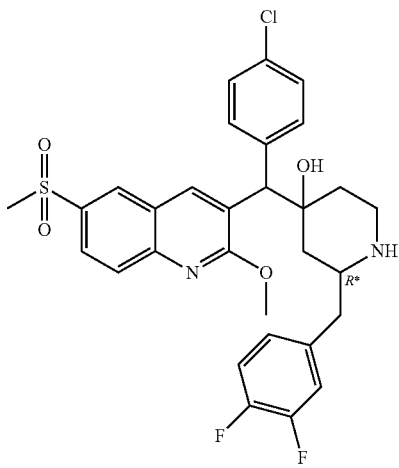

SFC Chiralpak AD-H (5 µm, 20 × 250 mm),
CO₂ 70% EtOH 30% and iPA 0.3%(in MeOH)
Co. 209; (2R*), cis-1; Ex. B24
Co. 210; (2R*), cis-3; Ex. B24

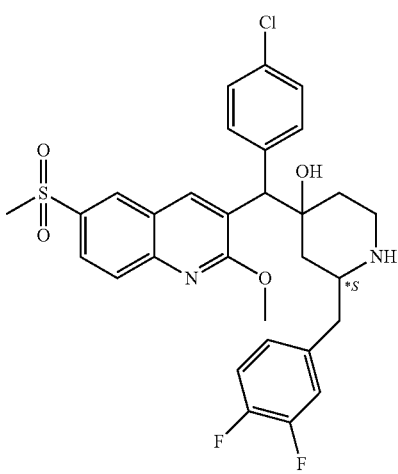

Silica gel 20-45 µm, 450 g, Cyclo/EtOAc 90/10
Co. 211; (2*S), cis-1; Ex. B24

TABLE 1-continued

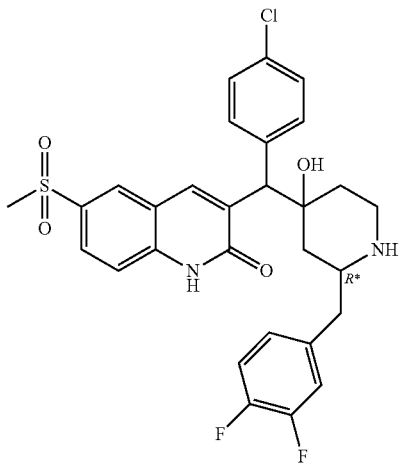

Silica gel, 20-45 µm, 450 g, Cyclo/EtOAc 90/10
Co. 212; hydrochloride; (2R*), trans-2;
Ex. B36
SFC Chiralpak AD-H (5 µm 20 × 250 mm), CO₂
60% EtOH 40% and iPA 0.3% (in MeOH)
Co. 213; fumarate; (2R*), trans-4; Ex. B36
SFC Chiralpak AD-H (5 µm, 20 × 250 mm), CO₂
70% EtOH 30% and iPA 0.3% (in MeOH)
Co. 214; fumarate; (2R*), cis-1; Ex. B36
Co. 215; fumarate; (2R*), cis-3; Ex. B36

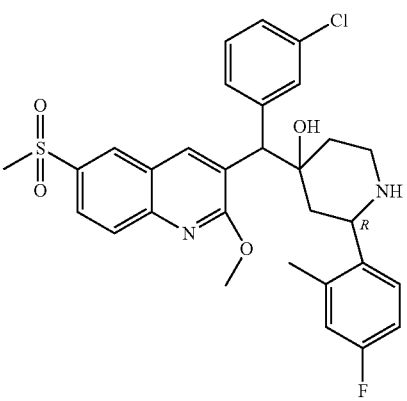

SFC Chiralpack AD-H (5 µm 20 × 250 mm),
CO₂ 65% EtOH 17.5% iPrOH 17.5% and iPA
0.3% (in MeOH)
Co. 44; (2R), trans-1; Ex. B30*
Co. 45; (2R), trans-2; Ex. B30*
Co. 46; (2R), cis-3; Ex. B30*
Co. 47; (2R), cis-4; Ex. B30*

TABLE 1-continued

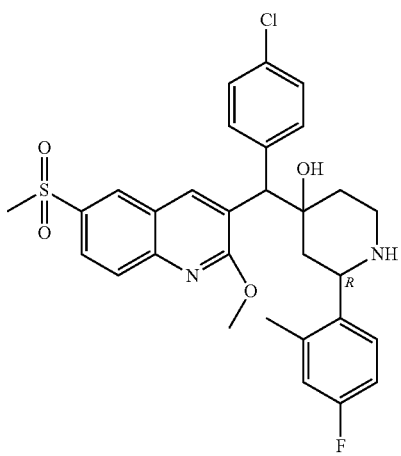

Silica gel, 15-40 μm, 300 g,
DCM/MeOH/NH₄OH: 95/5/0.1
Co. 216; (2R), cis-1; Ex. B30
Co. 217; (2R), trans-2; Ex. B30
SFC Chiralpak AD-H (5 μm 20 × 250 mm), CO₂
60% EtOH 40% and iPA 0.3% (in MeOH)
Co. 218; (2R), trans-3; Ex. B30
Co. 219; (2R), cis-4; Ex. B30

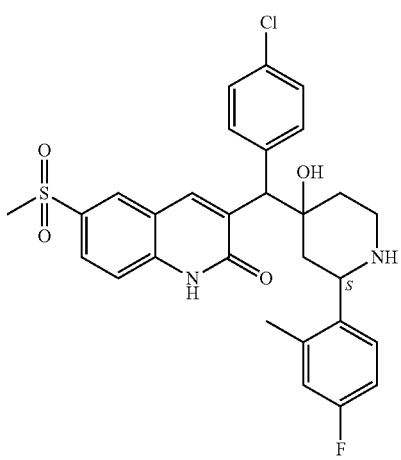

SFC Chiralpak AD-H (5 μm 20 × 250 mm),
CO₂ 75% EtOH 25% and iPA 0.3% (in MeOH)
Co. 220; hydrochloride; (2S), trans-4;
Ex. B28
SFC Chiralpak AD-H (5 μm 20 × 250 mm),
CO₂ 60% EtOH 40% and iPA 0.3% (in MeOH)
Co. 221; hydrochloride; (2S), cis-3;
Ex. B28
Co. 222; hydrochloride; (2S), trans-2;
Ex. B28
Silica gel, 15-40 μm, 90 g,
DCM/MeOH/NH₄OH: 97/3/0.1
Co. 223; hydrochloride; (2S), cis-1;
Ex. B28

TABLE 1-continued

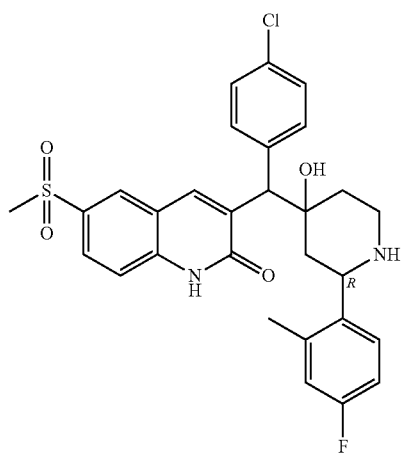

Silica gel, 15-40 μm, 300 g,
DCM/MeOH/NH₄OH: 95/5/0.1
Co. 224; hydrochloride; (2R), trans-2;
Ex. B28
SFC Chiralpak AD-H (5 μm 20 × 250 mm), CO₂
60% EtOH 40% and iPA 0.3% (in MeOH)
Co. 225; hydrochloride; (2R), trans-3;
Ex. B28

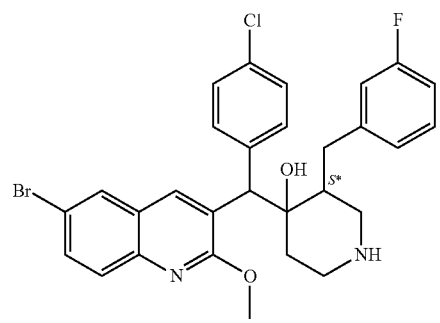

High-performance liquid chromatography
(Irregular SiOH, 20-45 μm, 450 g MATREX),
DCM 80%/Cyclo 20%
Co. 226; (3S*), (B); Ex. B31
Co. 227; (3S*), (A); Ex. B31

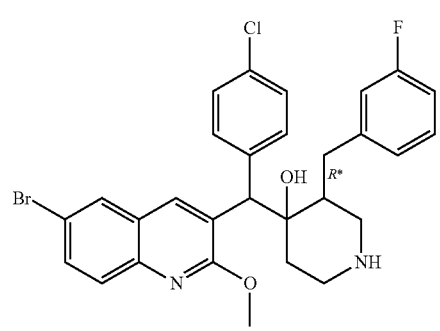

High-performance liquid chromatography
(Irregular SiOH, 20-45 μm, 450 g MATREX),
DCM 80%/Cyclo 20%
Co. 48; (3R*), (B); Ex. B31*
Co. 228; (3R*), (A); Ex. B31

TABLE 1-continued

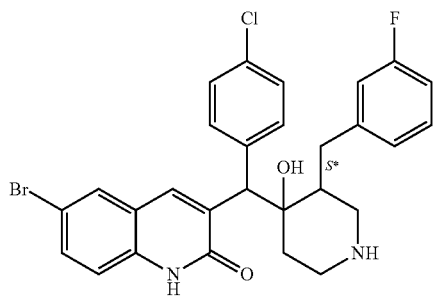

High-performance liquid chromatography (Irregular SiOH 20-45 μm, 450 g MATREX), DCM 80%/Cyclo 20%
Co. 49; hydrochloride; (3S*), (A); Ex. B32*

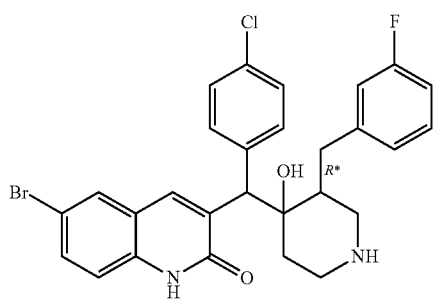

High-performance liquid chromatography (Irregular SiOH 20-45 μm, 450 g MATREX), DCM 80%/Cyclo 20%
Co. 229; hydrochloride; (3R*), (B); Ex. B32

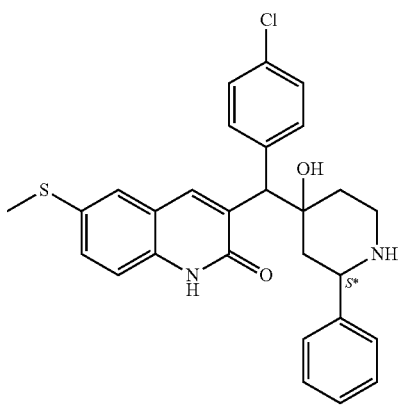

SFC Chiralpak AD-H (5 μm 20 × 250 mm), 3 ml/min, 35° C., 100 bars, CO₂ 50% MeOH 25% and iPrOH 25%
Co. 230; hydrochloride; (2S*), cis-3; Ex. B28
SiO₂, 15-40 μm, 300 g, Cyclo/EtOAc 95/5 to 85/15
Co. 231; hydrochloride; (2S*), trans-2; Ex. B28
Co. 232; hydrochloride; (2S*), trans-1; Ex. B28

TABLE 1-continued

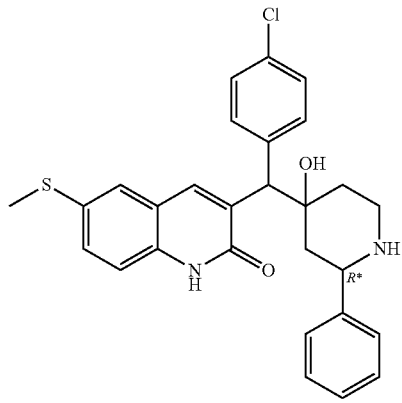

SFC Chiralpak AD-H (5 μm 20 × 250 mm), 3 ml/min, 35° C., 100 bars, CO₂ 60% MeOH 20% and iPrOH 20%
Co. 233; hydrochloride; (2R*), cis-3; Ex. B28
Silica gel, 15-40 μm, 300 g, Cyclo/EtOAc 85/15
Co. 234; hydrochloride; (2R*), trans-1; Ex. B28
SFC Chiralpak AD-H (5 μm 20 × 250 mm), 3 ml/min, 35° C., 100 bars, CO₂ 60% MeOH 20% and iPrOH 20%
Co. 235; hydrochloride; (2R*), cis-2; Ex. B28

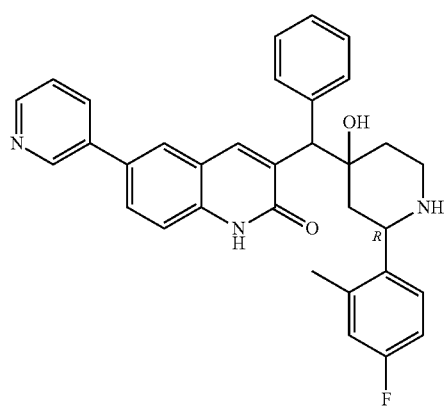

SFC Chiralpak AD-H (5 μm 20 × 250 mm), CO₂ 75% EtOH 25% and iPA 0.3% (in MeOH) in isocratic mode
Co. 236; hydrochloride; (2R), trans-1; Ex. B28

TABLE 1-continued

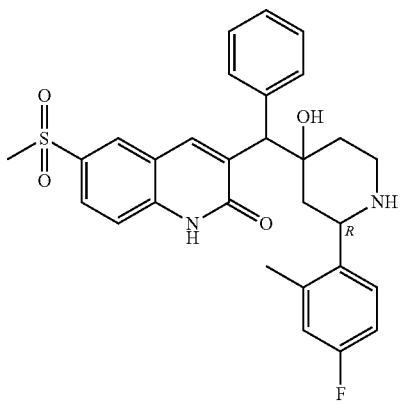

SFC Chiralpak AD-H (5 μm 20 × 250 mm), CO2
60% iPrOH 40% and iPA 0.3% (in MeOH)
Co. 237; hydrochloride; (2R), trans-3;
Ex. B28
Co. 238; hydrochloride; (2R), trans-1;
Ex. B28

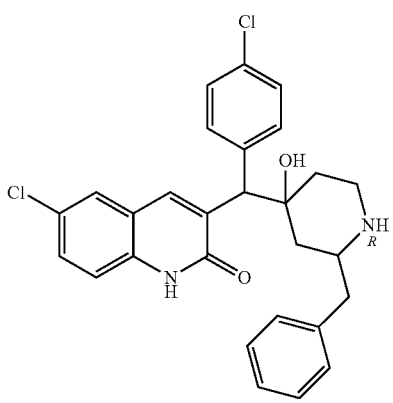

SFC Chiralpak AD-H (5 μm 250 × 20 mm), iPA
0.3%; CO2 70% iPrOH 30%
Co. 239; hydrochloride; (2R), cis-4;
Ex. B2
Co. 5; hydrochloride; (2R), trans-3; Ex.
B2*
SFC Chiralpak IC (5 μm, 250 × 20 mm), iPA
0.3%; CO2 60% iPrOH 40%
Co. 240; hydrochloride; (2R), cis-2;
Ex. B2
Co. 241; hydrochloride; (2R), trans-1;
Ex. B2

TABLE 1-continued

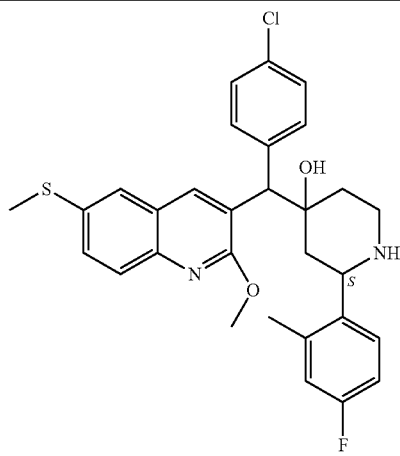

SFC Chiralpak AD-H (5 μm 20 × 250 mm), CO2
70% EtOH 15% IPrOH 15% and iPA 0.3% (in
MeOH)
Co. 242; (2S), trans-1; Ex. B33
Co. 243; (2S), cis-2; Ex. B33
SFC Chiralpak AD-H (5 μm, 20 × 250 mm),
CO2 60% EtOH 40% and iPA 0.3% (in MeOH)
Co. 244; (2S), cis-3; Ex. B33
Co. 245; (2S), trans-4; Ex. B33

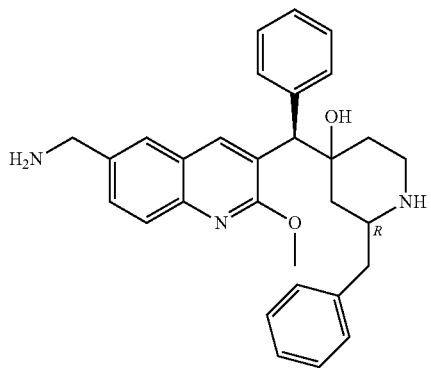

Silica gel (B6927, 20-45 μm, 450 g,
Cyclo/EtOAc 90/10)
Co. 246; (2R), cis-1; Ex. B20

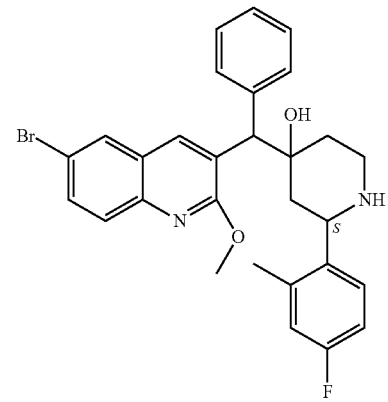

SFC Chiralpak AD-H (5 μm 20 × 250 mm), CO2
65% EtOH 35% and iPA 0.3% (in MeOH)
Co. 247; (2S), trans-1; Ex. B1
Co. 248; (2S), trans-2; Ex. B1
Co. 249; (2S), cis-3; Ex. B1
Co. 250; (2S), cis-4; Ex. B1

TABLE 1-continued

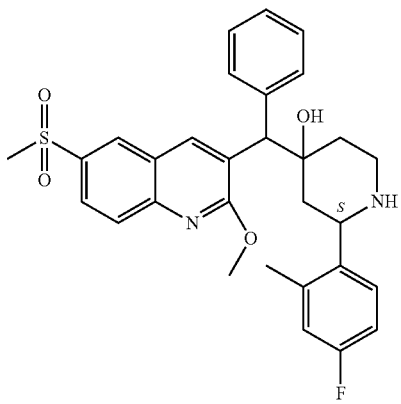

SFC Chiralpak AD-H (5 μm, 20 × 250 mm),
CO₂ 60% MeOH 40% and iPA 0.3% (in
MeOH)
Co. 251; (2S), cis-1; Ex. B30
SFC Chiralpak AD-H (5 μm, 20 × 250 mm),
CO₂ 50% MeOH 50% and iPA 0.3% (in
MeOH)
Co. 252; (2S), trans-2; Ex. B30
SFC Chiralpak AD-H (5 μm, 20 × 250 mm),
CO₂ 65% MeOH 35% and iPA 0.3% (in
MeOH)
Co. 253; (2S), trans-4; Ex. B30

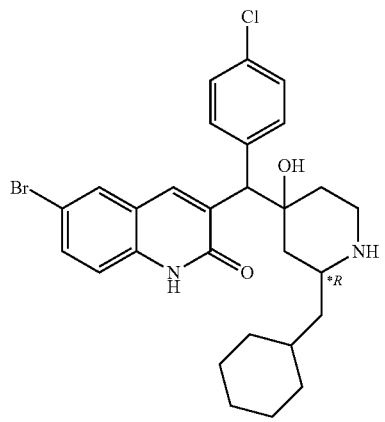

High-performance liquid chromatography
(Irregular SiOH 15-40 μm 300 g MERCK), DCM
98% EtOAc 2%
Co. 254; hydrochloride; (2R*), (A); Ex. B3
Co. 255; hydrochloride; (2R*), (B); Ex. B3

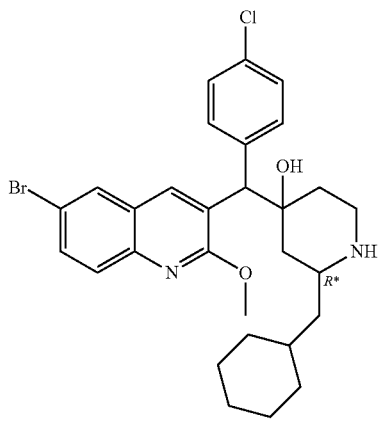

High-performance liquid chromatography
(Irregular SiOH 15-40 μm, 300 g MERCK),
DCM 98% EtOAc 2%
Co. 256; (2R*), (A); Ex. B18
Co. 257; (2R*), (B); Ex. B18

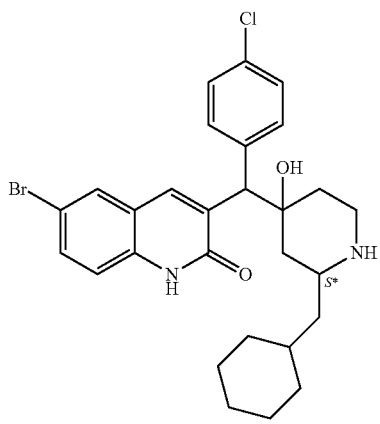

High-performance liquid chromatography
(Irregular SiOH 15-40 μm, 300 g MERCK), DCM
98% EtOAc 2%
Co. 6; hydrochloride; 41873312(2S*), (A);
Ex. B3*
Co. 258; hydrochloride; (2S*), (B); Ex. B3

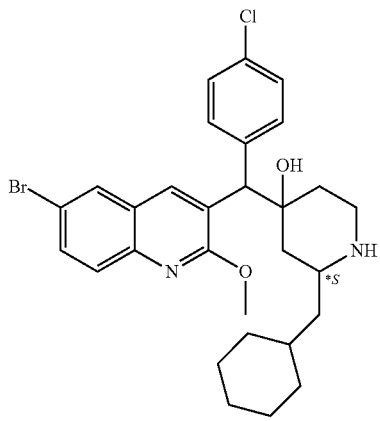

High-performance liquid chromatography
(Irregular SiOH 15-40 μm, 300 g MERCK),
DCM 98% EtOAc 2%
Co. 259; (2S*), (A); Ex. B18

TABLE 1-continued

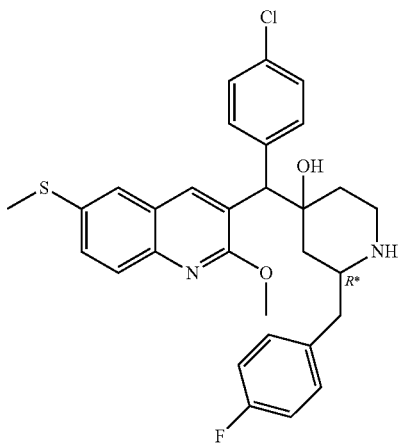

SFC Chiralpak AD-H (5 μm 250 × 20 mm), iPA
0.3%; CO₂ 65% EtOH 35%
Co. 260; (2R*), trans-1; Ex. B24
Co. 261; (2R*), cis-2; Ex. B24
Co. 262; (2R*), cis-4; Ex. B24

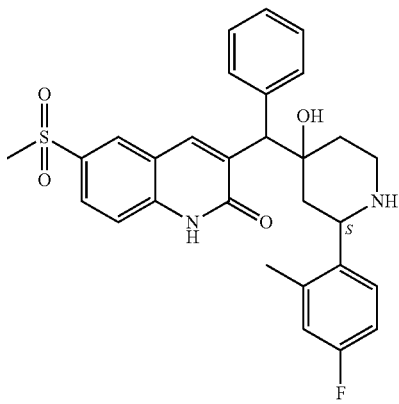

SFC Chiralpak AD-H (5 μm 20 × 250 mm),
CO₂ 50% MeOH 50% and iPA 0.3% (in
MeOH)
Co. 263; hydrochloride; (2S), trans-2;
Ex. B28
SFC Chiralpak AD-H (5 μm 20 × 250 mm),
CO₂ 65% MeOH 35% and iPA 0.3% (in
MeOH)
Co. 264; hydrochloride; (2S), cis-3;
Ex. B28
Co. 265; hydrochloride; (2S), trans-4;
Ex. B28

TABLE 1-continued

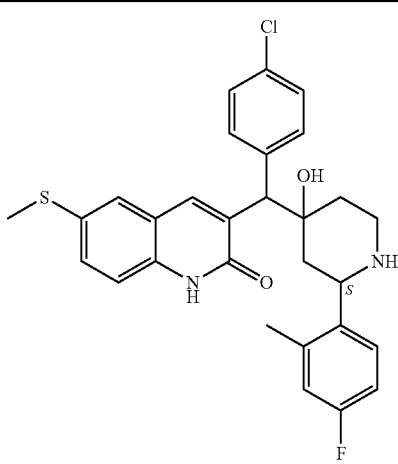

SFC Chiralpak AD-H (5 μm 20 × 250 mm), CO₂
60% EtOH 40% and iPA 0.3% (in MeOH)
Co. 266; hydrochloride; (2S), trans-4;
Ex. B28
SFC Chiralpak AD-H (5 μm 20 × 250 mm), CO₂
70% EtOH 15% iPrOH 15% and iPA 0.3% (in
MeOH)
Co. 267; hydrochloride; (2S), cis-2; Ex. B28
Co. 268; hydrochloride; (2S), trans-1;
Ex. B28

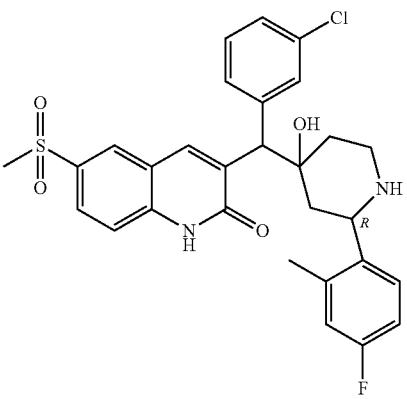

SFC Chiralpak AD-H (5 μm 20 × 250 mm),
CO₂ 65% EtOH 17.5% iPrOH 17.5% and iPA
0.3% (in MeOH)
Co. 269; hydrochloride; (2R), cis-4;
Ex. B28
Co. 270; hydrochloride; (2R), cis-3;
Ex. B28
Co. 271; hydrochloride; (2R), trans-2;
Ex. B28
Co. 272; hydrochloride; (2R), trans-1;
Ex. B28

TABLE 1-continued

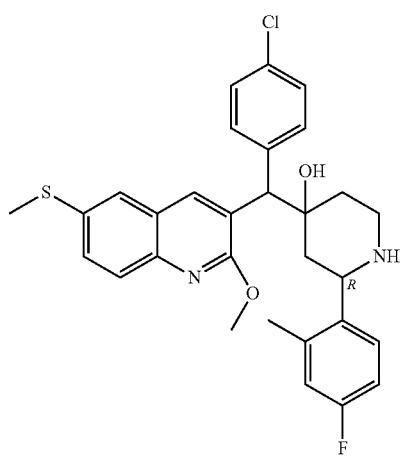

Silica gel, 15-40 µm, 300 g,
DCM/MeOH/NH₄OH: 97.5/2.5/0.1
Co. 273; (2R), cis-1; Ex. B30
SFC Chiralpak AD-H (5 µm, 20 × 250 mm),
CO₂ 60% MeOH 40% and iPA 0.3% (in MeOH)
Co. 274; (2R), cis-2; Ex. B30
SFC Chiralpak AD-H (5 µm, 20 × 250 mm),
CO₂ 60% MeOH 40% and iPA 0.3% (in MeOH)
Co. 275; (2R), trans-3; Ex. B30
Co. 276; (2R), trans-4; Ex. B30

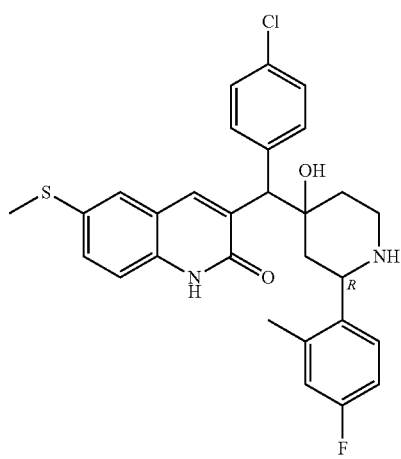

SFC Chiralpak AD-H (5 µm, 20 × 250 mm),
CO₂ 60% MeOH 40% and iPA 0.3% (in MeOH)
Co. 277; hydrochloride; (2R), trans-4;
Ex. B28
Co. 278; hydrochloride; (2R), trans-3;
Ex. B28

TABLE 1-continued

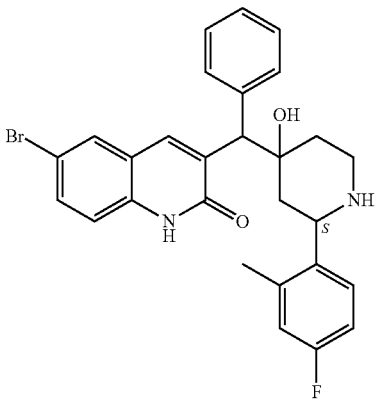

SFC Chiralpak AD-H (5 µm, 20 × 250 mm),
CO₂ 65% EtOH 35% and iPA 0.3% (in MeOH)
Co. 279; hydrochloride; (2S), trans-2;
Ex. B29
Co. 280; hydrochloride; (2S), trans-1;
Ex. B29

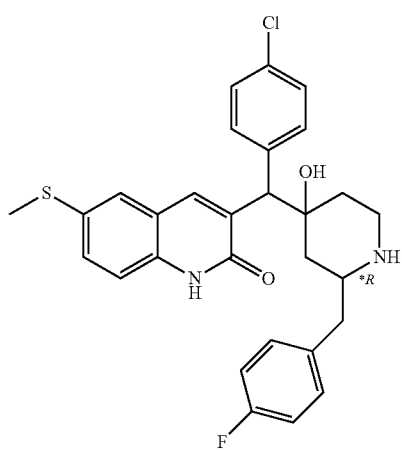

SFC Chiralpak AD-H (5 µm, 250 × 20 mm), iPA
0.3%; CO₂ 65% EtOH 35%
Co. 281; hydrochloride; (2R*), cis-2;
Ex. B26
Co. 282; hydrochloride; (2R*), cis-4;
Ex. B26

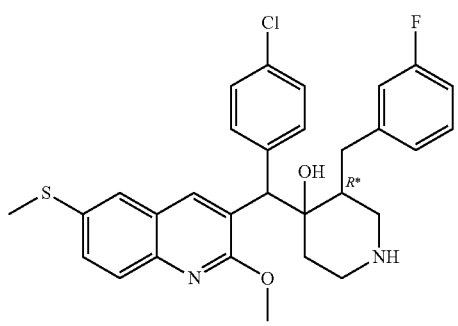

High-performance liquid chromatography
(Irregular SiOH 15-40 µm, 300 g MERCK), DCM
98% EtOAc 2%
Co. 283; (3R*), (A); Ex. B31
Co. 284; fumarate; (3R*), (B); Ex. B31

TABLE 1-continued

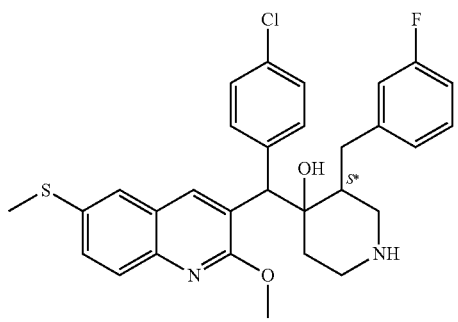

High-performance liquid chromatography
(Irregular SiOH 15-40 µm, 300 g MERCK),
DCM 98% EtOAc 2%
Co. 285; (3S*), (A); Ex. B27 Co. 286;
fumarate; (3S*), (B); Ex. B27

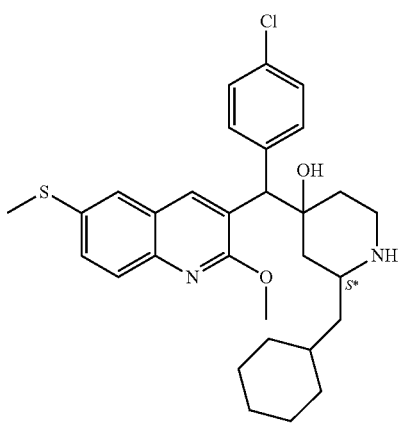

High-performance liquid chromatography
(Irregular SiOH 20-45 µm, 450 g MATREX),
Cyclo 90% EtOAc 10%
Co. 287; (2S*), (B); Ex. B20
Co. 288; fumarate; (2S*), (A); Ex. B20

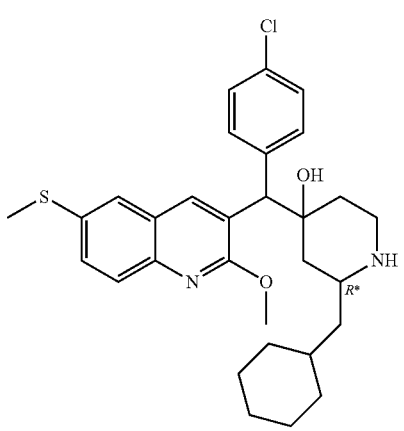

High-performance liquid chromatography
(Irregular SiOH 20-45 µm, 450 g MATREX),
Cyclo 90% EtOAc 10%
Co. 289; fumarate; (2R*), (A); Ex. B18
Co. 290; (2R*), (B); Ex. B18

TABLE 1-continued

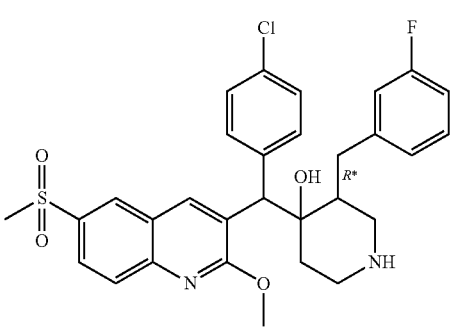

High-performance liquid chromatography
(Irregular SiOH 15-40 µm, 300 g MERCK), DCM
98% EtOAc 2%
Co. 291; (3R*), (A); Ex. B31
Co. 292; (3R*), (B); Ex. B31

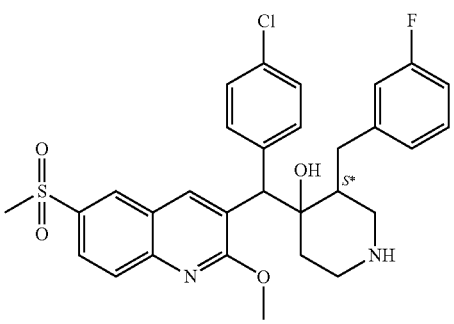

High-performance liquid chromatography
(Irregular SiOH 15-40 µm, 300 g MERCK),
DCM 98% EtOAc 2%
Co. 293; (3S*), (A); Ex. B31 Co. 294;
(3S*), (B); Ex. B31

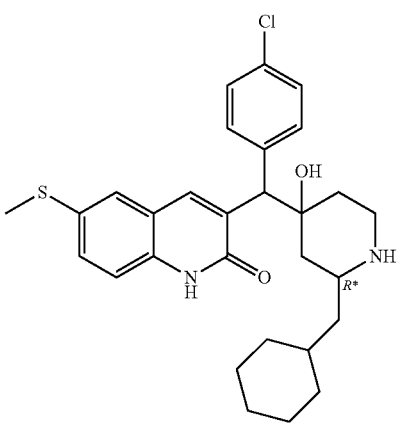

High-performance liquid chromatography
(Irregular SiOH 20-45 µm, 450 g MATREX),
Cyclo 90% EtOAc 10%
Co. 295; hydrochloride; (2R*), (A); Ex. B3
Co. 296; hydrochloride; (2R*), (B); Ex. B3

TABLE 1-continued

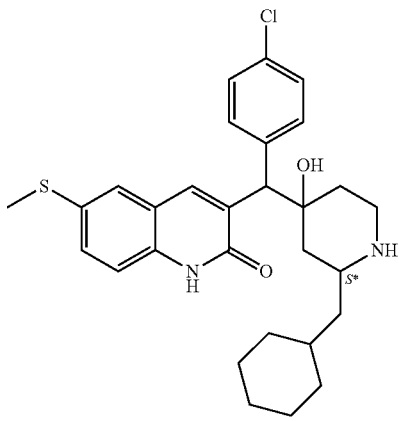

High-performance liquid chromatography
(Irregular SiOH 20-45 µm, 450 g MATREX),
Cyclo 90% EtOAc 10%
Co. 297; hydrochloride; (2S*), (B); Ex. B3
Co. 298; hydrochloride; (2S*), (A); Ex. B3

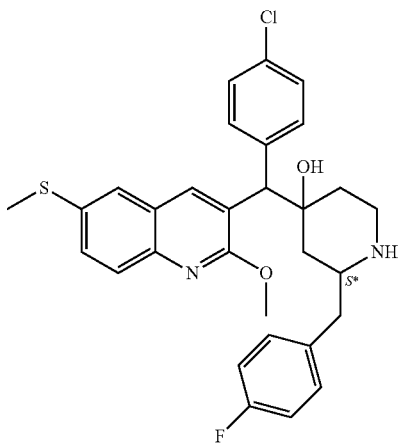

SFC Chiralpak AD-H (5 µm, 250 × 20 mm), iPA
0.3%; $CO_2$ 70% EtOH 30%
Co. 299; (2S*), trans-1; Ex. B33
Co. 300; (2S*), cis-2; Ex. B33
Co. 301; (2S*), cis-3; Ex. B33
Co. 302; (2S*), trans-4; Ex. B33

TABLE 1-continued

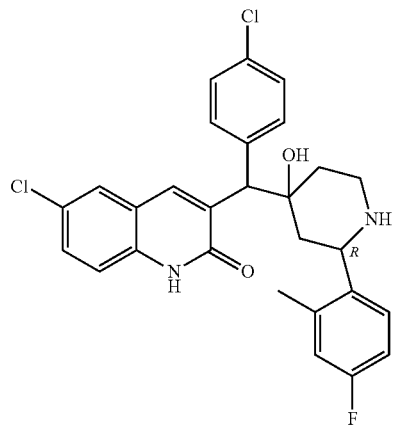

SFC Chiralpak AD-H (5 µm, 250 × 20 mm), iPA
0.3%; $CO_2$ 75% MeOH 12.5% iPrOH 12.5%
Co. 303; hydrochloride; (2R), trans-3;
Ex. B4
SFC Chiralpak AD-H (5 µm, 250 × 20 mm), iPA
0.3%; $CO_2$ 60% MeOH 40%
Co. 304; hydrochloride; (2R), trans-2;
Ex. B4

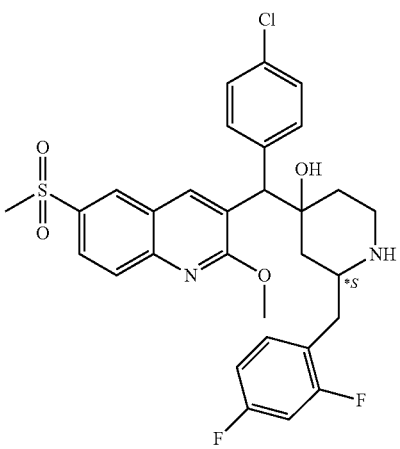

SFC Chiralcel OD-H (5 µm, 250 × 20 mm), iPA
0%; $CO_2$ 70% MeOH 30%
Co. 305; trifluoroacetate; (2S*), cis-2;
Ex. B24
Co. 306; trifluoroacetate; (2S*), cis-1;
Ex. B24

TABLE 1-continued

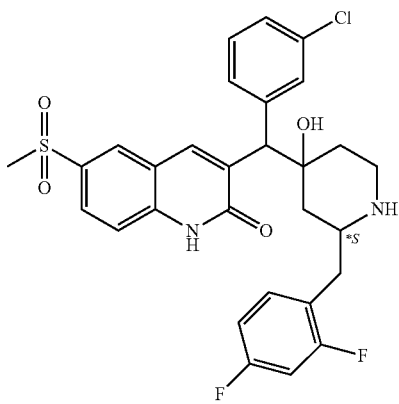

SFC Chiralcel OD-H (5 μm, 250 × 20 mm), iPA
0%; CO₂ 70% MeOH 30%
Co. 307; hydrochloride; (2S*), cis-2;
Ex. B36
Co. 308; hydrochloride; (2S*), cis-1;
Ex. B36

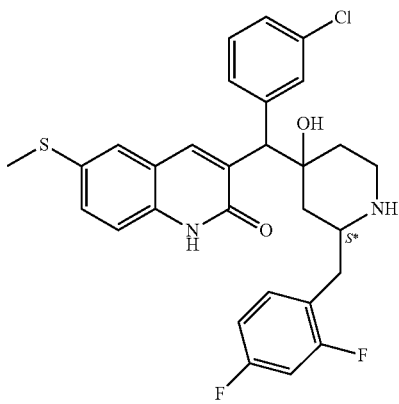

SFC Chiralcel OD-H (5 μm, 250 × 20 mm), iPA
0%; CO₂ 70% MeOH 30%
Co. 309; hydrochloride; (2S*), cis-2;
Ex. B36
Co. 310; hydrochloride; (2S*), cis-1;
Ex. B36
SFC Chiralpak AD-H (5 μm, 250 × 20 mm), iPA
0%; CO₂ 70% iPrOH 30%
Co. 311; hydrochloride; (2S*), trans-4;
Ex. B36
Co. 312; hydrochloride; (2S*), trans-3;
Ex. B36

TABLE 1-continued

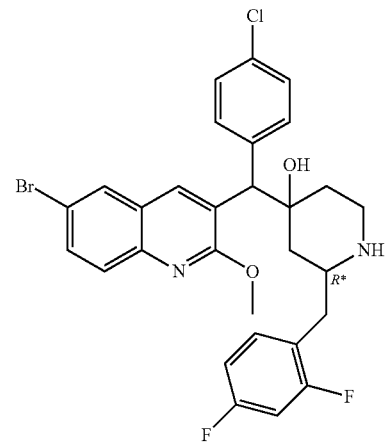

SFC Chiralpak AD-H (5 μm, 250 × 20 mm), iPA
0%; CO₂ 70% EtOH 15% iPrOH 15%
Co. 313; trifluoroacetate; (2R*), cis-4;
Ex. B34
Co. 51; trifluoroacetate; (2R*), cis-3; Ex.
B34*

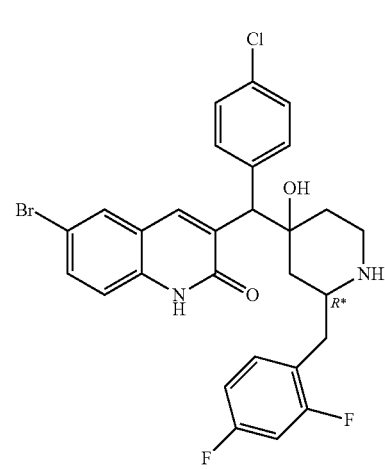

SFC (Chiralpak AD-H 5 μm, 250 × 20 mm), iPA
0%; CO₂ 70% EtOH 15% iPrOH 15%
Co. 314; hydrochloride; (2R*), cis-4;
Ex. B28
Co. 315; hydrochloride; (2R*), cis-3;
Ex. B28
Co. 316; hydrochloride; (2R*), trans-
1; ExB28.
Co. 317; hydrochloride; (2R*), trans-
2; ExB28.

TABLE 1-continued

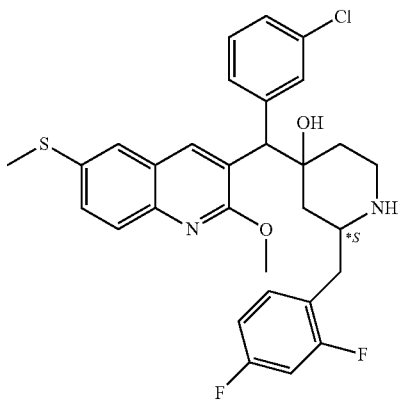

SFC Chiralpak AD-H (5 µm, 250 × 20 mm), iPA 0%; CO$_2$ 70% iPrOH 30%
Co. 50; trifluoroacetate; (2S*), cis-2; Ex. B33*
Co. 318; (2S*), cis-1; Ex. B33

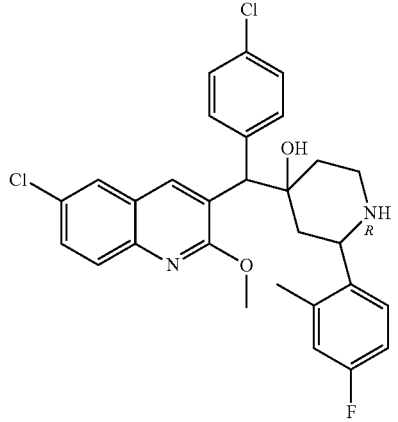

SFC Chiralpak AD-H (5 µm, 250 × 20 mm), iPA 0.3%; CO$_2$ 60% MeOH 40%
Co. 1; (2R), cis-1; Ex. B1*
SFC Chiralpak AD-H (5 µm, 250 × 20 mm), iPA 0.3%; CO$_2$ 75% MeOH 12.5% iPrOH 12.5%
Co. 2; (2R), trans-2; Ex. B1*
Co 3.; (2R), trans-3; Ex. B1*
Co. 4; (2R), cis-4; Ex. B1*

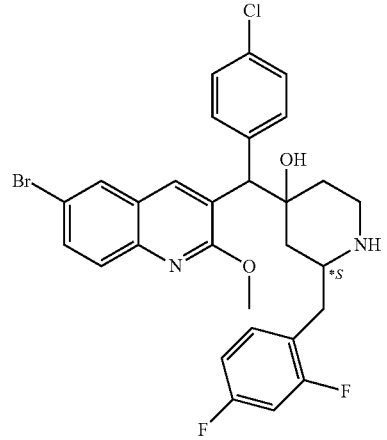

SFC Chiralpak IC (5 µm, 250 × 20 mm), iPA 0.3%; CO$_2$ 70% MeOH 15% iPrOH 15%
Co. 319; trifluoroacetate; (2S*), cis-2; Ex. B34
Co. 320; (2S*), cis-1; Ex. B34

TABLE 1-continued

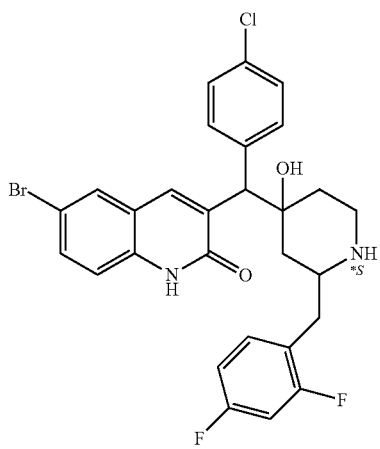

SFC Chiralpak IC (5 µm, 250 × 20 mm), iPA 0.3%; CO$_2$ 70% MeOH 15% iPrOH 15%
Co. 321; hydrochloride; (2S*), cis-2; Ex. B28
Co. 322; hydrochloride; (2S*), cis-1; Ex. B28
SFC Chiralpak AD-H (5 µm, 250 × 20 mm), iPA 0%; CO$_2$ 70% EtOH 30%
Co. 323; hydrochloride; (2S*), trans-4; Ex. B28
Co. 324; hydrochloride; (2S*), trans-3; Ex. B28

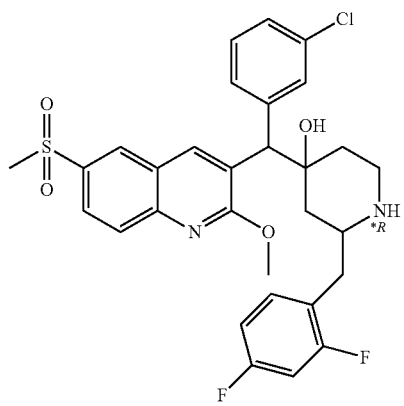

SFC Chiralpak IC (5 µm, 250 × 20 mm), iPA 0%; CO$_2$ 80% MeOH 20%
Co. 325; trifluoroacetate; (2R*), cis-3; Ex. B24
SFC Chiralpak AD-H (5 µm, 250 × 20 mm), iPA 0%; CO$_2$ 70% iPrOH 30%
Co. 326; trifluoroacetate; (2R*), cis-2; Ex B24.

TABLE 1-continued

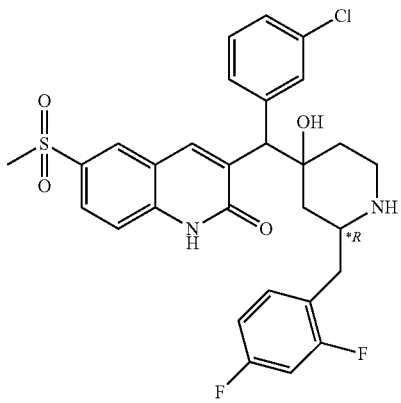

SFC Chiralpak IC (5 µm, 250 × 20 mm), iPA 0%;
CO₂ 80% MeOH 20%
Co. 327; hydrochloride; (2R*), cis-3; Ex.
B36
SFC Chiralpak AD-H (5 µm, 250 × 20 mm), iPA
0%; CO₂ 70% iPrOH 30%
Co. 328; hydrochloride; (2R*), cis-2; Ex.
B36

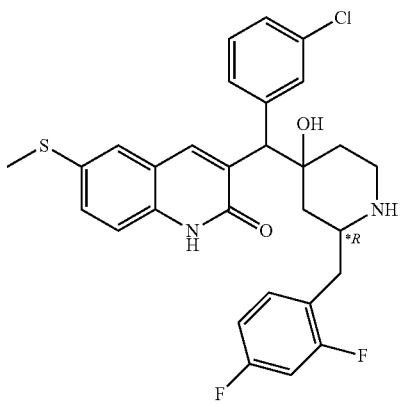

SFC Chiralpak AD-H (5 µm, 250 × 20 mm), iPA
0%; CO₂ 70% iPrOH 30%
Co. 329; hydrochloride; (2R*), trans-1;
Ex. B26

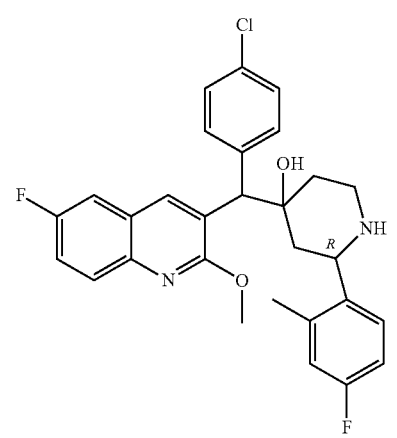

SFC Chiralpak AD-H (5 µm, 250 × 20 mm), iPA
0.3%; CO₂ 60% iPrOH 40%
Co. 330; fumarate; (2R), trans-1; Ex. B35
Co. 331; fumarate; (2R), trans-2; Ex. B35
Co. 332; fumarate; (2R), cis-3; Ex. B35

TABLE 1-continued

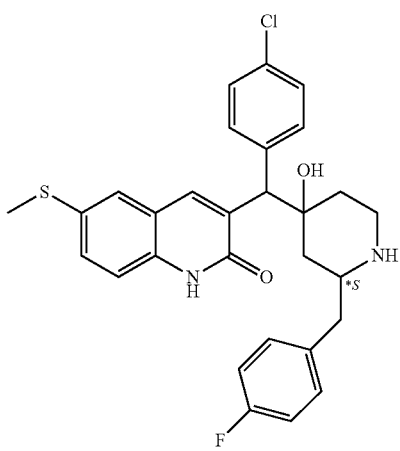

SFC Chiralpak AD-H (5 µm 250 × 20 mm), iPA
0.3%; CO₂ 70% EtOH 30%
Co. 333; hydrochloride; (2S*), cis-3; Ex.
B26
Co. 334; hydrochloride; (2S*), cis-2; Ex.
B26

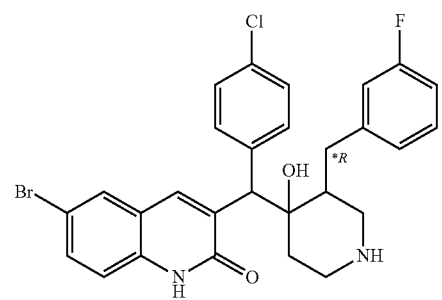

High-performance liquid chromatography
(Irregular SiOH 20-45 µm, 450 g MATREX).
Mobile phase (DCM 80%/Cyclo 20%)
Co. 335; (3R*), (A); Ex. B32

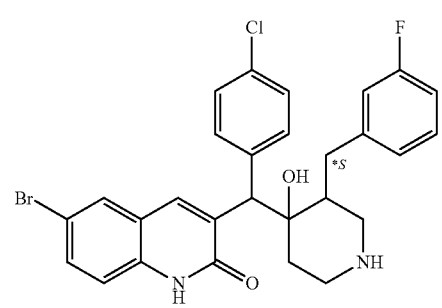

High-performance liquid chromatography
(Irregular SiOH 20-45 µm 450 g MATREX),
DCM 80%/Cyclo 20%
Co. 336; (3S*), (B); Ex. B32

TABLE 1-continued

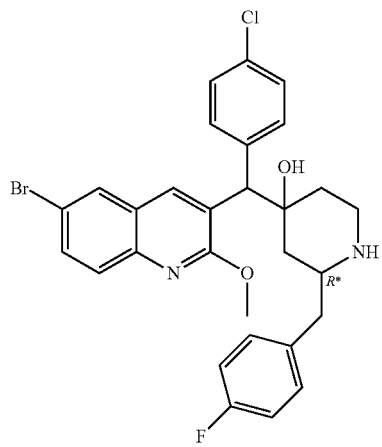

SFC Chiralpak AD-H (5 µm, 250 × 20 mm), iPA
0.3%; CO2 60% EtOH 20% iPrOH 20%
Co. 337; (2R*), trans-1; Ex. B25
Co. 338; (2R*), cis-2; Ex. B25
Co. 339; (2R*), trans-3; Ex. B25
Co. 340; (2R*), cis-4; Ex. B25.

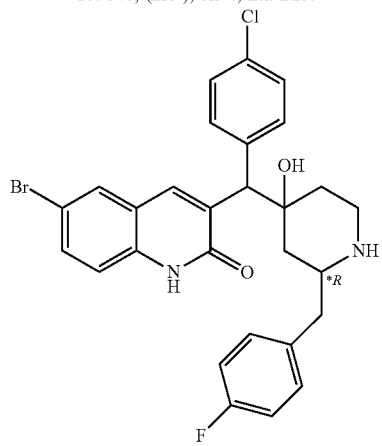

SFC Chiralpak AD-H (5 µm 250 × 20 mm), iPA
0.3%; CO2 60% EtOH 20% iPrOH 20%
Co. 341; hydrochloride; (2R*), cis-2;
Ex. B26
Co. 342; hydrochloride; (2R*), cis-4; Ex.
B26

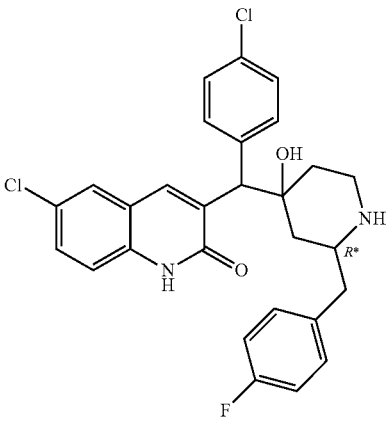

SFC Chiralpak AD-H (5 µm 250 × 20 mm), iPA
0.3%; gradient CO2/ETIP from 80/20 to 60/40)
Co. 343; hydrochloride; (2R*), cis-4; Ex. B2
Co. 344; hydrochloride; (2R*), cis-2; Ex.
B2

TABLE 1-continued

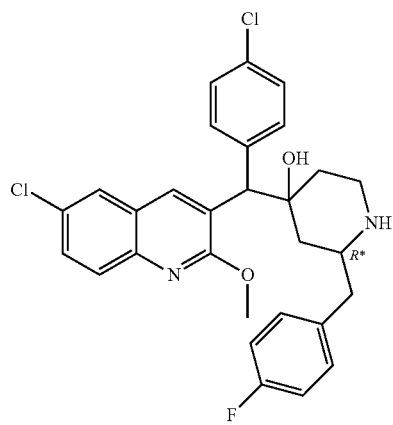

SFC Chiralpak AD-H (5 µm, 250 × 20 mm), iPA
0.3%; gradient CO2/ETIP from 80/20 to 60/40
Co. 345; fumarate; (2R*), trans-1; Ex. B23
Co. 346; fumarate; (2R*), cis-2; Ex. B23
Co. 347; fumarate; (2R*), trans-3; Ex. B23
Co. 348; fumarate; (2R*), cis-4; Ex. B23

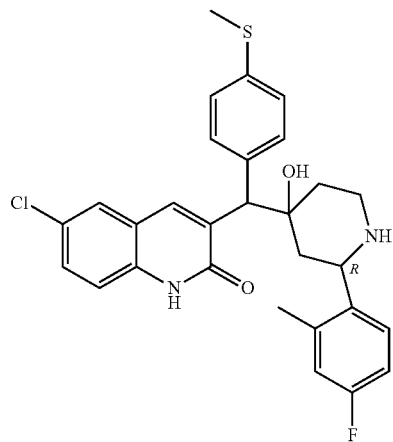

SFC Chiralpak AD-H (5 µm, 250 × 20 mm), iPA
0.3%; CO2 60% iPrOH 40%
Co. 349; hydrochloride; (2R), trans-1; Ex.
B2
Co. 350; hydrochloride; (2R), trans-2; Ex.
B2

TABLE 1-continued

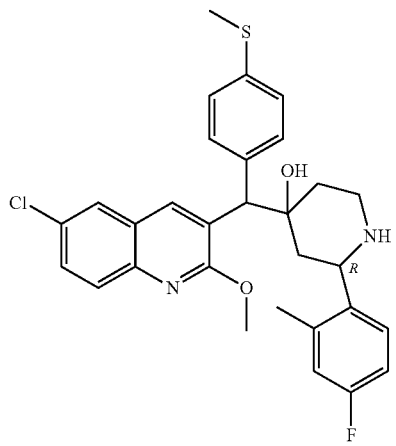

SFC Chiralpak AD-H (5 μm, 250 × 20 mm), iPA 0.3%; CO2 60% iPrOH 40%
Co. 351; (2R), trans-1; Ex. B1
Co. 352; (2R), trans-2; Ex. B1
Co. 353; fumarate; (2R), cis-3; Ex. B1
Co. 354; fumarate; (2R), cis-4; Ex. B1

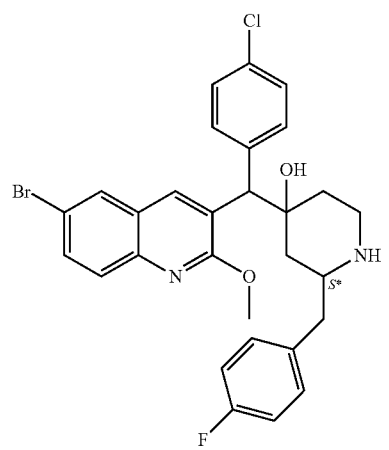

SFC Chiralpak IC (5 μm, 250 × 20 mm), iPA 0.3%; CO2 80% ETIP 20%
Co. 355; (2S*), cis-1; Ex. B25
Co. 356; (2S*), cis-2; Ex. B25
Co. 357; (2S*), trans-3; Ex. B25
Co. 358; (2S*), trans-4; Ex. B25

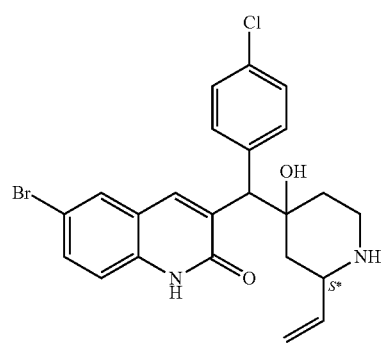

SFC Chiralpak AD-H (5 μm, 250 × 20 mm), iPA 0.3%; CO2 70% EtOH 15% iPrOH 15%
Co. 359; hydrochloride; (2S*), (A); Ex. B6
Co. 360; hydrochloride; (2S*), (B); Ex. B6

TABLE 1-continued

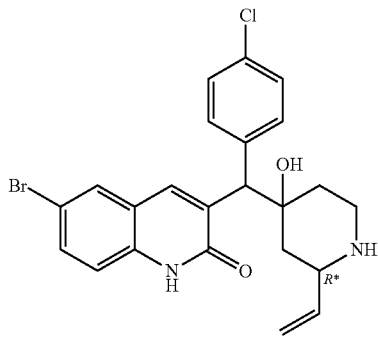

SFC Chiralpak AD-H (5 μm, 250 × 20 mm), iPA 0.3%; CO2 70% EtOH 30%
Co. 361; hydrochloride; (2R*), (A); Ex. B6
Co. 362; hydrochloride; (2R*), (B); Ex. B6

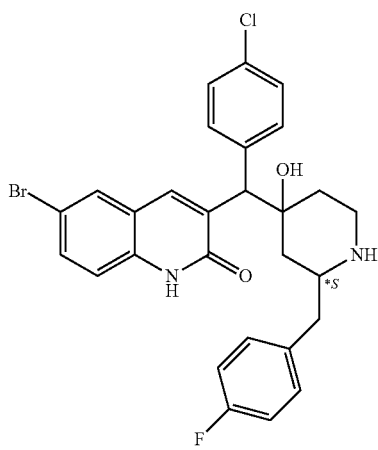

SFC Chiralpak IC (5 μm, 250 × 20 mm), iPA 0.3%; CO2 80% ETIP 20%
Co. 363; hydrochloride; (2S*), cis-1; Ex. B26
Co. 364; hydrochloride; (2S*), trans-4; Ex. B26
Co. 365; hydrochloride; (2S*), cis-2; Ex. B26

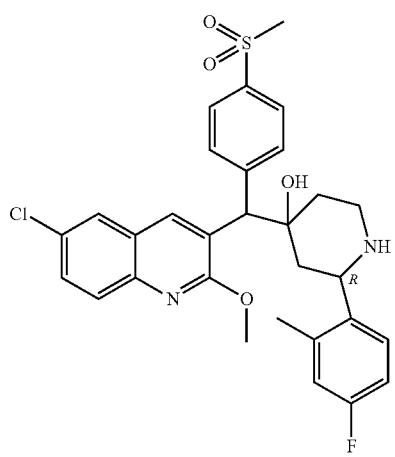

SFC Chiralpak AD-H (5 μm, 250 × 20 mm), iPA 0.3%; CO2 65% EtOH 17.5% iPrOH 17.5%
Co. 366; (2R), trans-1; Ex. B1
Co. 367; (2R), trans-2; Ex. B1
Co. 368; fumarate; (2R), cis-3; Ex. B1
Co. 369; fumarate; (2R), cis-4; Ex. B1

TABLE 1-continued

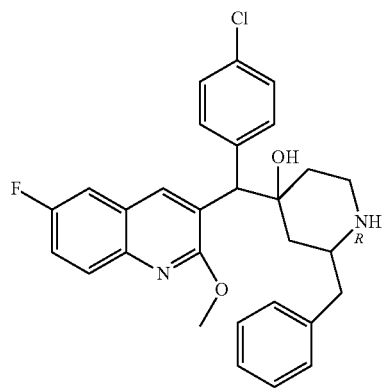

SFC Chiralpak AD-H (5 μm, 250 × 20 mm), iPA
0.3%; CO$_2$ 70% EtOH 15% iPrOH 15%
Co. 52; (2R), cis-1; Ex. B35*
Co. 53; (2R), cis-2; Ex. B35*
Co. 54; fumarate; (2R), trans-3; Ex. B35*
Co. 55; fumarate; (2R), trans-4; Ex. B35*

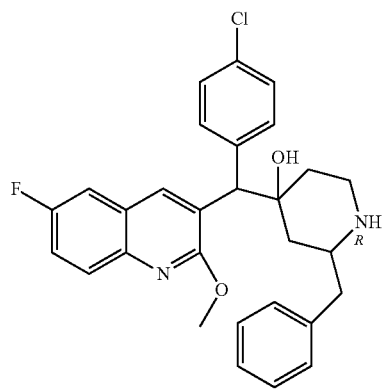

High-performance liquid chromatography
(Irregular SiOH 15-40 μm 300 g MERCK), DCM
98% EtOAc 2%
Co. 370; (B); Ex. B1

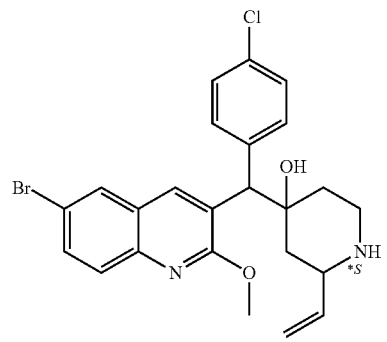

SFC Chiralpak AD-H (5 μm 250 × 20 mm), iPA
0.3%; CO$_2$ 70% EtOH 15% iPrOH 15%
Co. 371; (2S*), (A); Ex. B6
Co. 372; (2S*), (B); Ex. B6

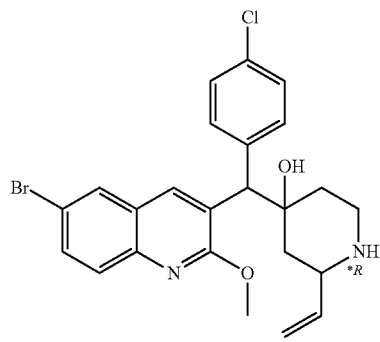

SFC Chiralpak AD-H (5 μm 250 × 20 mm), iPA
0.3%; CO$_2$ 70% EtOH 30%
Co. 373; (2R*), (A); Ex. B6
Co. 374; (2R*), (B); Ex. B6

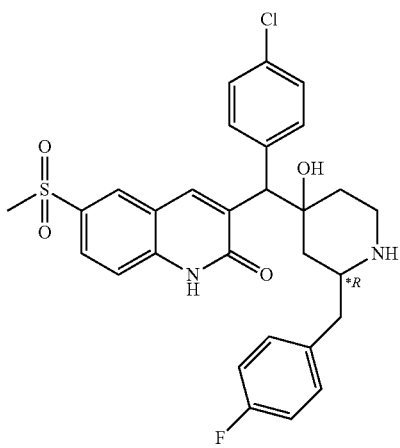

Normal phase on Irregular SiOH (15-40 μm,
300 g MERCK), NH$_4$OH 1%, 90% DCM, 10%
MeOH
Co. 56; (2R*), cis-1; Ex. B36*
Co. 57; (2R*), cis-2; Ex. B36*
Normal phase on Irregular SiOH (15-40 μm,
300 g MERCK), NH$_4$OH 1%, 90% DCM, 10%
MeOH
Co. 58; (2R*), trans-3; Ex. B36*
Co. 59; (2R*), trans-4; Ex. B36*

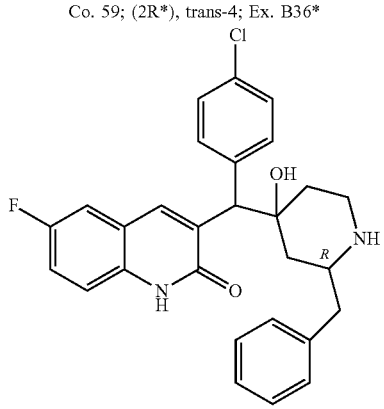

SFC Chiralpak ALPAK AD-H (5 μm,
250 × 20 mm), iPA 0.3%; CO$_2$ 70% EtOH 15%
iPrOH 15%
Co. 375; hydrochloride; (2R), cis-2; Ex.
B36
Co. 376; hydrochloride; (2R), cis-1; Ex.
B36

TABLE 1-continued

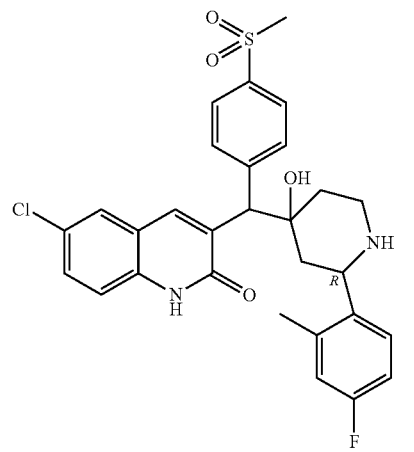

SFC Chiralpak AD-H (5 µm, 250 × 20 mm), iPA
0.3%; CO$_2$ 65% EtOH 17.5% iPrOH 17.5%
Co. 377; hydrochloride; (2R), trans-2;
Ex. B4
Co. 378; hydrochloride; (2R), trans-1; Ex.
B4

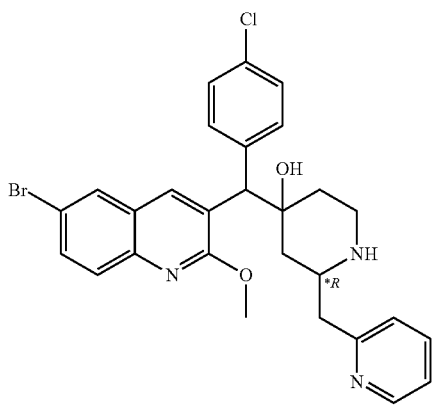

SFC Irregular SiOH (15-40 µm, 300 g MERCK),
Cyclo 80% EtOAc 20%
Co. 60; (2R*), cis-1; Ex. B37*
Co. 379; (2R*), cis-2; Ex. B37

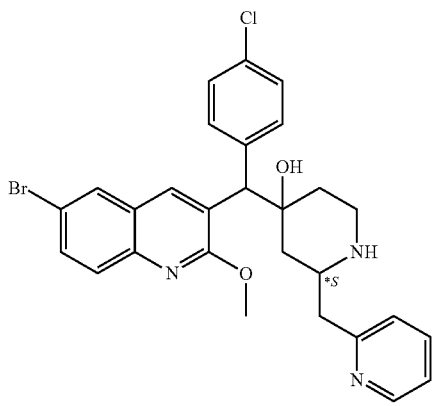

High-performance liquid chromatography
Irregular SiOH (15-40 µm, 300 g MERCK),
Cyclo 80% EtOAc 20%
Co. 380; fumarate; (2S*), cis-1; Ex. B37
Co. 381; (2S*), cis-2; Ex. B37

TABLE 1-continued

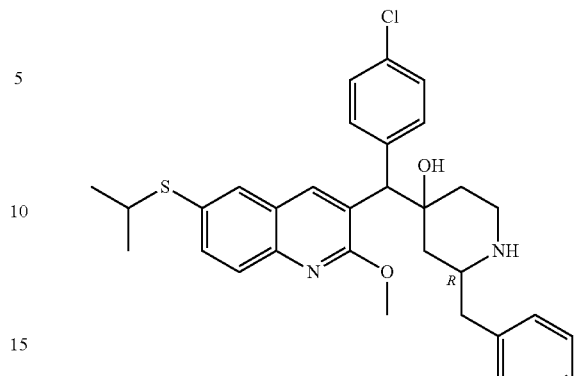

SFC Chiralpak IC (5 µm, 250 × 20 mm), iPA 0.3%;
CO$_2$ 75% MeOH 25%
Co. 382; (2R), cis-4; Ex. B33
Co. 383; (2R), cis-1; Ex. B33
Co. 384; (2R), trans-2; Ex. B33
Co. 385; (2R), trans-3; Ex. B33

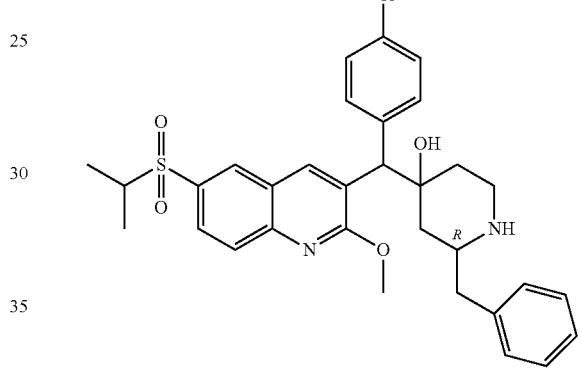

SFC Chiralpak IC (5 µm, 250 × 20 mm), iPA
0.3%; CO$_2$ 75% MeOH 25%
Co. 386; (2R), cis-1; Ex. B24
Co. 387; (2R), cis-4; Ex. B24

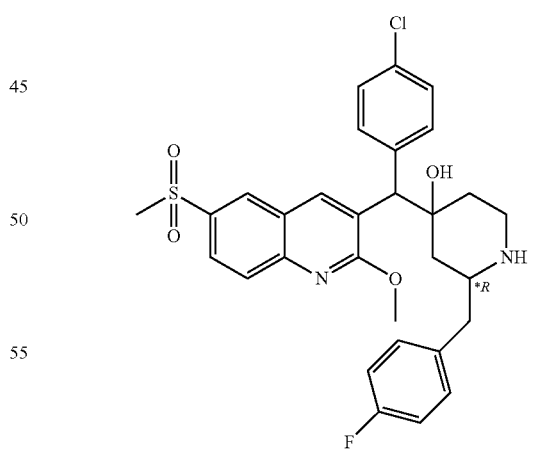

Silica gel (15-40 µm, 300 g MERCK), NH$_4$OH
0.5%, 92% DCM, 8% MeOH
Co. 388; (2R*), cis-1; Ex. B24
SFC Chiralpak AD-H (5 µm, 250 × 20 mm), iPA
0.3%, 65% CO$_2$, 35% (EtOH 50% iPrOH 50%)
Co. 389; (2R*), trans-2; Ex. B24
Co. 390; (2R*), cis-3; Ex. B24
Co. 391; (2R*), trans-4; Ex. B24

TABLE 1-continued

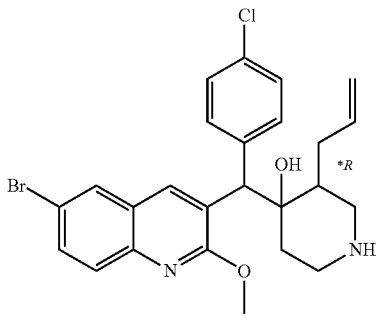

SFC Chiralpak AD-H (5 μm, 250 × 20 mm), iPA
0.3%, 70% CO$_2$, 30% iPrOH
Co. 392; (3R*), (A); Ex. B31
Co. 393; (3R*), (B); Ex. B31

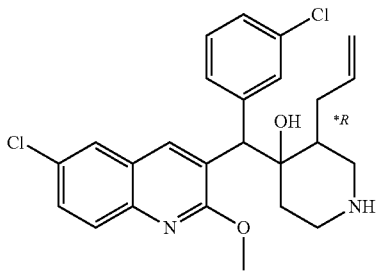

SFC Chiralpak AD-H (5 μm, 250 × 20 mm), iPA
0.3%, 70% CO$_2$, 30% iPrOH
Co. 394; (3R*), (A); Ex. B31
Co. 395; (3R*), (B); Ex. B31

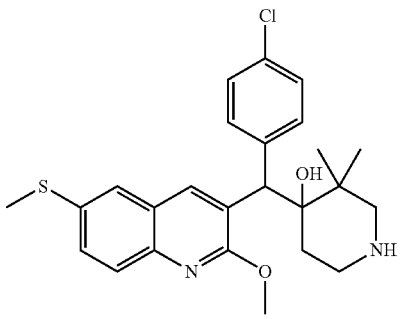 [SMILES: COc1nc2ccc(SC)cc2cc1C(c1ccc(Cl)cc1)C1(O)CCNCC1(C)C]

SFC (Chiralpak AD-H 5 μm, 250 × 20 mm), iPA
0.3%, 70% CO$_2$, 30% EtOH
Co. 62; (S1); Ex B38*
Co. 396; (S2); Ex B38

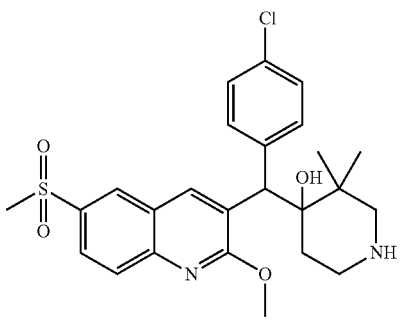 [SMILES: COc1nc2ccc(S(C)(=O)=O)cc2cc1C(c1ccc(Cl)cc1)C1(O)CCNCC1(C)C]

SFC (Chiralpak AD-H 5 μm, 250 × 20 mm), iPA
0.3%, 70% CO$_2$, 30% EtOH
Co. 397; (S1); Ex B38
Co. 398; (S2); Ex B38

TABLE 1-continued

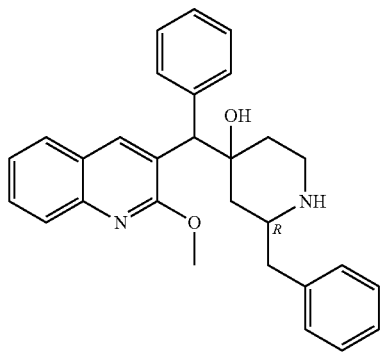

SFC Chiralpak IC (5 μm, 250 × 20 mm), iPA
0.3%, 60% CO$_2$, 40% (EtOH 50% iPrOH 50%)
Co. 399; fumarate; (2R), trans-1; Ex. B12
Co. 400; fumarate; (2R), trans-2; Ex. B12
SFC Chiralpak AD-H (5 μm, 250 × 20 mm), iPA
0.3%, 65% CO$_2$, 35% EtOH
Co. 401; fumarate; (2R), cis-3; Ex. B12
Co. 402; fumarate; (2R), cis-4; Ex. B12

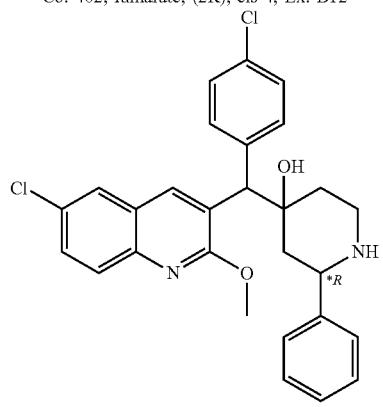

SFC Chiralpak AD-H (5 μm, 250 × 20 mm), iPA
0.3%, 65% CO$_2$, 35% MeOH
Co. 403; fumarate; (2R*), cis-1; Ex. B1
SFC Chiralpak AD-H (5 μm, 250 × 20 mm), iPA
0.3%, 65% CO$_2$, 35% EtOH
Co. 404; fumarate; (2R*), trans-2; Ex. B1
Co. 405; fumarate; (2R*), cis-3; Ex. B1

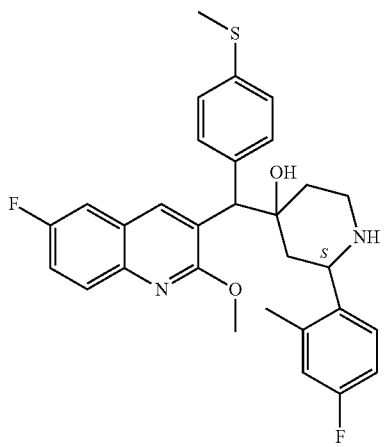

SFC Chiralpak AD-H (5 μm, 250 × 20 mm), 0%
iPA 0.3%, 75% CO$_2$, 25% EtOH
Co. 406; (2S), trans-1; Ex. B1
Co. 407; (2S), trans-2; Ex. B1

TABLE 1-continued

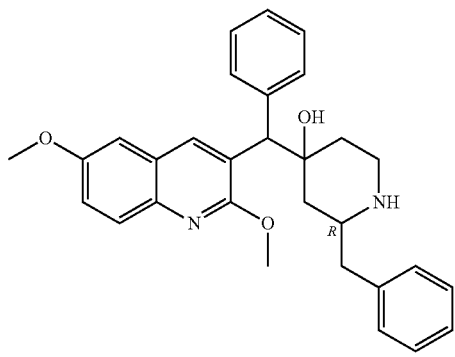

SFC Chiralpak AD-H (5 μm, 250 × 20 mm), iPA
0.3%, 65% CO₂, 35% iPrOH
Co. 408; fumarate; (2R), cis-1; Ex. B23

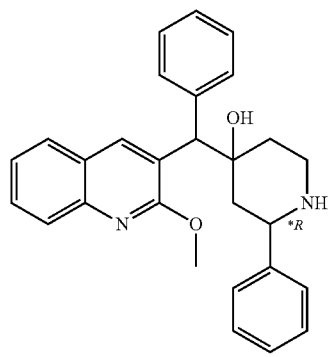

SFC Chiralpak AD-H (5 μm 250 × 20 mm), iPA
0.3%, 70% CO₂, 30% MeOH
Co. 413; fumarate; (2R*), cis-1; Ex. B10
Co. 414; fumarate; (2R*), cis-2; Ex. B10
SFC Chiralpak AD-H (5 μm 250 × 20 mm), iPA
0.3%, 70% CO₂, 30% iPrOH
Co. 415; fumarate; (2R*), trans-1; Ex. B10

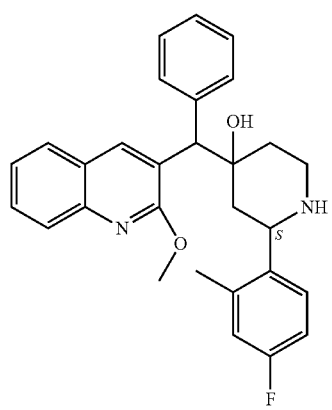

SFC Chiralpak AD-H (5 μm 20 × 250 mm), CO₂
65% EtOH 35% and iPA 0.3% (in MeOH) in
isocratic mode.
Co. 16; fumarate; (2S), trans-2; Ex. B10*

SFC Chiralpak AD-H (5 μm, 250 × 20 mm), iPA
0.3%, 70% CO₂, 30% (EtOH 50% iPrOH 50%)
Co. 409; fumarate; (3R*), (A); Ex. B31
Co. 410; fumarate; (3R*), (B); Ex. B31

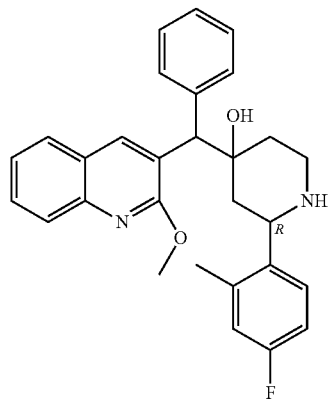

SFC Chiralpak AD-H (5 μm, 250 × 20 mm), iPA
0.3%, 80% CO₂, 20% EtOH
Co. 411; fumarate; (3S*), (A); Ex. B27
Co. 412; fumarate; (3S*), (B); Ex. B27

SFC Chiralpak AD-H (5 μm, 20 × 250 mm),
CO₂ 75% EtOH 25% and iPA 0.3% (in MeOH)
in isocratic mode.
Co. 416; fumarate; (2R), trans-1; Ex. B10

TABLE 1-continued

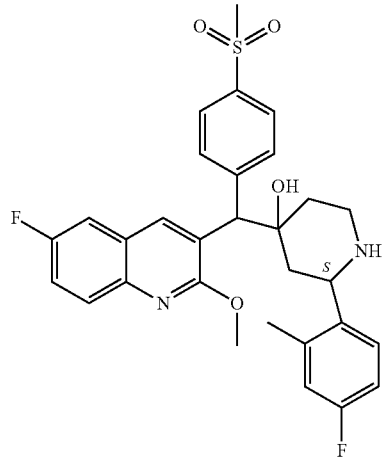

SFC Chiralpak AD-H (5 μm, 250 × 20 mm), iPA
0.3%, 75% CO$_2$, 25% EtOH
Co. 417; (2S), trans-1; Ex. B1
Co. 418; fumarate; (2S), cis-2; Ex. B1
SFC Chiralpak AD-H (5 μm, 250 × 20 mm), iPA
0.3%, 60% CO$_2$, 40% EtOH
Co. 419; (2S), trans-2; Ex. B1

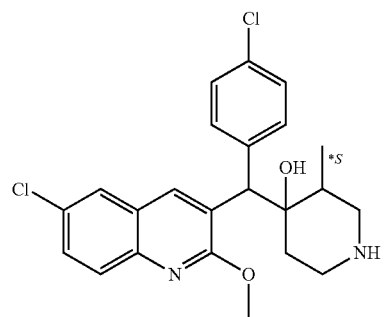

SFC Chiralpak AD-H (5 μm, 250 × 20 mm), 0.3%
iPA, 25% CO$_2$, 75% MeOH
Co. 420; (3S*), (A); Ex. B27
Co. 421; (3S*), (B); Ex. B27

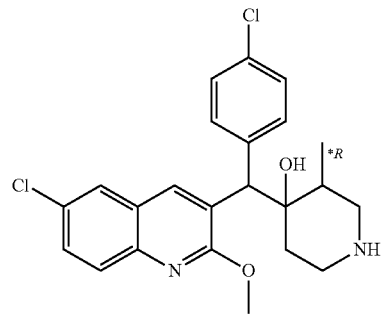

SFC Chiralpak AD-H (5 μm, 250 × 20 mm), 0.3%
iPA, 60% CO$_2$, 40% iPrOH
Co. 422; (3R*), (A); Ex. B27
Co. 423; (3R*), (B); Ex. B27

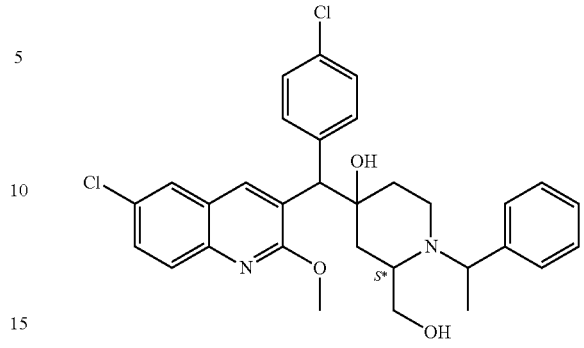

SFC Chiralpak AD-H (5 μm, 250 × 20 mm),
gradient from 0.3% iPA, 60% CO$_2$, 40% EtOH
to 0.3% iPA, 60% CO$_2$, 40% EtOH
Co. 8; (1'S, 2S*), cis-2; Ex. B5*
Co. 9; (1'S, 2S*), cis-1; Ex. B5*

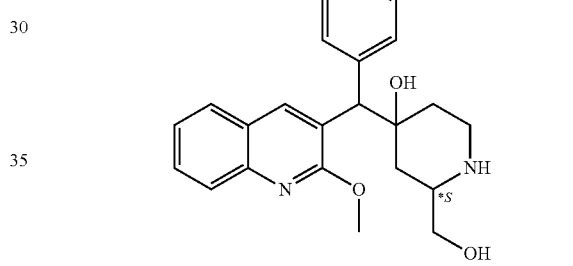

SFC Chiralpak AD-H (5 μm, 250 × 20 mm);
gradient from 0.3% iPA, 60% CO$_2$, 40% EtOH
to 0.3% iPA, 60% CO$_2$, 40% EtOH
Co. 10; (2S*), cis-2; Ex. B5*
Co. 424; (2S*), cis-1; Ex. B5

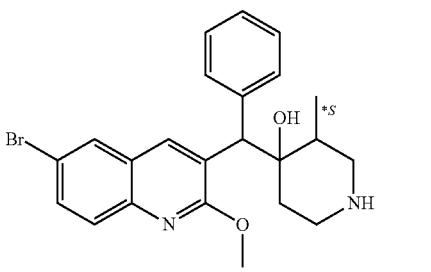

SFC Chiralpak AD-H (5 μm, 250 × 20 mm);
gradient from 0.3% iPA, 70% CO$_2$, 30% iPrOH
to 0.3% iPA, 70% CO$_2$, 30% iPrOH
Co. 425; (3S*), (A); Ex B27
Co. 426; (3S*), (B); Ex. B27

TABLE 1-continued

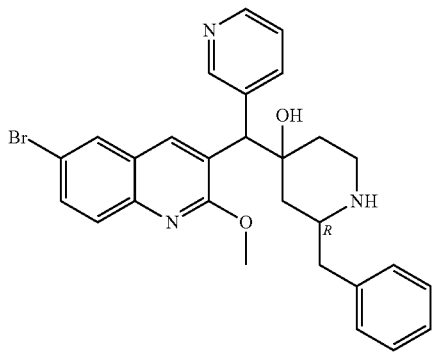

Normal phase on Irregular SiOH (20-45 µm, 450 g MATREX); gradient from 0.1% NH₄OH, 99% DCM, 1% MeOH to 0.1% NH₄OH, 96% DCM, 4% MeOH
Co. 427; fumarate; (2R), cis-1; Ex B35
Co. 428; fumarate; (2R), cis-3; Ex B35

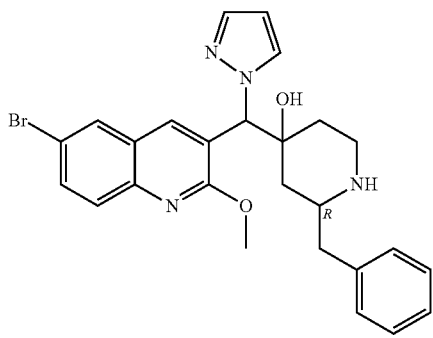

SFC Chiralpak AD-H (5 µm, 250 × 20 mm); gradient from 0.3% iPA, 75% CO₂, 25% MeOH to 0.3% iPA, 75% CO₂, 25% MeOH)
Co. 67; fumarate; (2R), (A); Ex B41*
Co. 429; fumarate; (2R), (B); Ex B41.

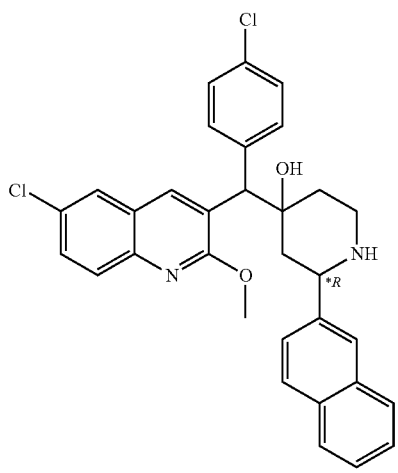

SFC Chiralpak AD-H (5 µm, 250 × 20 mm), 0.3% iPA, 60% CO₂, 40% (EtOH 50% iPrOH 50%)
Co. 43 0; fumarate; (2R*), trans-1; Ex. B 1
Co. 431; fumarate; (2R*), cis-2; Ex. B1
Co. 432; fumarate; (2R*), cis/trans, 25/75; Ex. B1

TABLE 1-continued

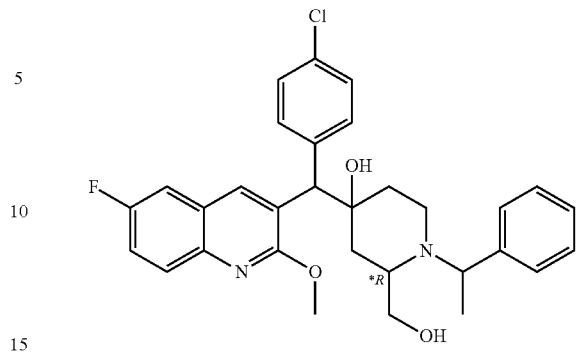

SFC Chiralpak AD-H (5 µm, 250 × 20 mm), 3% iPA, 70% CO₂, 30% EtOH
Co. 13; (2R*), cis-1; Ex. B8*
Co. 14; (2R*), cis-2; Ex. B8*

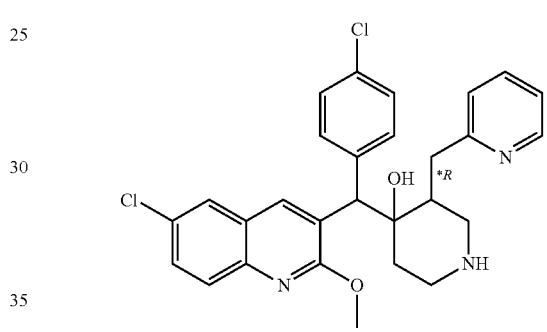

SFC Chiralpak AD-H (5 µm, 250 × 20 mm), 3% iPA, 60% CO₂, 40% (EtOH 50% iPrOH 50%)
Co. 433; (3R*), (A); Ex. B27
Co. 434; (3R*), (B); Ex. B27

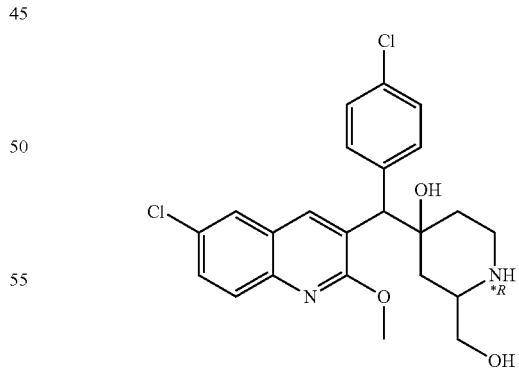

SFC Chiralpak AD-H (5 µm, 250 × 20 mm), 0.3% iPA, 70% CO₂, 30% (EtOH 50% iPrOH 50%)
Co. 12; (2R*), cis-2; Ex. B7*

TABLE 1-continued

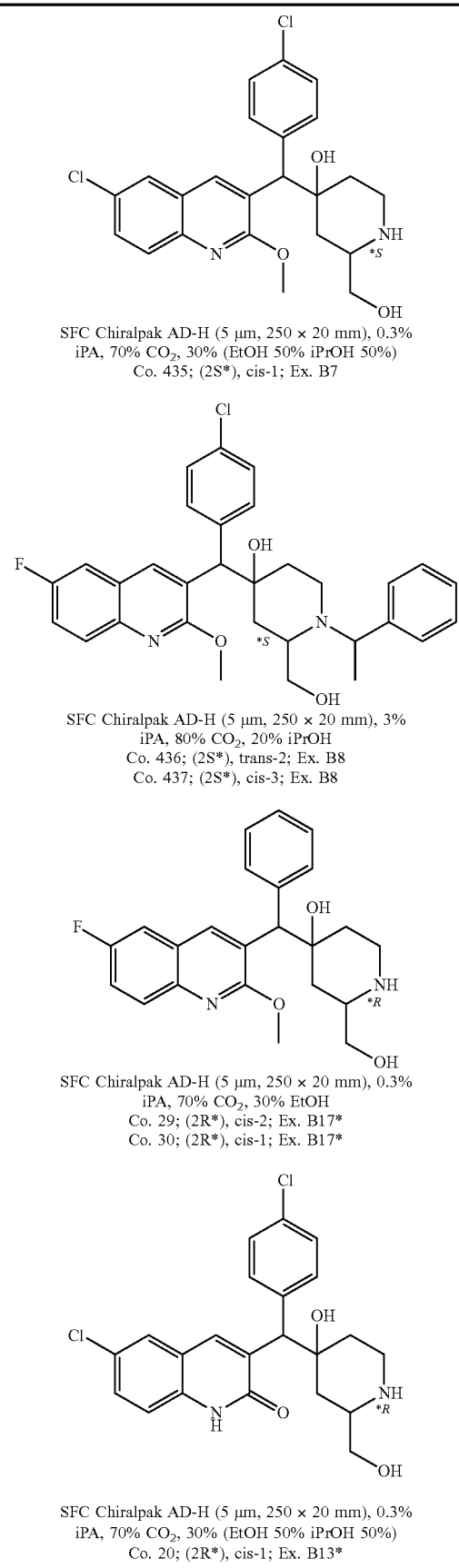

SFC Chiralpak AD-H (5 µm, 250 × 20 mm), 0.3%
iPA, 70% CO$_2$, 30% (EtOH 50% iPrOH 50%)
Co. 435; (2S*), cis-1; Ex. B7

SFC Chiralpak AD-H (5 µm, 250 × 20 mm), 3%
iPA, 80% CO$_2$, 20% iPrOH
Co. 436; (2S*), trans-2; Ex. B8
Co. 437; (2S*), cis-3; Ex. B8

SFC Chiralpak AD-H (5 µm, 250 × 20 mm), 0.3%
iPA, 70% CO$_2$, 30% EtOH
Co. 29; (2R*), cis-2; Ex. B17*
Co. 30; (2R*), cis-1; Ex. B17*

SFC Chiralpak AD-H (5 µm, 250 × 20 mm), 0.3%
iPA, 70% CO$_2$, 30% (EtOH 50% iPrOH 50%)
Co. 20; (2R*), cis-1; Ex. B13*

TABLE 1-continued

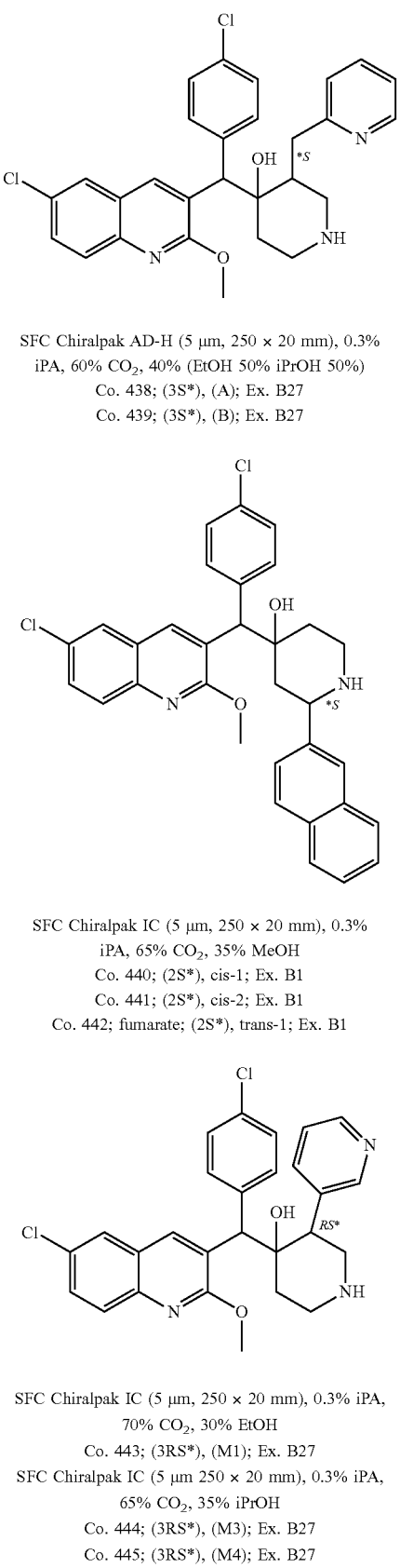

SFC Chiralpak AD-H (5 µm, 250 × 20 mm), 0.3%
iPA, 60% CO$_2$, 40% (EtOH 50% iPrOH 50%)
Co. 438; (3S*), (A); Ex. B27
Co. 439; (3S*), (B); Ex. B27

SFC Chiralpak IC (5 µm, 250 × 20 mm), 0.3%
iPA, 65% CO$_2$, 35% MeOH
Co. 440; (2S*), cis-1; Ex. B1
Co. 441; (2S*), cis-2; Ex. B1
Co. 442; fumarate; (2S*), trans-1; Ex. B1

SFC Chiralpak IC (5 µm, 250 × 20 mm), 0.3% iPA,
70% CO$_2$, 30% EtOH
Co. 443; (3RS*), (M1); Ex. B27
SFC Chiralpak IC (5 µm 250 × 20 mm), 0.3% iPA,
65% CO$_2$, 35% iPrOH
Co. 444; (3RS*), (M3); Ex. B27
Co. 445; (3RS*), (M4); Ex. B27

TABLE 1-continued

SFC Chiralpak AD-H (5 μm, 250 × 20 mm), 0.3%
iPA, 70% CO$_2$, 30% (EtOH 50% iPrOH 50%)
Co. 446; (2S*), cis-2; Ex. B13

Silica gel (15-40 μm, 30 g), 0.5% NH$_4$OH, 95%
DCM, 5% MeOH
Co. 65; (3R*), (A); Ex B40*.
Co. 66; (3R*), (B); Ex B40*

Silica gel (Cartridge 15-40 μm 30 g), 0.5%
NH$_4$OH, 95% DCM, 5% MeOH
Co. 447; (3S*), (A); Ex B40
Co. 448; (3S*), (B); Ex B40.

TABLE 1-continued

SFC Chiralpak IC (5 μm, 250 × 20 mm), 0.3% iPA,
75% CO$_2$, 25% (EtOH 50% iPrOH 50%)
Co. 449; (3R*), cis-2; Ex. B27
SFC Chiralpak IC (5 μm, 250 × 20 mm), 0.3% iPA,
70% CO$_2$, 30% iPrOH
Co. 450; (3R*), cis-3; Ex. B27
SFC Chiralpak AD-H (5 μm, 250 × 20 mm), 0.3%
iPA, 75% CO$_2$, 25% MeOH
Co. 451; (3R*), trans-1; Ex. B27
SFC Chiralpak IC (5 μm, 250 × 20 mm), 0.3% iPA,
70% CO$_2$, 30% iPrOH
Co. 452; (3R*), trans-2; Ex. B27

SFC Chiralpak IC (5 μm, 250 × 20 mm), 0.3%
iPA, 75% CO$_2$, 25% (EtOH 50% iPrOH 50%)
Co. 453; (3S*), cis-1; Ex. B27
SFC Chiralpak IC (5 μm, 250 × 20 mm), 0.3%
iPA, 70% CO$_2$, 30% iPrOH
Co. 454; (3S*), cis-4; Ex. B27
SFC Chiralpak IC (5 μm, 250 × 20 mm), 0.3%
iPA, 70% CO$_2$, 30% iPrOH
Co. 455; (3S*), trans-3; Ex. B27
Co. 456; (3S*), trans-4; Ex. B27

TABLE 1-continued

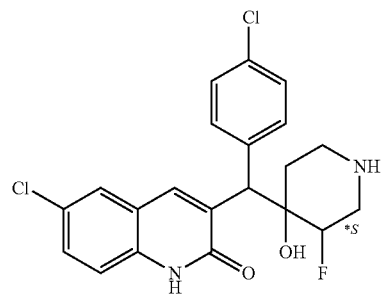

SFC Chiralpak IC (5 µm, 250 × 20 mm), 0.3% iPA,
75% CO₂, 25% (EtOH 50% iPrOH 50%)
Co. 457; hydrochloride; (3S*), cis-1;
Ex. B32

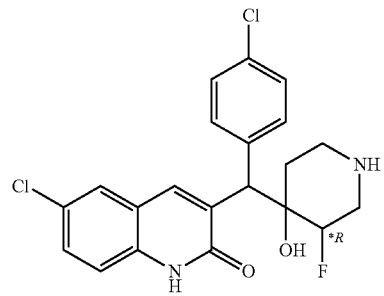

SFC Chiralpak IC (5 µm, 250 × 20 mm), 0.3%
iPA, 75% CO₂, 25% (EtOH 50% iPrOH 50%)
Co. 458; hydrochloride; (3R*), cis-2; Ex.
B32

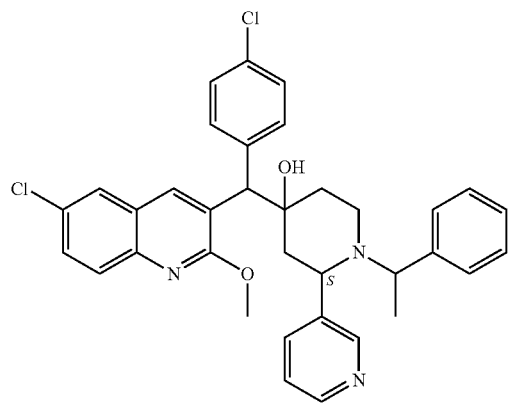

SFC Chiralpak AD-H (5 µm, 250 × 20 mm), 0.3%
iPA, 50% CO₂, 50% (EtOH 50% iPrOH 50%)
Co. 22; (2S), trans-2; Ex. B14*
Co. 23; (2S), cis-3; Ex. B14*
Co. 24; (2S), cis-4; Ex. B14*
Co. 21; (2S), trans-1; Ex. B14*

TABLE 1-continued

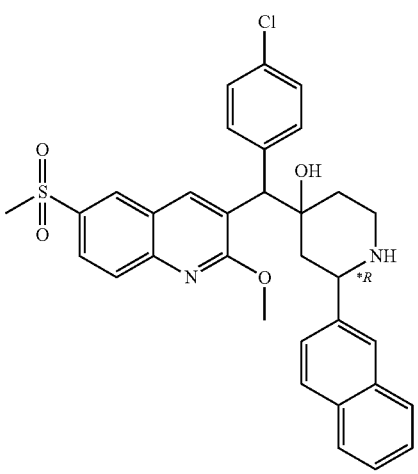

SFC Chiralpak AD-H (5 µm, 250 × 20 mm), 0.3%
iPA, 50% CO₂, 50% iPrOH
Co. 459; (2R*), cis-1; Ex. B24
SFC Chiralpak AD-H (5 µm, 250 × 20 mm), 0.3%
iPA, 55% CO₂, 45% iPrOH
Co. 460; (2R*), cis-2; Ex. B24
Co. 461; (2R*), trans-1; Ex. B24
SFC Chiralpak AD-H (5 µm, 250 × 20 mm), 0.3%
iPA, 50% CO₂, 50% iPrOH
Co. 462; (2R*), trans-2; Ex. B24

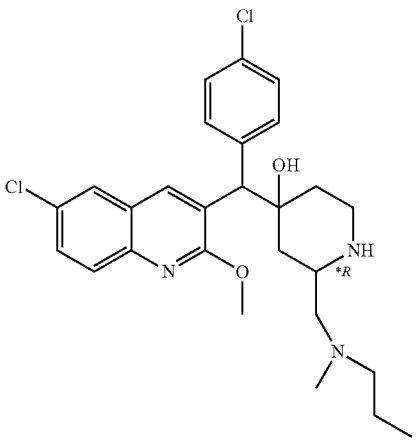

SFC Chiralpak AD-H (5 µm, 250 × 20 mm), 0.3%
iPA, 60% CO₂, 40% EtOH
Co. 63; (2R*), cis-1; Ex B39*
Co. 64; fumarate; (2R*), cis-2; Ex B39*.

TABLE 1-continued

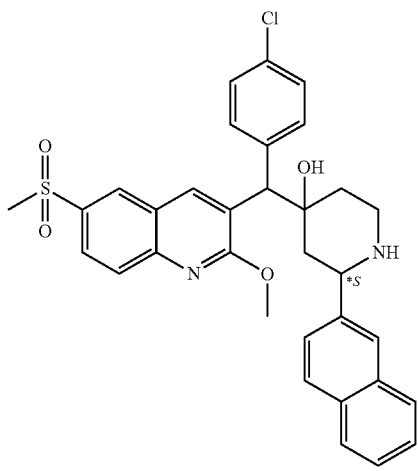

Normal phase on Irregular SiOH (20-45 µm,
450 g MATREX); gradient from 97% NH₄OH,
3% DCM, 0.1% MeOH to 93% NH₄OH, 7%
DCM, 0.5% MeOH).
Co. 463; (2S*), cis-1; Ex. B36
Co. 464; (2S*), cis-2; Ex. B36
Co. 465; (2S*), trans-3; Ex. B36
SFC Chiralpak AD-H (5 µm 250 × 20 mm), 0.3%
iPA, 65% CO₂, 35% EtOH 50% iPrOH 50%
Co. 466; (2S*), trans-4; Ex. B36

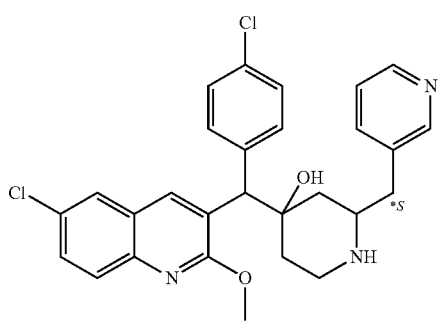

Silica gel (15-40 µm, 437mg), Cyclo/EtOAc
60/40
Co. 467; (2S*), cis-mixture 45/55; Ex. B37

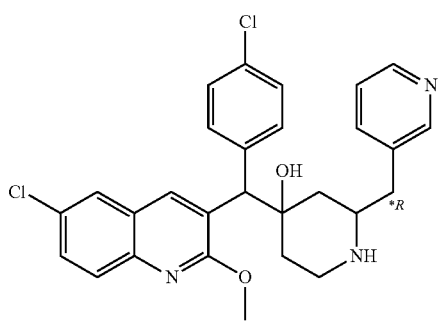

Silica gel (15-40 µm, 540 mg), Cyclo/EtOAc
60/40
Co. 468; (2R*), cis-mixture 60/40; Ex.
B37

TABLE 1-continued

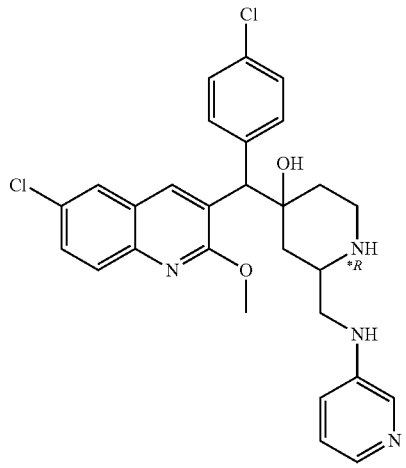

Silica gel (15-40 µm, 400 g), Cyclo 100 to
Cyclo/EtOAc 90/10
Co. 469; (2R*), cis; Ex B39.

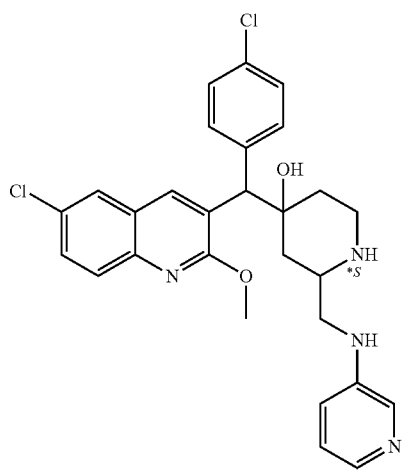

Silica gel (15-40 µm, 400 g), Cyclo 100 to
Cyclo/EtOAc 90/10)
Co. 470; (2S*), cis; Ex B39.

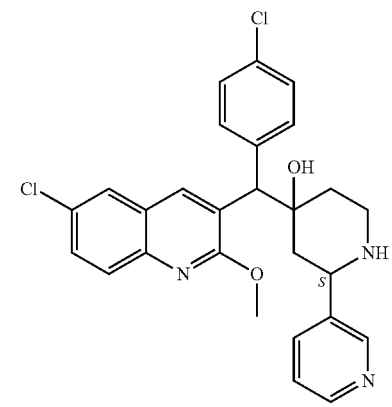

SFC Chiralpak AD-H (5 µm 250 × 20 mm), 0.3%
iPA, 50% CO₂, 50% (EtOH 50% iPrOH 50%)
Co. 471; (2S), cis-4; Ex. B16
Co. 28; (2S), cis-3; Ex. B16*

TABLE 1-continued

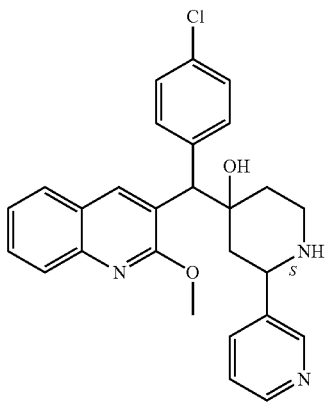

SFC Chiralpak AD-H (5 μm, 250 × 20 mm), 0.3%
iPA, 50% CO₂, 50% (EtOH 50% iPrOH 50%)
Co. 27; (2S), cis-3; Ex. B16*

C. Analytical Methods

C 1. LCMS

The mass of some compounds was recorded with LCMS (liquid chromatography mass spectrometry). The methods used are described below.

General Procedure A:

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters—for method 1, and 3.15 kV at 110° C. on the ZQ™ (simple quadrupole Zspray™ mass spectrometer from Waters—for methods 2 and 3. Nitrogen was used as the nebulizer gas. Data acquisition was performed with a Waters-Micromass MassLynx-Openlynx data system.

General Procedure B

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method 1

In Addition to the General Procedure A:

Reversed phase HPLC was carried out on a Kromasil C18 column (5 μm, 4.6×150 mm) with a flow rate of 1.0 ml/min. Three mobile phases (mobile phase A: 100% 7 mM ammonium acetate; mobile phase B: 100% acetonitrile; mobile phase C: 0.2% formic acid+99.8% ultra-pure Water) were employed to run a gradient condition from 30% A, 40% B and 30% C (hold for 1 minute) to 100% B in 4 minutes, 100% B for 5 minutes and reequilibrated with initial conditions for 3 minutes. An injection volume of 5 μl was used. Cone voltage was 20 V for positive and negative ionization mode. Mass spectra were acquired by scanning from 100 to 900 in 0.8 seconds using an interscan delay of 0.08 seconds.

Method 2

In Addition to the General Procedure A:

Reversed phase HPLC was carried out on a X-Bridge C18 column (3.5 μm, 4.6×100 mm) with a flow rate of 0.8 ml/min. Two mobile phases (mobile phase A: 100% 7 mM ammonium acetate; mobile phase B: 100% acetonitrile; were employed to run a gradient condition from 80% A, 20% B (hold for 0.5 minute) to 10% A, 90% B in 4.5 minutes, hold at 10% A and 90% B for 4 minutes and reequilibrated with initial conditions for 3 minutes. An injection volume of 10 μl was used. Cone voltage was 20 V for positive and negative ionization mode. Mass spectra were acquired by scanning from 100 to 1000 in 0.4 seconds using an interscan delay of 0.3 seconds.

Method 3

In Addition to the General Procedure A:

Reversed phase HPLC was carried out on a Sunfire C18 column (3.5 μm, 4.6×100 mm) with an initial flow rate of 0.8 ml/min. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A (hold for 1 minute) to 100% B in 4 minutes, hold at 100% B at a flow rate of 1.2 ml/min for 4 minutes and reequilibrated with initial conditions for 3 minutes. An injection volume of 10 μl was used. Positive ionization mode was used with four different cone voltages (20,40,50,55 V). Mass spectra were acquired by scanning from 100 to 1000 in 0.4 seconds using an interscan delay of 0.1 seconds.

Method 4

In Addition to the General Procedure B:

Reversed phase UPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

Method 5

In Addition to the General Procedure B:

Reversed phase UPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltages were 20, 30, 45, 60 V for positive ionization mode. Mass spectra were acquired by scanning from 100 to 1000 in 0.2 seconds using an interscan delay of 0.1 seconds.

Method 6

In Addition to the General Procedure B:

Reversed phase UPLC was carried out on a Thermo Hypersil Gold C18 column (1.9 μm, 2.1×100 mm) with a flow rate of 0.40 ml/min. Two mobile phases (mobile phase A: 95% 7 mM ammonium acetate/5% acetonitrile; mobile phase B: 100% acetonitrile) were employed to run a gradient condition from 72% A and 28% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

Method 7

In Addition to the General Procedure B:

Reversed phase UPLC was carried out on a Thermo Hypersil Gold C18 column (1.9 μm, 2.1×100 mm) with a flow rate of 0.40 ml/min. Two mobile phases (mobile phase A: 95% 7 mM ammonium acetate/5% acetonitrile; mobile phase B: 100% acetonitrile) were employed to run a gradient condition from 72% A and 28% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltages were 20, 30, 45, 60 V for positive ionization mode. Mass spectra were acquired by scanning from 100 to 1000 in 0.2 seconds using an interscan delay of 0.1 seconds.

Method 8

In Addition to the General Procedure B:

Reversed phase UPLC was carried out on a Thermo Hypersil Gold C18 column (1.9 μm, 2.1×100 mm) with a flow rate of 0.50 ml/min. Two mobile phases (mobile phase A: 95% 7 mM ammonium acetate/5% acetonitrile; mobile phase B: 100% acetonitrile) were employed to run a gradient condition from 40% A and 60% B (hold for 0.5 minutes) to 5% A and 95% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

Method 9

In Addition to the General Procedure B:

Reversed phase UPLC was carried out on a Waters HSS (High Strength Silica) C18 column (1.8 μm, 2.1×100 mm) with a flow rate of 0.40 ml/min. Two mobile phases (mobile phase A: 95% 7 mM ammonium acetate/5% acetonitrile; mobile phase B: 100% acetonitrile) were employed to run a gradient condition from 72% A and 28% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

Method 10

In Addition to the General Procedure B:

Reversed phase UPLC was carried out on a Waters HSS (High Strength Silica) C18 column (1.8 μm, 2.1×100 mm) with a flow rate of 0.40 ml/min. Two mobile phases (mobile phase A: 95% 7 mM ammonium acetate/5% acetonitrile; mobile phase B: 100% acetonitrile) were employed to run a gradient condition from 50% A and 50% B (hold for 0.5 minutes) to 3% A and 97% B in 3.5 minutes, hold for 4.5 min and back to the initial conditions in 0.5 min, hold for 1.0 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

When a compound is a mixture of isomers which give different peaks in the LCMS method, only the retention time of the main component is given in the LCMS table. In the following table the LCMS data is given as (MH$^+$), protonated molecular ion (of the free base), and retention time (Rt, in minutes).

C2. Optical Rotation

The optical rotation was measured using a polarimeter. $[\alpha]_D^{20}$ indicates the optical rotation measured with light at the wavelength of the D-line of sodium (589 nm) at a temperature of 20° C. The cell pathlength is 1 dm. After $[\alpha]_D^{20}$ value the temperature, concentration and solvent of the solution which was used to measure the optical rotation are indicated.

C3. Melting Points

For a number of compounds, melting points were obtained with a Kofler hot bench, consisting of a heated plate with linear temperature gradient, a sliding pointer and a temperature scale in degrees Celsius.

TABLE 2

| Co. | Optical Rotation $[\alpha]_D^{20}$ | MP (° C.) (Kofler) | Rt | (MH+) | LCMS Method |
|---|---|---|---|---|---|
| 25 | | 154 | 5.91 | 567 | 1 |
| 26 | | 238 | 5.77 | 567 | 1 |
| 68 | | | 5.67 | 629 | 3 |
| 69 | | | 5.47 | 629 | 3 |
| 70 | +116.21° (589 nm, c 0.3485 w/v %, DMF, 20° C.) | 112 | 4.53 | 553 | 5 |
| 31 | −210.78° (589 nm, c 0.3525 w/v %, DMF, 20° C.) | 183 | 4.21 | 553 | 9 |
| 71 | −133.33° (589 nm, c 0.3075 w/v %, DMF, 20° C.) | 138 | 4.49 | 553 | 5 |
| 32 | +132.57° (589 nm, c 0.307 w/v %, DMF, 20° C.) | | 4.5 | 553 | 5 |
| 72 | +92.09° (589 nm, c 0.493 w/v %, DMF, 20° C.) | | 3.56 | 519 | 7 |
| 73 | −104.74° (589 nm, c 0.2635 w/v %, DMF, 20° C.) | | 3.48 | 519 | 7 |
| 74 | −226.18° (589 nm, c 0.3935 w/v %, DMF, 20° C.) | 157 | 3.59 | 519 | 7 |

TABLE 2-continued

| Co. | Optical Rotation $[\alpha]_D^{20}$ | MP (° C.) (Kofler) | Rt | (MH+) | LCMS Method |
|---|---|---|---|---|---|
| 75 | | 192 | 5.4 | 641 | 7 |
| 76 | | 148 | 5.36 | 641 | 7 |
| 77 | −108.52° (589 nm, c 0.399 w/v %, DMF, 20° C.) | 155 | 4.21 | 553 | 6 |
| 78 | +132.15° (589 nm, c 0.311 w/v %, DMF, 20° C.) | 130 | 4.18 | 553 | 6 |
| 79 | −141.91° (589 nm, c 0.241 w/v %, DMF, 20° C.) | | 4.14 | 551 | 6 |
| 33 | +232.66° (589 nm, c 0.297 w/v %, DMF, 20° C.) | 177 | 4.28 | 551 | 6 |
| 80 | | | 3.95 | 550 | 4 |
| 81 | | 233 | 3.02 | 537 | 6 |
| 82 | | 230 | 4.11 | 565 | 6 |
| 83 | | 219 | 4.08 | 567 | 6 |
| 19 | | | 3.68 | 473 | 6 |
| 84 | | 238 | 3.34 | 551 | 6 |
| 17 | | | 4.77 | 567 | 6 |
| 35 | +77.49° (589 nm, c 0.422 w/v %, DMF, 20° C.) | 145 | 4.6 | 553 | 6 |
| 34 | −188.97° (589 nm, c 0.435 w/v %, DMF, 20° C.) | 152 | 4.71 | 553 | 6 |
| 85 | | >260 | 3.19 | 539 | 6 |
| 86 | | >260 | 3.54 | 539 | 6 |
| 87 | | 227 | 5.08 | 569 | 6 |
| 88 | | 194 | 5.91 | 569 | 4 |
| 89 | | | 4.75 | 569 | 6 |
| 36 | | 120 | 3.6 | 550 | 6 |
| 15 | | 220 | 3.74 | 550 | 6 |
| 90 | +123.45° (589 nm, DMF, 20° C.) | 140 | 4.26 | 519 | 6 |
| 91 | −312.78° (589 nm, DMF, 20° C.) | 214 | 4.42 | 519 | 6 |
| 92 | −168.5° (589 nm, DMF, 20° C.) | 114 | 4.4 | 519 | 6 |
| 93 | +170.91° (589 nm, DMF, 20° C.) | >250 | 4.44 | 519 | 6 |
| 37 | | 107 | 3.91 | 507 | 9 |
| 94 | | 168 | 4.61 | 507 | 6 |
| 95 | +67.75° (589 nm, c 0.276 w/v %, DMF, 20° C.) | | 5.02 | 507 | 4 |
| 96 | | 114 | 3.88 | 507 | 9 |
| 97 | | 120 | 1.12 | 551 | 8 |
| 38 | | 130 | 3.02 | 551 | 9 |
| 98 | +175.98° (589 nm, c 0.358 w/v %, DMF, 20° C.) | | 4.58 | 565 | 6 |
| 99 | −277.47° (589 nm, c 0.435 w/v %, DMF, 20° C.) | 214 | 4.61 | 565 | 6 |
| 100 | −172.22° (589 nm, c 0.36 w/v %, DMF, 20° C.) | 143 | 4.65 | 565 | 6 |
| 101 | | | 3.71 | 565 | 9 |
| 102 | | 145 | 3.04 | 597 | 9 |
| 103 | | 135 | 2.8 | 597 | 9 |
| 104 | +77.22° (589 nm, c 0.259 w/v %, DMF, 20° C.) | 160 | 4.65 | 571 | 9 |
| 105 | −200.57° (589 nm, c 0.348 w/v %, DMF, 20° C.) | 149 | 4.57 | 571 | 9 |
| 106 | +7.14° (589 nm, c 0.364 w/v %, DMF, 20° C.) | >250 | 3.92 | 557 | 4 |
| 107 | | | 4.24 | 555 | 4 |
| 7 | +78.57° (589 nm, c 0.224 w/v %, DMF, 20° C.) | | 3.96 | 557 | 4 |
| 108 | +129.48° (589 nm, c 0.363 w/v %, DMF, 20° C.) | | 4.57 | 571 | 9 |
| 109 | | | 3.83 | 575 | 4 |
| 110 | −59.06° (589 nm, c 0.254 w/v %, DMF, 20° C.) | | 3.95 | 557 | 4 |
| 111 | +185.84° (589 nm, c 0.353 w/v %, DMF, 20° C.) | 111 | 5.05 | 589 | 4 |
| 39 | −115.3° (589 nm, c 0.3365 w/v %, DMF, 20° C.) | 106 | 4.98 | 589 | 4 |
| 112 | +78.52° (589 nm, c 0.284 w/v %, DMF, 20° C.) | 124 | 5.24 | 589 | 4 |
| 113 | −178.74° (589 nm, c 0.334 w/v %, DMF, 20° C.) | 130 | 5.07 | 589 | 4 |
| 114 | | | 3.9 | 553 | 9 |
| 115 | | | 4.39 | 542 | 4 |
| 116 | | 153 | 4.26 | 544 | 4 |
| 41 | | | 3.9 | 553 | 9 |
| 117 | | | 3.82 | 553 | 9 |
| 118 | | | 2.48 | 517 | 4 |

TABLE 2-continued

| Co. | Optical Rotation $[\alpha]_D^{20}$ | MP (° C.) (Kofler) | Rt | (MH+) | LCMS Method |
|---|---|---|---|---|---|
| 119 | | 215 | 1.76 | 537 | 9 |
| 120 | −109.96° (589 nm, c 0.281 w/v %, DMF, 20° C.) | | 5.33 | 537 | 2 |
| 121 | | >260 | 3.93 | 539 | 4 |
| 122 | | >260 | 3.96 | 539 | 4 |
| 123 | −182.89° (589 nm, c 0.339 w/v %, DMF, 20° C.) | 210 | 3.33 | 477 | 9 |
| 11 | +189.15° (589 nm, c 0.3225 w/v %, DMF, 20° C.) | 143 | 3.34 | 477 | 9 |
| 124 | −203.73° (589 nm, c 0.295 w/v %, DMF, 20° C.) | 164 | 3.32 | 477 | 9 |
| 125 | +183° (589 nm, c 0.3235 w/v %, DMF, 20° C.) | 210 | 3.32 | 477 | 9 |
| 126 | | >260 | 2.96 | 575 | 9 |
| 127 | | >260 | 3.09 | 575 | 9 |
| 40 | +48.62° (589 nm, c 0.3435 w/v %, DMF, 20° C.) | 224 | 3.74 | 575 | 4 |
| 128 | | | 3.84 | 539 | 4 |
| 129 | | 240 | 3.39 | 463 | 4 |
| 130 | | 200 | 3.44 | 463 | 4 |
| 131 | | 241 | 3.45 | 463 | 4 |
| 132 | | 244 | 3.39 | 463 | 4 |
| 133 | −57.52° (589 nm, c 0.412 w/v %, DMF, 20° C.) | >260 | 3.81 | 575 | 4 |
| 134 | +32.2° (589 nm, c 0.1615 w/v %, DMF, 20° C.) | 233 | 4.04 | 575 | 4 |
| 135 | | >250 | 3.49 | 557 | 9 |
| 136 | | >250 | 3.26 | 557 | 9 |
| 137 | | >250 | 3.26 | 557 | 9 |
| 138 | | >250 | 3.06 | 557 | 9 |
| 139 | | 130 | 3.66 | 509 | 9 |
| 140 | | | 3.6 | 509 | 9 |
| 141 | | 155 | 3.35 | 485 | 9 |
| 142 | | 190 | 3.43 | 485 | 9 |
| 143 | | >250 | 3.44 | 557 | 9 |
| 144 | | >250 | 3.2 | 557 | 9 |
| 145 | | >250 | 3.2 | 557 | 9 |
| 146 | | >250 | 3 | 557 | 9 |
| 147 | | | 4.19 | 537 | 9 |
| 148 | | | 4.22 | 537 | 9 |
| 149 | | 178 | 4.85 | 571 | 9 |
| 150 | | 184 | 4.52 | 571 | 9 |
| 151 | | 156 | 4.89 | 571 | 9 |
| 152 | | 170 | 4.65 | 571 | 9 |
| 153 | +63.31° (589 nm, c 0.387 w/v %, DMF, 20° C.) | 183 | 2.54 | 503 | 4 |
| 154 | +63.19° (589 nm, c 0.288 w/v %, DMF, 20° C.) | 250 | 2.94 | 503 | 4 |
| 155 | −67.85° (589 nm, c 0.3095 w/v %, DMF, 20° C.) | 194 | 2.65 | 503 | 4 |
| 156 | −128.4° (589 nm, c 0.3715 w/v %, DMF, 20° C.) | 254 | 2.94 | 503 | 4 |
| 157 | +85.21° (589 nm, c 0.311 w/v %, DMF, 20° C.) | 100 | 2.28 | 517 | 9 |
| 158 | −202.71° (589 nm, c 0.295 w/v %, DMF, 20° C.) | 198 | 2.53 | 517 | 9 |
| 159 | | >250 | 3.05 | 555 | 4 |
| 42 | | >250 | 3.44 | 555 | 4 |
| 160 | | >250 | 3.99 | 523 | 4 |
| 161 | | >250 | 3.8 | 523 | 4 |
| 162 | | >250 | 3.78 | 523 | 4 |
| 163 | | | 4.24 | 537 | 9 |
| 164 | | 170 | 4.55 | 537 | 9 |
| 165 | | 168 | 4.57 | 537 | 9 |
| 166 | | 168 | 5.01 | 537 | 4 |
| 167 | | | 3.74 | 503 | 9 |
| 168 | | 169 | 3.79 | 503 | 9 |
| 169 | | 169 | 4.15 | 503 | 9 |
| 170 | | 176 | 4.1 | 503 | 9 |
| 171 | | 161 | 3.29 | 569 | 9 |
| 172 | | 170 | 3.11 | 569 | 9 |
| 173 | | | 4.7 | 571 | 9 |
| 174 | | 171 | 3.79 | 523 | 4 |
| 175 | | 194 | 4.05 | 523 | 4 |
| 176 | | 192 | 3.78 | 523 | 4 |
| 177 | | >250 | 4.01 | 523 | 4 |

TABLE 2-continued

| Co. | Optical Rotation $[\alpha]_D^{20}$ | MP (° C.) (Kofler) | Rt | (MH+) | LCMS Method |
|---|---|---|---|---|---|
| 178 | | >250 | 3.7 | 489 | 4 |
| 179 | | >250 | 3.52 | 489 | 4 |
| 180 | | 186 | 3.75 | 489 | 4 |
| 181 | | 173 | 3.52 | 489 | 4 |
| 182 | −5.55° (589 nm, c 0.3605 w/v %, DMF, 20° C.) | >250 | 3.58 | 489 | 4 |
| 183 | −93.86° (589 nm, c 0.3175 w/v %, DMF, 20° C.) | >250 | 3.72 | 489 | 4 |
| 184 | | 172 | 2.71 | 535 | 9 |
| 185 | | 162 | 3.17 | 535 | 9 |
| 186 | | 166 | 2.88 | 535 | 9 |
| 187 | | 167 | 3.1 | 535 | 9 |
| 188 | −129.97° (589 nm, c 0.397 w/v %, DMF, 20° C.) | | 3.99 | 555 | 9 |
| 189 | +286.5° (589 nm, c 0.4185 w/v %, DMF, 20° C.) | 160 | 3.95 | 555 | 9 |
| 190 | +143.71° (589 nm, c 0.318 w/v %, DMF, 20° C.) | | 4 | 555 | 9 |
| 191 | −281.85° (589 nm, c 0.336 w/v %, DMF, 20° C.) | 162 | 3.94 | 555 | 9 |
| 192 | −16.33° (589 nm, c 0.3735 w/v %, DMF, 20° C.) | >250 | 3.69 | 523 | 4 |
| 43 | −94.13° (589 nm, c 0.4685 w/v %, DMF, 20° C.) | >250 | 3.84 | 523 | 4 |
| 193 | +23.43° (589 nm, c 0.397 w/v %, DMF, 20° C.) | 147 | 4.18 | 537 | 9 |
| 61 | −153.89° (589 nm, c 0.3535 w/v %, DMF, 20° C.) | 141 | 4.06 | 537 | 9 |
| 194 | +109.12° (589 nm, c 0.34 w/v %, DMF, 20° C.) | 149 | 4.42 | 537 | 9 |
| 195 | +50.76° (589 nm, c 0.461 w/v %, DMF, 20° C.) | 153 | 3.8 | 503 | 9 |
| 196 | +163.61° (589 nm, c 0.2995 w/v %, DMF, 20° C.) | | 4.11 | 503 | 9 |
| 197 | −195.04° (589 nm, c 0.282 w/v %, DMF, 20° C.) | 138 | 3.78 | 503 | 9 |
| 198 | −173.72° (589 nm, c 0.293 w/v %, DMF, 20° C.) | 187 | 4.16 | 503 | 9 |
| 199 | −61.7° (589 nm, c 0.4895 w/v %, DMF, 20° C.) | 192 | 3.13 | 569 | 9 |
| 200 | +171.12° (589 nm, c 0.4225 w/v %, DMF, 20° C.) | 187 | 3.34 | 569 | 9 |
| 201 | +130.34° (589 nm, c 0.267 w/v %, DMF, 20° C.) | 195 | 3.52 | 569 | 9 |
| 202 | −131.7° (589 nm, c 0.265 w/v %, DMF, 20° C.) | 186 | 3.61 | 569 | 9 |
| 203 | −72.45° (589 nm, c 0.363 w/v %, DMF, 20° C.) | >250 | 3.7 | 541 | 4 |
| 204 | +38.18° (589 nm, c 0.4165 w/v %, DMF, 20° C.) | >250 | 3.93 | 541 | 4 |
| 205 | −53.25° (589 nm, c 0.4 w/v %, DMF, 20° C.) | >250 | 2.98 | 573 | 4 |
| 206 | +31.72° (589 nm, c 0.476 w/v %, DMF, 20° C.) | 245 | 3.13 | 573 | 4 |
| 207 | −73.96° (589 nm, c 0.3975 w/v %, DMF, 20° C.) | >250 | 3.39 | 573 | 4 |
| 208 | +38.88° (589 nm, c 0.2855 w/v %, DMF, 20° C.) | >250 | 3.31 | 573 | 4 |
| 209 | +111.67° (589 nm, c 0.3385 w/v %, DMF, 20° C.) | | 2.98 | 587 | 9 |
| 210 | −180.75° (589 nm, c 0.3325 w/v %, DMF, 20° C.) | | 3.04 | 587 | 9 |
| 211 | −113.84° (589 nm, c 0.419 w/v %, DMF, 20° C.) | 150 | 2.98 | 587 | 9 |
| 212 | +71.23° (589 nm, c 0.2485 w/v %, DMF, 20° C.) | >250 | 3.39 | 573 | 4 |
| 213 | −27.33° (589 nm, c 0.3 w/v %, DMF, 20° C.) | | 3.12 | 573 | 4 |
| 214 | +58.16° (589 nm, c 0.392 w/v %, DMF, 20° C.) | 213 | 2.99 | 573 | 4 |
| 215 | −43.95° (589 nm, c 0.43 w/v %, DMF, 20° C.) | | 3.29 | 573 | 4 |
| 44 | +46.5° (589 nm, c 0.329 w/v %, DMF, 20° C.) | 148 | 3.12 | 569 | 9 |
| 45 | −162.08° (589 nm, c 0.327 w/v %, DMF, 20° C.) | 160 | 3.3 | 569 | 9 |

TABLE 2-continued

| Co. | Optical Rotation $[\alpha]_D^{20}$ | MP (° C.) (Kofler) | Rt | (MH+) | LCMS Method |
|---|---|---|---|---|---|
| 46 | +126.22° (589 nm, c 0.286 w/v %, DMF, 20° C.) | 145 | 3.6 | 569 | 9 |
| 47 | −141.92° (589 nm, c 0.291 w/v %, DMF, 20° C.) | 174 | 3.51 | 569 | 9 |
| 216 | −164.98° (589 nm, c 0.277 w/v %, DMF, 20° C.) | 152 | 3.53 | 569 | 9 |
| 217 | −169.84° (589 nm, c 0.368 w/v %, DMF, 20° C.) | 169 | 3.35 | 569 | 9 |
| 218 | +66.54° (589 nm, c 0.272 w/v %, DMF, 20° C.) | 174 | 3.13 | 569 | 9 |
| 219 | +105.06° (589 nm, c 0.336 w/v %, DMF, 20° C.) | 156 | 3.61 | 569 | 9 |
| 220 | −27.88° (589 nm, c 0.452 w/v %, DMF, 20° C.) | >250 | 3.09 | 555 | 4 |
| 221 | +33.44° (589 nm, c 0.311 w/v %, DMF, 20° C.) | >250 | 3.49 | 555 | 4 |
| 222 | +30.1° (589 nm, c 0.4485 w/v %, DMF, 20° C.) | >250 | 3.08 | 555 | 4 |
| 223 | +72.28° (589 nm, c 0.368 w/v %, DMF, 20° C.) | >250 | 3.09 | 555 | 4 |
| 224 | −95.7° (589 nm, c 0.3835 w/v %, DMF, 20° C.) | >250 | 3.46 | 555 | 4 |
| 225 | −25.06° (589 nm, c 0.423 w/v %, DMF, 20° C.) | >250 | 3.07 | 555 | 4 |
| 226 | +198.48° (589 nm, c 0.394 w/v %, DMF, 20° C.) | 221 | 3.91 | 571 | 9 |
| 227 | −41.67° (589 nm, c 0.312 w/v %, DMF, 20° C.) | 196 | 4.08 | 572 | 9 |
| 48 | −207.64° (589 nm, c 0.275 w/v %, DMF, 20° C.) | 221 | 3.88 | 571 | 9 |
| 228 | +41.36° (589 nm, c 0.295 w/v %, DMF, 20° C.) | 196 | 4.1 | 571 | 9 |
| 49 |  | 183 | 4.09 | 557 | 4 |
| 229 | −114.24° (589 nm, c 0.344 w/v %, DMF, 20° C.) | >250 | 3.92 | 557 | 4 |
| 230 | −32.93° (589 nm, c 0.1154 w/v %, DMF, 20° C.) | >250 | 3.82 | 491 | 4 |
| 231 | +107.46° (589 nm, c 0.228 w/v %, DMF, 20° C.) | >250 | 3.82 | 491 | 4 |
| 232 | +19.57° (589 nm, c 0.1022 w/v %, DMF, 20° C.) | >250 | 3.64 | 491 | 4 |
| 233 | +25.99° (589 nm, c 0.277 w/v %, DMF, 20° C.) | >250 | 3.82 | 491 | 4 |
| 234 | −29.57° (589 nm, c 0.1116 w/v %, DMF, 20° C.) | >250 | 3.64 | 491 | 4 |
| 235 | −46.73° (589 nm, c 0.0749 w/v %, DMF, 20° C.) | >250 | 3.4 | 491 | 4 |
| 236 |  | >250 | 3.06 | 520 | 4 |
| 237 | −100.34° (589 nm, c 0.294 w/v %, DMF, 20° C.) | >250 | 3.16 | 521 | 4 |
| 238 | −38.06° (589 nm, c 0.31 w/v %, DMF, 20° C.) | >250 | 2.81 | 521 | 4 |
| 239 |  | >250 | 3.94 | 493 | 4 |
| 5 |  | >250 | 3.93 | 103 | 4 |
| 240 |  | >250 | 3.67 | 493 | 4 |
| 241 |  | >250 | 3.78 | 493 | 4 |
| 242 | +235.76° (589 nm, c 0.302 w/v %, DMF, 20° C.) |  | 4.3 | 537 | 9 |
| 243 | −89.78° (589 nm, c 0.186 w/v %, DMF, 20° C.) | 140 | 3.16 | 553 | 9 |
| 244 | +217.8° (589 nm, c 0.337 w/v %, DMF, 20° C.) | 205 | 4.58 | 537 | 9 |
| 245 | −98.05° (589 nm, c 0.257 w/v %, DMF, 20° C.) | 147 | 4.28 | 537 | 9 |
| 246 |  | 100 | 2.38 | 468 | 4 |
| 247 | +144.41° (589 nm, c 0.286 w/v %, DMF, 20° C.) | 132 | 4.05 | 537 | 9 |
| 248 | −53.47° (589 nm, c 0.303 w/v %, DMF, 20° C.) | 134 | 4.16 | 537 | 9 |
| 249 | +136.02° (589 nm, c 0.2485 w/v %, DMF, 20° C.) | 178 | 4.2 | 537 | 9 |
| 250 | −148.58° (589 nm, c 0.2645 w/v %, DMF, 20° C.) | 125 | 4.42 | 537 | 9 |
| 251 | +115.43° (589 nm, c 0.324 w/v %, DMF, 20° C.) | 183 | 3.08 | 535 | 9 |

TABLE 2-continued

| Co. | Optical Rotation $[\alpha]_D^{20}$ | MP (° C.) (Kofler) | Rt | (MH+) | LCMS Method |
|---|---|---|---|---|---|
| 252 | −35.99° (589 nm, c 0.439 w/v %, DMF, 20° C.) | 152 | 2.71 | 535 | 9 |
| 253 | +136.81° (589 nm, c 0.432 w/v %, DMF, 20° C.) | 167 | 2.88 | 535 | 9 |
| 254 | +40.58° (589 nm, c 0.067 w/v %, DMF, 20° C.) | >250 | 3.54 | 545 | 4 |
| 255 | −42.8° (589 nm, c 0.0514 w/v %, DMF, 20° C.) | >250 | 4 | 545 | 4 |
| 256 | +153.1° (589 nm, c 0.258 w/v %, DMF, 20° C.) | 118 | 4.63 | 559 | 9 |
| 257 | −181.51° (589 nm, c 0.292 w/v %, DMF, 20° C.) | 108 | 4.57 | 559 | 9 |
| 6 |  | >250 | 3.94 | 545 | 4 |
| 258 | −64.24° (589 nm, c 0.0576 w/v %, DMF, 20° C.) | >250 | 3.58 | 545 | 4 |
| 259 | +186.75° (589 nm, c 0.302 w/v %, DMF, 20° C.) | 168 | 4.63 | 559 | 9 |
| 260 | +154.66° (589 nm, c 0.247 w/v %, DMF, 20° C.) | 104 | 3.7 | 537 | 9 |
| 261 | +298.07° (589 nm, c 0.2845 w/v %, DMF, 20° C.) | 122 | 3.81 | 537 | 9 |
| 262 | −142.69° (589 nm, c 0.253 w/v %, DMF, 20° C.) | 94 | 3.83 | 537 | 9 |
| 263 | +35.09° (589 nm, c 0.2565 w/v %, DMF, 20° C.) | >250 | 2.61 | 521 | 4 |
| 264 | +30.18° (589 nm, c 0.275 w/v %, DMF, 20° C.) | >250 | 3.02 | 521 | 4 |
| 265 | +98.69° (589 nm, c 0.306 w/v %, DMF, 20° C.) | >250 | 2.94 | 521 | 4 |
| 266 | +10.59° (589 nm, c 0.34 w/v %, DMF, 20° C.) | >250 | 3.5 | 523 | 4 |
| 267 | +28.99° (589 nm, c 0.276 w/v %, DMF, 20° C.) | >250 | 3.86 | 539 | 4 |
| 268 | +98.19° (589 nm, c 0.3035 w/v %, DMF, 20° C.) | >250 | 3.72 | 523 | 4 |
| 269 | −67.05° (589 nm, c 0.349 w/v %, DMF, 20° C.) | >250 | 2.94 | 555 | 4 |
| 270 | −43.13° (589 nm, c 0.2365 w/v %, DMF, 20° C.) | >250 | 3.29 | 555 | 4 |
| 271 | −105.62° (589 nm, c 0.267 w/v %, DMF, 20° C.) | >250 | 3.19 | 555 | 4 |
| 272 | −36.69° (589 nm, c 0.357 w/v %, DMF, 20° C.) | >250 | 2.85 | 555 | 4 |
| 273 | −206.07° (589 nm, c 0.2635 w/v %, DMF, 20° C.) | 204 | 4.58 | 537 | 9 |
| 274 |  |  | 4.56 | 537 | 9 |
| 275 | +95.58° (589 nm, c 0.407 w/v %, DMF, 20° C.) | 140 | 4.26 | 537 | 9 |
| 276 | −246.45° (589 nm, c 0.31 w/v %, DMF, 20° C.) |  | 4.29 | 537 | 9 |
| 277 | −96.53° (589 nm, c 0.259 w/v %, DMF, 20° C.) | >250 | 3.73 | 523 | 4 |
| 278 | −16.47° (589 nm, c 0.3035 w/v %, DMF, 20° C.) | >250 | 3.51 | 523 | 4 |
| 279 |  | >250 | 3.37 | 523 | 4 |
| 280 | +91.43° (589 nm, c 0.28 w/v %, DMF, 20° C.) | >250 | 3.49 | 523 | 4 |
| 281 | +42.67° (589 nm, c 0.3 w/v %, DMF, 20° C.) | >250 | 3.5 | 523 | 4 |
| 282 | −78.27° (589 nm, c 0.382 w/v %, DMF, 20° C.) | 206 | 3.35 | 523 | 4 |
| 283 | +54.55° (589 nm, c 0.297 w/v %, DMF, 20° C.) | 184 | 3.84 | 537 | 9 |
| 284 | −180.15° (589 nm, c 0.393 w/v %, DMF, 20° C.) | 163 | 3.73 | 537 | 9 |
| 285 | −57.81° (589 nm, c 0.384 w/v %, DMF, 20° C.) | 184 | 3.78 | 537 | 9 |
| 286 | +190.64° (589 nm, c 0.299 w/v %, DMF, 20° C.) | 177 | 3.74 | 537 | 9 |
| 287 | +255.83° (589 nm, c 0.283 w/v %, DMF, 20° C.) | 185 | 4.26 | 525 | 9 |
| 288 | −139.37° (589 nm, c 0.287 w/v %, DMF, 20° C.) | 150 | 4.2 | 525 | 9 |
| 289 | +139.65° (589 nm, c 0.401 w/v %, DMF, 20° C.) | 150 | 4.18 | 525 | 9 |

TABLE 2-continued

| Co. | Optical Rotation [α]$_D^{20}$ | MP (° C.) (Kofler) | Rt | (MH+) | LCMS Method |
|---|---|---|---|---|---|
| 290 | −253.69° (589 nm, c 0.298 w/v %, DMF, 20° C.) | 185 | 4.29 | 525 | 9 |
| 291 | +34.21° (589 nm, c 0.342 w/v %, DMF, 20° C.) | 150 | 2.91 | 569 | 9 |
| 292 | −172.52° (589 nm, c 0.262 w/v %, DMF, 20° C.) | 150 | 2.97 | 610 | 9 |
| 293 | −31.14° (589 nm, c 0.411 w/v %, DMF, 20° C.) | 150 | 2.9 | 569 | 9 |
| 294 | +175.47° (589 nm, c 0.322 w/v %, DMF, 20° C.) | 150 | 2.96 | 610 | 9 |
| 295 | +61.22° (589 nm, c 0.294 w/v %, DMF, 20° C.) | >250 | 3.49 | 511 | 4 |
| 296 | −42.04° (589 nm, c 0.3235 w/v %, DMF, 20° C.) | >250 | 3.88 | 511 | 4 |
| 297 | +35.65° (589 nm, c 0.2805 w/v %, DMF, 20° C.) | >250 | 3.88 | 511 | 4 |
| 298 | −61.26° (589 nm, c 0.302 w/v %, DMF, 20° C.) | >250 | 3.49 | 511 | 4 |
| 299 | +206.14° (589 nm, c 0.342 w/v %, DMF, 20° C.) | 110 | 3.76 | 537 | 9 |
| 300 | +185.42° (589 nm, c 0.295 w/v %, DMF, 20° C.) | 90 | 3.87 | 537 | 9 |
| 301 | −233.7° (589 nm, c 0.3175 w/v %, DMF, 20° C.) | 170 | 3.8 | 537 | 9 |
| 302 | −118.37° (589 nm, c 0.283 w/v %, DMF, 20° C.) | 120 | 3.72 | 537 | 9 |
| 303 | | >250 | 3.78 | 511 | 4 |
| 304 | | >250 | 3.59 | 511 | 4 |
| 305 | +80.67° (589 nm, c 0.269 w/v %, DMF, 20° C.) | 133 | 2.95 | 587 | 9 |
| 306 | −75.99° (589 nm, c 0.2645 w/v %, DMF, 20° C.) | 157 | 3.06 | 587 | 9 |
| 307 | +50.35° (589 nm, c 0.286 w/v %, DMF, 20° C.) | 232 | 2.76 | 573 | 4 |
| 308 | −31.76° (589 nm, c 0.2645 w/v %, DMF, 20° C.) | >260 | 3.08 | 573 | 4 |
| 309 | +85.04° (589 nm, c 0.254 w/v %, DMF, 20° C.) | >260 | 3.42 | 541 | 4 |
| 310 | −30.37° (589 nm, c 0.349 w/v %, DMF, 20° C.) | 126 | 3.59 | 541 | 4 |
| 311 | −45.25° (589 nm, c 0.263 w/v %, DMF, 20° C.) | >260 | 3.46 | 541 | 4 |
| 312 | | >260 | 3.57 | 541 | 4 |
| 313 | +100° (589 nm, c 0.25 w/v %, DMF, 20° C.) | 147 | 4.34 | 589 | 9 |
| 51 | −101.43° (589 nm, c 0.28 w/v %, DMF, 20° C.) | 176 | 4.35 | 589 | 9 |
| 314 | +39.29° (589 nm, c 0.3385 w/v %, DMF, 20° C.) | 234 | 3.69 | 575 | 4 |
| 315 | −69.76° (589 nm, c 0.3125 w/v %, DMF, 20° C.) | >260 | 3.54 | 575 | 4 |
| 316 | +45.65° (589 nm, c 0.23 w/v %, DMF, 20° C.) | >260 | 3.57 | 575 | 4 |
| 317 | | >260 | 3.68 | 575 | 4 |
| 50 | +109.94° (589 nm, c 0.322 w/v %, DMF, 20° C.) | 208 | 4.01 | 555 | 9 |
| 318 | −243.94° (589 nm, c 0.264 w/v %, DMF, 20° C.) | 133 | 4.03 | 555 | 9 |
| 1 | −153.8° (589 nm, c 0.342 w/v %, DMF, 20° C.) | | 4.79 | 525 | 9 |
| 2 | +76.76° (589 nm, c 0.37 w/v %, DMF, 20° C.) | 126 | 4.53 | 525 | 9 |
| 3 | −182.79° (589 nm, c 0.3835 w/v %, DMF, 20° C.) | 146 | 4.5 | 525 | 9 |
| 4 | +140.04° (589 nm, c 0.2835 w/v %, DMF, 20° C.) | | 4.76 | 525 | 9 |
| 319 | +103.95° (589 nm, c 0.329 w/v %, DMF, 20° C.) | 169 | 4.36 | 589 | 9 |
| 320 | −188.97° (589 nm, c 0.3625 w/v %, DMF, 20° C.) | 159 | 4.34 | 589 | 9 |
| 321 | +70.56° (589 nm, c 0.3685 w/v %, DMF, 20° C.) | >260 | 3.55 | 575 | 4 |
| 322 | −37.96° (589 nm, c 0.3925 w/v %, DMF, 20° C.) | 248 | 3.71 | 575 | 4 |
| 323 | −46.53° (589 nm, c 0.303 w/v %, DMF, 20° C.) | >260 | 3.57 | 575 | 4 |

TABLE 2-continued

| Co. | Optical Rotation $[\alpha]_D^{20}$ | MP (° C.) (Kofler) | Rt | (MH+) | LCMS Method |
|---|---|---|---|---|---|
| 324 | +83.03° (589 nm, c 0.2505 w/v %, DMF, 20° C.) | >260 | 3.69 | 575 | 4 |
| 325 | −73.27° (589 nm, c 0.318 w/v %, DMF, 20° C.) | 144 | 2.96 | 587 | 9 |
| 326 | +71.7° (589 nm, c 0.3975 w/v %, DMF, 20° C.) | 166 | 3.07 | 587 | 9 |
| 327 | −52.79° (589 nm, c 0.3675 w/v %, DMF, 20° C.) | 248 | 2.76 | 573 | 4 |
| 328 | +29.8° (589 nm, c 0.2685 w/v %, DMF, 20° C.) | >260 | 3.08 | 573 | 4 |
| 329 | +41.8° (589 nm, c 0.244 w/v %, DMF, 20° C.) | >260 | 3.46 | 541 | 4 |
| 330 | +28.89° (589 nm, c 0.27 w/v %, DMF, 20° C.) | 170 | 4.07 | 509 | 9 |
| 331 | −89.4° (589 nm, c 0.3255 w/v %, DMF, 20° C.) | 166 | 4.08 | 509 | 9 |
| 332 | −89.97° (589 nm, c 0.289 w/v %, DMF, 20° C.) | 164 | 4.39 | 509 | 9 |
| 333 | −37° (589 nm, c 0.327 w/v %, DMF, 20° C.) | | 3.4 | 523 | 4 |
| 334 | +69.77° (589 nm, c 0.354 w/v %, DMF, 20° C.) | 232 | 3.38 | 523 | 4 |
| 335 | Rotation: 0 | 180 | 3.62 | 226 | 4 |
| 336 | +84.24° (589 nm, c 0.311 w/v %, DMF, 20° C.) | | 3.54 | 557 | 4 |
| 337 | +121.82° (589 nm, c 0.307 w/v %, DMF, 20° C.) | 186 | 4.01 | 571 | 9 |
| 338 | +228.63° (589 nm, c 0.255 w/v %, DMF, 20° C.) | 198 | 4.15 | 571 | 9 |
| 339 | | 176 | 4.03 | 571 | 9 |
| 340 | −121.01° (589 nm, c 0.276 w/v %, DMF, 20° C.) | 132 | 4.17 | 571 | 9 |
| 341 | +35.29° (589 nm, c 0.136 w/v %, DMF, 20° C.) | >260 | 3.66 | 557 | 4 |
| 342 | −66.76° (589 nm, c 0.3655 w/v %, DMF, 20° C.) | >260 | 3.49 | 557 | 4 |
| 343 | | >250 | 3.42 | 511 | 4 |
| 344 | | >250 | 3.59 | 511 | 4 |
| 345 | +66.41° (589 nm, c 0.262 w/v %, DMF, 20° C.) | 152–154 | 3.92 | 525 | 9 |
| 346 | +120.83° (589 nm, c 0.36 w/v %, DMF, 20° C.) | 151–153 | 4.02 | 525 | 9 |
| 347 | −117.61° (589 nm, c 0.301 w/v %, DMF, 20° C.) | 148–150 | 3.93 | 525 | 9 |
| 348 | −98.33° (589 nm, c 0.3 w/v %, DMF, 20° C.) | 145 | 4.06 | 525 | 9 |
| 349 | | >250 | 3.57 | 523 | 4 |
| 350 | | >250 | 3.7 | 523 | 4 |
| 351 | | 128–130 | 4.39 | 537 | 9 |
| 352 | | 123–125 | 4.23 | 537 | 9 |
| 353 | | 166–168 | 4.63 | 537 | 9 |
| 354 | | 168–170 | 4.49 | 537 | 9 |
| 355 | −225.37° (589 nm, c 0.339 w/v %, DMF, 20° C.) | 190 | 4.17 | 571 | 9 |
| 356 | +129.45° (589 nm, c 0.2835 w/v %, DMF, 20° C.) | 98 | 4.2 | 571 | 9 |
| 357 | | 104 | 4.05 | 571 | 9 |
| 358 | −110.02° (589 nm, c 0.2945 w/v %, DMF, 20° C.) | 138 | 4.07 | 571 | 9 |
| 359 | +24.72° (589 nm, c 0.267 w/v %, DMF, 20° C.) | | 3.26 | 475 | 4 |
| 360 | −35.65° (589 nm, c 0.345 w/v %, DMF, 20° C.) | | 3.33 | 475 | 4 |
| 361 | +40.13° (589 nm, c 0.309 w/v %, DMF, 20° C.) | | 3.33 | 475 | 4 |
| 362 | −23.46° (589 nm, c 0.2515 w/v %, DMF, 20° C.) | | 3.26 | 475 | 4 |
| 363 | −40.04° (589 nm, c 0.1124 w/v %, DMF, 20° C.) | >260 | 3.61 | 557 | 4 |
| 364 | −34.57° (589 nm, c 0.269 w/v %, DMF, 20° C.) | >260 | 3.51 | 557 | 4 |
| 365 | +62.08° (589 nm, c 0.3415 w/v %, DMF, 20° C.) | 242 | 3.45 | 557 | 4 |
| 366 | | 146 | 3.43 | 569 | 9 |
| 367 | | 175 | 3.03 | 569 | 9 |
| 368 | | 144 | 3.29 | 569 | 9 |

TABLE 2-continued

| Co. | Optical Rotation [α]$_D^{20}$ | MP (° C.) (Kofler) | Rt | (MH+) | LCMS Method |
|---|---|---|---|---|---|
| 369 | | 138 | 3.71 | 569 | 9 |
| 52 | | 176 | 3.6 | 491 | 9 |
| 53 | | 102 | 3.57 | 491 | 9 |
| 54 | | 209 | 3.42 | 491 | 9 |
| 55 | | 120 | 3.34 | 491 | 9 |
| 370 | | | 3.63 | 491 | 9 |
| 371 | +146.51° (589 nm, c 0.258 w/v %, DMF, 20° C.) | 158 | 3.72 | 489 | 9 |
| 372 | −224.56° (589 nm, c 0.285 w/v %, DMF, 20° C.) | 194 | 3.81 | 489 | 9 |
| 373 | +226.53° (589 nm, c 0.2865 w/v %, DMF, 20° C.) | 193 | 3.82 | 489 | 9 |
| 374 | −146.07° (589 nm, c 0.28 w/v %, DMF, 20° C.) | 162 | 3.72 | 489 | 9 |
| 56 | −65.4° (589 nm, c 0.367 w/v %, DMF, 20° C.) | | 2.77 | 555 | 4 |
| 57 | +121.07° (589 nm, c 0.261 w/v %, DMF, 20° C.) | | 3.08 | 555 | 4 |
| 58 | +59.23° (589 nm, c 0.287 w/v %, DMF, 20° C.) | | 2.87 | 555 | 4 |
| 59 | −70.18° (589 nm, c 0.285 w/v %, DMF, 20° C.) | | 3.11 | 555 | 4 |
| 375 | | >250 | 3.19 | 477 | 4 |
| 376 | | >250 | 3.42 | 477 | 4 |
| 377 | | | 2.97 | 555 | 4 |
| 378 | | | 3.1 | 555 | 4 |
| 60 | +245.07° (589 nm, c 0.2685 w/v %, DMF, 20° C.) | 161 | 3.64 | 554 | 9 |
| 379 | −104.1° (589 nm, c 0.293 w/v %, DMF, 20° C.) | | 3.65 | 554 | 9 |
| 380 | +71.83° (589 nm, c 0.284 w/v %, DMF, 20° C.) | | 3.67 | 554 | 9 |
| 381 | −228.26° (589 nm, c 0.276 w/v %, DMF, 20° C.) | | 3.65 | 554 | 9 |
| 382 | +142.29° (589 nm, c 0.253 w/v %, DMF, 20° C.) | | 4.53 | 547 | 9 |
| 383 | −267.89° (589 nm, c 0.246 w/v %, DMF, 20° C.) | | 4.53 | 547 | 9 |
| 384 | −138.01° (589 nm, c 0.271 w/v %, DMF, 20° C.) | | 4.34 | 547 | 9 |
| 385 | +168.79° (589 nm, c 0.282 w/v %, DMF, 20° C.) | | 4.42 | 547 | 9 |
| 386 | −211.7° (589 nm, c 0.2735 w/v %, DMF, 20° C.) | 125 | 3.38 | 579 | 9 |
| 387 | +118.66° (589 nm, c 0.343 w/v %, DMF, 20° C.) | 204 | 3.22 | 579 | 9 |
| 388 | +188.25° (589 nm, c 0.3065 w/v %, DMF, 20° C.) | 103 | 2.92 | 569 | 9 |
| 389 | +97.98° (589 nm, c 0.3225 w/v %, DMF, 20° C.) | 128 | 2.76 | 569 | 9 |
| 390 | −112.32° (589 nm, c 0.276 w/v %, DMF, 20° C.) | 170 | 2.81 | 569 | 9 |
| 391 | −131.97° (589 nm, c 0.2925 w/v %, DMF, 20° C.) | 120 | 2.94 | 569 | 9 |
| 392 | | 162-164 | 3.66 | 503 | 9 |
| 393 | | 159-161 | 3.55 | 503 | 9 |
| 394 | | | 3.53 | 457 | 9 |
| 395 | | 150-152 | 3.45 | 457 | 9 |
| 62 | | 212 | 4.01 | 457 | 4 |
| 396 | | | 4.06 | 457 | 4 |
| 397 | | 180 | 3.16 | 489 | 4 |
| 398 | | | 3.36 | 489 | 4 |
| 399 | | 222-224 | 3.68 | 439 | 4 |
| 400 | | 157 | 3.7 | 439 | 4 |
| 401 | | 240 | 3.7 | 439 | 4 |
| 402 | | 175-177 | 3.75 | 439 | 4 |
| 403 | | 176 | 4.4 | 493 | 9 |
| 404 | | 168 | 4.1 | 493 | 9 |
| 405 | | 184 | 4.38 | 493 | 9 |
| 406 | | 206 | 3.84 | 522 | 9 |
| 407 | | | 3.93 | 521 | 9 |
| 408 | | 135 | 3.67 | 469 | 4 |
| 409 | | 190 | 4.34 | 493 | 4 |
| 410 | | 155 | 4.24 | 493 | 4 |
| 411 | | 168 | 4.21 | 493 | 4 |
| 412 | | 166 | 4.34 | 493 | 4 |

TABLE 2-continued

| Co. | Optical Rotation $[\alpha]_D^{20}$ | MP (° C.) (Kofler) | Rt | (MH+) | LCMS Method |
|---|---|---|---|---|---|
| 413 | | >250 | 3.84 | 425 | 4 |
| 414 | | 196 | 3.84 | 425 | 4 |
| 415 | | 160 | 3.69 | 425 | 4 |
| 16 | | 166-168 | 3.4 | 457 | 9 |
| 416 | | 160-162 | 3.4 | 457 | 9 |
| 417 | | 150 | 2.64 | 553 | 9 |
| 418 | | 164-166 | 3.28 | 553 | 9 |
| 419 | | 154 | 3.01 | 553 | 9 |
| 420 | | | 3.19 | 431 | 9 |
| 421 | | | 3.24 | 431 | 9 |
| 422 | | | 3.25 | 431 | 9 |
| 423 | | 174 | 3.16 | 431 | 9 |
| 10 | | | 2.61 | 413 | 9 |
| 424 | | | 2.61 | 413 | 9 |
| 425 | | 125 | 2.98 | 441 | 9 |
| 426 | | 174 | 3.1 | 443 | 9 |
| 427 | | 174 | 3.51 | 520 | 4 |
| 428 | | 217 | 3.63 | 520 | 4 |
| 67 | | 245 | 4.06 | 509 | 4 |
| 429 | | >260 | 4.06 | 509 | 4 |
| 430 | | 184 | 4.71 | 543 | 9 |
| 431 | | 178 | 4.87 | 543 | 9 |
| 432 | | 167 | 4.67 | 543 | 9 |
| 13 | +99.45° (589 nm, c 0.2735 w/v %, DMF, 20° C.) | 162 | 4.67 | 535 | 9 |
| 14 | −87.9° (589 nm, c 0.281 w/v %, DMF, 20° C.) | | 4.69 | 535 | 9 |
| 433 | | 114 | 3.55 | 508 | 9 |
| 434 | | 197 | 3.71 | 508 | 9 |
| 12 | −134.65° (589 nm, c 0.303 w/v %, DMF, 20° C.) | 135 | 3.8 | 447 | 4 |
| 435 | +132.68° (589 nm, c 0.306 w/v %, DMF, 20° C.) | 140 | 3.13 | 447 | 9 |
| 436 | | 135 | 4.02 | 535 | 9 |
| 437 | | | 4.62 | 535 | 9 |
| 29 | | 135 | 2.29 | 397 | 9 |
| 30 | | | 2.74 | 431 | 9 |
| 20 | | 232 | 3.08 | 433 | 4 |
| 438 | | 188 | 3.69 | 508 | 9 |
| 439 | | 132 | 3.52 | 508 | 9 |
| 440 | | | 4.86 | 543 | 9 |
| 441 | | | 4.89 | 543 | 9 |
| 442 | | 178 | 4.78 | 543 | 9 |
| 443 | | 156 | 3.05 | 494 | 9 |
| 444 | | 172 | 2.93 | 494 | 9 |
| 445 | | 154 | 3.08 | 494 | 9 |
| 446 | | 210 | 3.08 | 433 | 4 |
| 65 | | 240 | 2.09 | 568 | 9 |
| 66 | | 184 | 2.1 | 568 | 9 |
| 447 | | 234 | 2.09 | 568 | 9 |
| 448 | | 182 | 2.09 | 568 | 9 |
| 449 | +195.05° (589 nm, c 0.283 w/v %, DMF, 20° C.) | 190 | 3.76 | 435 | 9 |
| 450 | +163.97° (589 nm, c 0.297 w/v %, DMF, 20° C.) | 200 | 3.78 | 435 | 9 |
| 451 | −216.99° (589 nm, c 0.1825 w/v %, DMF, 20° C.) | 110 | 3.6 | 435 | 9 |
| 452 | −179.09° (589 nm, c 0.1865 w/v %, DMF, 20° C.) | 114 | 3.68 | 435 | 9 |
| 453 | −160.6° (589 nm, c 0.302 w/v %, DMF, 20° C.) | 210 | 3.78 | 435 | 9 |
| 454 | −180.34° (589 nm, c 0.295 w/v %, DMF, 20° C.) | 186 | 3.77 | 435 | 9 |
| 455 | +179.5° (589 nm, c 0.161 w/v %, DMF, 20° C.) | 118 | 3.69 | 435 | 9 |
| 456 | +224.84° (589 nm, c 0.153 w/v %, DMF, 20° C.) | 115 | 3.58 | 435 | 9 |
| 457 | | >250 | 3.35 | 421 | 4 |
| 458 | | >250 | 3.29 | 421 | 4 |
| 22 | | | 4.83 | 598 | 10 |
| 23 | | | 4.69 | 598 | 10 |
| 24 | | | 4.68 | 598 | 10 |
| 459 | | 211 | 3.65 | 587 | 9 |
| 460 | | 197 | 3.83 | 587 | 9 |
| 461 | | 208 | 3.38 | 587 | 9 |
| 462 | | 192 | 3.6 | 587 | 9 |

TABLE 2-continued

| Co. | Optical Rotation $[\alpha]_D^{20}$ | MP (° C.) (Kofler) | Rt | (MH+) | LCMS Method |
|---|---|---|---|---|---|
| 63 | | 157 | 4.24 | 502 | 9 |
| 64 | | 141 | 4.25 | 502 | 9 |
| 463 | | 160 | 2.57 | 587 | 10 |
| 464 | | 154 | 2.8 | 587 | 10 |
| 465 | | 168 | 2.19 | 587 | 10 |
| 466 | | 188 | 2.49 | 587 | 10 |
| 467 | | 148 | 2.19 | 508 | 10 |
| 468 | | 148 | 2.2 | 508 | 10 |
| 469 | | | 3.49 | 523 | 9 |
| 470 | | | 3.48 | 523 | 9 |
| 471 | | | 3.84 | 494 | 9 |
| 28 | | | 3.83 | 494 | 9 |
| 27 | | | 3.31 | 460 | 9 |

D. Pharmacological Examples

D.1. In-Vitro Method for Testing Compounds for Anti-Bacterial Activity Against Strain M. Smegmatis ATCC607

Flat-bottom, sterile 96-well plastic microtiter plates were filled with 180 µl of sterile deionized water, supplemented with 0.25% BSA. Subsequently, stock solutions (7.8× final test concentration) of compounds were added in 45 µl volumes to a series of duplicate wells in column 2 so as to allow evaluation of their effects on bacterial growth. Serial five-fold dilutions (45 µl in 180 µl) were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 250 CFU per well of bacteria inoculum, in a volume of 100 µl in 2.8× Mueller-Hinton broth medium, was added to the rows A to H, except column 12. The same volume of broth medium without inoculum was added to column 12 in row A to H. The cultures were incubated at 37° C. for 48 hours in a humidified 5% $CO_2$ atmosphere (incubator with open air valve and continuous ventilation). At the end of incubation, two days after inoculation, the bacterial growth was quantitated fluorometrically. Therefore Alamar Blue (10×) was added to all wells in a volume of 20 µl and plates were incubated for another 2 hours at 50° C.

The fluorescence was read in a computer-controlled fluorometer (Cytofluor, Biosearch) at an excitation wavelength of 530 nm and an emission wavelength of 590 nm (gain 30). The percentage growth inhibition achieved by the compounds was calculated according to standard methods and expressed as $IC_{90}$ (µg/ml) which defines the 90% inhibitory concentration for bacterial growth. The results are shown in Table 3.

D.2. In-Vitro Method for Testing Compounds for Anti-Bacterial Activity Against Various Non-Mycobacterial Strains Preparation of Bacterial Suspensions for Susceptibility Testing:

The bacteria used in this study were grown overnight in flasks containing 100 ml Mueller-Hinton Broth (Becton Dickinson—cat. no. 275730) in sterile de-ionized water, with shaking, at 37° C. Stocks (0.5 ml/tube) were stored at −70° C. until use. Bacteria titrations were performed in microtiter plates to detect the $TCID_{50}$, in which $TCID_{50}$ represents the dilution that gives rise to bacterial growth in 50% of inoculated cultures. In general, an inoculum level of approximately 100 $TCID_{50}$ was used for susceptibility testing.

Anti Bacterial Susceptibility Testing: $IC_{90}$ Determination Microtitre Plate Assay Flat-bottom, sterile 96-well plastic microtiter plates were filled with 180 µl of sterile deionized water, supplemented with 0.25% BSA. Subsequently, stock solutions (7.8× final test concentration) of compounds were added in 45 µl volumes in column 2 Serial five-fold dilutions (45 µl in 180 µl) were made directly in the microtiter plates from column 2 to reach column 11. Untreated control samples with (column 1) and without (column 12) inoculum were included in each microtiter plate. Depending on the bacteria type, approximately 10 to 60 CFU per well of bacteria inoculum (100 TCID50), in a volume of 100 µl in 2.8× Mueller-Hinton broth medium, was added to the rows A to H, except column 12. The same volume of broth medium without inoculum was added to column 12 in row A to H. The cultures were incubated at 37° C. for 24 hours under a normal atmosphere (incubator with open air valve and continuous ventilation). At the end of incubation, one day after inoculation, the bacterial growth was quantitated fluorometrically. Therefore resazurin (0.6 mg/ml) was added in a volume of 20 µl to all wells 3 hours after inoculation, and the plates were re-incubated overnight. A change in colour from blue to pink indicated the growth of bacteria. The fluorescence was read in a computer-controlled fluorometer (Cytofluor Biosearch) at an excitation wavelength of 530 nm and an emission wavelength of 590 nm. The % growth inhibition achieved by the compounds was calculated according to standard methods. The $IC_{90}$ (expressed in µg/ml) was defined as the 90% inhibitory concentration for bacterial growth. The results are shown in Table 3.

Agar Dilution Method.

$MIC_{99}$ values (the minimal concentration for obtaining 99% inhibition of bacterial growth) can be determined by performing the standard Agar dilution method according to NCCLS standards* wherein the media used includes Mueller-Hinton agar.

* Clinical laboratory standard institute. 2005. Methods for dilution Antimicrobial susceptibility tests for bacteria that grows Aerobically: approved standard—sixth edition Time Kill Assays Bactericidal or bacteriostatic activity of the compounds may be determined in a time kill assay using the broth microdilution method *. In a time kill assay on *Staphylococcus aureus*, the starting inoculum of *S. aureus* is $10^6$ CFU/ml in Muller Hinton broth. The antibacterial compounds are used at the concentration of 0.1 to 10 times the MIC (i.e. $IC_{90}$ as determined in microtitre plate assay). Wells receiving no antibacterial agent constitute the culture growth control. The plates containing the microorganism and the test compounds are incubated at 37° C. After 0, 3, 6, and 24 hrs of incubation samples are removed for determination of viable counts by serial dilution ($10^{-1}$ to $10^{-6}$) in sterile PBS and plating (200 µl) on Mueller Hinton agar. The plates are incubated at 37° C. for 24 hrs and the number of colonies are determined Killing curves can be constructed by plotting the $\log_{10}$ CFU per ml versus time. A bactericidal effect is commonly defined as 3-$\log_{10}$ decrease in number of CFU per ml as compared to untreated inoculum. The potential carryover effect of the drugs is removed by serial dilutions and counting the colonies at highest dilution used for plating.

* Zurenko, G. E. et al. In vitro activities of U-100592 and U-100766, novel oxazolidinone antibacterial agents. *Antimicrob. Agents Chemother.* 40, 839-845 (1996).

Determination of Cellular ATP Levels

In order to analyse the change in the total cellular ATP concentration (using ATP bioluminescence Kit, Roche), assays are carried out by growing a culture of *S. aureus* (ATCC29213) stock in 100 ml Mueller Hinton flasks and incubate in a shaker-incubator for 24 hrs at 37° C. (300 rpm). Measure $OD_{405}$ and calculate the CFU/ml. Dilute the cultures to $1\times10^6$ CFU/ml (final concentration for ATP measurement: $1\times10^5$ CFU/100 µl per well) and add test compound at 0.1 to 10 times the MIC (i.e. $IC_{90}$ as determined in microtitre plate assay). Incubate these tubes for 0, 30 and 60 minutes at 300 rpm and 37° C. Use 0.6 ml bacterial suspension from the snap-cap tubes and add to a new 2 ml eppendorf tubes. Add 0.6 ml cell lysis reagent (Roche kit), vortex at max speed and incubate for 5 minutes at room temperature. Cool on ice. Let the luminometer warm up to 30° C. (Luminoskan Ascent Labsystems with injector). Fill one column (=6 wells) with 100 µl of the same sample. Add 100 µl Luciferase reagent to each well by using the injector system. Measure the luminescence for 1 sec.

TABLE 3

$IC_{90}$ values (µg/ml).

| Compound number | STA B29213 | SPN 6305 | MSM 607 |
|---|---|---|---|
| 25 | >19.87 | | >19.87 |
| 26 | >44.79 | | |
| 70 | 4.38 | | |
| 31 | 3.48 | | 1.90 |
| 71 | 4.38 | | |
| 32 | 3.48 | | 1.56 |
| 72 | 4.11 | | |
| 73 | 4.11 | | |
| 77 | 5.49 | | 4.36 |
| 33 | 3.48 | | >3.48 |
| 80 | 4.37 | | |
| 81 | 8.52 | | |
| 82 | 2.84 | | 1.60 |
| 19 | 5.95 | | 3.76 |
| 89 | 3.58 | | 1.80 |
| 84 | 6.95 | | 5.52 |
| 18 | 19.96 | | 10.00 |
| 35 | 2.76 | 4.37 | 2.19 |
| 34 | 3.48 | | 2.20 |
| 85 | 7.23 | | 3.62 |

TABLE 3-continued $IC_{90}$ values (µg/ml).

| Compound number | STA B29213 | SPN 6305 | MSM 607 |
|---|---|---|---|
| 86 | 1.82 | 4.56 | 4.07 |
| 83 | 7.12 | | 3.57 |
| 87 | 3.58 | 7.15 | 2.85 |
| 36 | 3.47 | | 2.19 |
| 15 | 1.74 | 6.93 | 1.38 |
| 88 | 2.63 | 8.32 | 1.66 |
| 90 | 3.18 | 8.00 | 3.18 |
| 91 | 1.64 | 4.63 | 1.64 |
| 92 | 1.64 | 6.54 | 1.64 |
| 93 | 3.18 | 5.66 | 2.01 |
| 37 | 1.14 | | 0.90 |
| 94 | 3.13 | 4.95 | 1.76 |
| 97 | >13.84 | | 13.84 |
| 38 | 3.48 | 6.94 | 3.48 |
| 98 | 1.78 | 6.32 | 1.12 |
| 99 | 1.78 | 6.32 | 1.42 |
| 100 | 7.09 | | 7.09 |
| 109 | 1.49 | | 1.49 |
| 101 | 3.56 | 6.32 | 1.59 |
| 102 | 3.76 | 7.50 | 3.76 |
| 103 | 14.96 | | 14.96 |
| 107 | 1.87 | | 2.65 |
| 104 | 1.80 | | 1.14 |
| 106 | 1.87 | | <0.93 |
| 7 | 1.49 | | 0.94 |
| 108 | 2.41 | | 1.36 |
| 110 | 1.87 | | 1.87 |
| 105 | 1.80 | | 0.90 |
| 39 | 1.17 | 5.24 | 0.93 |
| 40 | 3.42 | 6.83 | 1.93 |
| 113 | 2.02 | 4.04 | 1.01 |
| 112 | 1.66 | 6.60 | 0.93 |
| 95 | 2.02 | | 1.43 |
| 114 | 1.75 | 4.38 | 0.98 |
| 115 | 3.30 | 4.16 | 2.08 |
| 116 | 3.42 | 6.83 | 1.72 |
| 41 | 3.48 | 6.95 | 3.48 |
| 117 | 3.48 | 5.52 | 2.77 |
| 118 | >20.58 | | >20.58 |
| 119 | >16.90 | | >16.90 |
| 121 | 3.62 | 3.62 | 3.62 |
| 122 | 2.88 | 3.62 | 3.62 |
| 11 | 3.00 | | 3.00 |
| 124 | 3.00 | | 3.00 |
| 125 | 3.00 | | 3.00 |
| 126 | 3.85 | | 3.06 |
| 127 | 1.93 | | 3.06 |
| 128 | 4.56 | | 3.62 |
| 129 | 12.52 | | 7.90 |
| 130 | 11.60 | | 5.81 |
| 131 | >6.27 | | 4.98 |
| 132 | | | 9.21 |
| 133 | 3.85 | | 3.06 |
| 134 | 3.07 | | 3.86 |
| 120 | 6.76 | | 5.37 |
| 135 | 1.84 | | 1.84 |
| 136 | 2.08 | | 1.47 |
| 137 | 3.69 | | 1.65 |
| 138 | 2.35 | | 1.18 |
| 141 | 7.77 | | 4.37 |
| 139 | 2.00 | | 1.78 |
| 140 | 2.55 | | 0.72 |
| 142 | 3.06 | | 2.16 |
| 143 | 1.82 | | 2.04 |
| 144 | 3.63 | | 3.24 |
| 145 | 2.92 | | 2.32 |
| 146 | 2.35 | | 1.87 |
| 147 | 3.39 | | 1.51 |
| 148 | 3.39 | | 1.70 |
| 149 | 5.63 | | 2.52 |
| 150 | 2.63 | | 1.66 |
| 151 | 5.26 | | 2.35 |
| 152 | 2.78 | | 1.76 |

TABLE 3-continued

IC$_{90}$ values (μg/ml).

IC90 μg/ml

| Compound number | STA B29213 | SPN 6305 | MSM 607 |
|---|---|---|---|
| 153 | >12.63 | | >12.63 |
| 157 | >12.98 | | >12.98 |
| 154 | >12.63 | | >12.63 |
| 155 | >12.63 | | >12.63 |
| 156 | >12.63 | | 11.25 |
| 158 | >12.98 | | >12.98 |
| 159 | >14.69 | | >14.69 |
| 160 | 3.51 | | 2.48 |
| 162 | 3.52 | | 2.49 |
| 42 | 7.34 | | 2.60 |
| 163 | 1.70 | | 1.20 |
| 164 | 4.23 | | 2.38 |
| 165 | 5.10 | | 3.61 |
| 166 | 3.09 | | 1.95 |
| 161 | 6.90 | | 6.90 |
| 167 | 3.17 | | 1.26 |
| 168 | 3.17 | | 1.42 |
| 169 | 4.96 | | 3.94 |
| 170 | 5.27 | | 4.69 |
| 171 | 7.16 | | 5.69 |
| 173 | 2.86 | | 3.20 |
| 174 | 3.30 | | 3.30 |
| 175 | 2.34 | | 3.30 |
| 176 | 3.30 | | 3.30 |
| 177 | 1.76 | | 2.78 |
| 178 | 6.15 | | 4.89 |
| 179 | 8.69 | | 6.15 |
| 180 | 3.08 | | 3.08 |
| 181 | 6.15 | | 9.75 |
| 172 | 7.16 | | 3.59 |
| 182 | 6.60 | | 6.60 |
| 184 | 13.43 | | 13.43 |
| 185 | 13.43 | | 8.47 |
| 186 | 9.51 | | 8.47 |
| 187 | >13.43 | | 13.43 |
| 188 | 2.20 | | 2.77 |
| 190 | 1.39 | | 1.76 |
| 189 | 1.76 | | 2.78 |
| 191 | 3.50 | | 3.50 |
| 183 | 3.31 | | 3.31 |
| 192 | 7.00 | | 13.96 |
| 43 | 3.48 | | 3.48 |
| 193 | 5.35 | | 5.35 |
| 61 | 1.69 | | 0.85 |
| 194 | 1.69 | | 2.68 |
| 195 | 3.17 | | 2.00 |
| 196 | 3.17 | | 2.52 |
| 197 | 1.59 | | 1.59 |
| 198 | 3.17 | | 3.17 |
| 199 | 7.16 | | 7.16 |
| 200 | 5.69 | | 5.69 |
| 201 | >19.28 | | >19.28 |
| 202 | 1.80 | | 2.27 |
| 203 | 10.80 | | 6.81 |
| 204 | 3.63 | | 7.23 |
| 205 | >15.22 | | >15.22 |
| 209 | 14.75 | | 14.75 |
| 213 | >17.31 | | >17.31 |
| 206 | >15.08 | | >15.08 |
| 207 | 3.83 | | 3.83 |
| 208 | 7.60 | | 9.57 |
| 212 | 7.60 | | 6.04 |
| 210 | 1.86 | | 2.94 |
| 211 | 14.75 | | 7.39 |
| 214 | >17.57 | | >17.57 |
| 215 | 13.66 | | 17.19 |
| 44 | 7.16 | | 3.59 |
| 45 | 1.80 | | 1.14 |
| 46 | 3.59 | | 1.80 |
| 47 | 14.30 | | 5.69 |
| 216 | 7.16 | | 5.69 |
| 217 | 1.27 | | 0.90 |
| 218 | 5.69 | | 2.85 |
| 219 | 3.59 | | 1.80 |
| 220 | >14.80 | | >14.80 |
| 221 | 3.73 | | 2.96 |
| 222 | >14.78 | | >14.78 |
| 223 | >14.83 | | >14.83 |
| 224 | 3.73 | | 5.92 |
| 225 | >14.77 | | >14.77 |
| 226 | 1.80 | | 0.90 |
| 227 | 1.80 | | 2.86 |
| 48 | 0.90 | | 0.72 |
| 228 | 1.80 | | 2.86 |
| 49 | 2.25 | | 1.79 |
| 229 | 1.86 | | 3.31 |
| 230 | 1.67 | | 1.18 |
| 231 | 3.30 | | 2.62 |
| 232 | 6.65 | | 5.93 |
| 233 | 1.67 | | 1.32 |
| 234 | 5.24 | | 3.71 |
| 236 | 10.26 | | 7.26 |
| 237 | >13.93 | | 11.06 |
| 238 | >13.99 | | >13.99 |
| 96 | 1.60 | | 1.01 |
| 239 | 1.67 | | 2.97 |
| 5 | 1.67 | | 1.67 |
| 240 | 6.67 | | 4.21 |
| 241 | 4.72 | | 3.34 |
| 242 | 1.51 | | 1.20 |
| 243 | 2.14 | | 2.40 |
| 244 | 2.40 | | 1.51 |
| 245 | 1.91 | | 1.07 |
| 246 | >11.75 | | >11.75 |
| 247 | 3.38 | | 1.69 |
| 248 | 3.38 | | 2.68 |
| 249 | 1.69 | | 1.07 |
| 250 | 1.69 | | 1.35 |
| 251 | 13.43 | | 10.67 |
| 252 | >13.43 | | >13.43 |
| 253 | >13.43 | | >13.43 |
| 235 | 4.17 | | 6.60 |
| 254 | 3.60 | | 3.60 |
| 256 | 2.49 | | 2.22 |
| 6 | 1.83 | | 9.18 |
| 258 | 3.66 | | 3.66 |
| 259 | 1.76 | | 1.40 |
| 257 | 4.97 | | 3.14 |
| 260 | 3.39 | | 3.39 |
| 261 | 1.70 | | 1.70 |
| 262 | 7.59 | | 3.39 |
| 263 | >13.89 | | >13.89 |
| 264 | >13.88 | | 3.49 |
| 265 | >13.92 | | 13.92 |
| 266 | 2.50 | | 2.22 |
| 267 | 1.76 | | 1.40 |
| 268 | 1.76 | | 1.40 |
| 269 | >14.75 | | >14.75 |
| 270 | 7.42 | | 5.89 |
| 271 | 7.42 | | 9.34 |
| 272 | >14.78 | | >14.78 |
| 273 | 3.39 | | 1.70 |
| 274 | 1.91 | | 1.07 |
| 275 | 0.85 | | 1.35 |
| 276 | 1.70 | | 1.07 |
| 277 | 1.76 | | 1.40 |
| 278 | 1.77 | | 1.40 |
| 279 | 7.00 | | 7.00 |
| 280 | 1.75 | | 1.10 |
| 281 | 3.53 | | 7.03 |
| 283 | 3.39 | | 3.39 |
| 284 | 4.25 | | 3.38 |
| 285 | >13.49 | | >13.49 |
| 286 | 4.22 | | 2.12 |
| 287 | 3.31 | | 2.63 |
| 289 | 4.23 | | 3.36 |

TABLE 3-continued

IC$_{90}$ values (µg/ml).

| Compound number | STA B29213 | SPN 6305 | MSM 607 |
|---|---|---|---|
| 290 | 2.35 | | 2.63 |
| 288 | 4.29 | | 3.41 |
| 255 | 3.65 | | 7.28 |
| 291 | 7.16 | | 7.16 |
| 292 | 7.16 | | 5.69 |
| 293 | 7.16 | | 7.16 |
| 294 | 11.36 | | 14.30 |
| 295 | 3.43 | | 3.43 |
| 296 | 3.43 | | 6.85 |
| 297 | 3.43 | | 13.65 |
| 298 | 6.88 | | 6.88 |
| 282 | 7.02 | | 7.02 |
| 299 | 1.70 | | 1.35 |
| 300 | 1.07 | | 1.70 |
| 301 | 6.76 | | 6.76 |
| 302 | 2.14 | | 1.35 |
| 303 | 6.88 | | 5.47 |
| 304 | 3.45 | | 1.73 |
| 305 | 18.76 | | 18.76 |
| 307 | >15.12 | | >15.12 |
| 50 | 1.15 | | 1.15 |
| 309 | 14.50 | | 11.52 |
| 310 | 3.62 | | 3.62 |
| 313 | 2.40 | | 1.91 |
| 314 | 3.05 | | 4.83 |
| 51 | 2.34 | | 1.17 |
| 315 | 3.84 | | 3.84 |
| 316 | 3.84 | | 3.05 |
| 308 | 7.65 | | 6.08 |
| 311 | 7.24 | | 3.63 |
| 312 | 3.62 | | 3.62 |
| 317 | 1.92 | | 1.92 |
| 306 | 4.70 | | 4.70 |
| 318 | 1.76 | | 1.76 |
| 1 | 3.32 | | 1.66 |
| 2 | 13.20 | | 13.20 |
| 3 | 0.83 | | 0.83 |
| 4 | 2.63 | | 2.09 |
| 319 | 2.40 | | 2.40 |
| 320 | 3.71 | | 2.95 |
| 321 | 15.33 | | 12.18 |
| 322 | 2.43 | | 3.85 |
| 323 | 7.68 | | 6.10 |
| 324 | 1.93 | | 3.43 |
| 325 | >19.04 | | 19.04 |
| 327 | >15.31 | | >15.31 |
| 326 | 5.37 | | 4.78 |
| 328 | 15.31 | | 12.16 |
| 329 | 7.27 | | 7.27 |
| 330 | 2.08 | | 1.04 |
| 331 | 1.06 | | 0.94 |
| 332 | 4.38 | | 2.20 |
| 333 | 2.50 | | 3.53 |
| 334 | 8.87 | | 7.04 |
| 335 | 1.76 | | 2.21 |
| 336 | 3.51 | | 7.00 |
| 337 | 1.80 | | 0.90 |
| 338 | 1.80 | | 1.43 |
| 339 | 3.60 | | 1.80 |
| 340 | 2.86 | | 1.43 |
| 341 | 2.36 | | 4.71 |
| 343 | 6.90 | | 4.35 |
| 344 | 3.46 | | 8.68 |
| 345 | 4.38 | | 3.48 |
| 346 | 2.13 | | 1.69 |
| 347 | 4.27 | | 1.70 |
| 348 | 4.19 | | 1.67 |
| 349 | 7.04 | | 7.04 |
| 350 | 2.80 | | 1.77 |
| 351 | 1.70 | | 1.35 |
| 352 | 1.70 | | 0.85 |
| 353 | 2.18 | | 1.73 |
| 354 | 3.95 | | 3.14 |
| 342 | 7.46 | | 3.74 |
| 355 | 3.60 | | 1.43 |
| 356 | 1.80 | | 1.80 |
| 357 | 5.70 | | 3.60 |
| 358 | 3.60 | | 1.43 |
| 359 | 12.82 | | 10.18 |
| 360 | 12.82 | | 6.42 |
| 361 | 12.82 | | 6.42 |
| 362 | 12.82 | | 10.18 |
| 363 | 1.87 | | 3.74 |
| 364 | 3.74 | | 2.97 |
| 366 | 7.16 | | 3.59 |
| 367 | 7.16 | | 5.69 |
| 368 | 17.71 | | 14.06 |
| 369 | 9.12 | | 4.57 |
| 52 | 1.23 | | 0.62 |
| 53 | 1.55 | | 2.46 |
| 54 | 3.54 | | 1.77 |
| 55 | 6.19 | | 3.90 |
| 370 | 3.09 | | 1.55 |
| 371 | 3.08 | | 2.44 |
| 372 | 6.14 | | 3.08 |
| 373 | 3.08 | | 3.08 |
| 374 | 3.08 | | 1.23 |
| 365 | 3.74 | | 3.74 |
| 56 | >13.94 | | >13.94 |
| 57 | 3.50 | | 3.50 |
| 58 | >13.94 | | >13.94 |
| 59 | 6.99 | | 5.55 |
| 375 | >12.90 | | 12.90 |
| 376 | 3.24 | | 2.57 |
| 377 | >14.86 | | >14.86 |
| 378 | 14.86 | | 11.80 |
| 60 | 2.77 | | 1.39 |
| 379 | 3.49 | | 2.77 |
| 380 | 5.16 | | 4.10 |
| 381 | 3.49 | | 1.75 |
| 382 | 3.45 | | 2.18 |
| 383 | 3.45 | | 2.74 |
| 384 | 3.45 | | 2.18 |
| 385 | 1.73 | | 1.37 |
| 386 | 3.65 | | 2.90 |
| 387 | 14.55 | | 7.29 |
| 388 | 1.80 | | 3.59 |
| 389 | 7.16 | | 7.16 |
| 390 | 14.30 | | 11.36 |
| 391 | 3.59 | | 1.80 |
| 392 | 6.32 | | 3.17 |
| 393 | 10.01 | | 6.32 |
| 394 | 2.89 | | 2.29 |
| 395 | 5.76 | | 2.89 |
| 62 | 5.75 | | 4.57 |
| 396 | 5.75 | | 5.75 |
| 397 | >12.28 | | >12.28 |
| 398 | >12.28 | | >12.28 |
| 399 | >12.47 | | >12.47 |
| 400 | >12.47 | | >12.47 |
| 401 | >12.77 | | >12.77 |
| 402 | >12.47 | | 12.47 |
| 403 | 9.72 | | 8.66 |
| 404 | 2.99 | | 1.68 |
| 405 | 5.26 | | 2.63 |
| 406 | 3.29 | | 2.61 |
| 407 | 1.65 | | 1.17 |
| 408 | >19.18 | | >19.18 |
| 409 | 2.01 | | 6.36 |
| 410 | 12.25 | | 7.73 |
| 411 | 4.10 | | 6.50 |
| 412 | 4.02 | | 2.02 |
| 413 | 18.24 | | 18.24 |
| 414 | 18.39 | | 18.39 |
| 415 | 15.47 | | >15.47 |
| 16 | 7.21 | | 9.08 |

TABLE 3-continued

IC90 values (μg/ml).

| Compound number | STA B29213 | SPN 6305 | MSM 607 |
|---|---|---|---|
| 416 | 9.25 | | 9.25 |
| 417 | >13.88 | | >13.88 |
| 418 | >17.6721 | | 17.67 |
| 419 | 11.03 | | 11.03 |
| 420 | 5.43 | | 5.43 |
| 421 | 5.43 | | 5.43 |
| 422 | 7.67 | | 8.61 |
| 423 | 5.43 | | 3.43 |
| 9 | 4.92 | | 3.48 |
| 10 | >10.37 | | >10.37 |
| 424 | >10.37 | | >10.37 |
| 425 | >11.09 | | >11.09 |
| 426 | >11.09 | | >11.09 |
| 427 | >16.08 | | >16.08 |
| 428 | 15.06 | | 10.66 |
| 67 | 14.90 | | 7.47 |
| 429 | 7.72 | | 3.87 |
| 430 | 3.39 | | 3.39 |
| 431 | 8.60 | | 7.66 |
| 432 | 7.41 | | 5.24 |
| 13 | 8.48 | | 4.77 |
| 14 | 6.74 | | 3.79 |
| 442 | 11.37 | | 3.60 |
| 433 | 6.40 | | 4.04 |
| 434 | 3.21 | | 3.21 |
| 12 | 7.09 | | 2.82 |
| 435 | 5.63 | | 3.99 |
| 436 | 13.44 | | |
| 29 | >9.96 | | |
| 20 | >10.89 | | |
| 437 | 13.44 | | |
| 30 | >10.82 | | |
| 438 | 3.21 | | |
| 439 | 12.77 | | |
| 440 | 8.61 | | |
| 441 | 12.17 | | |
| 443 | 4.41 | | |
| 444 | 12.42 | | |
| 445 | 3.50 | | |
| 446 | 10.89 | | 5.46 |
| 65 | >14.27 | | >14.27 |
| 66 | >14.27 | | >14.27 |
| 447 | >14.27 | | >14.27 |
| 448 | >14.27 | | >14.27 |
| 453 | 5.48 | | 2.75 |
| 449 | 5.48 | | 2.75 |
| 450 | 8.69 | | 4.35 |
| 454 | 10.94 | | 4.35 |
| 451 | 5.48 | | 2.18 |
| 452 | 9.75 | | 4.35 |
| 455 | 7.74 | | 5.48 |
| 456 | 10.94 | | 10.94 |
| 457 | 11.50 | | 5.76 |
| 458 | 11.50 | | 11.50 |
| 22 | >15.036 | | >15.036 |
| 23 | >15.036 | | >15.036 |
| 24 | >15.036 | | >15.036 |
| 459 | 13.14 | | 3.70 |
| 460 | 3.70 | | 1.86 |
| 461 | 2.62 | | 1.47 |
| 462 | 1.86 | | 0.93 |
| 63 | 3.17 | | 1.59 |
| 64 | 7.93 | | 3.98 |
| 463 | 14.75 | | 2.34 |
| 464 | 1.47 | | 1.17 |
| 465 | 5.87 | | 2.62 |
| 466 | 3.70 | | 1.47 |
| 467 | 3.21 | | 2.55 |
| 468 | 3.21 | | 3.21 |
| 469 | 8.30 | | 4.16 |
| 470 | 5.23 | | 3.08 |
| 471 | 4.94 | | 2.91 |
| 27 | 11.55 | | 7.29 |
| 28 | 6.22 | | 3.12 |

STA B29213 means *Staphylococcus aureus* (ATCC29213); SPN 6305 means *Streptococcus pneumoniae* (ATCC6305); MSM 607 means *Mycobacterium smegmatis* (ATCC607); ATCC means American Type Tissue Culture.

The invention claimed is:

1. A compound of formula (Ia) or (Ib):

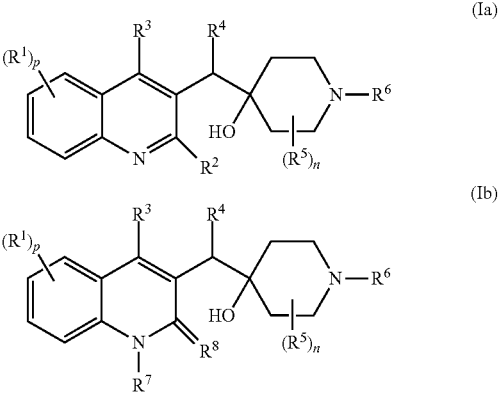

including any stereochemically isomeric form thereof, wherein p is an integer equal to 1, 2, 3 or 4;

n is an integer equal to 1 or 2; provided that if n is 2 then both $R^5$ substituents are linked to the same carbon atom of the piperidine moiety;

$R^1$ is hydrogen, cyano, cyano$C_{1-6}$alkyl, formyl, carboxyl, halo, $C_{1-6}$alkyl, $C_{2-6}$alkenyl, $C_{2-6}$alkynyl, polyhalo$C_{1-6}$alkyl, hydroxy, hydroxy$C_{1-6}$alkyl, $C_{1-6}$alkyloxy, $C_{1-6}$alkyloxy$C_{1-6}$alkyl, $C_{1-6}$alkylthio, $C_{1-6}$alkylthio$C_{1-6}$alkyl, —C=N—$OR^{11}$, amino, mono or di($C_{1-6}$alkyl)amino, amino$C_{1-6}$alkyl, mono or di($C_{1-6}$alkyl)amino$C_{1-6}$alkyl, $C_{1-6}$alkylcarbonylamino$C_{1-6}$alkyl, $R^{9b}R^{10b}$N—C(=O)—, aryl$C_{1-6}$alkyl, arylcarbonyl, $R^{9a}R^{10a}$N—$C_{1-6}$alkyl, di(aryl)$C_{1-6}$alkyl, aryl, $C_{3-6}$cycloalkyl, $R^{9a}R^{10a}$N—, $R^{9a}R^{10a}$N—C(O)—, $C_{1-4}$alkyl-S(=O)$_2$—, or Het;

$R^2$ is hydrogen, $C_{1-6}$alkyloxy, aryl, aryloxy, hydroxy, mercapto, $C_{1-6}$alkyloxy$C_{1-6}$alkyloxy, $C_{1-6}$alkylthio, mono or di($C_{1-6}$alkyl)amino, amino, pyrrolidino or a radical of formula

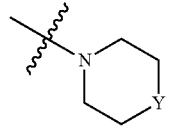

wherein Y is $CH_2$, O, S, NH or N—$C_{1-6}$alkyl;

$R^3$ is hydrogen, halo, $C_{1-6}$alkyl, aryl or Het;

is aryl$^1$ or Het;

$R^5$ is aryl, aryl$C_{1-6}$alkyl, $C_{3-6}$cycloalkyl, $C_{3-6}$cycloalkyl$C_{1-6}$alkyl, Het, Het$C_{1-6}$alkyl, $C_{1-6}$alkyl, hydroxy$C_{1-6}$alkyl, amino$C_{1-6}$alkyl, mono- or di($C_{1-4}$alkyl)amino$C_{1-6}$alkyl, aryl-NH—$C_{1-6}$alkyl, Het-NH—$C_{1-6}$alkyl, $C_{2-6}$alkenyl or halo;

$R^6$ is hydrogen, $C_{1-6}$alkyl, aryl$C_{1-6}$alkyl, Het$^1$, Het$^1$$C_{1-6}$alkyl or —C(=NH)—NH$_2$;

$R^7$ is hydrogen or $C_{1-6}$alkyl;

$R^8$ is oxo; or $R^7$ and $R^8$ together form the radical CH=CH—N=;

$R^{9a}$ and $R^{10a}$ together with the nitrogen atom to which they are attached form a radical selected from the group consisting of pyrrolidinyl, piperidinyl, piperazinyl, morpholinyl, 4-thiomorpholinyl, 2,3-dihydroisoindol-1-yl, thiazolidin-3-yl, 1,2,3,6-tetrahydropyridyl, hexahydro-1H-azepinyl, hexahydro-1H-1,4-diazepinyl, hexahydro-1,4-oxazepinyl, 1,2,3,4-tetrahydroisoquinolin-2-yl, pyrrolinyl, pyrrolyl, imidazolidinyl, pyrazolidinyl, 2-imidazolinyl, 2-pyrazolinyl, imidazolyl, pyrazolyl, triazolyl, pyridinyl, pyridazinyl, pyrimidinyl, pyrazinyl and triazinyl, each radical being optionally substituted with 1, 2, 3 or 4 substituents, each substituent being independently selected from $C_{1-6}$alkyl, polyhalo$C_{1-6}$alkyl, halo, aryl$C_{1-6}$alkyl, hydroxy, $C_{1-6}$alkyloxy, amino, mono- or di($C_{1-6}$alkyl)amino, $C_{1-6}$alkylthio, $C_{1-6}$alkylthio$C_{1-6}$alkyl, aryl, pyridyl or pyrimidinyl;

$R^{9b}$ and $R^{10b}$ each independently represent hydrogen, $C_{1-6}$alkyl, aryl or Het;

$R^{11}$ is hydrogen or $C_{1-6}$alkyl;

aryl is a homocycle selected from phenyl, naphthyl, acenaphthyl or tetrahydronaphthyl, each being optionally substituted with 1, 2 or 3 substituents, each substituent being independently selected from hydroxy, hydroxy$C_{1-6}$alkyl, halo, cyano, cyano$C_{1-6}$alkyl, nitro, amino, mono- or di($C_{1-6}$alkyl)amino, $C_{1-6}$alkyl, $C_{2-6}$alkenyl optionally substituted with phenyl, polyhalo$C_{1-6}$alkyl, $C_{1-6}$alkyloxy, $C_{1-6}$alkyloxy$C_{1-6}$alkyl, polyhalo$C_{1-6}$alkyloxy, carboxyl, $C_{1-6}$alkyloxycarbonyl, aminocarbonyl, morpholinyl or mono- or di($C_{1-6}$alkyl)aminocarbonyl;

aryl$^1$ is a homocycle selected from phenyl, naphthyl, acenaphthyl or tetrahydronaphthyl, each being optionally substituted with 1, 2 or 3 substituents, each substituent being independently selected from hydroxy, hydroxy$C_{1-6}$alkyl, halo, cyano, cyano$C_{1-6}$alkyl, nitro, amino, mono- or di($C_{1-6}$alkyl)amino, $C_{1-6}$alkyl, polyhalo$C_{1-6}$alkyl, $C_{1-6}$alkyloxy, $C_{1-6}$alkyloxy$C_{1-6}$alkyl, $C_{1-6}$alkylthio, polyhalo$C_{1-6}$alkyloxy, carboxyl, $C_{1-6}$alkyloxycarbonyl, aminocarbonyl, Het, mono- or di($C_{1-6}$alkyl)aminocarbonyl, or $C_{1-4}$alkyl-S(=O)$_2$—;

Het is a monocyclic heterocycle selected from N-phenoxypiperidinyl, piperidinyl, piperazinyl, morpholinyl, 4-thiomorpholinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle being optionally substituted with 1, 2 or 3 substituents, each substituent being independently selected from halo, hydroxy, $C_{1-6}$alkyl or $C_{1-6}$alkyloxy;

Het$^1$ is a monocyclic saturated heterocycle selected from pyrrolidinyl, piperidinyl, piperazinyl, morpholinyl, 4-thiomorpholinyl, imidazolidinyl, pyrazolidinyl; each monocyclic saturated heterocycle being optionally substituted with $C_{1-6}$alkyl or aryl$C_{1-6}$alkyl;

a N-oxide thereof, a pharmaceutically acceptable salt thereof or a solvate thereof.

2. A compound according to claim 1 wherein $R^1$ is hydrogen, carboxyl, halo, $C_{1-6}$alkylthio, amino$C_{1-6}$alkyl or Het.

3. A compound according to claim 1 wherein p is 1.

4. A compound according to claim 1 wherein $R^2$ is $C_{1-6}$alkyloxy.

5. A compound according to claim 1 wherein $R^3$ is hydrogen.

6. A compound according to claim 1 wherein $R^4$ is phenyl optionally substituted with 1 substituent, said substituent being selected from halo, cyano, $C_{1-4}$alkyl-S(=O)$_2$— or $C_{1-6}$alkylthio.

7. A compound according to claim 1 wherein $R^4$ is a monocyclic heterocycle selected from piperidinyl, pyrazolyl, furanyl or pyridinyl, especially pyrazolyl or pyridinyl; each monocyclic heterocycle being optionally substituted with 1 substituent selected from halo, hydroxy, $C_{1-6}$alkyl or $C_{1-6}$alkyloxy.

8. A compound according to claim 1 wherein $R^5$ is phenyl; phenyl substituted with 1 or 2 substituents each being independently selected from halo or $C_{1-6}$alkyl; benzyl; or benzyl wherein the phenyl moiety is substituted with 1 or 2 substituents each being independently selected from halo or $C_{1-6}$alkyl.

9. A compound according to claim 1 wherein $R^6$ is hydrogen, $C_{1-6}$alkyl or benzyl.

10. A compound according to claim 1 wherein $R^7$ is hydrogen and $R^8$ is oxo.

11. A compound according to claim 1 wherein the compound is a compound of formula (Ia).

12. A compound according to claim 1 wherein $R^1$ is placed in position 6 of the quinoline ring.

13. A compound according to claim 1 wherein n is 1.

14. A compound according to claim 1 wherein aryl is phenyl, optionally substituted with one or two substituents each being independently selected from halo; cyano; alkyl; or alkyloxy.

15. A compound according to claim 1 wherein

Het is pyridinyl or pyrazolyl.

16. A compound according to claim 1 wherein p is 1;

n is 1;

$R^1$ is halo; $C_{1-6}$alkylthio; $C_{1-4}$alkyl-S(=O)$_2$; or Het;

$R^2$ is $C_{1-6}$alkyloxy;

$R^3$ is hydrogen;

$R^4$ is phenyl optionally substituted with halo;

$R^5$ is aryl; aryl$C_{1-6}$alkyl; $C_{3-6}$cycloalkyl$C_{1-6}$alkyl; Het$C_{1-6}$alkyl; or $C_{1-6}$alkyl; and wherein $R^5$ is placed in position 2 of the piperdine ring; and $R^6$ is hydrogen.

17. A compound according to claim 1 wherein the compound is selected from the following compounds:

217
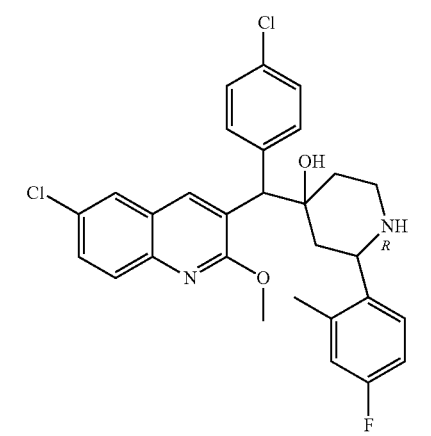
(2R), trans-3
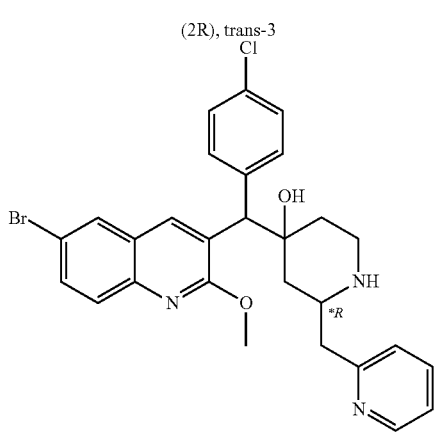
(2R*), cis-1
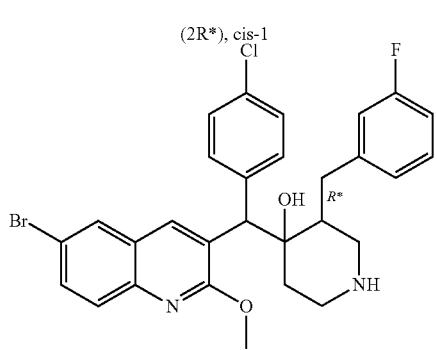
(3R*), (B)
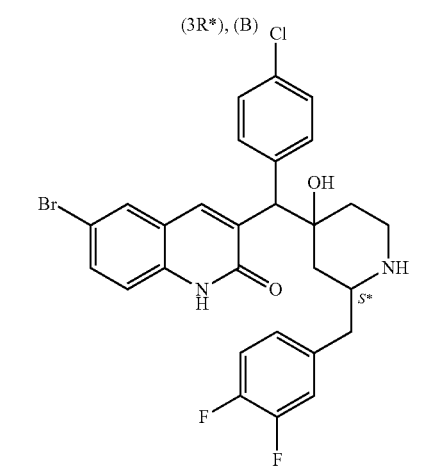
(2S*), cis-1
218
-continued
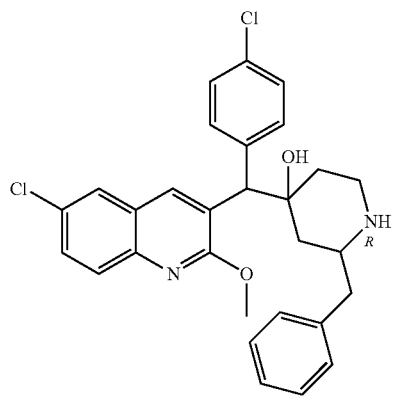
(2R), trans-3
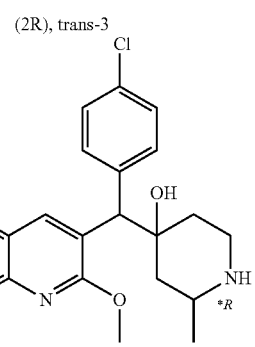
(2R*), cis-2
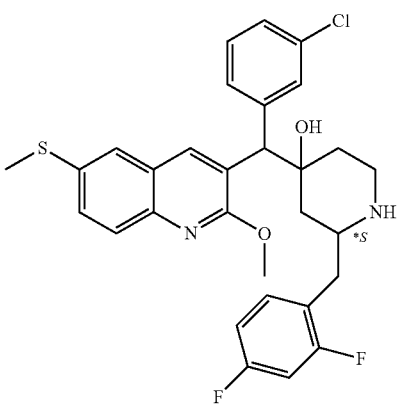
(2S*), cis-2
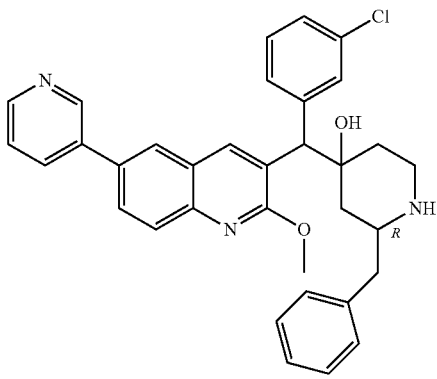
(2R), cis-1

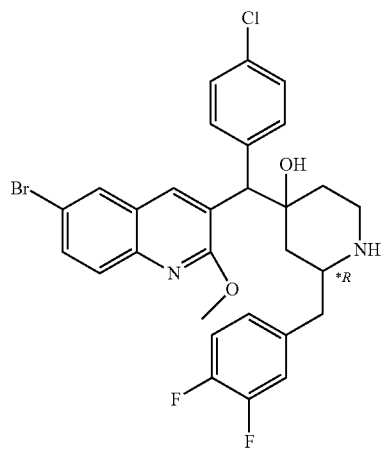
(2R*), cis-2
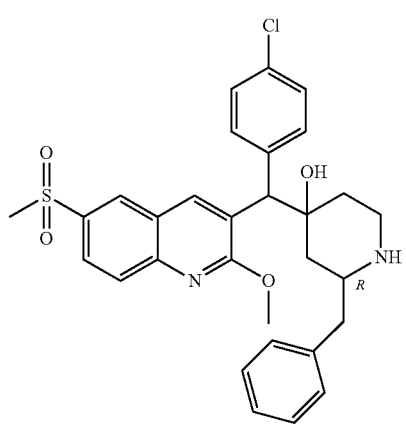
(2R), cis-3
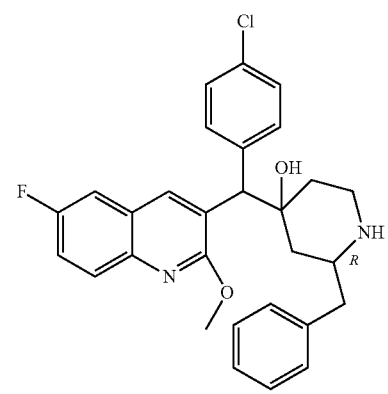
(2R), cis-1
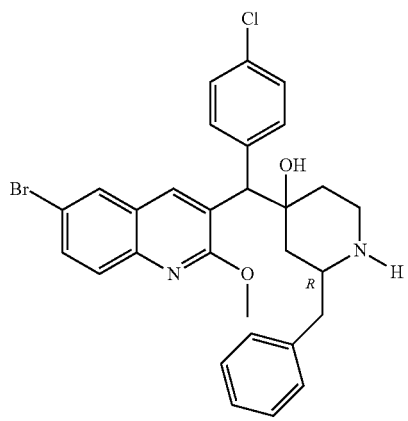
(2R), cis-4
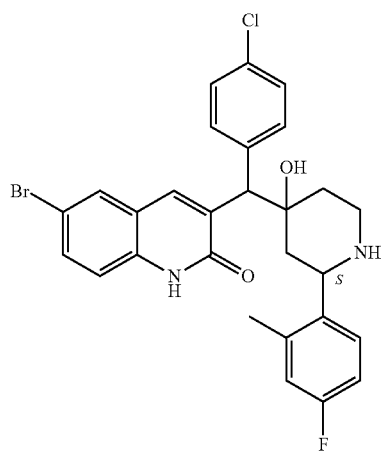
(2S), cis-2
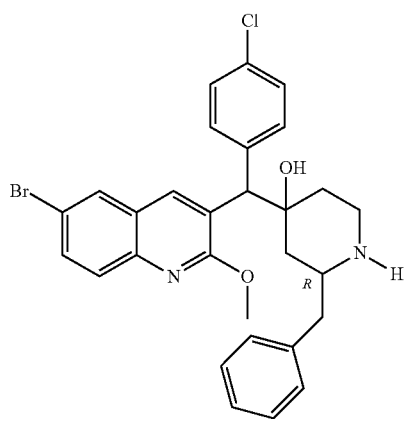
(2R), trans-2

-continued
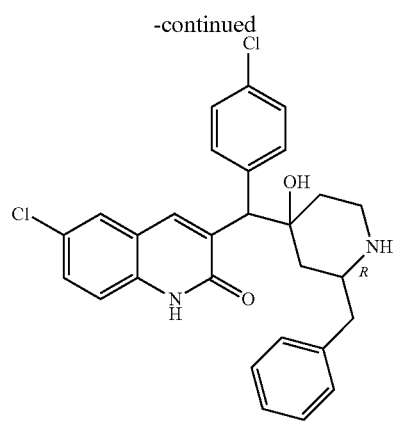
(2R), trans-3
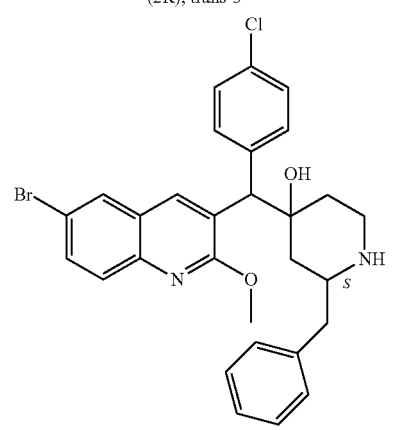
(2S), cis-4
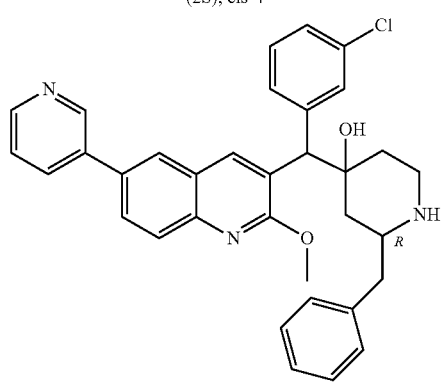
(2R), cis-4
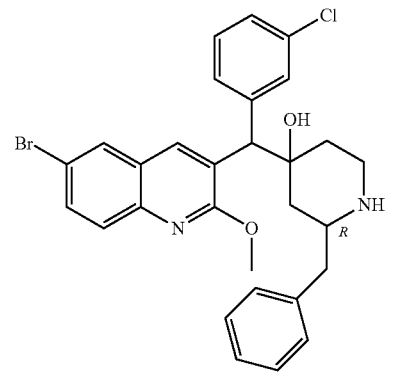
(2R), cis-4
-continued
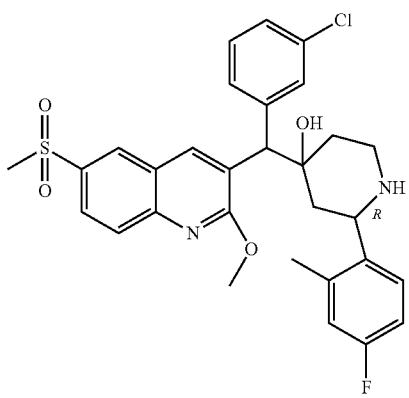
(2R), trans-2
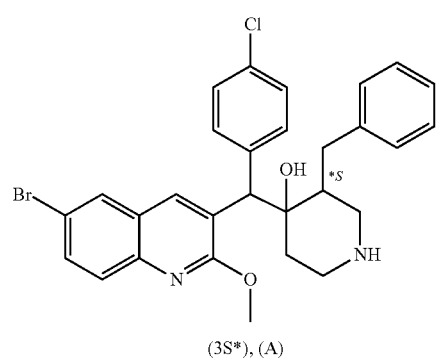
(3S*), (A)
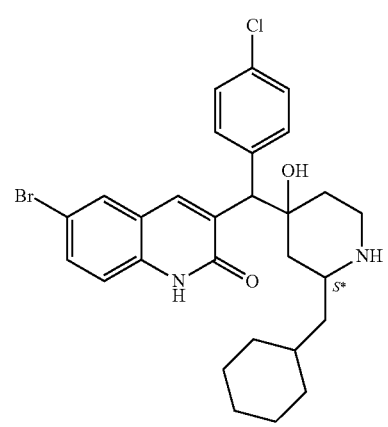
(2S*), (A)
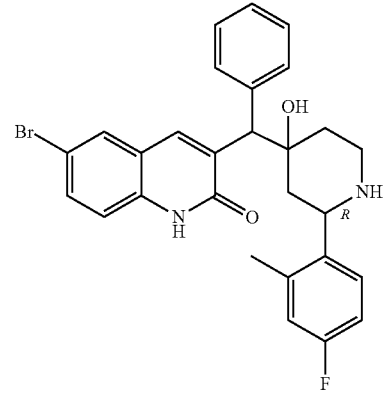
(2R), trans-2

223
-continued

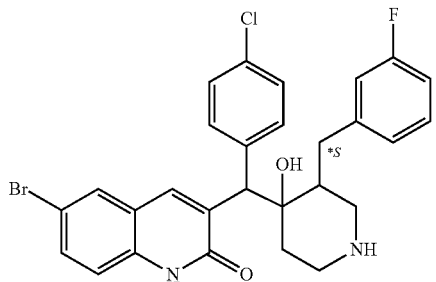

(3S*), (A)

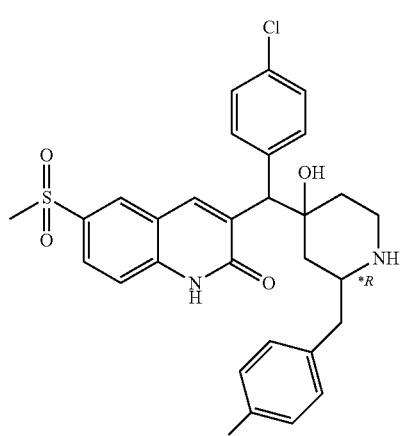

(2R*), cis-2

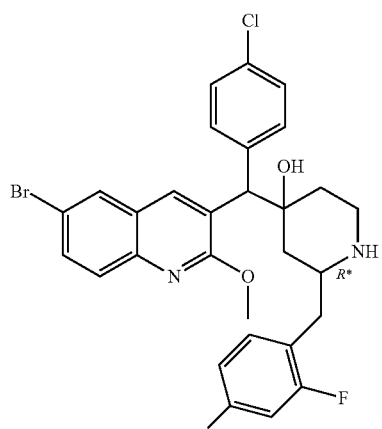

(2R*), cis-3

224
-continued

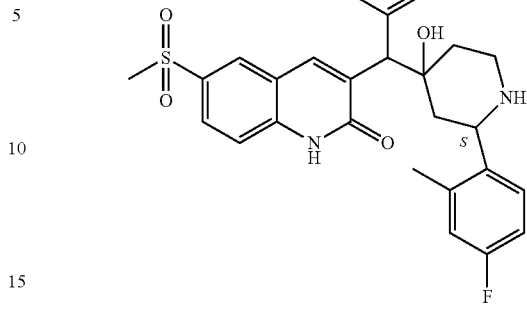

(2S), cis-4 including any stereochemically isomeric form thereof; a N-oxide thereof, a pharmaceutically acceptable salt thereof or a solvate thereof.

18. A pharmaceutical composition comprising a pharmaceutically acceptable carrier and, as active ingredient, a therapeutically effective amount of a compound as defined in claim 1.

19. A method for treating a bacterial infection comprising administering a therapeutic amount of a compound according to claim 1 to a patient having a bacterial infection.

20. The method of claim 19 wherein the bacterial infection is an infection with a gram-positive bacterium.

21. The method of claim 20 wherein the gram-positive bacterium is *Streptococcus pneumoniae*.

22. The method of claim 20 wherein the gram-positive bacterium is *Staphylococcus aureus*.

23. The method of claim 22 wherein the gram-positive bacterium is methicillin-resistant *Staphylococcus aureus*.

24. The method of claim 19 wherein the bacterial infection is a mycobacterial infection.

25. The method of claim 24 wherein the mycobacterial infection is an infection with *Mycobacterium tuberculosis*.

26. A process for the preparation of a compound according to claim 1 characterized by:
a) deprotecting an intermediate of formula (II-a) wherein $P^1$ is a suitable protecting group

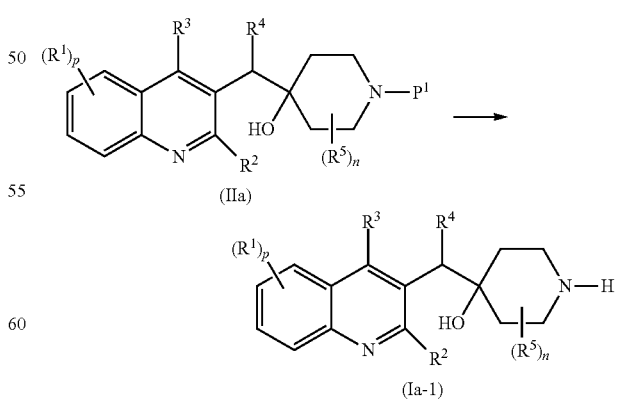

to prepare compounds of formula (Ia) wherein $R^6$ is hydrogen, said compounds being represented by formula (Ia-1);

b) deprotecting an intermediate of formula (IIa) with a suitable acid

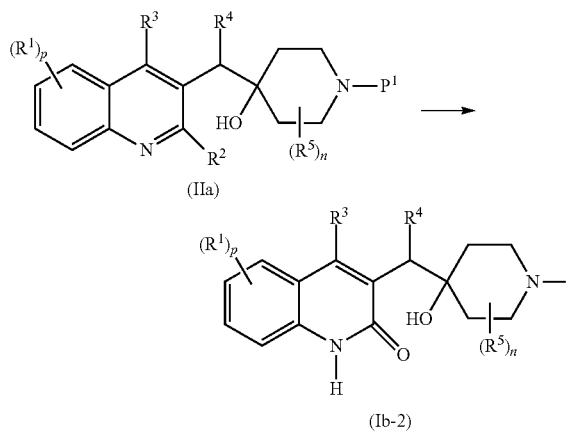

(IIa)

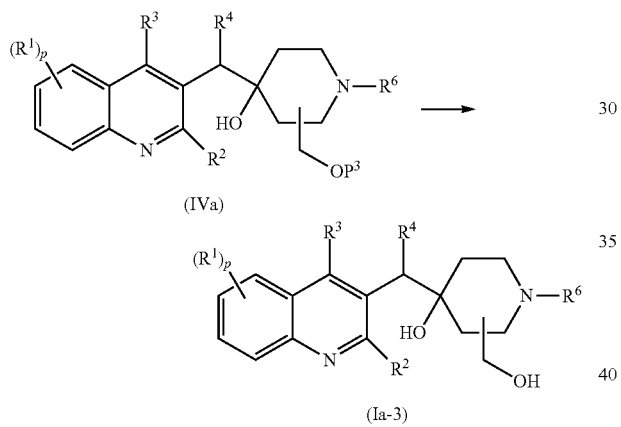

(Ib-2)

to prepare compounds of formula (Ib) wherein $R^6$ is hydrogen, $R^7$ is hydrogen and $R^8$ is oxo, said compounds being represented by formula (Ib-2);

c) treating an intermediate of formula (IV-a) wherein $P^3$ is a suitable protecting group with a quaternary ammonium salt (IVa)

(Ia-3)

to prepare compounds of formula (Ia) wherein $R^5$ is a hydroxymethyl group, said compounds being represented by formula (Ia-3);

c) reacting an intermediate of formula (Va) with a compound of formula (VIa)

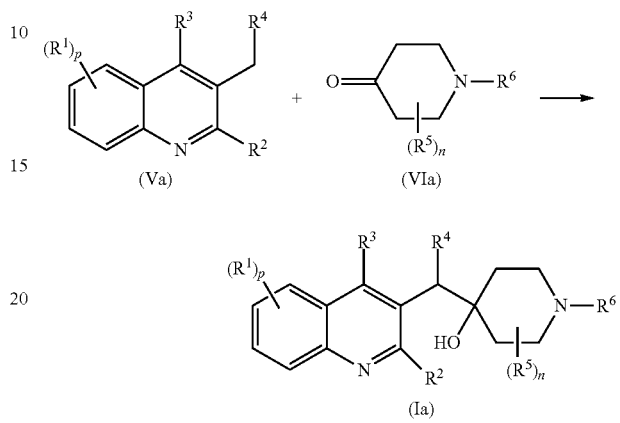

(Va)  (VIa)

(Ia)

to prepare compounds of formula (Ia);

or, if desired, converting compounds of formula (Ia) or (Ib) into each other following art-known transformations, and further, if desired, converting the compounds of formula (Ia) or (Ib), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms or N-oxide forms thereof.

* * * * *